(12) United States Patent
Principe et al.

(10) Patent No.: US 10,531,806 B2
(45) Date of Patent: Jan. 14, 2020

(54) BRAIN STATE ADVISORY SYSTEM USING CALIBRATED METRICS AND OPTIMAL TIME-SERIES DECOMPOSITION

(71) Applicant: University of Florida Research Foundation, Inc., Gainesville, FL (US)

(72) Inventors: Jose Principe, Gainesville, FL (US); Austin J. Brockmeier, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 834 days.

(21) Appl. No.: 14/574,320

(22) Filed: Dec. 17, 2014

(65) Prior Publication Data

US 2016/0242690 A1    Aug. 25, 2016

Related U.S. Application Data

(60) Provisional application No. 61/916,919, filed on Dec. 17, 2013.

(51) Int. Cl.
| | | |
|---|---|---|
| *A61B 5/04* | (2006.01) | |
| *A61B 5/00* | (2006.01) | |
| *A61B 5/0476* | (2006.01) | |

(52) U.S. Cl.
CPC .......... *A61B 5/04012* (2013.01); *A61B 5/742* (2013.01); *A61B 5/0476* (2013.01)

(58) Field of Classification Search
CPC .............. A41D 19/0037; A63C 11/222; A45B 2009/025
See application file for complete search history.

(56) References Cited

U.S. PATENT DOCUMENTS

| | | | |
|---|---|---|---|
| 4,201,224 A | 5/1980 | John | |
| 5,406,957 A | 4/1995 | Tansey | |
| 6,898,582 B2 | 5/2005 | Lange | |
| 6,988,056 B2 | 1/2006 | Cook | |
| 8,073,534 B2 | 12/2011 | Low | |
| 8,512,240 B1 * | 8/2013 | Zuckerman-Stark | ................. G16H 50/30 600/301 |
| 2005/0007091 A1 * | 1/2005 | Makeig | ................. A61B 5/048 324/76.13 |
| 2007/0260151 A1 * | 11/2007 | Clifford | ............. A61B 5/04017 600/509 |

(Continued)

OTHER PUBLICATIONS

S. Mallat and Z. Zhang, "Matching pursuits with time-frequency dictionaries," Signal Processing, IEEE Transactions on, vol. 41, No. 12, pp. 3397-3415, Dec. 1993.

(Continued)

*Primary Examiner* — Jacqueline Cheng
*Assistant Examiner* — Tho Q Tran
(74) *Attorney, Agent, or Firm* — Thomas Horstemeyer, LLP

(57) ABSTRACT

Various examples are provided for brain state advisory systems using calibrated metrics and optimal time-series decompositions. In one embodiment, a method includes monitoring brainwave activity of a subject and classifying a brain state of the subject based upon the brainwave activity and a model of the brainwave activity. In another embodiment, brain states of the subject are modeled based upon the brainwave activity of the subject.

18 Claims, 64 Drawing Sheets

(56) References Cited

U.S. PATENT DOCUMENTS

| | | | | |
|---|---|---|---|---|
| 2011/0295332 | A1* | 12/2011 | Osorio | A61B 5/0476 607/3 |
| 2012/0130266 | A1* | 5/2012 | Mathan | A61B 5/4833 600/544 |
| 2012/0184869 | A1* | 7/2012 | Chiang | A61B 5/7278 600/544 |
| 2015/0005839 | A1* | 1/2015 | Sabesan | A61N 1/36064 607/45 |
| 2015/0065839 | A1* | 3/2015 | Farah | A61B 5/0478 600/383 |
| 2018/0310854 | A1* | 11/2018 | Geva | A61B 5/04012 |

OTHER PUBLICATIONS

S. S. Chen, D. L. Donoho, and M. A. Saunders, "Atomic decomposition by basis pursuit," SIAM journal on scientific computing, vol. 20, No. 1, pp. 33-61, 1998.

E. Smith and M. Lewicki, "Efficient auditory coding," Nature, vol. 439, No. 7079, pp. 978-982, Feb. 2006.

J. L. Roux, A. D. Cheveigne, and L. C. Parra, "Adaptive template matching with shift-invariant semi-nmf," in Advances in Neural Information Processing Systems 21, D. Koller, D. Schuurmans, Y. Bengio, and L. Bottou, Eds., 2009, pp. 921-928.

R. Grosse, R. Raina, H. Kwong, and A. Y. Ng, "Shift-invariance sparse coding for audio classification," in Proc. UAI, 2007.

M. Lewicki, "Efficient coding of natural sounds," Nature Neuroscience, vol. 5, No. 4, pp. 356-363, Apr. 2002.

D. C. Balcan, M. S. Lewicki et al., "Point coding: Sparse image representation with adaptive shiftable-kernel dictionaries," in SPARS'09—Signal Processing with Adaptive Sparse Structured Representations, Apr. 2009.

C. Ekanadham, D. Tranchina, and E. Simoncelli, "Recovery of sparse translation-invariant signals with continuous basis pursuit," Signal Processing, IEEE Transactions on, vol. 59, No. 10, pp. 4735-4744, Oct. 2011.

O. Shalvi and E. Weinstein, "New criteria for blind deconvolution of nonminimum phase systems (channels)," Information Theory, IEEE Transactions on, vol. 36, No. 2, pp. 312-321, Mar. 1990.

A. Bell and T. Sejnowski, "Learning the higher-order structure of a natural sound*," Network: Computation in Neural Systems, vol. 7, No. 2, pp. 261-266, Jan. 1996.

M. Davies and C. James, "Source separation using single channel ICA," Signal Processing, vol. 87, No. 8, pp. 1819-1832, Aug. 2007.

F. Lucena, A. Barros, J. Principe, and N. Ohnishi, "Statistical coding and decoding of heartbeat intervals," PLoS One, vol. 6, No. 6, p. e20227, Jun. 2011.

P. Smaragdis, B. Raj, and M. Shashanka, "Sparse and shift-invariant feature extraction from non-negative data," in Acoustics, Speech and Signal Processing, IEEE International Conference on, Mar. 2008, pp. 2069-2072.

M. O'Brien, A. Sinclair, and S. Kramer, "Recovery of a sparse spike time series by L1 norm deconvolution," Signal Processing, IEEE Transactions on, vol. 42, No. 12, pp. 3353-3365, Dec. 1994.

P. Comon, "Independent component analysis, a new concept?" Signal processing, vol. 36, No. 3, pp. 287-314, Apr. 1994.

A. Hyvarinen, "Fast and robust fixed-point algorithms for independent component analysis," Neural Networks, IEEE Transactions on, vol. 10, No. 3, pp. 626-634, May 1999.

B. Mailhe' et al., "Shift-invariant dictionary learning for sparse representations: extending k-SVD," in 16th European Signal Processing Conference, Aug. 2008.

A. J. Brockmeier, B. Mahmoudi, J. C. Sanchez, and J. C. Principe, "Efficient temporal decomposition of local field potentials," in Machine Learning for Signal Processing (MLSP), 2011 IEEE International Workshop on, Sep. 2011, pp. 1-6.

A. J. Brockmeier, M. K. Hazrati, W. J. Freeman, and J. C. Principe, "Locating spatial patterns of waveforms during sensory perception in scalp EEG," in Engineering in Medicine and Biology Society (EMBC), 2012 Annual International Conference of the IEEE, Sep. 2012, pp. 2531-2534.

A. J. Brockmeier, L. G. Sanchez Giraldo, M. S. Emigh, J. Bae, J. S. Choi, J. T. Francis, and J. C. Principe, "Information-theoretic metric learning: 2-D linear projections of neural data for visualization," in Engineering in Medicine and Biology Society (EMBC), 2013 35th Annual International Conference of the IEEE, Jul. 2013, pp. 5586-5589.

Blumensath, Thomas, and Mike Davies. "Sparse and shift-invariant representations of music." IEEE Transactions on Audio, Speech, and Language Processing 14.1 (Jan. 2006): 50-57.

Stoica, Petre, and Yngve Selen. "Cyclic minimizers, majorization techniques, and the expectation-maximization algorithm: a refresher." IEEE Signal Processing Magazine 21.1 (Jan. 2004): 112-114.

* cited by examiner

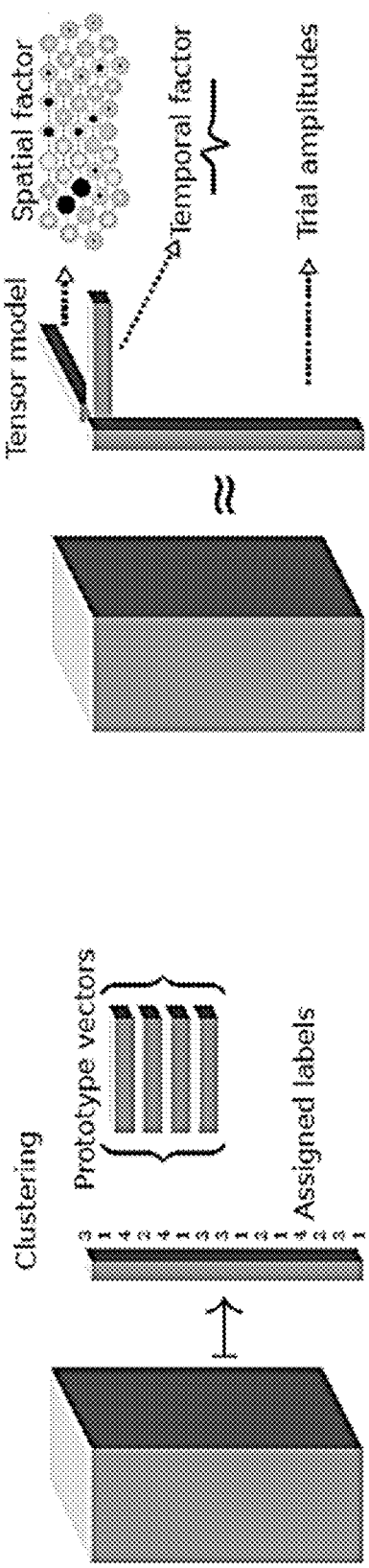
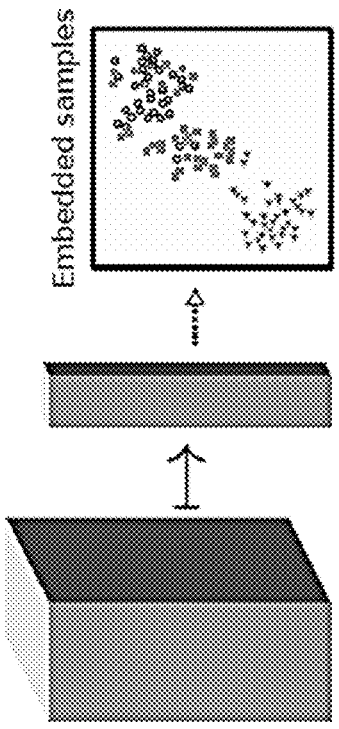
FIG. 6A
FIG. 6B
FIG. 6C

|     | Spectral Clustering | | | | | k-means | | | | |
| --- | --- | --- | --- | --- | --- | --- | --- | --- | --- | --- |
| L | k=4 | k=6 | k=8 | k=10 | k=16 | k=4 | k=6 | k=8 | k=10 | k=16 |
| 1 | 43.7 | 51.6 | 47.4 | 45.1 | 47.3 | 45.4 | 47.9 | 46.8 | 44.3 | 49.7 |
| 5 | 43.8 | 56.6 | 58.2 | 56.9 | 52.2 | 44.6 | 51.2 | 57.1 | 51.3 | 47.9 |
| 10 | 50.0 | 46.3 | 51.2 | 51.7 | 52.0 | 44.6 | 49.9 | 51.5 | 48.3 | 45.2 |
| 20 | 43.9 | 48.2 | 51.3 | 55.3 | 52.9 | 42.1 | 49.1 | 45.4 | 48.8 | 48.1 |
FIG. 7D
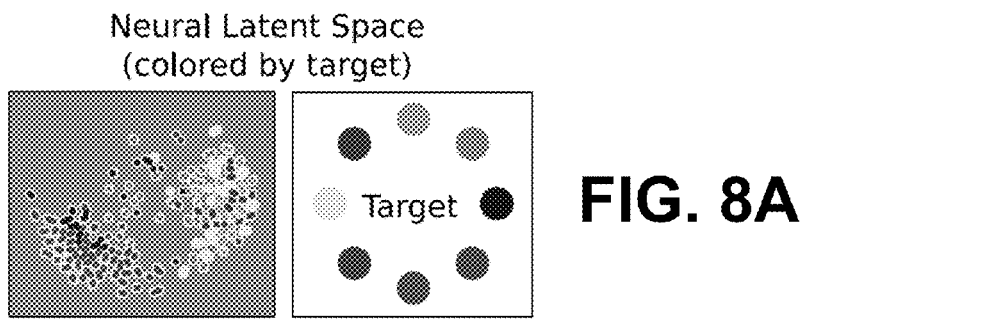
FIG. 8A
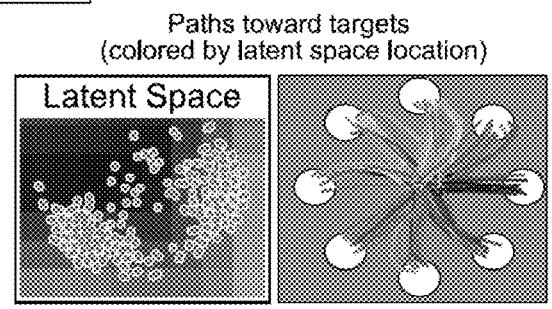
FIG. 8B
| Space | Area | Start cue | Target cue | During reach | | | | Target hold | Reward |
| --- | --- | --- | --- | --- | --- | --- | --- | --- | --- |
| Original | M1 | 9.2 | 15.2 | 51.2 | 53.7 | 52.9 | 48.8 | 43.8 | 20.4 |
| Latent | M1 | 10.8 | 18.4 | 31.4 | 50.4 | 59.5 | 52.1 | 49.6 | 27.8 |
| Original | PMd | 7.7 | 11.2 | 36.4 | 29.8 | 24.8 | 23.1 | 19.0 | 7.4 |
| Latent | PMd | 12.3 | 11.2 | 12.4 | 16.5 | 16.5 | 13.2 | 14.1 | 14.8 |
| Original | S1 | 15.4 | 13.6 | 23.1 | 25.6 | 29.8 | 26.5 | 18.2 | 20.4 |
| Latent | S1 | 13.9 | 12.0 | 16.5 | 18.2 | 22.3 | 17.4 | 19.0 | 16.7 |
FIG. 8C

Algorithm 3.1 Matching pursuit (MP).

$r \leftarrow x$
for $i = 1, \ldots, L$ do
　　$r \leftarrow x - \tilde{x}$
　　$c_q \leftarrow \frac{1}{\|a_q\|}(a_q, r) \quad q = 1, \ldots, P$
　　$p_i \leftarrow \arg\max_q = |c_q|$
　　$\tilde{A} \leftarrow \begin{bmatrix} \tilde{A}, a_{p_i} \end{bmatrix}$
　　$\tilde{s}_i \leftarrow c_{p_i}$
　　$r \leftarrow r - \tilde{s}_i a_{p_i}$
end for

FIG. 10A

Algorithm 3.2 Orthogonal matching pursuit (OMP).

$\hat{x} = 0$
for $i = 1, \ldots, L$ do
　　$r \leftarrow x - \hat{x}$
　　$c_q \leftarrow \frac{1}{\|a_q\|}(a_q, r) \quad q = 1, \ldots, P$
　　$p_i \leftarrow \arg\max_q = |c_q|$
　　$\tilde{A} \leftarrow \begin{bmatrix} \tilde{A}, a_{p_i} \end{bmatrix}$
　　$\tilde{s} \leftarrow \tilde{A}^\dagger x$
　　$\hat{x} \leftarrow \tilde{A}\tilde{s}$
end for

FIG. 10B

Algorithm 3.3 Time-series MP $r(t) \leftarrow x(t)$
for $i = 1, \ldots, L$ do
　　$c_q(t) = \frac{1}{\int_{-\infty}^{\infty} a_q^2(u) du}(a_q * r)(t) \quad q = 1, \ldots, P$
　　$p_i \leftarrow \arg\max_q \max_t |c_q(t)|$
　　$\tau_i \leftarrow \arg\max_t |c_{p_i}(t)|$
　　$\alpha_i \leftarrow c_{p_i}(\tau_i)$
　　$r(t) \leftarrow r(t) - \int_{-\infty}^{\infty} \alpha_i \delta(t - \tau_i - u) a_{p_i}(u) du$
end for

FIG. 10C

Algorithm 3.4 Timing extraction with a $B$-length censoring period.

$z_q(t) \leftarrow 1 \quad \forall t, q = 1, \ldots, P$
$i \leftarrow 1$
for $q = 1, \ldots, P$ do
   $c_q(t) = (a_q * x)(t)$
   while $\exists t : z_q(t) = 1$ do
     $i \leftarrow i + 1$
     $p_i = q$
     $\tau_i \leftarrow \arg\max_t |c_q(t) z_q(t)|$
     $z_q(t) \leftarrow 0 \quad t \in (\tau_i - \frac{B}{2}, \tau_i + \frac{B}{2})$
   end while
end for
$L \leftarrow i$

FIG. 10D

Algorithm 3.5 OMP Select
for $k = 1, \ldots, K$ do
   $\{(\alpha_i, \tau_i)\}_{i=1}^L \leftarrow \text{MP}(r, v_k, L)$
   $y_k \leftarrow \sum_{i=1}^L \alpha_i T_{\tau_i} v_k$
end for
$\{p_i\}_{i=1}^P \leftarrow \text{OMP}(x, \{v_k\}_{k=1}^K, P)$
$\{v_p\}_{p=1}^P \leftarrow \{v_j\}_{j \in \{p_i : i=1, \ldots, P\}}$

FIG. 10E

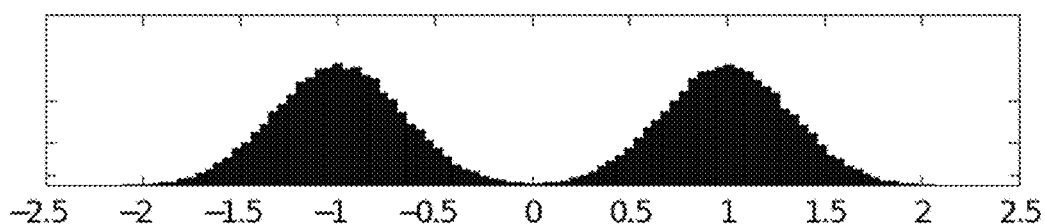

FIG. 11

Algorithm 3.6 MP-SVD $\mathbf{v}_p \leftarrow \text{randn}(M,1) \quad \forall p = 1,\ldots,P$
repeat
 $\{(p_i, \alpha_i, \tau_i)\}_{i=1}^{L} \leftarrow \text{MP}\left(\mathbf{x}, \{\mathbf{v}_p\}_{p=1}^{P}, L\right)$
 $\mathbf{e} \leftarrow \mathbf{x} - \sum_{i=1}^{L} \alpha_i T_{\tau_i} \mathbf{v}_{p_i}$
 for $p = 1,\ldots,P$ do
  $\mathcal{I}_p \leftarrow \{i : p_i = p\}$
  $\mathbf{x}^{(p)} \leftarrow \mathbf{e} + \sum_{j \in \mathcal{I}_p} \alpha_j T_{\tau_j} \mathbf{v}_p$
  $\check{X}_p \leftarrow \left[T_{\tau_j}^* \mathbf{x}^{(p)}\right]_{j \in \mathcal{I}_p}$
  $\mathbf{v}_p \leftarrow \arg\max_{\mathbf{w}} \dfrac{\mathbf{w}^T \check{X}_p \check{X}_p^T \mathbf{w}}{\mathbf{w}^T \mathbf{w}}$
 end for
until Convergence of the filters or other stopping criterion

Algorithm 3.7 Greedy MP-SVD $\mathbf{r} \leftarrow \mathbf{x}$
for $p = 1,\ldots,P$ do
 $\mathbf{v}_p \leftarrow \text{randn}(M,1)$
 repeat
  $\{(\alpha_i, \tau_i)\}_{i=1}^{L} \leftarrow \text{MP}(\mathbf{r}, \mathbf{v}_p, L)$
  $\check{R} \leftarrow \left[T_{\tau_i}^* \mathbf{r}\right]_{i=1}^{L}$
  $\mathbf{v}_p \leftarrow \arg\max_{\mathbf{w}} \dfrac{\mathbf{w}^T \check{R} \check{R}^T \mathbf{w}}{\mathbf{w}^T \mathbf{w}}$
 until Convergence of the filter or other stopping criterion
 $\{(\alpha_i, \tau_i)\}_{i=1}^{L} \leftarrow \text{MP}(\mathbf{r}, \mathbf{v}_p, L)$
 $\mathbf{r} \leftarrow \mathbf{r} - \sum_{i=1}^{L} \alpha_i T_{\tau_i} \mathbf{v}_p$
end for

FIG. 10G

| Method | Training PVE (%) | | | | | Testing PVE (%) | | | | |
|---|---|---|---|---|---|---|---|---|---|---|
| | 1[a] | 2 | 3 | 4 | Total[b] | 1 | 2 | 3 | 4 | Total |
| MP-SVD | 24 | 45 | 21 | 22 | 89 | 25±4 | 35±4 | 24±2 | 24±1 | 86±2 |
| FastICA | 37 | 34 | 16 | 15 | 84 | 29±4 | 32±1 | 19±1 | 16±1 | 82±1 |
| Greedy | 60 | 27 | 10 | 2 | 92 | 52±3 | 34±2 | 11±1 | 3±1 | 90±1 |

[a]Per component.
[b]Using all components at once.

FIG. 16A

| Method | Learning time (s) | Approximation time (s) |
|---|---|---|
| MP-SVD | 243 | 64±5 |
| FastICA | 12 | 52±3 |
| Greedy | 60 | 5±0.03 |

FIG. 16B

| Method | Training PVE (%) | | | | | | Testing PVE (%) | | | | | |
|---|---|---|---|---|---|---|---|---|---|---|---|---|
| | 1[a] | 2 | 3 | 4 | Total[b] | All[c] | 1 | 2 | 3 | 4 | Total | All |
| MP-SVD | 18 | 18 | 16 | 18 | 66 | 53 | 18±4 | 15±2 | 12±4 | 19±2 | 61±4 | 48±4 |
| FastICA | 25 | 22 | 21 | 18 | 61 | 49 | 23±1 | 17±2 | 19±1 | 17±3 | 56±3 | 44±3 |
| Greedy | 52 | 15 | 0 | 0 | 64 | 60 | 45±4 | 18±2 | 0±0 | 0±0 | 59±4 | 56±3 |
[a]Per component on select channel.
[b]Using all components on select channel.
[c]Across all channels.
FIG. 20D
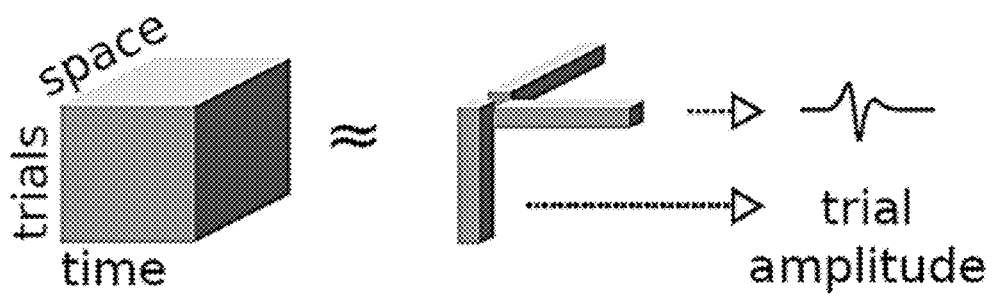
FIG. 21A
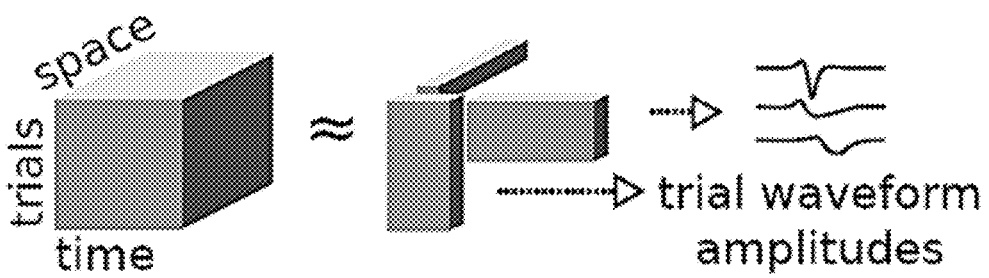
FIG. 21B

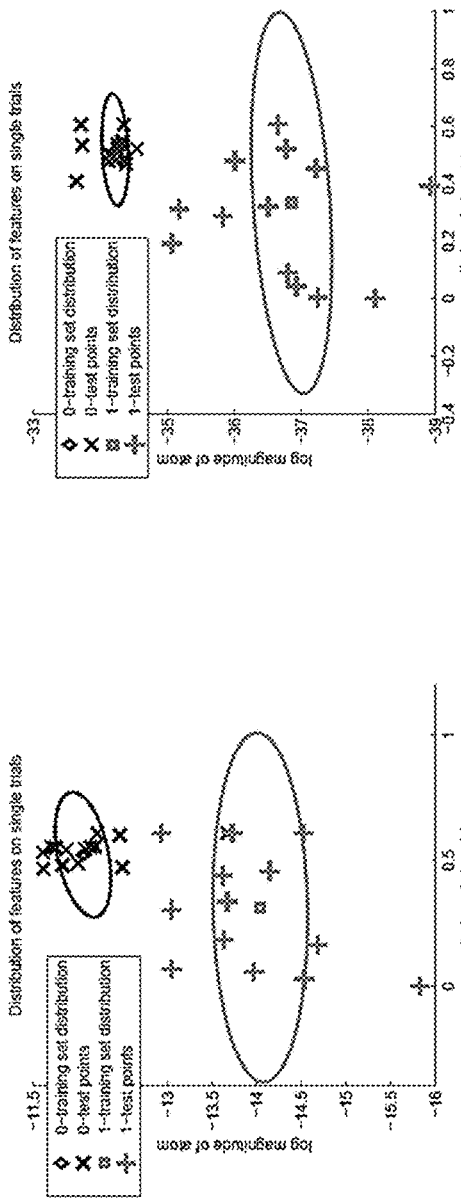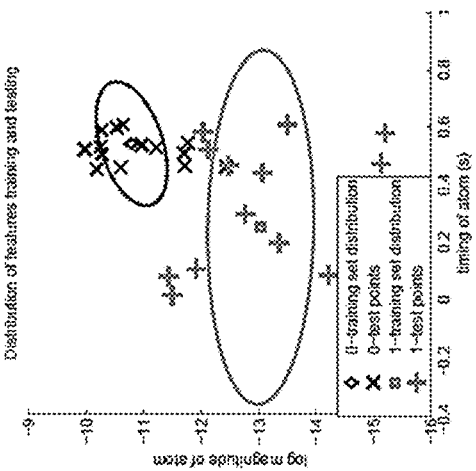
FIG. 28A
FIG. 28B
FIG. 28C

| Model | Time | Amplitude | Power | Time and amplitude |
|---|---|---|---|---|
| A | 71.7±4.7 | 94.0±2.8 | 93.5±2.4 | 94.1±3.3 |
| B | 73.5±4.0 | 95.7±1.8 | 94.0±4.0 | 96.6±2.0 |
| C | 75.4±3.5 | 92.8±2.8 | 93.6±2.5 | 95.8±1.8 |
FIG. 31
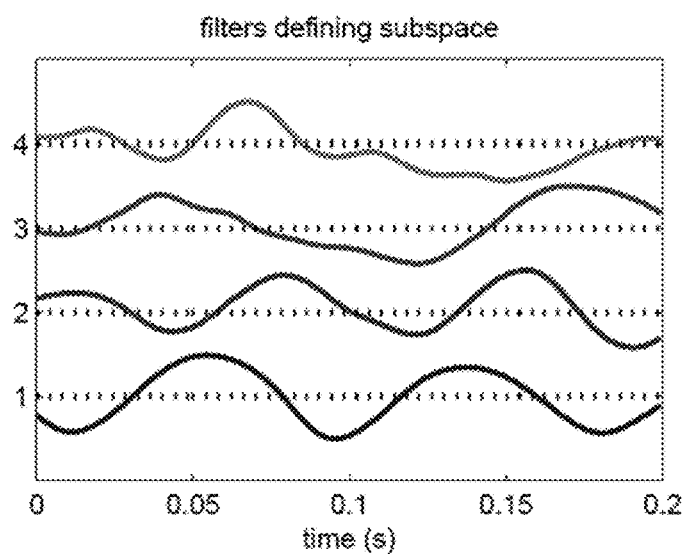
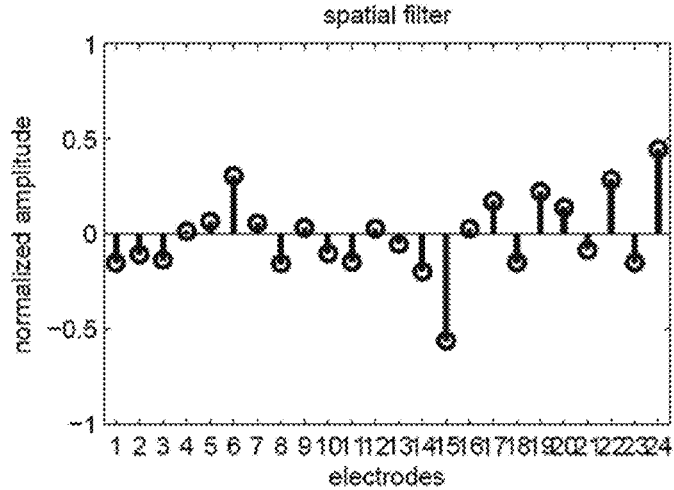
FIG. 32

| Dataset[a] | Dimension | Model[b] | Waveform length | BIC × 10^6 | SNR (dB) | Run time[c] (s) |
|---|---|---|---|---|---|---|
| A | 16×1017×43 | | | | | |
| | | CPD | 1017 | -14.88 | 6.36 | 0.32 |
| | | SVS | 512 | -14.80 | 5.06 | 2.66 |
| | | dVCA | 512 | -14.84 | 5.69 | 2.47 |
| | | gVCA | 512 | *-14.89 | 6.36 | 7.77 |
| B | 24×400×48 | | | | | |
| | | CPD | 400 | -1.76 | 1.62 | 0.32 |
| | | SVS | 128 | -1.80 | 2.40 | 1.21 |
| | | dVCA | 64 | *-1.83 | 3.00 | 1.79 |
| | | gVCA | 128 | -1.83 | 2.95 | 2.49 |
| C | 64×240×340 | | | | | |
| | | CPD | 240 | 24.21 | 2.88 | 1.57 |
| | | SVS | 12 | 23.99 | 3.29 | 12.77 |
| | | dVCA | 64 | *23.74 | 3.77 | 37.63 |
| | | gVCA | 64 | 23.87 | 3.54 | 28.09 |
| D | 64×240×340 | | | | | |
| | | CPD | 240 | 22.74 | 1.68 | 1.60 |
| | | SVS | 64 | 22.15 | 2.80 | 22.04 |
| | | dVCA | 64 | *21.80 | 3.48 | 50.12 |
| | | gVCA | 64 | 21.84 | 3.40 | 62.62 |

* Indicates best model with 2 components in terms of BIC.
[a] Datasets: A) LFPs in ventral striatum during non-rewarding object trials. B) LFPs in motor cortex for non-rewarding passive observation trials. C) Scalp EEGs for subject A during BCI operation. D) Scalp EEGs for subject B during BCI operation.
[b] Models consist of the canonical polyadic decomposition (CPD), shift-varying subspace (SVS) with a single spatial factor, differentially variable component analysis (dVCA) with a single spatial factor, and greedy dVCA (gVCA) that has a unique spatial factor for each component.
[c] Concurrent computing load may have affected run times.

FIG. 39A

| Dataset[a] | Dimension | Model[b] | Waveform length | BIC ×10⁶ | SNR (dB) | Run time[c] (s) |
|---|---|---|---|---|---|---|
| A | 16×1017×43 | | | | | |
| | | CPD | 1017 | -15.06 | 10.29 | 1.41 |
| | | SVS | 512 | -14.79 | 5.63 | 4.97 |
| | | dVCA | 128 | -14.93 | 7.05 | 28.32 |
| | | gVCA | 512 | *-15.16 | 10.93 | 35.18 |
| B | 24×400×48 | | | | | |
| | | CPD | 400 | -1.86 | 4.66 | 0.61 |
| | | SVS | 256 | -1.87 | 4.52 | 1.76 |
| | | dVCA | 64 | *-2.00 | 6.90 | 17.87 |
| | | gVCA | 64 | -1.98 | 6.56 | 18.53 |
| C | 64×240×340 | | | | | |
| | | CPD | 240 | 22.06 | 7.10 | 3.94 |
| | | SVS | 64 | 22.35 | 6.53 | 28.47 |
| | | dVCA | 64 | 21.43 | 8.33 | 513.62 |
| | | gVCA | 64 | *21.40 | 8.41 | 180.36 |
| D | 64×240×340 | | | | | |
| | | CPD | 240 | 21.36 | 4.43 | 4.37 |
| | | SVS | 200 | 21.12 | 4.88 | 24.70 |
| | | dVCA | 64 | 20.32 | 6.44 | 480.10 |
| | | gVCA | 64 | *20.03 | 7.02 | 338.37 |

* Indicates best model with 8 components in terms of BIC.
[a]Datasets: A) LFPs in ventral striatum during non-rewarding object trials. B) LFPs in motor cortex for non-rewarding passive observation trials. C) Scalp EEGs for subject A during BCI operation. D) Scalp EEGs for subject B during BCI operation.
[b]Models consist of the canonical polyadic decomposition (CPD), shift-varying subspace (SVS) with a single spatial factor, differentially variable component analysis (dVCA) with a single spatial factor, and greedy dVCA (gVCA) that has a unique spatial factor for each component.
[c]Concurrent computing load may have affected run times.

FIG. 39B

| Dataset | C | P | n | SOPFW[a] | Euclid.[b] | CAML[c] | ~CAML[d] |
|---|---|---|---|---|---|---|---|
| Pen-Based Recog. | 10 | 16 | 10992 | 1.1 | *1.0±0.2 | N/A | 1.2±0.2 |
| Breast Wisc. (Diag.) | 2 | 30 | 569 | *4.0 | 4.8±1.7 | 4.4±1.5 | 4.3±1.4 |
| Page Blocks | 5 | 10 | 5473 | 4.6 | *4.1±0.5 | 4.6±0.5 | 4.3±0.5 |
| Image Segmentation | 7 | 18 | 2310 | 5.2 | 6.2±1.0 | *3.3±0.8 | 4.6±0.8 |
| Ionosphere | 2 | 33 | 351 | 12.2 | 16.3±3.9 | *10.7±4.9 | 13.7±3.5 |
| Parkinsons | 2 | 22 | 195 | *10.2 | 12.1±4.3 | 13.6±4.7 | 11.5±3.9 |
| Spambase | 2 | 57 | 4601 | *10.4 | 11.0±0.9 | 14.6±4.7 | *10.4±0.8 |
| Waveform (ver. 1) | 3 | 21 | 5000 | 18.4 | 19.0±0.9 | *17.9±0.9 | 18.5±0.8 |
| Connectionist (Sonar) | 2 | 60 | 208 | 22.1 | *20.8±5.4 | 27.5±4.9 | 22.4±5.4 |
| Wine Quality | 7 | 11 | 6497 | 46.3 | 46.3±1.0 | 48.9±1.2 | *46.0±1.0 |

Entries are classification error as percent incorrect, average and standard deviation taken across Monte Carlo runs, using a k-nearest neighbor classifier. Columns denoted |C|, P, and n indicate the number of classes, features, and samples, respectively.
[a]Sequential quadratic program-based feature weighting
[b]Unweighted normalized Euclidean distance
[c]Centered alignment metric learning optimizing a product kernel
[d]Centered alignment metric learning with mini-batch approximation
*Indicates best performing methods, which were not significantly different, p-value greater than 0.05, for either a one-sample t-test versus SQPFW, or a two-sample t-test between other methods.

FIG. 40

FIG. 41

| Dataset | VP metric unweighted 1-NN | SVM | mCI metric unweighted 1-NN | SVM | VP metric $\theta$ 1-NN | $\theta$ SVM | $\Theta$ SVM | mCI metric $\theta$ 1-NN | $\theta$ SVM | $\Theta$ SVM |
|---|---|---|---|---|---|---|---|---|---|---|
| 1 | 53±9 | 69±9 | 60±9 | 59±8 | 86±6 | 87±5 | 85±9 | 85±4 | *90±6 | *92±5 |
| 2 | 35±4 | 80±5 | 70±5 | 78±5 | 77±5 | 87±5 | *91±4 | 78±4 | 87±5 | *89±3 |
| 3 | 28±5 | 50±4 | 43±4 | 50±6 | 44±6 | 53±4 | *59±5 | 48±5 | 58±6 | *61±4 |
| 4 | 22±4 | 28±6 | 25±4 | 27±5 | 22±5 | *38±5 | *38±5 | 22±4 | 29±9 | 34±4 |

Entries indicate the mean and standard deviation of percent correct computed across 20 Monte Carlo runs. Victor-Purpura (VP) and kernel-based (mCI) metrics in unweighted combinations are compared alongside of using centered alignment metric learning (CAML) to optimize a product kernel ($\theta$) or sum of 5 weighted product kernels ($\Theta$). Nearest-neighbor (1-NN) and support vector machine (SVM) were used as classifiers.
*Indicates methods with highest accuracy with or without binning

FIG. 42

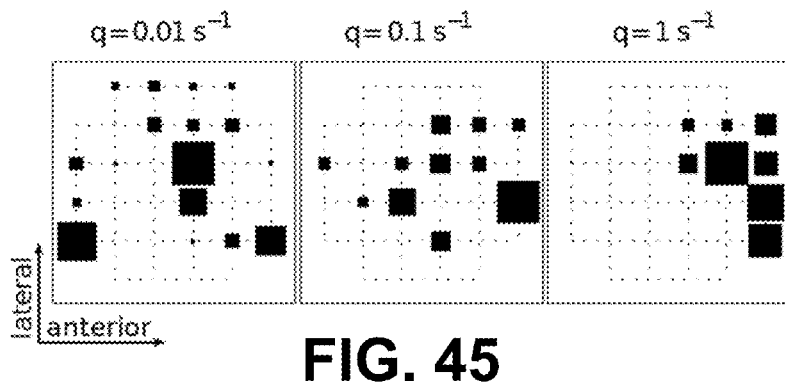

FIG. 45

| Dataset | Euclidean | $\theta$-CAML | $\Theta$-CAML | A-CA | A-FDA | A-LMNN |
|---|---|---|---|---|---|---|
| 1 | 89±4.4 | 94±3.7 | 97±2.2 | *98±2.0 | *98±2.0 | 97±2.4 |
| 2 | 75±5.0 | 84±3.0 | 89±2.4 | 95±2.6 | *97±1.9 | 94±5.0 |
| 3 | 61±5.4 | 79±4.9 | 83±4.0 | *91±4.7 | *92±3.5 | 87±2.9 |
| 4 | 54±5.1 | 81±4.2 | *85±3.8 | *86±3.8 | *86±4.5 | 80±5.9 |

Entries indicate the mean and standard deviation of percent correct computed across 20 Monte Carlo runs. SVM is used as classifier. Centered alignment metric learning (CAML) is used to optimize a single temporal weight vector $\theta$ or a sum kernel with multiple temporal weightings $\Theta$ Mahalanobis-based metrics (parametrized by a matrix $A$) optimized using Fisher discriminant analysis (FDA), centered alignment (CA), and large margin nearest neighbor (LMNN).
* indicates highest performing methods for each dataset.

FIG. 46

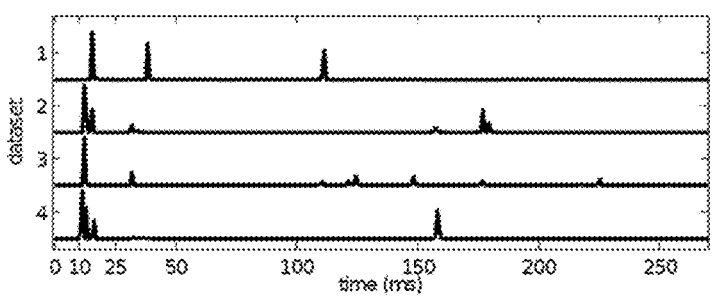

FIG. 47

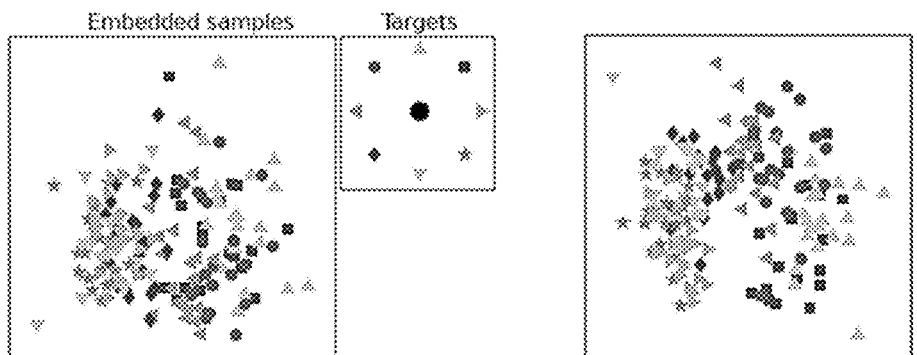

Entries indicate the mean and standard deviation of percent correct computed across 80 Monte Carlo runs. For each unit, the spike train kernel induced distance is computed. An unweighted combination of these distances is compared to using centered alignment metric learning (CAML) to optimize a weighted distance. Results for the third nearest neighbor (3NN) and support vector machine (SVM) are reported.

FIG. 48

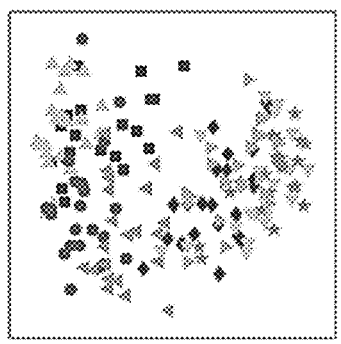

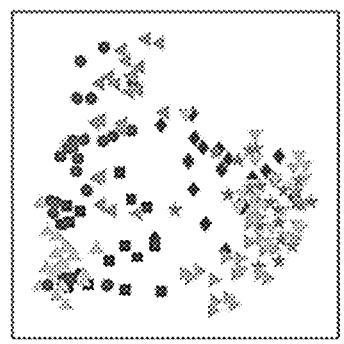

BRAIN STATE ADVISORY SYSTEM USING CALIBRATED METRICS AND OPTIMAL TIME-SERIES DECOMPOSITION

CROSS REFERENCE TO RELATED APPLICATIONS

This application claims priority to U.S. provisional application entitled "BRAIN STATE ADVISORY SYSTEM USING CALIBRATED METRICS AND OPTIMAL TIME-SERIES DECOMPOSITION" having Ser. No. 61/916,919, filed Dec. 17, 2013, which is hereby incorporated by reference in its entirety.

STATEMENT REGARDING FEDERALLY SPONSORED RESEARCH OR DEVELOPMENT

This invention was made with government support under agreement N66001-10-C-2008 awarded by the Defense Advanced Research Projects Agency (DARPA). The Government has certain rights in the invention.

BACKGROUND

Electrocorticograms and/or electroencephalograms are used by physicians to monitor brainwave activity for medical evaluation of a patient. Micro-electrode arrays can be implanted into the brain to record the electrical potentials corresponding to the activity of neurons and neural populations. These recordings can be used to understand how a subject's brain represents different conditions such as external stimuli or movement intention. Brain-machine interfaces may be utilized to decode the signals from the micro-electrode arrays.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 6A through 6C are examples of spatiotemporal data analysis in accordance with various embodiments of the present disclosure.

FIG. 7D is a table illustrating examples of classifying rewarding and non-rewarding trials in accordance with various embodiments of the present disclosure.

FIGS. 8A and 8B are visual representations of subject trial results in accordance with various embodiments of the present disclosure.

FIG. 8C is a table illustrating examples of performance of reach target decoding in accordance with various embodiments of the present disclosure.

FIGS. 10A through 10G are examples of various algorithms for classification in accordance with various embodiments of the present disclosure.

FIG. 11 is an example of source excitation amplitude distribution in accordance with various embodiments of the present disclosure.

FIGS. 16A and 16B are tables illustrating examples of training performance in accordance with various embodiments of the present disclosure.

FIGS. 17A-17C and 20A-20D are examples of decomposition of motor cortex LFP in accordance with various embodiments of the present disclosure.

FIGS. 21A and 21B are examples of tensor models in accordance with various embodiments of the present disclosure.

FIGS. 28A-28C and 34 are examples of scatter plots for atomic decompositions in accordance with various embodiments of the present disclosure.

FIGS. 29A-29C, 30A-30C, 31, 40, 42, 43A-43B and 46 are examples of classification performance in accordance with various embodiments of the present disclosure.

FIG. 32 includes examples of spatiotemporal models in accordance with various embodiments of the present disclosure.

FIGS. 38A-38D and 39A-39B illustrate model performance in accordance with various embodiments of the present disclosure.

FIG. 41 includes images illustrating the setup for subject testing in accordance with various embodiments of the present disclosure.

FIGS. 44 and 49A-49D illustrate examples of metric-based dimensionality reduction in accordance with various embodiments of the present disclosure.

FIGS. 45 and 47 are examples of learned weighting in accordance with various embodiments of the present disclosure.

FIG. 48 is an example of multi-unit metrics in accordance with various embodiments of the present disclosure.

DETAILED DESCRIPTION

Figure 1:
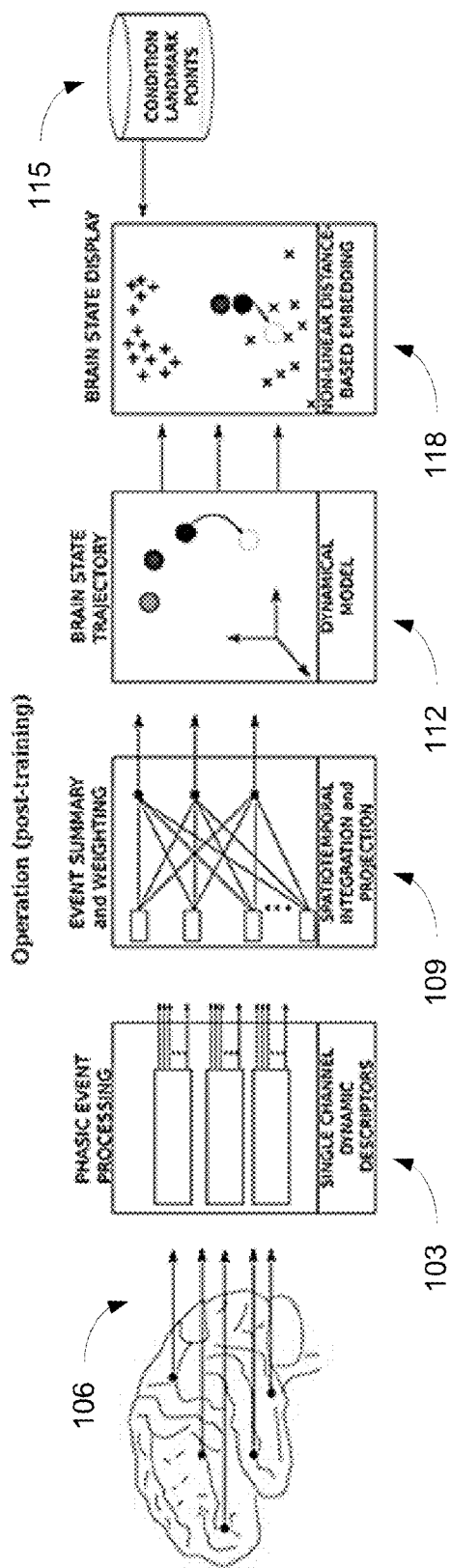
FIG. 1 is an example of a brain state advisory system in accordance with various embodiments of the present disclosure.

Disclosed herein are various examples related to brain state advisory systems using calibrated metrics and optimal time-series decompositions. Reference will now be made in detail to the description of the embodiments as illustrated in the drawings, wherein like reference numbers indicate like parts throughout the several views.

Referring to FIG. 1, shown is an example of a brain state advisory system for determining and displaying the current and predicted brain state referenced to clinically determined states. The brain state is determined through patient-specific signal processing and mapping functions. The blocks of processing include a patient-specific optimal decomposition 103, which accurately and sparsely describes the spatiotemporal dynamics of the collected brainwaves 106 (local field potentials, electrocorticogram, and/or electroencephalogram (EEG)) through phasic events; followed by spatiotemporal integration of the phasic events' energy into a multidimensional vector 109; finally, the energy vectors are mapped to a low-dimensional representation 112 that retains the maximal information regarding the clinically determined states.

First, in 103 time-series decomposition separates the multichannel neural electric recordings into set of waveform descriptors. The decomposition corresponds to a generative model of the subject's brain activity: a linear superposition of sparse independent sources filtered by distinct waveforms. The decomposition is designed to: be tuned, through training, to a given subjects brainwaves; quantify transients and temporally localized oscillations; avoid any assumptions regarding the distribution or stationarity in signals; and does not decrease the temporal resolution versus the original discretely sampled time-series. This decomposition can be applied to even a single channel to produce the features for the analysis to quantify brain state in health (circadian rhythms) and in disease states. Each waveform may correspond either evoked potentials or temporally localized brain rhythms (e.g., delta, theta, alpha, sigma/sleep spindles, beta, gamma, high gamma, and fast ripples), since the sources are sparse the waveforms are typically separated in time and their occurrence are treated as "phasic events". This brain-rhythm decomposition allows the original signals to be reconstructed with high fidelity from the sparse phasic events. Because the decomposition is tuned to each subject, the methodology is able to achieve both diagnostic sensitivity and specificity.

In 109, short-term summaries of the phasic events are constructed by low-pass filtering the energy of events and pooling the energy between nearby channels with similar waveforms. Following this spatiotemporal integration, vectors of the pooled energy are linearly projected to a lower dimensional space. This projection is optimized within the framework of metric-learning, a supervised dimensionality reduction algorithm. The metric can be calibrated for the objective such as separating abnormal and normal brain states or brain states corresponding to different stimuli.

After projection, in 112 a probabilistic model is made for each clinical diagnostic condition of interest. This can be implemented using a set a landmark points 115 (e.g., component means in a Gaussian mixture model). The distance to the nearest landmark point for a given condition is proportional to the likelihood of that condition. Furthermore, a dynamical model can be used to track the trajectory of the current brain state relative to the landmark points. The past and current brain state can be displayed on a portable device in 118, or watch-form factor, in conjunction with the landmark points as part of a brain state advisory system. The two-dimensional representation is implemented by non-linear distance embedding.

One embodiment, among others, includes a method of EEG or intracranial EEG data representation, transmission, analysis, and display for brainwave activity for clinical diagnostic using the steps of:

(a) Modeling segments of multichannel EEG as a linear superposition of time-localized waveforms compactly recorded as a vector of the waveform index, time index, spatial amplitude vector, a so-called atomic decomposition and inferred using an greedy iterative approach;

(b) Learning the set of waveforms and spatial amplitude vectors using an alternating optimization, on a training segment, with one or a combination of the following criterion: minimizing the mean square error of the reconstruction, independence among the coefficients for different waveforms, or maximizing the difference between the magnitude of the coefficients under different conditions;

(c) Using the atomic decomposition to achieve data compression and low-bandwidth transmission; assuming the set of waveforms is known at the receiver, only the vector of waveform index, time index, spatial amplitude vector are sent;

(d) Summarizing the atomic decomposition by low-pass filtering the squared magnitude of amplitude coefficients; the energy from very similar waveforms, or proximal channels/electrodes, may be added together (pooled) to provide invariance to the exact temporal waveform or spatial location and reduce the dimensions, the pooled energy across remaining dimensions is concatenated into a vector; and (e) Using metric-learning to optimize a linear projection of the energy vector that is either low-rank or full-rank, but comprising a non-negative weight for each dimension; the projection is calibrated so that after projection the Euclidean distance between energy vectors that are nearby occur during the same brain (cognitive, pathological, sensory) state; the projection corresponds to changing the metric in the original space; the low-rank projection intrinsically reduces the dimension of this space, in the non-negative weighting dimensions whose weight is below a threshold may be removed.

In operation, the current brain state is classified by minimum distance, using the calibrated metric, to a set of points indicative of each brain state (these points are defined as landmarks). Using a probabilistic dynamical system to predict the trajectory of the brain state in the future, this can be used to advise the user. An advisory system comprising textual information and a two-dimensional display of the relative location of the current and recent brain states relative to the landmark points, along with the estimated trajectory, may be used. This representation can be formed by using a non-linear embedding that preserves the distances using the calibrated metric.

This example can achieve data compression and reconstruction with high fidelity (in terms of signal to noise ratio) and low data transmission rates along with discrimination between different patient conditions using steps (a) and (b). Using a processing and display device with a handheld or watch form-factor, the device can be used in ambulatory conditions to record the representation (a), process it (c-f), and display some information regarding the representation (e).

Testing and evaluation of the disclosed system was performed. Different stages of processing on LFPs under two unknown conditions were investigated for disambiguating conditions from phasic descriptors. The two conditions were separable using the multiscale processing analysis.

It was demonstrated how discriminative methods can be used to extract shift-invariant spatio-temporal features from multichannel local field potentials (LFPs). The discrimination comes from the fact that the spatio-temporal component filters are learned on a training segment from only one condition. Thus, the resulting filters efficiently describe only this one condition. Then the entire recording under both conditions is decomposed using these component filters.

The short-term energy for each decomposition (i.e., the component energy) can used as the descriptor at temporal scales a magnitude longer than the component filters. The statistics of the component energy in the training set is used to learn a projection to a two-dimensional state in which the states for the two conditions are maximally separated.

Figure 2:
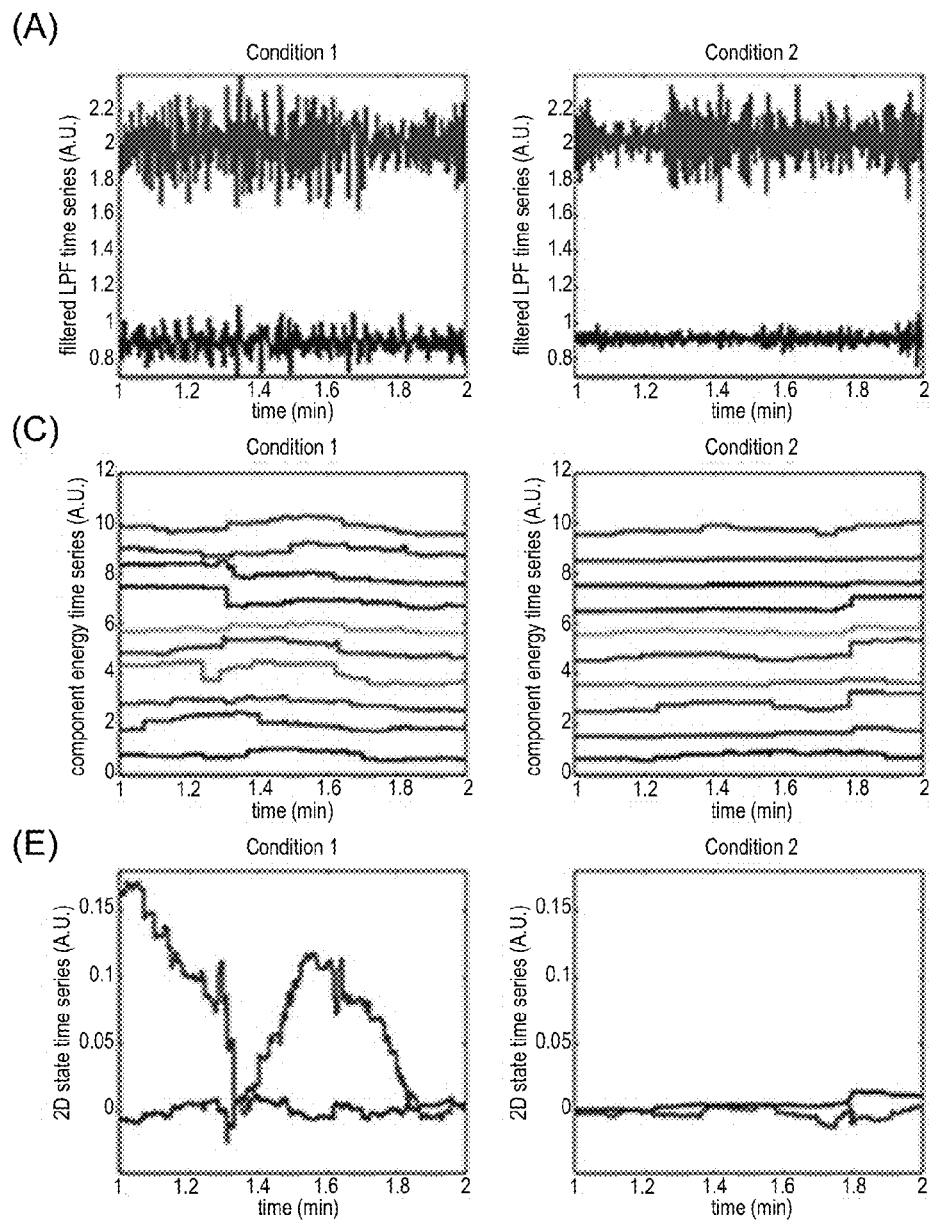
FIG. 2 illustrates examples of signal processing for discrimination of brain states in accordance with various embodiments of the present disclosure.
Figure 2:
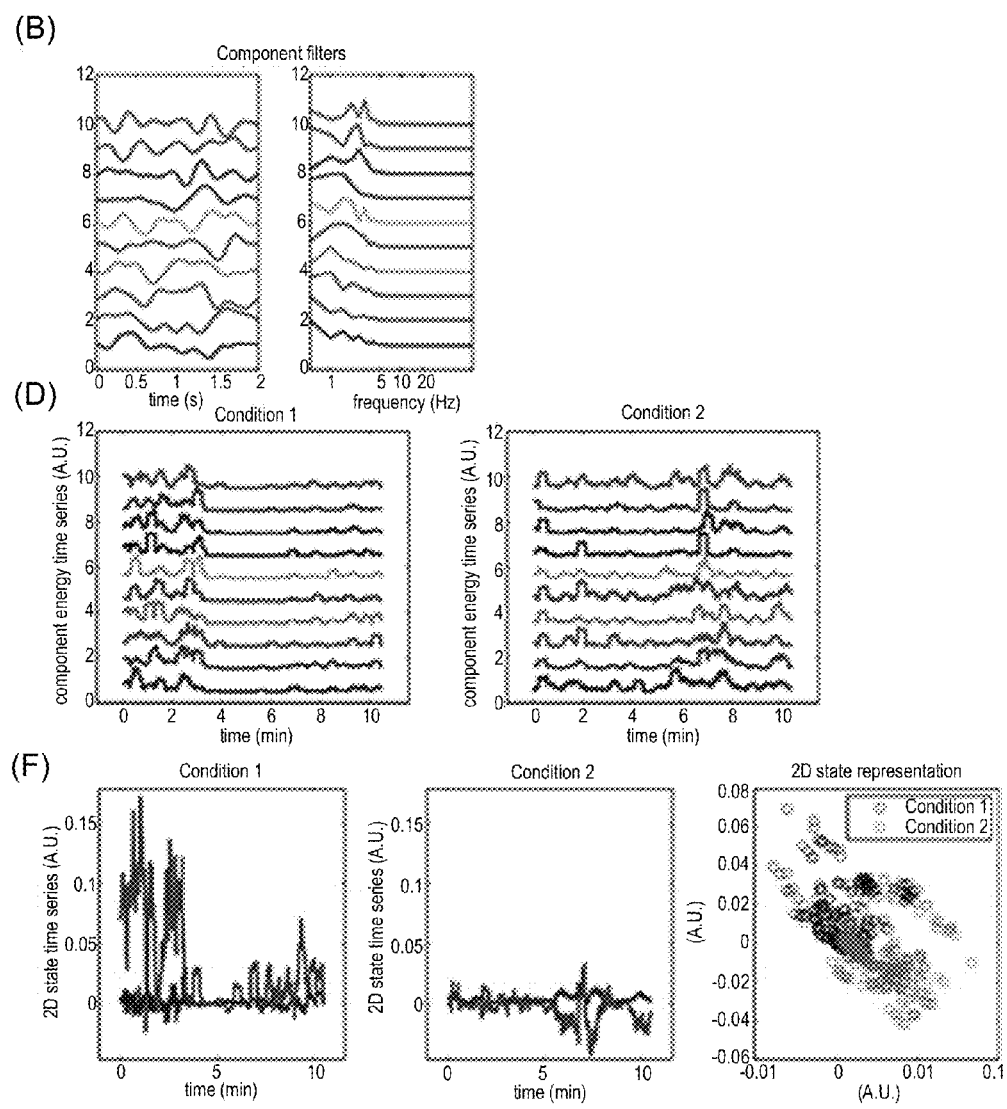

Referring to FIG. 2, shown is an example of a signal processing tool chain for discrimination of brain states. Two conditions are examined. In FIG. 2(A), shown are one-minute segments of the LFPs under each condition filtered with a low-pass filter. In FIG. 2(B), shown are the component filters learned under condition 1. In FIG. 2(C), shown is the short-term energy of each component in the same one-minute segment under each condition. In FIG. 2(D), shown is the short-term energy across the entire recording under each condition. In FIG. 2(E), shown is a linear projection of the component energies in the one-minute segment under each condition. In FIG. 2(F), shown are the state representation time series and the 2D state representation across the full recording. The two conditions are clearly separable in this representation.

Neural signals can be recorded at multiple scales: the action potentials, or spikes, from individual neurons, and the local field potentials corresponding to neural populations. In addition, the neural responses can have a natural variability even for the same condition. With these diverse and high-dimensional signals, pinpointing the indicators of different conditions can be a challenge. Furthermore, a portion, or even a majority, of the neural signals may pertain to other cognitive processes. To a naive brain-machine interface, this background activity may appear to be inexplicable noise.

These challenges can be addressed by proposing a set of methods that learn new representations of the neural data. These representations can be adapted to both the recurrent patterns in the neural signals and the decoding task. These methods include clustering and dimensionality reduction, which label or group reoccurring spatiotemporal patterns without supervision. Similarly, generative models can be used to parsimoniously explain both the spatial and temporal patterns in neural potentials. In particular, models can account for variability in amplitude, waveform shape, and timing, and exploit spatial filters to separate different conditions. Finally, a new approach for learning metrics on population activity can be used to exploit information jointly represented across space and time and to highlight the most informative dimensions.

These tools can be applied to neural recordings of both spike trains and local field potentials in different brain regions of animal models. The approaches may improve data visualization and decoding performance, aiding researchers in their quest to understand the brain from increasingly complex neural recordings.

Systematic analysis of neural activity is used to investigate the brain's representation of different conditions such as stimuli, actions, intentions, cognitive states, or affective states. Motor brain-machine interfaces (BMIs) attempt to decode upper-limb movements from neural data. Applications of BMIs include delivering lost sensation back to the brain or deriving training signals for motor decoders directly from the brain's representation of reward. In these cases, the fundamental role of a BMI is to decode motor intention, location of touch, or cognitive features such as anticipation of reward solely from the recorded neural signals.

Electrophysiology recordings use multiple electrodes and high-sampling rates to accurately record neural signals as they vary across time and space. The neural responses may be recorded either invasively or non-invasively. Surgically implanted micro-electrode arrays allow invasive recordings to capture both the timing of action potentials (spike trains) across many neurons, and local field potentials (LFPs) across many electrodes. Only the action potential waveforms of neurons in the close vicinity of the electrode are captured, providing a minute fraction of the neurons contributing in the implanted region.

Estimating the decoding models utilized by BMIs is difficult on this diverse, high-dimensional data. In addition, there are multiple modalities by which the signal characteristics differ between conditions. These include the energy at certain frequencies, the spatial or temporal patterns of evoked potentials following a stimulus presentation, and the rate or pattern of individual neuronal spiking patterns.

Instead of treating the representation of the neural response as given and attempting to solve a very difficult classification or regression task, an alternative, possibly low-dimensional, representation of the neural signals can be optimized. Ideally, with this new representation it will be easier to perform the subsequent classification or regression problem, investigate the important dimensions of the neural response, and/or gauge the information content relevant to the experimental condition. In this disclosure, a number of algorithms are proposed that learn useful representations of neural signals based on their underlying statistics among responses to the same condition and between responses of different conditions. These approaches can be specifically tailored to handle both the complexity and diversity of the neural signals and the high-dimensionality found in real neural recordings.

Neural Spiking Activity. Interneuronal communication is often characterized by a series of action potentials, or spikes. In very general terms, a relatively large and rapid change in one neuron's potential can be generated by the dynamic activation of ion channels in a neuron. Action potentials in the peripheral nerve carry information back to the central nervous system via their timing and rate of generation. In the central nervous system the initial impulse is generated near the neuron's cell body, and the impulse travels along its axon toward where other neurons are synaptically connected. As the relative amplitude of the spike carries less information than the timing, the amplitude of spikes is discarded and only the spike timing recorded. Statistically, spike trains are formally modeled as a point process.

Electrophysiological Recordings. Microelectrode arrays capture the time-varying extracellular potential at each recording location. Single-unit action potential waveforms are relatively short and impulse-like, thus their contribution is spread over the spectrum; however, they can be distinguished by their contribution to the high portion of the spectrum (e.g., over the range of 300 Hz to 6 KHz). Single-unit action potentials, or spikes, can be isolated from the high frequency portion of the voltage trace in two steps. Initially, the potential spike times can be found by identifying when the signal crosses a threshold. Then the spikes from each specific neuron can be discriminated based on the shape of the action potential wave-form. This second process is called spike sorting. Sorting involves matching the waveforms surrounding a threshold crossing to a set of shape templates. Defining the shape templates for the different units can be done as either a supervised or unsupervised process. Since noise can also cause a spurious threshold crossing, waveforms that do not sufficiently match any of the templates can be discarded. Whether sorted to separate the different units or not, spiking activity no longer contains amplitude information and can be encoded solely in a sequence of time called a spike train.

In the last couple decades, it has become possible to sample from large numbers of neurons. This is largely due to the development of multi-electrode arrays, better instrumentation, and faster computing that allows the simultaneous recording and processing of multiple neurons. A neuron can spike multiple times in a second, so recording from a large population can yield hundreds of thousands of action potential over a short period of time (e.g., in the course of 20 minute experiment). To handle this amount of data, intensive computing is used for spike identification and spike sorting.

Figure 3:
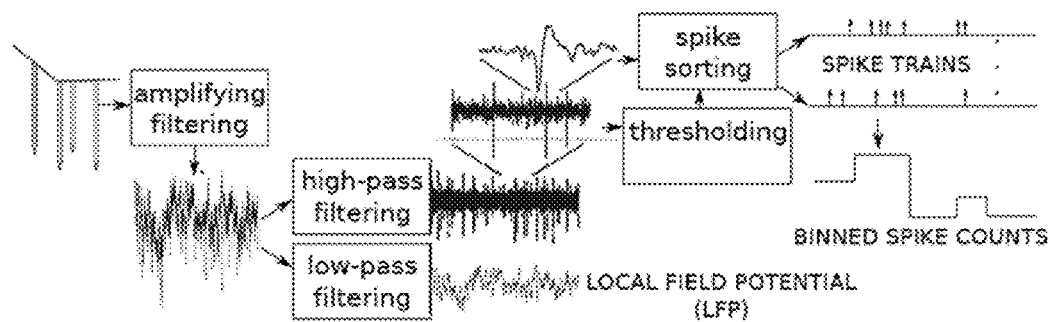
FIG. 3 is an example of processing for spike trains and local field potentials (LFPs) in accordance with various embodiments of the present disclosure.

Spike Training Binning. Even after spike sorting, the spiking activity cannot be directly used in algorithms that require real-valued vectors or scalars. Many algorithms are designed for real-valued vectors not spike trains. To use spike times as real-valued vectors, they are transformed into a discrete-time rate function by either smoothing, similar to kernel density estimation, or binning, using a time histogram of non-overlapping windows with a pre-specified bin width. Referring to FIG. 3, shown is an example of the preprocessing steps and signal flow for extracting spike trains and LFPs. After initial amplification, filtering, and sampling, the signal can be low-pass filtered if destined for LFP analysis and high-pass filtered for spike detection. To resolve a spike train, the signal can be thresholded and sorted. Using a histogram in time to bin the spike train is an optional final step. A bin width or kernel width in the hundreds of milliseconds can be used for a smooth estimate of the firing rate.

Spike Training Binning. Even after spike sorting, the spiking activity is not ready to be directly used in algorithms that utilize real-valued vectors or scalars rather than spike trains. To use spike times as real-valued vectors, they can be transformed into a discrete-time rate function by either smoothing, similar to kernel density estimation, or binning, using a time histogram of non-overlapping windows with a pre-specified bin width as illustrated in FIG. 3. A bin width or kernel width in the hundreds of milliseconds can be used for a smooth estimate of the firing rate.

Neural Electrical Potentials. Brain waves are measurements of the time-varying electrical currents occurring in the brain. The electrical potential produced by the combined electric fields of neurons in the central nervous system can be measured at varying locations and scales: the electroenchephogram (EEG), the electrocorticogram (ECoG), and the local field potential (LFP). These neural potentials are a combination of local and distributed neural activity. The meaningful frequency ranges for analysis can range from less than one cycle per second to hundreds of cycles per second (e.g., 0.5 Hz to 300 Hz). Neural potentials offer a unique window into the operation of the neural circuits of the brain.

An EEG measures the potentials across the scalp, and can be used to analyze cortical processing. Classically, EEGs have been studied in terms of event-locked evoked potentials or in terms of power spectral density of the oscillations across the alphabetic frequency bands (alpha, beta, gamma, delta, mu). Brain waves can also be measured intracranially via an ECoG, sometimes referred to as intracranial EEG, or from penetrating electrodes within brain tissue, where the LFPs directly measure the extracellular potential.

At each of the scales/locations, the electrical potential measurement at each electrode is the superposition of electrical potential from multitudes of individual current sources. Additionally, the measurements are subject to noise from facial and neck muscle activity, movement artifacts, and external noise sources. To discern the underlying brain activity, these sources are first separated. Consequently, analysis of the electrical potentials relies heavily on signal processing to resolve the raw signals into usable forms. In certain cases, it is possible to identify the contributions of individual sources to the measured signal via various decomposition techniques.

One theory of how masses of neurons generate oscillations in the electric potential uses a series of hierarchical dynamical system models. Essentially, the waveforms in evoked potentials can be characterized by the synchronous activity of large numbers of neurons with both excitatory and inhibitory connections with varying time constants. In principle, the electric fields of the brain can be described by vector fields. A given dimension of the electric field in any coordinate system is a scalar field, since there are three dimensions of the electric field the complete electric field is a three-dimensional vector field. However, at each electrode only the scalar electric potential is measured, and the spatial sampling is limited by the position and number of electrodes. Understanding how currents contribute to the recorded electric potential allows an understanding of the sources of brain waves.

Due to the relatively slow speed of ion transport, the magnetic and electric waves are decoupled in electric fields in the brain. Thus, electric fields passively propagating through biological media (with possibly heterogeneous conductance) will only experience linear filtering—that is, they will not experience any non-linear distortion. Consequently, with no active means of amplification, the power of a signal fades as it is recorded farther from its source. The power at any frequency cannot increase, nor can it be distributed to other frequencies (i.e., there is no chance of Doppler effects).

As a measure of the electric potential in a localized area of the brain, the LFP can be the smallest scale of analysis considered for electrical potentials. The LFP is closer to the origin of neural oscillations than either ECoG or EEG measurements. The physical location of ECoG above the cortex and the EEG above the scalp may further attenuate the signals. Due to the orientation of the electric field, some local oscillations may not make measurable contributions to the potentials recorded above the cortex or on the scalp. At these external locations, they can also be more prone to environmental noise sources and movement artifacts. Consequently, LFPs offer a unique opportunity to study neural electric potentials nearer their origins.

Neural data analysis has many challenges associated with the size, complexity, and unobservable nature of the central nervous system.

Heterogeneity: The central nervous system in vertebrates is a complex system composed of a richly structured and connected network of neurons and other cells that are specialized in form, function, and location. Even within a specific cortical region, such as the motor or somatosensory cortex, it is difficult to predict a priori how exactly a given neuron may behavior, what conditions may affect its operation, etc. Neurons in different systems may use the timing of their action potentials or their rate to deliver information to the next layer.

High-dimensionality: Multichannel neural recordings with high-sampling rates yield high-dimensional dataset; yet, they correspond to an extreme subsampling of the full brain.

Diversity across scales: The activity a population of neurons is set of timings, locations, and shapes of action potentials, or simply a set of spike spike train, whereas the electrical potentials is a continuous multivariate time-series with conditions affecting both the spatial and temporal patterns and the frequency content.

Network complexity: Neural data analysis has inherent dependencies at different scales and between different scales—e.g., the dependency between individual neurons, between neurons and the local field potential, between the field potentials in different brain regions, etc. There may exist many distinct neural ensembles whose activity is associated with processing similar information; however, the assignment of neurons to ensembles, or other dependencies, has to be inferred solely from their activity without known connectivity.

Variability: Unable to account for the activity of unobserved neural populations, and the distributed nature of neural circuits, the neural response to repeated conditions appears noisy and variable. This background activity is difficult to model, as it may be non-stationary, non-Gaussian, and non-linear. The relative contribution of the background activity can mask the activity relevant to the condition of interest. In addition, long term variability arises from the fact the central nervous system is itself plastic, and adapts over time. The neural plasticity may occur rapidly and it is difficult to predict these changes.

Neural Signal Variability. Neural signals are never wholly consistent across periods of time. When analyzing neural data when there is known external information, such as the timings of stimuli, it may be possible to identify a reliable response in the time-locked average. This is the most basic offline analysis approach when multiple presentations of the stimuli are available. This average is referred to as a peri-stimulus or pen-event time average, or in the case of binned spike time histogram.

Time-locked averages discard much of the underlying response. If there was a high-frequency content in the signal that was not phase-locked, or temporal patterns with various temporal alignments, then these patterns will not be present in the average. The signal itself may be the result of multiple unobserved sources impinging on each recording sensor. Averaging does not provide a means to separate the contribution of the other sources; and thus does not help in separating multiple sources on individual trials.

Disparity in the Information Rate. Another challenge is the disparity between the information rate of the external information and the sampling rate of the data. The exact timing window in which the neural response represents the condition of interest may be short compared to the length of the recording. Finding which portions can be important, especially if the lag between the stimulus and the response varies.

This is opposed to cases where there is known desired signal at every point in time, as in Wiener filtering or other system identification methods. These methods are well suited to identify one-to-one functions between time-varying signals and corresponding external variables of interest, but they are not well suited to capture the discriminating features of the diverse set of high-dimensional evoked signals associated with different stimuli classes.

For example, in a binary classification task a single bit of external information per trial is available; it may be possible to learn the patterns that characterize the signal per class. Assume each trial comprises a 4 second window of multi-channel recordings sampled at 500 Hz. Trying to classify each time point independently is a naive approach. Alternatively, treating the whole segment as a single observation provides only a single point in a sparse high dimensional space observation space. Thus, methods that extract information somewhere in between these extremes should be used.

As the details of neural signals differ between subject and recording location, a general 'one size fits all' BMI system will generally not succeed. Portions of the complete system may use predefined signal processing blocks, but a subset of system parameters should be adjusted, through training, for a specific subject. Often this training uses data from prior sessions where the desired outcomes are known. As the desired signals are known a priori they serve as a desired response for the system. The system parameters are trained to match as closely as possible this desired response. This form of adaptive training is known as supervised learning. The system may remain adaptive with the system parameters adjusted so that performance will be maintained as the underlying neural signals change over time.

Neural decoders can be used to assess the amount of information the recorded activity carries about the condition of interest. However, it can be difficult to determine whether poor performance is a result of lack of neural modulation or an inefficient decoder. If the performance is high then it is clear that the neural response carries information about the condition, but if the performance is not high it may be a poor decoder selection. Assessing the neural response in a decoder independent manner can be desirable to understand the degree to which the neural response varies among similar or repeated stimuli on a trial-to-trial basis.

Figure 4:
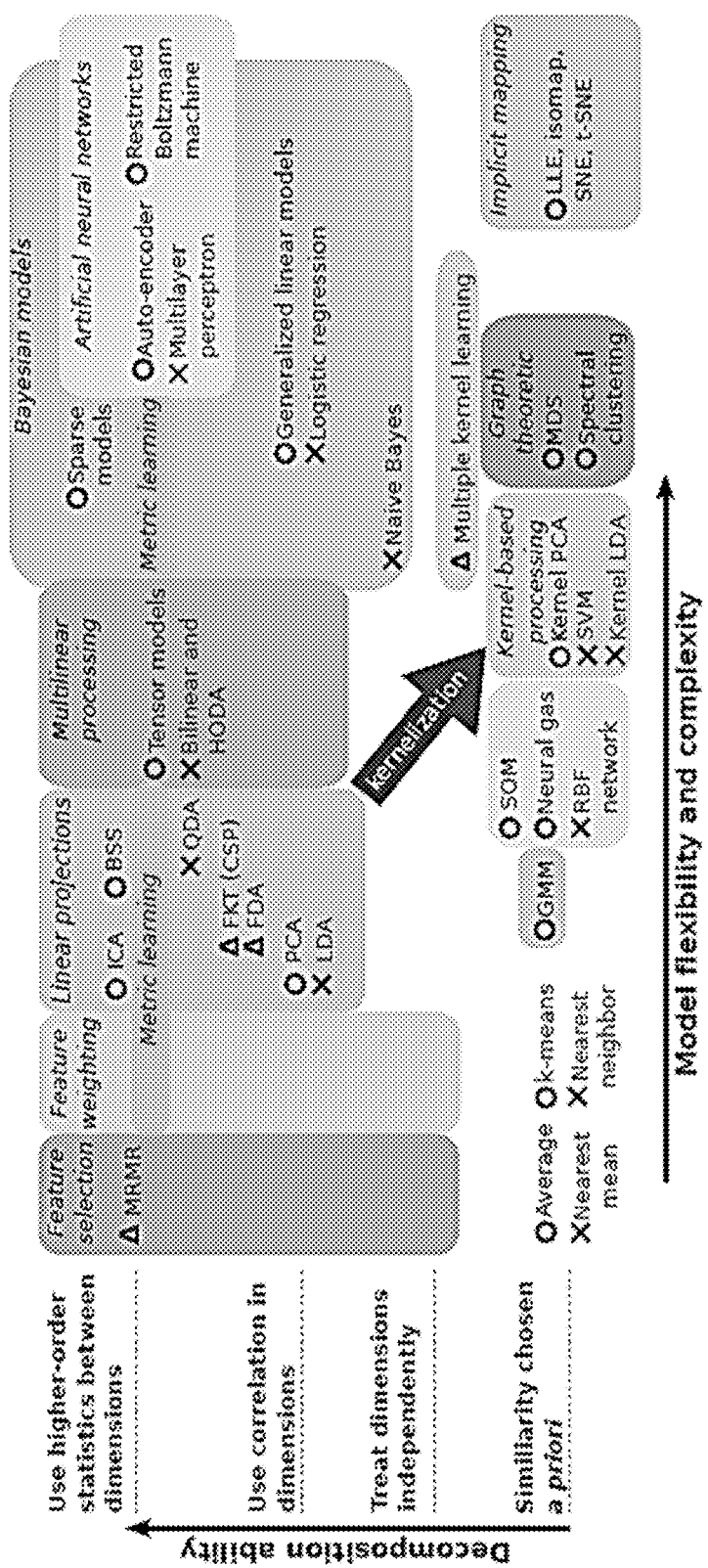
FIG. 4 is an example of classification and dimensionality reduction methods in accordance with various embodiments of the present disclosure.

Learning Representations for Neural Data. The methods for neural data analysis and decoding for BMIs can include the following: qualitatively capture the intrinsic relationship between the neural modulation and the variable to be decoded, highlight important features or dimensions of the neural response, and improve the performance of subsequent decoding. While neural data has certain unique characteristics, the analysis relies on the methods developed for general problems in the pattern recognition. FIG. 4 is a diagram illustrating examples of classification and dimensionality reduction methods organized by complexity and ability to use information among dimensions. FIG. 4 labels a number of pattern recognition methods for classification, clustering, dimensionality reduction, and modeling. ○ indicates an unsupervised method, x indicates a classification method, and Δ indicates a supervised dimensionality reduction approach.

In FIG. 4, the methods are oriented along two axes, with the x-axis detailing the underlying complexity in terms of number of parameters and computation time, and the y-axis detailing the ability of algorithms to be tuned to the specific dimensions thereby attenuating irrelevant dimensions or possibly linearly, or non-linearly, de-mixing the superpositions of multiple sources. Moving left to right, the methods involve more parameters or are more complex in terms of non-linearities of classification decision boundaries or functional mappings. In addition, methods on the right typically require longer computation. Moving bottom to top, methods are able to isolate components or dimensions relevant to a task using supervised information or show statistical structure without supervision.

A variety of methods consider the formation of features from the dimensions. Starting on the far left of FIG. 4, feature selection is the simplest approach as it comprises an inclusion or exclusion decision for each dimension. Although the relative importance of a feature is assessed, the information is used to select the features and then is lost; whereas feature weighting explicitly optimizes the relative contribution of the individual dimensions. Feature weighting can be used whenever there is an underlying distance metric. When applicable, linear projections can be used to find linear combinations, weighted sums, of the dimensions or, more generally, the correlation between dimensions that serve as better features then a weighted combination of features. Beyond linear projections, multilinear processing exploits the intrinsic organization of dimensions along multiple modes. For instance, features can be derived via bilinear projections for windows of multivariate time-series. Bilinear projections use a linear transformation along time and a linear projection across space.

Residing at the bottom of the diagram are methods that utilize a user-provided similarity measure. This similarity can be defined as inversely proportional to an intrinsic distance function, such as Euclidean distance. Another distance function could also be chosen a priori, but the methods do not modify this function in any way. The simplest approaches for summarizing data utilize averaging and clustering, which in the case of vector quantization coincides with local averages. Correspondingly, nearest-mean and nearest neighbor classifiers use the locations of samples in the training set without any optimization. The radial basis function (RBF) network learns a decision boundary function without changing the underlying measure, and can be a precursor to kernel-machines.

The kernel functions used in many popular kernel algorithms are bivariate similarity measures that the user chooses along with any hyper-parameters, e.g., Gaussian kernel size, associated with the kernels. Moving towards the top of FIG. 4, multiple kernel learning allows a convex combination of kernels to be automatically learned for a given task, and kernel-based metric learning allows the kernel functions themselves to be adapted. In the top right quadrant are the most versatile and powerful methods, such as auto-encoders for non-linear dimensionality reduction and multilayer perceptron. These methods comprise a priori selection of the architecture, but the optimal parameters and hyper-parameters are inferred from the data. These models typically utilize extensive computation time. Certain Bayesian models can be formulated that only comprise convex optimization, particularly with certain choices in generalized linear models.

Low-dimensional representations can be more informative. Although neural recordings may be very high-dimensional, often stimuli are applied or the behavior is performed in 2-D or 3-D space. This is especially true for motor and tactile experiments. The similarity among the conditions may correspond to similarity among behaviors or stimuli, such as spatial organization of the targets in a reaching task or the location of touches in a somatosensory task. In these cases, it may be possible to find a low-dimensional representation of the neural responses. If this representation preserves the relationships among the conditions, then there should be natural correspondence between the low-dimensional representation and the conditions. The representation can be used to assess the trial-to-trial variability and the similarity between neural responses to similar conditions—without explicit modeling. The neural response representation can be optimized in either a supervised or unsupervised manner.

Unsupervised Dimensionality Reduction. A number of unsupervised methods can be used for the exploratory analysis of neural data. Principal component analysis (PCA) can reveal patterns in neural data, but the results from PCA on neural data may be unsatisfactory, as the directions of largest variance may not contain any useful information. In the linear case, independent component analysis (ICA) can optimize a linear projection so the resulting vector has maximally independent elements. The activity projected along each of these dimensions may be informative, but as there is not a natural ranking of components the user is left to assess if any of the directions is meaningful.

Other non-linear approaches include distance embedding, kernel-based extension to PCA, and manifold learning algorithms that may preserve the similarity structure between samples in a low-dimensional representation. These methods tend to concentrate on preserving either local or structural-based similarities; but samples can be mapped to the representation space via explicit mappings.

Dynamical Modeling. State-space models with low-dimensional states can be used to model the temporal evolution and dependencies in neural responses. In a generative model, the low-dimensional states can be the latent process generating the high-dimensional neural activity. After training, the state-space models provide a means to explore the temporal evolution and variability of neural responses during single trials. The low-dimensional or discrete state variables, as in hidden Markov models (HMMs), can be visually depicted to track the dynamics of the neural response have shown how a combination of both temporal dynamics and a discrete state can efficiently capture the dynamics in a neural response. Ideally, the estimated states contain information regarding the experimental conditions, e.g., that they are indicative of the start of movement or intention. However, as unsupervised methods, state-space models are not guaranteed to capture aspects of the neural data actually related to the experimental condition.

Supervised Dimensionality Reduction. In the supervised case, Fisher discriminant analysis (FDA) and extensions use sample covariances from each class to form discriminative projections. The optimal projection can be a solution to a generalized eigenvalue problem that maximizes the spread between the means in different classes while minimizing the spread of samples within the same class. Local estimates of the class-covariance can be used for multimodal distributions. The dimensionality of the neural response can be reduced by feature selection. The simplest approach can be to find how informative each feature is for a given task and then select a set of informative, but not redundant features, or a set of features may be obtained by backward or forward-selection algorithms.

Decomposition of Spatiotemporal Signals. Models of stimulus evoked potentials can be used to separate the signal of interest from background activity. In some cases, tools developed for blind-source separation can identify separate spatially localized source spatial separation. In some implementations, separation can be performed in the time domain. Multiway or tensor models of the neural potentials allow for both spatial and temporal factors.

Representations for Spike Trains. The sequence of timings associated with neural action potentials are known as spike trains and can be a particularly challenging data type. Most processing algorithms deal with fixed-length vectors, whereas the spike trains are variable length data sets. The sequence of spike times (i.e., the spike train) can be modeled probabilistically as a point process in time. Point process models can be incredibly useful for building encoding models of how stimuli affect the spiking, and subsequently decoding the stimuli from the model. In other embodiments, decoding algorithms can be built directly off the geometric structure of the spike trains, without explicit probabilistic modeling, by exploiting measures of similarity and dissimilarity provided by spike train kernels and metrics, respectively.

The Victor-Purpura metric is an edit distance designed to weight the relative contribution of moving spikes to adding and deleting spikes. This weight is controlled by a temporal precision parameter. The van Rossum distance is the $\mathcal{L}_2$ distance between continuous rate functions, where the rate functions are estimated by convolving the spike trains with an impulse function comprising a one-sided exponential decay. Population versions of these metrics can also be utilized.

Following the success of kernel machines for machine learning, and the ability to define kernels on general spaces, such as graphs, spike train kernels may be used. In the reproducing kernel Hilbert space framework, linear algorithms in the Hilbert-space can implement non-linear processing in the input space. This can be used for spike trains where the input space does not permit linear operations. Of course linear operations can be applied to binned spike trains. After binning, spike trains are vectors in Euclidean space and general kernels can be used. In some cases, specialized kernels for spike count vectors, such as alignment-based kernels and/or spikernels that efficiently use population activity, can be used.

Although these metrics and kernels exploit the structure in individual neurons, the multi-unit approaches can be unsatisfactory when it comes to population activity. The main reason is that it is not straightforward how to design learning system that can differentially weight the individual contributions of units. In vector-valued patterns, a linear combination can be used to weight the different contribution of dimensions. Joint measures such as a tensor product spike train kernel, which uses the contribution of all units, can be useful. If only a few of the units are meaningful, then their activity can be diluted in the joint kernel. Thus, it can be beneficial to adapt joint measures toward a specific task.

To learn meaningful representations from raw neural data, the neural signals can be processed in a data-dependent manner, exploiting the structure of the signals. First, recurrent patterns in observed neural signals can indicate recurrent neural processing. By identifying the recurrent patterns, their occurrence can be used for later decoding. There are two paradigms for pattern recognition: summarizing the signal by a discrete or lower dimensional variable, and extracting a component under the assumption that the signal is a linear combination of components. In either case, the new representation corresponds to the pattern opposed to the raw signal.

Figure 5:
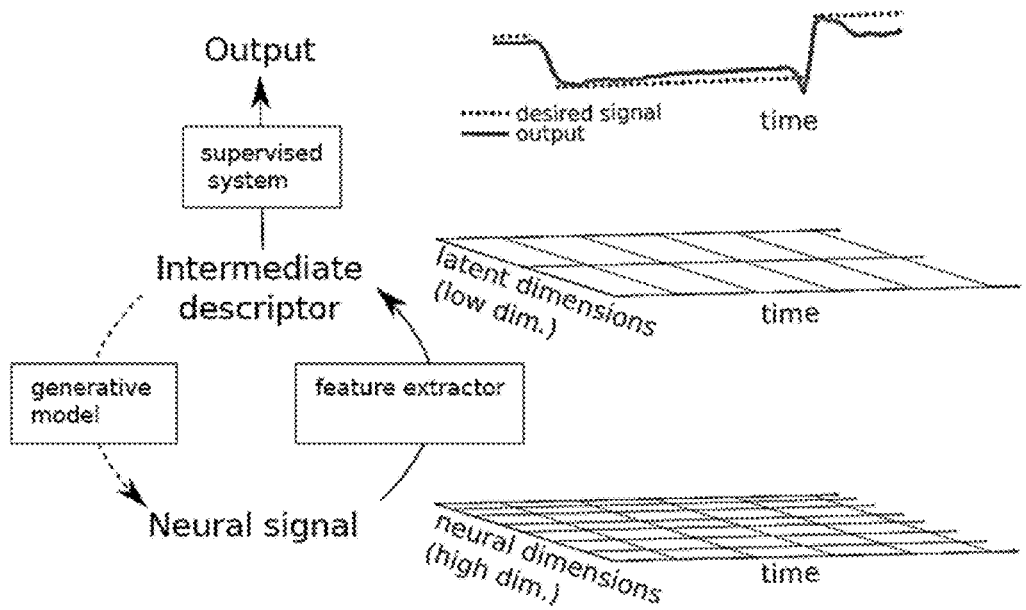
FIG. 5 illustrates an example of learning new representations of neural data in accordance with various embodiments of the present disclosure.

Second, for multi-electrode recordings, only a subset of the neural dimensions is relevant for a given decoding task. The relevant dimensions can be identified and combined in a manner that exploits their relative importance to maximize their joint information. These new representations can be learned based on the statistics of the data and possibly the decoding task. The new representations can serve as an intermediate descriptor for neural decoding that is better suited than using the raw signals. Specifically, intermediate descriptors can efficiently capture the characteristics of the signals or be estimates of latent, unobserved sources that are combined in the observed signals. FIG. 5 shows a diagram illustrating an example of learning new representations for neural data. An intermediate descriptor can be extracted from the signals prior to the classification task. The new representation is a common domain that can used for signals at multiple scales, e.g., for both neuronal spiking and electrical potentials.

The process can be matched to the type and complexity of the signals. For populations of spiking neurons, clustering and dimensionality reduction techniques can be used to summarize and capture recurring spatiotemporal firing rate patterns of populations of neurons. For local field potentials and EEG data, the signals can be modeled as an additive combination of background activity and relevant reoccurring patterns. In the case of spike trains and local field potentials, spatial and temporal dimensions can be identified. Graphical representations of these three approaches are shown in FIGS. 6A through 6C. FIG. 6A illustrates an example of clustering using spatiotemporal metrics, FIG. 6B illustrates an example of a tensor model for evoked potentials, and FIG. 6C illustrates an example of nonlinear dimensionality reduction using optimized metrics.

Unsupervised Learning for Neural Firing Rate Patterns. Multichannel neuron spike rates with a low-dimensional or discrete variable can be summarized such that the single-trial variability and cross-trial reliability can be assessed and task-relevant information is maintained. Clustering and dimensionality reduction-techniques can be applied as illustrated in FIG. 6A. Clustering assigns labels to recurrent patterns during and across multiple task trials. The sequence of labels can be used to identify cognitive processing, specifically reward expectation. Using dimensionality reduction, the trajectories of the high-dimensional neural data can be visualized in two- or three-dimensional representations—elucidating whether the neural data has consistent representations across multiple trials of a behavioral task.

Linear Models of Neural Electric Potentials. Condition-relevant spatiotemporal patterns from neural electric potentials can be extracted using linear synthesis models for the multichannel time-varying signals as illustrated in FIG. 6B. Two signal processing schemes can be used for extracting information from local field potential data: the first finds multiple recurrent patterns in continuous recordings, and the second assumes a single pattern per trial.

In the first scheme, the recurrent patterns in neural signals can be learned in an unsupervised manner. This approach can be used when external information is only available at much longer timescales so that the local activity can be summarized, but in a manner that can be tuned to the characteristics of the signals. Specifically, independent component analysis and/or sparse coding techniques can be used to identify sources of different multi-channel spatio-temporal patterns in the signals. Testing has indicated that this technique can identify recurrent patterns in single-channel LFPs.

In the second scheme, models can be used to explain the spatiotemporal waveforms evoked following stimuli presentations. The patterns occurring at random time points can be naturally captured and the spatiotemporal aspects of the signals leveraged. For these models, a balance can be struck between the cost between using simple models to summarize the neural responses and maintaining the diversity in the signal features. To find this balance, model selection criteria can be applied. The methods build of preliminary results that explored using predefined temporal waveforms and non-linear filtering via iterative optimization to extract spatial amplitude patterns in EEG on a single-trial basis.

These models can be used to identify coupling across scales, e.g., between neuronal data (spike trains) and electrical potential data. The relative temporal location of recurrent patterns in the LFP can be shown to be more predictive then the task timing for some neurons.

Optimized Representations. A general framework can also be developed for learning better representations of neural data as illustrated in FIG. 6C. Metric learning can be used as a general framework suitable for this task. Within this framework, approaches for learning joint kernels can be utilized that rely on the connection between metrics and reproducing kernel Hilbert spaces. The kernel framework may be used not only for kernel machine implementations—to perform non-linear classification and regression—but also for its connection with dependency measures and information theoretic quantities. Entropy and dependency measures can be empirically evaluated from kernel matrices, without explicit kernel density estimation. This approach allows Mahalanobis metrics on real-valued vectors to be optimized. This may be applied to binned spike trains and LFPs. The approach can be generalized to learning weighted product kernels on spike trains and LFPs. A computationally faster dependency measure can also be included. The framework can be used to learn the parameters of multi-unit spike train kernels.

Complexity of Representations. Brains are physical systems with real constraints, redundancies, and dependency between dimensions. Neural signals are more akin to audio recordings of natural sounds. As physical systems, they are constrained by their rate of change and limits in power or energy. The interaction of electrical potentials allows multiple sources impinging on the same sensors, just as multiple voices can be concurrently recorded on a single microphone.

The choice of modeling techniques or processing algorithms can be based on two considerations: first, whether the goal of the analysis is distilling the information to a more interpretable form, or extracting the relevant signals from a set or mixture; and second, the complexity of the signals based on an understanding of the underlying neurophysiology and generating process. In this disclosure, the analysis methods have been chosen such that the complexity of the model is matched to the complexity of the neural signals. For instance, if a subset of neural signals is desirable than a feature selection approach can be taken; or if the temporal alignment is desired then a shift-tolerant model can be employed. In certain cases, the modeling and post-hoc model selection itself can be used to understand the complexity of the data.

Unsupervised Analysis of Population Firing Rates

In the analysis of concurrent recordings of multiple units, recurrent patterns may be seen across the recorded population. A time course analysis tool, in the case of multiple stereotyped trials, is a peristimulus time histogram (PSTH), but it only provides the average for a discrete number of time-locked conditions. In addition, each neuron is treated separately, providing little intuition on the state of the ensemble of neurons. As it only explains the mean, it is unable to capture either the joint activity on a trial-to-trial basis.

Visualizing the collective modulation of multiple neurons can be useful for exploratory analysis, but visualizing a large number at once is challenging. In general, it is difficult to represent the joint neural activity in a single trial basis that is both understandable and informative. Often the patterns are only seen by assessing the patterns across many repeated trials; otherwise, the relevant modulation is lost by both the sheer dimensionality of the data and the intrinsic noise of neural spiking. One approach is to estimate a low-dimensional latent state variable that corresponds to the high dimensional data. Estimating latent states from multi-electrode neural data can be a general tool for characterizing the underlying network dynamics and can be used to find areas of interest (synchronization or correlation) over time.

Bayesian modeling is a natural approach for latent state estimation. This approach can deal with the natural variation and high dimensionality. Other state-estimation for multi-electrode recordings studies can be based on dynamical models such as hidden Markov models (HMMs), Kalman filters, and/or other dynamical models. State estimation for brain-machine interfaces can be used to decode movement type or plan timing. These approaches comprise explicit model formulation and estimation. Instead, data-driven approaches can be used for discrete state estimation or continuous state estimation where high-dimensional trajectories are projected to a low-dimensional space wherein trail-to-trail variability can be assessed visually.

Ignoring the temporal dynamics in the models, static via dimensionality reduction can find a lower dimensional representation of the neural activity. In the linear case, this corresponds to principal-component analysis (PCA), but with neural firing rates the results of applying PCA are often unsatisfactory. Nonlinear dimensionality reduction techniques such as local linear embedding (LLE) can be useful for preserving neural trajectories in other neuroscience analyses. Another method to avoid dynamical modeling is to apply clustering directly to the neural trajectories. Besides clustering of dynamical models, clustering has been an underutilized approach to find temporal structure in neural data.

Neural state estimation can be performed via unsupervised clustering. To do this, a joint domain can be defined for the spatiotemporal patterns in the neural firing rates. At each sample, a vector can be built with all the sampled neurons' estimated firing rates at a time step and some previous values. However, simply vectorizing the observations and applying a Euclidean distance metric ignores the relative contributions of space and time, which is not satisfactory. Thus, a dissimilarity measure in the combined spatiotemporal space can be used to cluster the data.

In addition, static dimensionality reduction techniques can be used on neural firing rate data. The dimensionality reduction techniques can be used to find a two-dimensional embedding that can be visualized and preserves aspects of the data in its original, high-dimensional space. The method can be applied to neural data recorded during a manual center-out reaching task. Meaningful visualization confirms the underlying structure in data, and the lower-dimensional representation can be just as useful as the original data in predicting the reach target. This technique can be a straightforward way to extract a useful visualization of the dynamics in neural recordings.

Learning without Supervision. A special case of statistical learning is the unsupervised case: no external information is given to system besides the input. The goal of unsupervised learning is to learn a function whose output preserves or captures the underlying distribution of the original data. For it to be considered learning, the function should be dependent on the data. By this definition, preprocessing such as Fourier or wavelet transforms are not learning.

Typical forms of unsupervised learning include clustering, auto-encoders, dimensionality reduction, and sparse/non-negative/independent component analysis. In a generative sense, unsupervised learning identifies latent variables that describe the structure of observed data while conforming to a set of a priori constraints. Often observations can be assumed to be drawn independently and identically distributed from an underlying generative model. In reality this is not the case as observations are taken from one continuous signal—e.g., windows drawn from a time-series, but the assumption is that it contains reoccurring and localized patterns.

Notation. Capital letters A will denote sets or matrices, |A| denotes the cardinality of set A, and boldface lowercase letters indicate vectors a. The inner product of real-valued column vectors is $(a, b) = a^T b$ where $^T$ denotes the matrix transpose. For compactness, the subset of the positive integers $\{1, \ldots, n\}$ is denoted as $[n]$.

With this notation, there is a purposeful ambiguity between finite indexed sets of equal length column vectors and a matrix composed of these vectors—i.e., the set $A = \{a_i\}_{i=1}^{|A|}$ is denoted the same as the matrix $A = [a_1 \, a_2 \, \ldots \, a_{|A|}]$. The same holds for double indexed finite sets of scalars: the set $S = \{s_{p,n}\}_{p=1,n=1}^{P,N}$ is denoted the same as the matrix:

$$S = \begin{bmatrix} s_{1,1} & \cdots & s_{1,N} \\ \vdots & \ddots & \vdots \\ s_{P,1} & \cdots & s_{P,N} \end{bmatrix}.$$

Clustering. Clustering can be described as the unsupervised partitioning of the indices of the observation vectors into a finite number of classes such that some form of similarity is maximized among vectors assigned to a given class and/or the dissimilarity between vectors of different classes is maximized.

For the case of real valued vectors, a single model vector can be used to approximate all vectors assigned to the class. The similarity function used to assign an observation to a class varies, but typically, a shift-invariant measure such as Euclidean distance is used. In alternate embodiments, for vector spaces a gain-invariant measure such as the angle between vectors may be used. In the gain-invariant case, the magnitude is discarded. This can be useful for waveforms, but may not be as useful for neural rate where the magnitude matters.

At its simplest, clustering amounts to learning a partition function such that each observation is more similar to those assigned to the same class than those observations assigned to other classes. In clustering, this similarity is assessed via a linkage function, which can be thought of a generalized distance function that can be defined between two sets of vectors cluster, including singleton sets. For example, centroid linkage assesses the similarity between the observation vector and the prototype vector, which is the average of all vectors already assigned to that class. An alternative is the average linkage, which is the average distance between the observation vector and all the observations assigned to that class. In the case of Euclidean distance, these two linkages are equivalent.

Let the assignments of samples to clusters be defined by S, a matrix with a single 1 per column, where:

$$s_{p,n} = \begin{cases} 1 & f(n) = p \\ 0 & f(n) \neq 0 \end{cases}. \tag{1}$$

Vector Quantization. In the case of a real valued vector, all samples assigned to the same class can be represented by a prototype vector. This is a way to compress the data. Let the set of prototype vectors be denoted $A = \{a_p\}_{p=1}^{P}$, $P \ll N$. With this, the similarity between the observations assigned to each class and their corresponding prototype vector can be maximized. In alternate implementations, the average distance, which for the Euclidean distance is equivalent to mean squared error (MSE) over the observation set, can be used as a cost function:

$$J_{MSE}(A, f) = \sum_{n=1}^{N} \|X_n - A_{f(n)}\|_2^2 = tr((X - AS)(X - AS)^T), \tag{2}$$

where $f:[N] \to [P]$ is the partition function that maps the index of an observation vector to a class index. The prototype vectors that minimize the mean squared error cost function are simply the class centroids—i.e., the averages of the vectors assigned to that class $$S_p = \{n \in [N] | f(n) = p\} = \{n \in [N] | s_{p,n} = 1\}$$

$$A_p = \sum_{n \in S_p} \frac{1}{|S_p|} X_n p \in [P], \tag{3}$$

$$A_p = \frac{\sum_{n \in [N]} s_{p,n} X_n}{\sum_{n \in [N]} s_{p,n}} p \in [P]. \tag{4}$$

All that remains is to choose the partition function f, but for a given number of clusters where there are $N^P$ choices an exhaustive search is out of the question. Once candidate prototype vectors are available, the simplest partition function is to return the index of the nearest prototype vector.

$$f(n) = \operatorname{argmin}_{p \in P} \|X_n - A_p\| \, n \in [N]. \tag{5}$$

Assignment and prototype vector update are the two underlying steps in the k-means algorithm. The algorithms alternate between adjusting the partition function based on the current prototype vectors and updating the prototype vectors based on the current partition function, and runs until convergence. An initial set of prototype vectors can be chosen as a subset of the observation vectors, and multiple initial sets can be tried and the best clustering, in terms of the cost function, can be used.

Clustering via a soft assignment function. The use of a hard assignment function $f:[N] \to [P]$ is not strictly necessary to compute the prototype vectors. For instance, probabilistic modeling assigns the value of $s_{p,n}$ as the posterior probability of assigning observation n to the pth class. A fuzzy or soft assignment provides another way of computing the prototypes. Instead, of assigning a "1" or "0" as the weight to compute the prototype, the prototypes can be computed with a local weighting of all observation vectors. By smoothly weighting all the samples with those observation vectors very close to the prototype vector receiving the largest weights, an implicit assignment is not necessary, and the prototypes can be found before assigning the final partition function f.

Let g: $\mathbb{R}^L \to \mathbb{R}^+$ be a symmetric positive definite function, then $h(X_i, X_j) = g(X_i - X_j)$ is a shift-invariant function of two variables. Redefine S using $g(\cdot)$ and the prototype vectors such that:

$$s_{p,n} = g(A_p - X_n). \tag{6}$$

A Gaussian mean-shift algorithm is the special case where $g_o(\cdot) = \exp(-\|\cdot\|^2/(2\sigma))$. The initial prototype vectors are some subset of the data vectors $A \subseteq X$ (often A=X), and Equation (4) with Equation (6) can be used to iteratively update the prototype vectors.

As mentioned, in a probabilistic setting such as a Gaussian mixture model, $s_{p,n}$ is the posterior probability of $X_n$ being in class $c_p$, with:

$$s_{p,n} = p(c_p | X_n, A, \theta) = \frac{p(c_p | A, \theta) p(X_n | c_p, A, \theta)}{p(X_n | A, \theta)}, \tag{7}$$

where the prototype vectors A are the means and the remaining parameters, e.g., covariances and priors, are stored in θ. The expectation maximization algorithm for the Gaussian mixture model comprises alternating the update in Equation (7) with the computation of Equation (4) for the means alongside another update for the covariances and priors $p(c_p | A, \theta) = N^{-1} \Sigma_{n \in [N]} p(c_p | X_n, A, \theta)$.

Graph-Theoretic Clustering. All three of the previously detailed algorithms rely on multiple iterations to identify prototype vectors that minimize a similarity cost function. As opposed to the aforementioned iterative methods, an analytic approach is to treat clustering as optimally dividing a weighted graph. Spectral clustering is a graph-theoretic approach that has yielded success in a variety of domains. Spectral clustering operates not on the observation nor prototype vectors in $\mathbb{R}^L$, but instead on an affinity matrix in $\mathbb{R}^{N \times N}$.

The affinity matrix is formed by applying a positive definite function $g(\cdot)$ to a distance matrix—where $d(\cdot)$ denotes the metric—between each vector in the dataset. The affinity matrix is a Gram matrix if positive definite kernels are used. Initially, by letting A=X and P=N this affinity matrix corresponds to the matrix S:

$$s_{p,n} = g(d(X_n, A_p)) \, p, n \in [P] = [N].$$

The matrix S then defines the weights of a graph (possibly disconnected). The aim of spectral clustering is to cut the graph into k subgraphs so each subgraph is maximally connected (minimum edge distances). Finding the best cut is the same as finding the best partition function f. Spectral clustering finds a cut, which is suboptimal, but it is guaranteed to be an approximation of the optimal partition. Essentially, spectral clustering finds a projection of the affinity matrix such that the points representing vectors within the same cluster are closely packed whereas those from distant clusters are separated. Running k-means in this space with P=k will return the partition function f. The formulation for the algorithm is in and not reproduced here for compactness. As this method can be applied on a space with a metric or at least a dissimilarity, it is agnostic to the original vectors and their prototypes.

Non-Linear Dimensionality Reduction. Dimensionality reduction techniques are a class of unsupervised learning algorithms that attempt to find a low dimensional embedding of high dimensional data that preserves aspects of the structure of the original data such as clusters or manifolds. The specific characteristics preserved can vary by method, e.g., local distances, local neighborhoods, pseudo-geodesic, and/or global distances. Here, the relative location of sets of observation vectors in the high-dimensional space can be preserved by their location on a low-dimensional latent space. The mapping from high-dimensional space to low-dimensional space can be an explicit function or implicitly defined. In either case, this mapping can be based on the statistics of data, without any supervision.

The dimensionality may be reduced such that the data can be visualized in two or three dimensions. Various cost functions quantify how well the high-dimensional topology can be represented in the low-dimensional projection. One approach is Sammon projections. Kohonen's self-organizing maps (SOMS) are artificial neural network implementations that can find non-linear mappings between units on a two dimensional lattice and the original space. Static dimensionality reduction techniques include local linear embedding (LLE). A popular approach for visualization (but with only an implicit mapping) is stochastic neighborhood embedding, t-SNE. The t-SNE algorithm can be useful for visualizing the aspects of high-dimensional datasets such as clusters and manifolds. The basic approach uses divergence between the two spaces as a cost function, but it may be extended.

Stochastic Neighborhood Embedding. The algorithm t-distributed stochastic neighborhood embedding, t-SNE, can produce useful visualizations of high-dimensional datasets. The algorithm uses a probabilistic formulation with the Kullback-Leibler divergence as the cost function. Specifically, all of the pairwise Euclidean distances in both spaces, original and latent, can be transformed to densities that represent the probability of points i and j being in the same neighborhood.

In the original space, the joint density can be formed as the symmetric combination of the conditional probability of finding j in the neighborhood of i and vice versa. See Equation (9) below. The conditional density can be considered a Gaussian density centered around point i, see Equation (8) below, where the scale parameter $\sigma_i$ is chosen so that the conditional density has a user-defined perplexity (e.g., the logarithm of perplexity can be the Shannon entropy). The perplexity corresponds to a smoothed estimate of number of neighbors each point has.

Let $\{x_i\}_{i=1}^N$ be the points in the original space and $\{a_i\}_{i=1}^N$ be the points in the embedded space. The original conditional densities can be represented by:

$$p_{j|i} = \frac{\exp(-\|x_j - x_i\|^2 / 2\sigma_i^2)}{\sum_{k \neq i} \exp(-\|x_k - x_i\|^2 / 2\sigma_i^2)}. \tag{8}$$

Then, the joint density is given by:

$$p_{ij} = (p_{i|j} + p_{j|i})/2N. \tag{9}$$

The embedded space has a joint density of:

$$q_{ij} = \frac{(1 + \|a_i - a_j\|^2)^{-1}}{\sum_{k \neq l}(1 + \|a_k - a_l\|^2)^{-1}}. \tag{10}$$

The cost function can be the Kullback-Leibler Divergence:

$$C = D_{KL}(P \| Q) = \sum_i \sum_{j \neq i} p_{ij} \log(p_{ij}/q_{ij}). \tag{11}$$

In the low-dimensional latent space, the density function centered at each point is the Student's t-distribution with one degree of freedom, i.e. the Cauchy distribution of Equation (10). Unlike the original space, the choice of scale is arbitrary, but the Cauchy distribution provides a much larger tail than that of the Gaussian, which avoids a "crowding" problem. In a high dimensional space, many points can exist at the same distance and density, but in the low dimensional space, the same number of points would have to crowd together to be at the same density with a Gaussian distribution. However, with the Cauchy distribution, the density falls off much slower with increasing distance, thereby increasing the range of distances that are within a given density range. The increase in range of distances allows the points to spread out resulting in more useful visualizations. The algorithm can initialize the latent space with a PCA projection, and proceed to minimize the KL divergence by gradient descent with a momentum term.

Clustering for State Estimation in the Nucleus Accumbens. Windows of spatiotemporal neural firing rats can be clustered during a reward deliver task. A sequence of estimated labels was used to investigate the neural representation preceding reward deliver and the differences between rewarding and non-rewarding trials were compared.

Nucleus Accumbens Data. Windows of spatiotemporal neural firing were clustered during a reward deliver task of a rat. A microwire electrode array recorded signals from the nucleus accumbens of the rat. Before implantation, the rat was trained in a two-lever choice task. By pressing the target lever, cued by LEDs, the rat could receive a water reward. Each trial was initiated by the rat with a nose poke.

During acquisition of the signals, the rat watched a robotic arm move toward one of the two levers, where the lever on each trial had been chosen pseudo-randomly. If the robotic arm moved toward the target lever as indicated by a LED, the rat would receive the water reward. But if the robotic arm moved to the wrong target, then no reward was given and the rat received a negative tone. The robot stopped moving when it reached the lever. Thus, the robotic arm replaced the rat's own lever pressing. The rat could identify the upcoming reward based on the robot movement.

The data used in the analysis was from a single day's recording where the same target lever was always cued. 102 trials were analyzed. On 43 trials the robot moved to the correct target lever, and the rat received reward; on 59 trials the robot moved to the wrong lever, and the rat received the negative tone. After spike sorting, there were 43 neurons isolated. In the analysis, a bin size of 100 ms with 150 bins (15 seconds per trial) surrounding was used.

Data Representation. Time embedding can be used to define a spatio-temporal space for the clustering. The neural data may be grouped into meaningful clusters that define the state of the ensemble. At each time step, a vector can be composed of the spike counts of all neurons over a window of time.

$$x_i = [r_1(i), r_2(i), \ldots, r_n(i), r_1(i-1), r_2(i-1), \ldots, r_n(i-1), r_n(i-2), \ldots, r_n(i-L+1)] \in \mathbb{Z}_+^{n \cdot L} \tag{12}$$

where $r_v(i)$ is bin count for neuron v at time step i, n is the number of neurons, and L−1 is the maximum lag of the time embedding. A set $X = \{x_1, \ldots x_N\}$ of N such vectors is analyzed. A label corresponding to the state or cluster can be assigned to each spike count vector at every time step. In order to cluster, a distance measure which works across different neurons at different time steps is used. The simplest approach would be to treat all dimensions as equal with Euclidean distance. This treats the neurons and successive times equivalently. Another approach is to use smaller weights for greater time lags. This approach can emphasize the recent data instead of treating all time lags in the window equally, while still providing more information than the instantaneous firing rate. A weighted Euclidean distance is of the form of:

$$d_w(x_i, x_j) = \left( \sum_{l=0}^{L-1} w_l \sum_{v=1}^{n} (r_v(i-1) - r_v(j-1))^2 \right)^{\frac{1}{2}}. \tag{13}$$

The weights for successive lags are decayed exponentially $w_i = e^{-i/L-1}$. The time constant is set to the maximum lag L−1.

Clustering. K-means and spectral clustering are compared for various embedding dimensions and number of clusters. For spectral clustering, the affinity matrix is formed using a Gaussian kernel $K_\tau(d) = 1/(\sqrt{2\pi}\tau)\exp(d^2/(2\tau^2))$. The value of τ can be found by doing a parameter sweep and using the value with the 'tightest' clusters in terms of mean-square error. Both methods of clustering are computationally straightforward, but utilize a user-defined number of clusters.

To speed computation, only samples between the start cue and when the robot stopped moving were used in clustering. The remaining samples can be assigned to the state corresponding to the nearest cluster center for visualization purposes. Let n task relevant samples out of N total samples points be divided into P clusters. For each cluster j the prototype vector $A_j \in \mathbb{R}^{N_r \cdot L}$ can be computed over all sample points assigned to that cluster. Then all N samples can be assigned to the closest cluster defined by the distance measure. The cluster assignment can be treated as a discrete random variable $S_i \in 1, 2, \ldots, P$; $i \in \{1, \ldots, N\}$. To summarize, the user-defined parameters can be the time embedding depth L, cluster count P, the time constant for the weighting, and the distance measure of Equation (13).

Figure 7B:
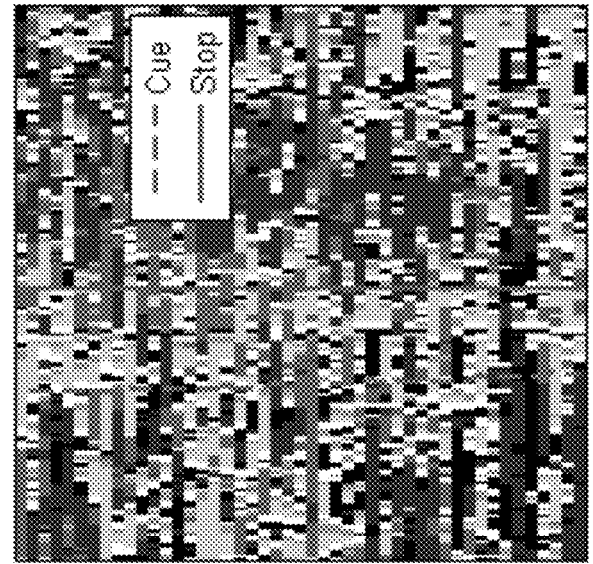
FIGS. 7A through 7C are examples of clustering results in accordance with various embodiments of the present disclosure.
Figure 7C:
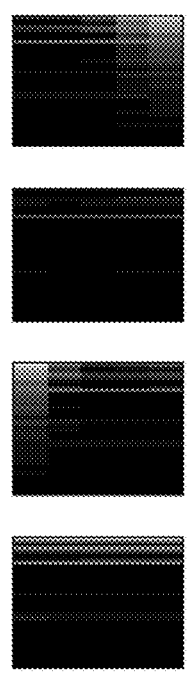
Figure 7A:
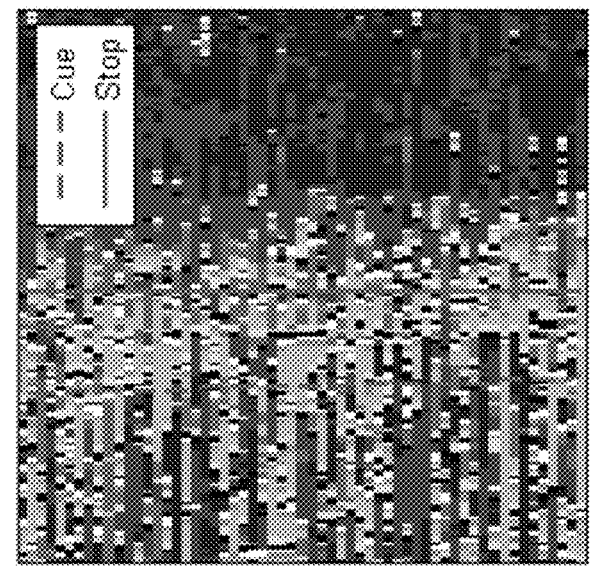

Results. The state estimation consistently finds recurrent sequences associated with the task timing. FIGS. 7A through 7C show the clustering results for the reward expectation experiment. These clusters can be used for single trial classification. Specifically, a trial was classified by the distribution of the cluster labels during the last 2.4 s of robot movement, as the robotic arm reached for the lever. The clustering was performed with k=8 clusters, a time window of L=5, and spectral clustering. Cluster labels were assigned for each time step across all trials and the grayscale color corresponds to an arbitrary state label. FIG. 7A shows cluster assignments across all non-rewarding trials, FIG. 7B shows cluster assignments across all rewarding trials, and FIG. 7C shows the spatio-temporal mean for each cluster.

For every trial a histogram of the labels was computed. Each bin in the histograms was normalized by the number of times that cluster was assigned across all trials and time indexes. Linear discriminant analysis with diagonal pooled covariance estimates was chosen as an off-the-shelf method. Across 1000 Monte Carlo runs, the trials were divided into a training set with two-thirds of the trials and the remaining one-third were used for testing. The average and standard deviation are reported in Table of FIG. 7D, which illustrates classifying rewarding versus non-rewarding trials using cluster labels. Entries indicate the percent of trials correctly classified, averaged across Monte Carlo runs. The maximum standard deviation across the runs was 7.8%. The time embedding dimension is denoted L, which varies across the rows. The number of clusters is denoted k and varies across the columns. Although, the classification rate was fairly small there is an interesting trend between the embedding length L and the number of clusters. In addition, spectral clustering appears to perform better than k-means across the board.

The results demonstrate that the discrete state estimation can capture trends in neural data using unsupervised clustering. In addition, it is able to capture trends in data with a small number of states and it does this with no supervised initialization or data segmentation. Although, a temporal weighting was explored in the distance, another consideration can be applying a weighting to the neurons as they are taken to be independent and equally important.

Nonlinear Dimensionality Reduction for Motor Cortex Representations during Reaching Tasks. A t-SNE can be used to produce a two-dimensional visualization of a subject's neural data while the subject performed a manual reaching task. As the underlying movement is in three-dimensions, it is a reasonable assumption that any relevant dynamics can be preserved in a visualization with equal or smaller dimension. A useful visualization would preserve any association between the neural modulation and the movement trajectories, e.g., whether nearby areas in the visualization correspond to similar portions of movement. Thus, the location in the visualization can serve as a predictor of the position during movement. How well the latent space preserves known external dynamics will be examined. Although visualization is inherently qualitative, it may be used to quantify how well the two-dimensional embedding can be used to predict the movement.

Data Collection. A female bonnet macaque was trained for a center-out reaching task using the right arm in a Kinarm exoskeleton using visual feedback of hand position and virtual targets provided by a computer display. The reaches to 8 virtual targets were constrained to be in two-dimensions. Every trial started at a center point, and the distance from the center to each of the equally-spaced targets was 4 cm. Each reach trial included the following steps: center target presentation, subject returns to center target and must hold for 300 ms; reach target is presented and subject must remain on center target for another 300 ms, this hold period ends when the center target vanishes and serves as the go-cue; reach to the target, successful reaches comprise a maximum duration with a hold period on the target; and finally liquid reward was delivered at the completion of the trial.

After the subject attained about an 80% success rate, micro-electrode arrays were implanted in motor cortex (M1), dorsal premotor (PMd), and somatosensory cortex (S1). Animal surgery was performed under the Institutional Animal Care and Use Committee (IACUC) regulations and assisted by the Division of Laboratory Animal Resources (DLAR) at SUNY Downstate Medical Center.

The data from each spiking unit is a sequence of action potential timings. Instead of using the exact time of each action potential, a time histogram was used and only the spikes in contiguous non-overlapping fixed-width bins with a bin width in the tens to hundreds of milliseconds counted. At each time step, a vector was composed of the spike counts of all neurons $x_i = [r_1(i), r_2(i), \ldots, r_n(i)] \in \mathbb{R}^n$ where $r_j(i)$ is the count for the jth neuron at the ith time step, and n is the number of neurons.

One of the difficulties using the time histogram is choosing a bin width that captures the dynamics while reducing the variability. For simplicity, a single choice of 100 ms bins and a 3-tap moving-average filter on each individual neural channel were used. In general, different choices of bin size and filter order need consideration depending on the data.

Results. For the neural data we are interested in preserving the neighborhoods of similar neural modulation by having them nearby in the latent space, while at the same time separating dissimilar neural activity into different portions of latent space. Specifically, we wish to find a visualization of a set $\{x_i\}_{i=1}^N$ of these vectors that results in a set $\{y_i\}_{i=1}^N \in \mathbb{R}^2$ such that the location of the $y_i$'s preserves the relative pairwise Euclidean distances between the $x_i$'s.

The t-distributed stochastic neighborhood embedding (t-SNE) algorithm was used for dimensionality reduction. For qualitative analysis, a 2-dimensional latent space mapped to a color-wheel was use. Thus, each point's location defined its color, and the corresponding point of the external dynamics was colored with the same color for easy visual analysis. The results are illustrated in FIGS. 8A and 8B. FIG. 8A shows the latent space embedding of samples during multiple trials during the movement portion of the center-out task. Each point in the latent space represents a time window during this portion of the task. The points are colored by the reach target. Clear segmentation between left versus right targets and top versus bottom targets is preserved in this mapping. FIG. 8B shows the movement trajectories, which are colored by the corresponding neural state's location in the latent space. Similar colors for similar movements indicate a useful latent space embedding. Position in latent space defines the color of the corresponding movement.

Table of FIG. 8C reports the performance of reach target decoding for latent and original space across time points. Entries indicate the accuracy (% correct). The nearest-neighbor in the training set was used as a classifier and was performed in a leave-one-trial-out fashion for the 54 trials. The classification rate is for 8 targets, with a chance rate of 12.5%. Classification was performed at different time points before, during, and after the reach. Three areas were recorded: M1 motor cortex (185 units), PMd dorsal premotor (158 units), and somatosensory cortex (122 units).

The results clearly highlight that similar reach movements have similar neural representation. The visualization also maintains the neighborhoods of the original data, which is useful for prediction. The method does not utilize explicit model or trial-based averaging. In addition, it can be used with minimal preprocessing, only spike binning and low-pass filtering of the rates. The t-SNE algorithm uses a single user-defined parameter, the perplexity of the original space. For the movement task, the visualization neatly segmented the different portions of movement. Similar attempts for visualization were made using PCA and ensemble averaging, but these methods were not successful in capturing any distinction between the segments of the movements. Overall, this technique was useful for exploratory analysis of neural recordings without assumptions or model formulation. However, since the method is stochastic the user is left with no explicit model for the embedding.

Learning Recurrent Patterns in Time Series

Sparsely-activated signals are evident in a number of natural signals: neural spike trains, electrocardiograms, and seismic recordings. Signals such as these have two key distinctions: they comprise the same waveforms which appear repeatedly, but only occasionally, throughout the signal. These time-series signals can be modeled as a sparse excitation of a single filter. A signal of this form is known as shot noise. Mathematically, it corresponds to the convolution of a train of Dirac delta functions (which can include varying amplitude) with a filter representing the system's impulse response. Even more real-world signals can be approximated by a combination of shot-noise processes such as, e.g., recordings from an electrode in the brain near multiple neurons. A summation of single-source signals forms a multiple-input single-output (MISO) linear system. In this system, each component has a unique filter, and each source is assumed to be independently and sparsely excited. This model can be used to explain signals (e.g., sound or electromagnetic waves) that are emitted in a passive physical environment with a linear medium.

Time-series analysis can be utilized to approximate a signal using a small 'dictionary' or basis of interpretable component waveforms, e.g., sinusoids, delta functions, etc. Both Fourier and wavelet analysis are of this form, but they differ by the choice of the basis used in the analysis. Using the correct basis allows both compression and meaningful representations. A dictionary can also be used to decompose a signal into multiple constituent components, which enables denoising and demixing.

The shot-noise model can be seen as a form of time-series analysis where the waveforms are not only temporally localized and sparsely activated, but where the same waveform is recurrent throughout the signal. By only recording the waveforms and their index, timing, and amplitude—a so-called atomic decomposition—this approach provides significant compression.

By learning the filter responses and matching them within the signal, the underlying timing and amplitude of the sources can be identified. Wavelet analysis is perfectly amenable to the given time-series model; truncating the wavelet coefficients approximates sparsely activated signals since the wavelets are temporally localized. However, a small number of coefficients will only be sufficient to approximate the signal if the wavelet family is properly chosen. Thus, a benefit of learning filters from data versus using predefined filters is that learning the filters ensures that the sparse inputs can describe the signal without an a priori design choice.

Two issues are considered when creating a sparse representation of a time series: learning the dictionary (i.e., a set of filters) to represent the signal, and inferring the timing and amplitudes for the train of Dirac deltas, which correspond to the source excitation. Together, these can be referred to as blind deconvolution or blind system identification. Two distinct approaches can be applied for blind system identification in the case of sparse sources.

The first approach to solve the blind system identification assumes a generative model for the signal, with constraints in the form of sparse priors for the sources. Using a normal distribution for the noise, the optimal model can be the one that minimizes the least-squares reconstruction cost with a sparsity constraint on the source signals. This approach can be referred to as sparse coding. Filters which describe natural signals can be efficiently estimated directly from data. In particular, using matching-pursuit as a proxy for a maximum a posterior estimate, an efficient algorithm for learning sparse bases can be extended to the time-series case.

The second approach avoids the explicit estimation of the sources and the reconstruction of the signal. Instead, statistical properties of the sparse sources can be used in the filter estimation. This approach for blind estimation uses a matrix-based projection pursuit, where windows of the time series can be treated as vectors in independent component analysis (ICA). In this way, the filters can be blindly estimated without estimating the sources or using a reconstruction cost function. Fast ICA can be used to efficiently estimate the filters. FastICA is particularly suited for this since its objective implicitly estimates the sources through a non-linear function of the projected signals.

This disclosure will present a systematic analysis of the subproblems involved in shift-invariant sparse coding are covered; a comparison of the ICA and sparse coding approaches for blind system estimation; and the application of these algorithms to neural potential data. A matrix-based system will be introduced for deconvolution and demixing. Blind deconvolution is considered for the case of a single source, and dictionary learning with sparse coding for the multiple source case. Matching pursuit as a solution to sparse coding for time series is examined. System identification is covered as a subproblem of filter estimation given the source estimates. Alternative optimization algorithms are also introduced and compared with the ICA approach.

Blind system identification on synthetic data is discussed considering the limiting case of a single source and single sensor in order to understand the effect of sparsity on both the shift-invariant sparse coding and ICA. The single-source case is a subproblem in some alternating estimation approaches wherein the estimation of a single source is performed assuming the contributions from all other sources have been removed. To ease the computation demand, a simple approximation of matching pursuit for time series can be used. A greedy approach can also be introduced.

These algorithms can be applied to the analysis of neural potential signals, specifically to local field potentials (LFPs) collected from the motor cortex of a non-human primate. Time-frequency analysis, via short-term Fourier analysis or wavelet decompositions, has been the standard tool to analyze neural potential signals. However, linear filtering does not offer the best tradeoff for localizing both the timing and frequency of events. Matching pursuit offers an algorithmic, and thus non-linear, form of analysis. Using a predefined and stochastic basis, matching pursuit can be an effective tool for neural signal analysis. Here, the filters that are then used in the matching pursuit framework for decomposing single-channel neural potentials can be learned. In addition, using principal component analysis, the approaches can be extended to multiple channels.

Modeling Systems Excited by Sparse Signals. A sparse signal stands in stark contrast to both the Wiener processes and their discretely-sampled counterpart described by Gaussian distributions. Stochastically, the distribution for a sparse signal is referred to as a point process. A realization of a point process can be a train of Dirac delta functions. Delta functions with different amplitudes can be modeled with a marked point process, which describes both the stochastic nature of the timing and the amplitude distribution of the impulses.

Let y(t) be a time series created by the sparse excitation of a single filter. The signal is formed by convolving a weighted train of delta functions $s(t)=\Sigma_i \alpha_i \delta(t-\tau_i)$ with a filter a(t).

$$y(t) = \int_{-\infty}^{\infty} s(t-u)a(u)du \tag{14}$$

Let x(t) be a combination of these component signals $\{y_p(t)\}$, $p \in \{1, \ldots, P\}$ observed in the presence of noise. This signal can be created by a multiple-input single-output (MISO) linear system with sparse inputs. Each component, $y_p(t)$, has a unique filter $a_p(t)$:

$$x(t) = e(t) + \hat{x}(t) = e(t) + \sum_{p=1}^{P} y_p(t) \tag{15}$$

$$y_p(t) = \int_{-\infty}^{\infty} s_p(t-u)a_p(u)du \tag{16}$$

$$s_p(t) = \sum_i \alpha_{p,i} \delta(t-\tau_{p,i}) \; p = 1, \ldots, P. \tag{17}$$

The combination of the components is a noise-free model $\hat{x}(t)$.

The atomic representation of the model signal, $\hat{x}(t)$, comprises a set of source indices, amplitudes, and timings $\{(p_i, \alpha_i, \tau_i)\}$. Using this set, the model signal can be rewritten as:

$$\hat{x}(t) = \sum_i \int_{-\infty}^{\infty} \alpha_i \delta(t-\tau_i-u) a_{p_i}(u) du. \tag{18}$$

Similarly, each component signals can be described by the impulse response of the filter ap(t) and the set of excitation times and amplitudes $\{(\alpha_j, \tau_j)\}_{j \in \mathcal{I}_p}$ where $\mathcal{I}_p = \{i : p_i = p\}$.

Given the atomic representation $\{(p_i, \alpha_i, \tau_i)\}_i$ or the sparse inputs $\{s_p(t)\}$, $p \in \{1, \ldots, P\}$, learning the filters is a system identification problem; however, estimating the sources is the primary challenge.

Estimating Sources. For a single source with a known filter, estimating the source signal is called deconvolution. Deconvolution with sparse sources can arise in many physical processes, e.g., biomedical time-series analysis and imaging. For sparse sources, the filtering spreads out the signal's energy in time. Recovering the input amounts to localizing this energy in time. For a low-pass filter, the goal of deconvolution is to delineate the exact timing of the source excitations.

For a MISO system, the analysis problem is estimating the full set of sources $\{s_p(t)\}_p$. Even without noise e(t)=0 and with known filters, estimating the sources can be difficult. Strictly linear solutions suffer from cross-talk between sources whose filters have similar spectra. In general, identifying the inputs to a MISO system may not be possible from a single output, but this is not the case when the filters are only sparsely active. Sparsity allows estimation through disjoint representations. This principle holds for a range of regimes in which it is possible to identify the inputs to a MISO system from a single output. At the extremes of this range are spectrally disjoint filters (corresponding to sparsity in the frequency domain) or sufficiently sparse input (corresponding to temporally disjoint inputs).

A linear solution fails because it only considers the second-order statistics of the sources, which does not contain any information on the sparsity. Non-linear analysis techniques that exploit the sparsity (e.g., matching-pursuit) perform better, but utilize many more computations. Recovering the source as a train of Dirac deltas uses an overcomplete basis of the signal: shifted versions of the underlying filters appearing at each time-shift. With an overcomplete basis, linear analysis is not possible, and non-linear optimization or iterative algorithms are used. However, these non-linear approaches for MISO deconvolution require the set of filters $\mathcal{A} = \{a_p(t)\}_p$ to be known. Thus, a solution for blind deconvolution first identifies the system, i.e., the set of filters.

Discrete Time Synthesis and Analysis. For practical digital implementation, consider the case where the time series of Equation (15) is discretely sampled, and the convolution operators are replaced by finite summations. The basis for the signal is assumed to be a set of filters $\{a_p\}_{p=1}^{P}$ excited by the sparse sources $\{s_p\}_{p=1}^{P}$. Let $x = [x_1, \ldots, x_T]^T$ denote the observed signal formed by the moving average model:

$$x = \sum_{p=1}^{P} s_p * a_p + e. \tag{19}$$

Matrix-Based Deconvolution and Demixing. Consider a component signal y=s*a formed from a single convolution. Assuming a has a finite impulse response (FIR) of length less than M, this convolution can be written as:

$$y_t = \sum_{\tau=1}^{M} s_{t-\tau+1} a_\tau = \sum_{\tau=0}^{t} s_\tau a_{t-\tau+1} \; t = 1, \ldots, N. \tag{20}$$

Let $Y \in \mathbb{R}^{N \times M}$ denote the Toeplitz matrix formed from the time-series vector y, where M is the window size and N is the number of samples.

$$Y = \begin{bmatrix} y_M & y_{M-1} & \ldots & y_1 \\ y_{M+1} & y_M & \ldots & y_2 \\ \vdots & & & \\ y_N & y_{N-1} & \ldots & y_{N-M+1} \end{bmatrix} \tag{21}$$

Then the convolution can be expressed in matrix notation as $$Y = SA = \begin{bmatrix} s_M & s_{M-1} & \cdots & 0 & \cdots & 0 \\ s_{M+1} & s_M & \cdots & s_1 & \ddots & 0 \\ \vdots & \vdots & \ddots & \vdots & \ddots & \\ s_{2M-1} & s_{2M-2} & \cdots & s_{M-1} & \cdots & s_1 \\ \vdots & \vdots & & \vdots & & \vdots \\ s_N & s_{N-1} & \cdots & s_{N-M} & \cdots & s_{N-2M+2} \end{bmatrix} \begin{bmatrix} a_1 & 0 & \cdots & 0 \\ a_2 & a_1 & \cdots & 0 \\ \vdots & \vdots & \ddots & \\ 0 & a_M & \cdots & a_2 \\ \vdots & \ddots & \ddots & \vdots \\ 0 & 0 & 0 & a_M \end{bmatrix},$$ (22)

where $Y \in \mathbb{R}^{N \times M}$, $S \in \mathbb{R}^{N \times (2M-1)}$, and $A \in \mathbb{R}^{(2M-1) \times M}$. This representation is redundant as the N×M matrix Y is no more than an arrangement of the N distinct values in y.

The rows of A form the support for the rows of Y. Let M' be the actual extent of the filter a. If M'=1, then the filter is a Kronecker delta and A is a complete basis for Y. For M'>1, then A will have M+M'−1 rows that are pairwise linearly independent. For M'=M, A is an overcomplete basis for the rows of Y with support along 2M−1 distinct vectors.

Deconvolution. Only a single column of S needs to be estimated to approximately find s up to a lag. Let ___ denote a solution to the deconvolution problem such that:

$$Yw_\tau = SAw_\tau \approx Se_\tau = s(t-\tau+1).$$ (23)

where $e_\tau$ is the τth column of the (2M−1)×(2M−1) identity matrix, i.e., $e_\tau$ is the standard basis vector such that $e_\tau$ is zero except having a 1 for the τth element. The set of deconvolution FIR filters $W=[w_1 \ldots w_{2M-1}]$ is found as the pseudoinverse of A, $W=A^\dagger$. Let B be a matrix with linearly independent columns then $B^\dagger=(B^TB)^{-1}B^T$ is its pseudoinverse. Each column of W resolves the source at a different lag. The best lag in terms of least squares can be found as arg $\min_\tau \|Aw_\tau - e_\tau\|_2$.

Multiple-source Matrix-based Formulation. Consider the signal ___ formed via a combination of sources convolved with different filters. Let $X \in \mathbb{R}^{M \times T}$ denote the transpose of the Toeplitz matrix formed from the time-series vector x, where M is the window size and N is the number of samples.

$$X = \begin{bmatrix} X_M & X_{M+1} & \cdots & X_N \\ X_{M-1} & X_M & \cdots & X_{N-1} \\ \vdots & & & \\ X_1 & X_2 & \cdots & X_{N-M+1} \end{bmatrix}$$ (24)

Assuming that the impulse response of all the filters is less than M, then the convolution in the synthesis of x can be expressed as:

$$X^T = \sum_{p=1}^P Y_p = \sum_{p=1}^P S_p A_p = [S_1, S_2, \ldots, S_P] \begin{bmatrix} A_1 \\ A_2 \\ \vdots \\ A_P \end{bmatrix},$$ (25)

where $S_p \in \mathbb{R}^{N \times (2M-1)}$, and $A_p \in \mathbb{R}^{(2M-1) \times M}$ are Toeplitz matrices formed from $s_1, \ldots, s_P$ and $a_1, \ldots, a_P$ as in Equation (22). This synthesis equation can be compactly written as $X^T = \overline{S}\overline{A}$ where $\overline{A}=[A_1^T|A_2^T| \ldots |A_P^T]^T$ and $\overline{S}=[S_1|S_2| \ldots |S_P]$.

Multiple Source Deconvolution and Demixing. In general, it is not possible to resolve the sources from a single channel of observation even if all the filters are known. First due to the FIR synthesis, FIR analysis will only be an approximation. Second, there will be cross-talk between sources unless the filters have disjoint spectral support, i.e., $\forall t \, (a_p * a_q)(t)=0$, but with FIR synthesis the filters can only have approximately disjoint spectra. Every block of 2M−1 columns in $\overline{S}=[s_1 \ldots s_{P(2M-1)}]$ corresponds to lagged versions of one source, $s_l(t)=s_p(t-\tau+1)$ $l=\tau+(2M-1)\cdot(p-1)$. Let $w_l$ be an approximate solution to the demixing/demodulation problem that extracts the lth column of $\overline{S}$:

$$X^T w_l = \overline{S}\overline{A}w_l \approx \overline{S}e_l = s_l,$$ (26)

where $e_l$ denotes a vector from the standard basis, where $e_i$ is zero for its elements except it has 1 as its ith element.

The matrix of FIR filters $W=[w_1 \ldots w_{P(2M-1)}]$ can be found as the pseudoinverse of $\overline{A}$. The matrix W is partitioned into 2M−1 blocks corresponding to each source. In each block, the column of W such that the corresponding column of $\overline{A}W$ best approximates the corresponding standard basis vector (e.g., the column of the identity matrix) will be the best, in a least-squares sense, linear solution to the multiple source deconvolution problem of Equation (26).

In alternative implementations, the source separation/demixing can be performed without deconvolution. Source separation attempts to minimize the cross-talk between sources. Its success is dependent on the cross-correlation between the source filters. If the filters have disjoint spectral support then perfect separation can be achieved, but filters can only have approximately disjoint spectral support if they have finite duration.

Let $\overline{Y}=[Y_1|Y_2| \ldots |Y_P]=[\overline{y}_1 \ldots \overline{y}_{P(2M-1)}]$ for compactness. Every block of 2M−1 columns in $\overline{Y}$ corresponds to lagged versions of one filtered source, e.g., $\overline{y}_l(t)=(s_p * a_p)(t-\tau+1)=y_p(t-\tau+1) l=\tau+M(p-1)$. Let $\dot{w}_l$ be an approximate solution to the demixing problem that extracts the lth column of $\overline{Y}$, where:

$$X^T \dot{w}_l = \overline{S}\overline{A}\dot{w}_l \approx \overline{S}\overline{a}_l = \overline{y}_l.$$ (27)

The source separation matrix is $\dot{W}=W\acute{A}$ where $\acute{A}$ a block diagonal matrix with the Toeplitz representations of the filters on the diagonal $\acute{A}=\text{blkdiag}(A_1, A_2, \ldots, A_P) \in \mathbb{R}^{(2M-1)P \times MP}$. The best lag for the pth source can be chosen as:

$$\arg\min_\tau \|\overline{A}\dot{w}'_{\tau+M(p-1)} - \acute{a}'_{\tau+M(p-1)}\|_2.$$ (28)

The quality of the separation is dependent on how close the spectral representations of the filter are. Cross-talk from one source to another occurs when the filters are similar, and thus the separation filters will have similar frequency response. Two filters with minimal cross-talk have $(a_p * a_q)(t)=0 \approx \forall t$ or using the Toeplitz form:

$$A_p^T A_q \approx \begin{bmatrix} 0 & \cdots & 0 \\ \vdots & \ddots & \vdots \\ 0 & \cdots & 0 \end{bmatrix}.$$ (29)

Figure 9:
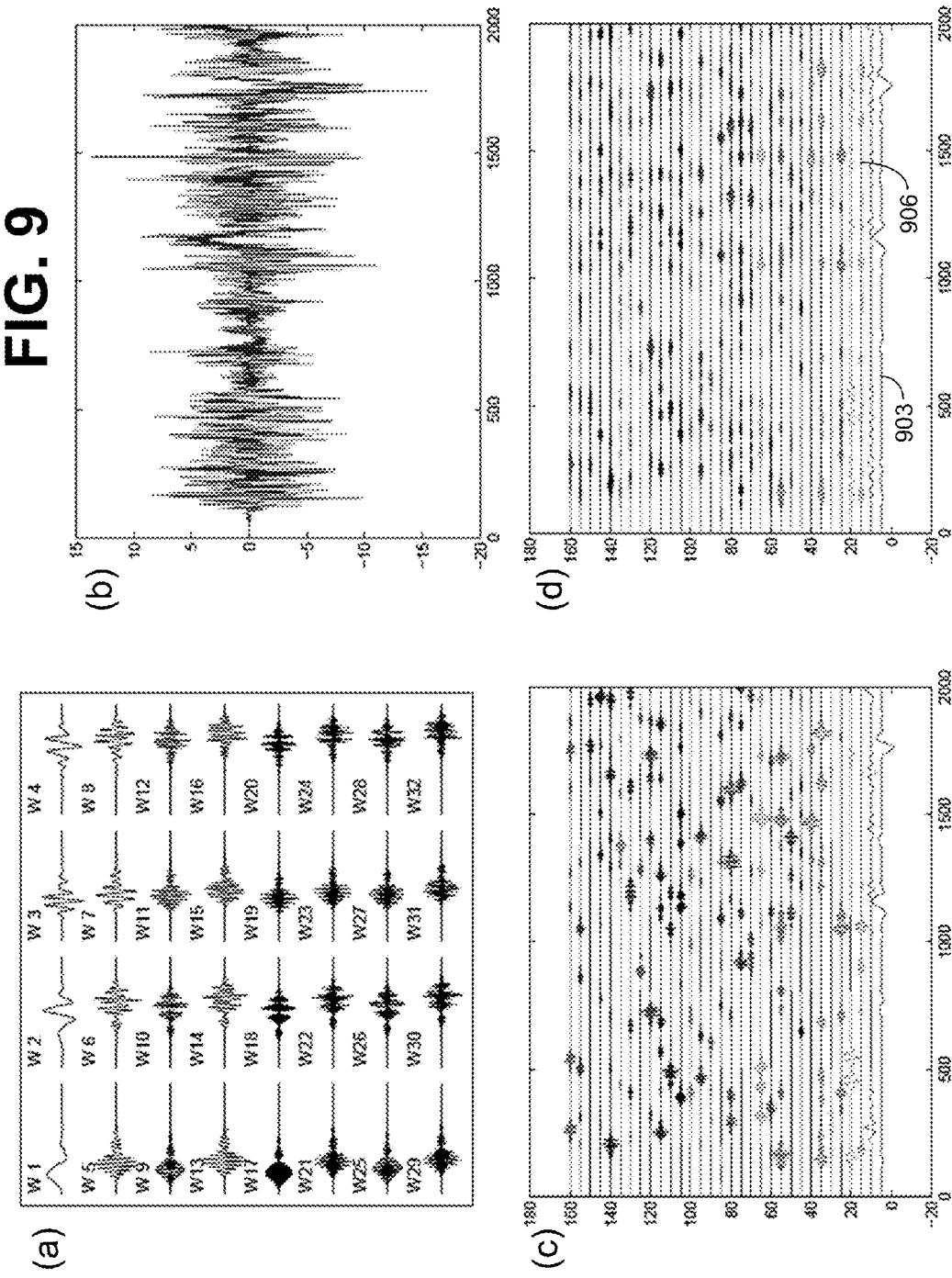
FIG. 9 illustrates demixing of a multiple input, single output system in accordance with various embodiments of the present disclosure.

An example of linearly demixing a MISO system with cross-talk is illustrated in FIG. 9. An example of a set of filters is shown in FIG. 9(a). True components are filters excited by sparse sources as illustrated in FIG. 9(b). A mixture of components observed as a single channel is shown in FIG. 9(c), with the linearly demixed components using known filters shown in FIG. 9(d). Some of the components can be linearly separated from the mixture if they have unique spectral support, such as the bottom component (903); whereas, if there are many filters with similar support there will be considerable cross-talk, such as the third from bottom component (906).

Iterative Deconvolution and Demixing. To introduce matching pursuit as an iterative deconvolution approach, consider a simple least-squares problem:

$$\min_{s} \|x - As\|_2^2, \tag{30}$$

where x is the vector to be approximated, $A=[a_1, a_2, \ldots, a_P]$, which can be a matrix with more columns than rows, and s represents the coefficients that minimize the least-squares cost. Matching pursuit is an iterative, and greedy, solution to the least-squares problem. Often it is posed as having an explicit constraint on sparsity, in terms of the number of non-zero elements in s. The $l_0$-'norm' of a vector can be considered the number of non-zero elements: $\|s\|_0 = |\{s_i : |s_i| > 0\}|$. In the simplest case, matching pursuit is a greedy approach to solve:

$$\min_{s: \|s\|_0 = L} \|x - As\|_2^2 \tag{31}$$

Referring to FIG. 10A, shown is an example of the iterative matching pursuit (MP) approach. Since the least-squares fit can be solved analytically once the non-zero elements are selected, the goal of the algorithm is to select a set of L column indices $p_1, p_2, \ldots, p_L$ corresponding to the columns of A:

$$\min_{\tilde{A} \in \{[a_{p_1}, a_{p_2}, \ldots, a_L]\}} \|x - \tilde{A}\tilde{A}^\dagger x\|_2^2 \tag{32}$$

Orthogonal matching pursuit (OMP) offers a theoretically better solution because it does not rely on coefficients estimated early on, which may have been biased. Thus, the optimal coefficients can be re-estimated at each iteration. All that needs to be stored at each iteration are the selected column indices, $p_1, p_2, \ldots, p_L$, as is detailed in the example OMP algorithm in FIG. 10B.

Returning to the time-series case, consider the following least-squares problem:

$$\min_{\{(p_i, \alpha_i, \tau_i)\}_{i=1}^{L}} \int_{-\infty}^{\infty} \left( x(t) - \sum_{i=1}^{L} \alpha_i \int_{-\infty}^{\infty} \delta(t - \tau_i) a_{p_i}(u) du \right)^2 dt. \tag{33}$$

The matching pursuit approach for time series is a greedy solution to this problem. At each iteration the solution is chosen as if only one source is active at only one point in time, and selects a single atom, comprising the timing, amplitude, and index of the base, that explains the most energy remaining in the residual of the signal. This criterion is equivalent to finding the filter with the highest normalized cross-correlation. At the end of each iteration, the residual signal is updated by removing the single-atom reconstruction. This updated residual is used as the input to the next iteration. The steps are detailed in the example algorithm in FIG. 10C.

Given atomic decomposition $\{(p_i, \alpha_i, \tau_i)\}_{i=1}^{L}$, the sources (deconvolution) or the individual components (demixing) can be computed easily via Equation (17) or Equation (16), respectively. In the naïve implementation, matching pursuit uses the cross-correlation between each filter and the signal to be computed for each iteration. As an approximation, only a single cross-correlation can be performed for each filter, and timings extracted for each source excitation that do not overlap with themselves. Given the timings for each filter a matrix of individual excitation waveforms can be constructed: $V=[v_1, v_2, \ldots, v_L]$, where $v_i$ is the discrete sample of $v_i(t) = \int_{-\infty}^{\infty} \delta(t - \tau_i - u) a_{p_i}(u) du$. The amplitudes can then be solved using a least-squares fit, $[\alpha_1, \alpha_2, \ldots, \alpha_L] = V^\dagger x$.

Although this approach utilizes only P cross-correlation computations, the timings may not be optimal, since they are computed for each filter independently. Additionally, the size of V can demand extensive computation for the least-squares solution. Nonetheless, this approximation can be used. Matching pursuit need not have a pre-defined '$l_0$-norm' for the sources. In alternate implementations, a threshold on the residual error can be used as a stopping criterion. However, choosing this threshold depends on the dynamic range of the signal and noise, and in practice it is simpler to predefine L.

System Identification. Assuming some estimates of the sources have been made, identifying the filters can be a system identification problem. Assuming the filters are all the same length, there are PM coefficients to be estimated from the N observations in x. In the sparse setting, the filter estimation poses a unique statistical challenge. At extreme sparsity, the filters do not overlap, which makes estimation easier, but since they appear very rarely, any noise can cause large variance in the estimation of the filters. As the rate of the sources increases, there are more realizations of the sources but they overlap with each other more frequently. Assuming that the sources are stationary, a Wiener filter can provide an optimal system identification in a least-squares sense. The source estimates can be the inputs and the observed signal x(t) can be treated as the desired signal.

The simplest solution comes from the extreme sparsity case, where the sources are independent Poisson processes of very low rate. In this case, the autocorrelation matrix of the input can be approximated as a diagonal matrix. By ignoring the scale of each filter, since it can never be determined unambiguously, this can be further simplified to the identity matrix. The estimated filter can be derived solely from the cross-correlation:

$$\hat{a}_p(\tau) = (s_p \star x)(\tau - 1) = \sum_t s_p(t) \times (t + \tau - 1). \tag{34}$$

If the sources are correlated in time or space, then ignoring the correlations can lead to a biased estimate of the filters. By analysis, the weighted average estimate can be a biased version of the Wiener filter. The bias decreases as the correlation matrix of the sources approaches a diagonal matrix. The Wiener filter and weighted average both assume the sources have been correctly estimated. In the case of source sparsity, the timing of source excitations can be used to form estimates of the filters. This approach can be used for the matching-pursuit-based algorithms, as will be discussed.

Methods for Blind MISO System Identification. In the blind setting, the values of the sources are unknown and thus unavailable for system identification. In addition, the filters associated with the sources $a_1, a_2, \ldots, a_P$ are also unknown and need to be estimated before any form of deconvolution can provide estimates of the sources. Thus, an unsupervised approach, one that can pull itself up by the bootstraps, can be used to estimate both the unknown sources and the unknown filters.

Estimating the filters corresponds to finding one row of each block of $\overline{A}$ corresponding to each unique filter. In the matrix formulation of Equation (25), it can be seen that the inner dimension of the matrix multiplication $X^T = \overline{AS}$ is greater the number of rows of X, even for one source. Thus using a low-rank approximation, e.g., principal component analysis, will fail to yield a useful channel estimation. Instead, the knowledge that the sources are sparse can be used to guide the estimation of the filters. When using the matrix notation, finding projections that result in sparse coefficients is equivalent to identifying the filters that form the basis of the signal. One way to identity sparsity is by evaluating the higher-order moments of a random variable; sparse random variable have very different higher-order moments than those of Gaussian random variables. As an alternative to the statistics of the sources, sufficiently sparse sources ensure that any observation window can be approximated by a small number of the elements. The optimization problem of minimizing the reconstruction error of the signal using only a few activations of the filter can be used to estimate the underlying filters.

Independent Component Analysis. Independent component analysis can be used to solve the blind deconvolution problem. In general, linear filtering induces temporal dependence in the resulting signal. Thus, blind deconvolution can be achieved by seeking a filter such that its output has minimal dependence. The clearest case is when the source has independent, identically distributed entries. As long as the source is not Gaussian, then higher-order statistics can be used to estimate the dependence. If the source vector is Gaussian, then the deconvolution filter can at best whiten the observed signal. In alternate implementations, the source may have weak and non-stationary dependence, in which case the changing second-order statistics can be used to estimate a demixing vector.

The deconvolution filter can be a demixing vector applied to a delay line of the signal. If it exists, the optimal deconvolution filter can be the filter inverse or a lagged version of it. Unlike instantaneous ICA, which would have a single vector for a single source, there can be many solutions to the single-channel deconvolution problem corresponding to different shifts of the demixing vector along the delay line. Each shift corresponds to a minimum of the dependence measure and a solution to the deconvolution problem. At which shifts it appears is an ambiguity in most blind deconvolution algorithms.

FastICA. In the FastICA algorithm, the dependence can be evaluated as an approximation of negentropy. Negentropy gauges the non-Gaussianity of a random variable in terms of its higher-order statistics. Since a Gaussian random variable only has second-order statistics these differences can be quantified by finding the expectation of a non-quadratic function such that the moment expansion will contain higher-order terms and subtracting the first and second-order moments that would appear for a Gaussian. The approximation of the negentropy of the random variable u is $J(u) \propto [E\{G(u)\} - E\{G(v)\}]$, where $G(\cdot)$ is the contrast function and v is a Gaussian random variable with the same mean and covariance as u. For random vectors, maximizing the sum of the negentropies, under the constraint of decorrelation, minimizes the mutual information between the elements. This is basic principle of contrast-function-based ICA approaches.

Recall the signal x is stored in the M×N matrix $X = [x_1\ x_2 \ldots x_N]$ where N corresponds to the number of samples and M the size of the inverse filter, and $X^T$ is Toeplitz. Let x denote a random vector corresponding to a patch of the signal, then $E\{f(x)\}$, the expected value of a function of this random vector, is estimated as $$\frac{1}{N} \sum_t f(x_t),$$

where the columns of X are treated as realizations of this random vector.

ICA algorithms typically require the estimated sources to be uncorrelated, before removing evaluating dependence. To enforce this constraint, the estimation is usually performed with whitened data; with whitened data uncorrelated sources means the demixing vectors are orthogonal. The eigen decomposition of the covariance matrix is $$E\{xx^T\} = \frac{1}{T} XX^T = U \Sigma U^T,$$

and $\psi = \Sigma^{-1/2} U^T$ is the whitening matrix such that $$E\{(\psi x)(\psi x)^T\} = \frac{1}{N}(\psi X)(\psi X)^T = I,$$

where I is the identity matrix.

Single-unit ICA uses one demixing vector, w, to estimate a single source, _____. With a sign and magnitude ambiguity in ICA, the source is constrained to have unit variance. This constraint is typically written as $$E\{(w^T x)^2\} = \frac{1}{N} w^T XX^T w = 1,$$

but can be written in terms of the whitening matrix as $\|w^T \psi^{-1}\|_2 = 1$ (using $1/N\ XX^T = \psi^{-1} \psi^{-T}$). The optimal w is one such that $w^T x$ has higher-order statistics far from those of a Gaussian of equal mean and variance. The optimization problem for single-unit FastICA can be written as:

$$\underset{\|w^T \psi^{-1}\|_2 = 1}{\operatorname{argmax}}\ [E\{G(w^T x)\} - E\{G(v)\}]^2, \qquad (35)$$

where $G(\cdot)$ is a suitably chosen contrast function. For super-gaussian sources, the contrast function is typically a symmetric sub-quadratic function such as, e.g., $G(u) = \log \cos h(u)$. While the vector w corresponds to a row of the demixing matrix, it also corresponds to the inverse of the filter such that $w^T X = \hat{s}_l^T$ is an estimate of the source signal as in Equation (26). The corresponding column of the mixing matrix is denoted v and is related by $$v = \frac{1}{N} X X^T w = E\{x\hat{s}\}.$$

Clearly, v is the weighted average of windows of the signal where the weighting assigned to each vector corresponds to the estimated source value.

Given a good demixing vector/filter w, the mixing vector should be equal to one of the rows of $\mathcal{V}$ corresponding to a time-reversed and shifted version of the R element FIR filter a, where $v=[0, \ldots, 0, a(R), \ldots, a(1), 0, \ldots, 0]^T$. Note that in terms of filters, w is not computed as the filter inverse as it was using the Toeplitz form of a as in Equation (23). In order to find a good demixing vector, an approximate solution to the single-unit ICA problem of Equation (35) yields an iterative update for w given by:

$$w \leftarrow \psi^T \psi E\{xg(w^T x)\} - E\{g'(w^T x)\}w \quad (36)$$

$$w \leftarrow \frac{w}{\sqrt{E\{w^T x x^T w\}}}, \quad (37)$$

where $$g(u) = \frac{\partial}{\partial u} G(u) \text{ and } g'(u) = \frac{\partial}{\partial u} g(u).$$

For G(u)=log cos h(u), g(u)=tan h(u) is a soft activation function, and g'(u)=1−tan $h^2$(u) is a symmetric function that peaks at 0. In terms of the mixing vector, this update is given by:

$$v \leftarrow E\{xg(\hat{s}) - vg'(\hat{s})\}, \quad (38)$$

where $w^T = v^T \psi^T \psi$ and $\hat{s} = w^T x$. This matches the interpretation of v as a weighted average, but gives an interpretation on its update. For a given realization, a large source magnitudes $|\hat{s}|>1$ implies $g(\hat{s}) \approx \text{sign}(\hat{s})$ and $g(\hat{s}) \approx 0$, this yields $v \approx x$. When the source coefficient is smaller such that $g'(\hat{s})$ dominates $g(\hat{s})$, the update moves the vector away from its current direction. Thus, single-unit FastICA can use a weighted average to estimate the filter, where the source estimates correspond to a source that is maximally non-Gaussian.

For the single-channel case, there appears to be no need to estimate the full demixing matrix. In practice, using a multiple-unit approach with a constraint that the sources are uncorrelated, can perform better than the single-unit approach. The multiple-unit approach, which maximizes the sum of negentropies, estimates multiple demixing vectors at once. Let the demixing matrix with K columns be denoted $W=[w_1 \ w_2 \ \ldots \ w_K]$. The multiple-unit optimization problem can be given by:

$$\operatorname*{argmax}_{E\{(w^T x)(w^T x)^T\}=I} \sum_{k=1}^{K} [E\{G(w_k^T x)\} - E\{G(v)\}]^2, \quad (39)$$

where I is the identify matrix. In the time-series setting, the true mixing matrix can be overcomplete, and the optimal vector for the single-unit case of Equation (35) will not necessarily correspond to a column of the matrix obtained for the multi-unit case of Equation (39). When using the multiple-unit approach for a single-source problem, a single vector can be selected to represent the filter. As ICA does not give a natural order for 'better' components, the mean squared error can be used as a cost function, and the filter can be chosen that has the best reconstruction of the signal using a single approximation iteration.

Multiple Source Case. In the multiple source case, an independent component analysis can be used to resolve multiple demixing vectors simultaneously. The projections that yield sparse values correspond to demixing vectors for each source at each permissible lag, as in Equation (26). Estimating a set of demixing vectors at once, to extract all the sources, greatly increases the dimensionality of the solution space. Since each source may have arbitrary lag, there is an even greater number of solutions that maximize the measure of independence. Consequently, the independent component analysis problem for multisource convolutive mixtures possesses a very complicated performance surface.

Another difficulty is the redundant estimation of the same filter at different lags. The constraint on correlation that avoids degenerate solutions in instantaneous ICA can be inadequate in the convolutive case. Different lags of the same source may be uncorrelated, thus a pair of demixing vectors that correspond to the same source at different lags can be a viable solution. For windows larger than the filter extent, the 'independence' between filters can be found by simply lagging the filters such that they do not overlap. Consequently, sets of demixing vectors that include multiple lags of the same source may optimize the independence criterion without estimating 'independent' components and missing some of the underlying source filters. Generally, multi-unit ICA in the single-channel case can yield a set of redundant shifts of a few unique filters and some spurious ones. The spurious filters are often noisy and may correspond to local optima caused by the correlation constraints of Equation (39). This does not completely limit estimating any lagged version of the filters. After running a multi-unit ICA, a subset of the filters can be selected.

Filter Subset Selection. In the blind estimation setting, it is unknown how many true sources there are. In practice, ICA can estimate as many filters as there are taps in the embedding window. However, this may yield many spurious filters that can be excluded by a relevance criterion. There is not a clear criterion for filter selection based on independence. It is easier for the user to provide how many filters are desired and use the reconstruction error to select a subset of the filters. Given the desired number of filters, the optimal subset that minimizes the reconstruction cost can be found. However, this problem has a combinatorial number of solutions. In practice, a greedy optimization such as orthogonal matching pursuit (OMP) can be used to find which set of filters that best explains the signal.

The primary aim is to find the filters that are most correlated with the data, but are not redundant copies of each other. To do this, an approximation of the signal can be made with each individual filter using time-series MP. Then these components can be treated as vectors in a dictionary, and standard vector-based OMP can be used to approximate the signal with these components. Thus, it is a simpler optimization since only the combination of components is optimized: the timing of the sources having already been estimated. The steps are detailed in the example algorithm in FIG. 10E. Using this approach it is unlikely that two filters that are simply shifted versions of each other will be selected, because their components will be the same. In addition, it does not require performing MP using all of the filters estimated by ICA at once. Once the subset has been selected, only those filters are needed if an approximation of the original signal is desired.

Matching Pursuit with K-SVD. Assuming the signal plus noise model in Equation (19), the blind deconvolution and filter estimation problem can be posed as a non-linear least-squares problem. The overall objective function can be written as:

$$\min_{\{v_p\}_{p=1}^{P},\{(p_i,\alpha_i,\tau_i)\}_{i=1}^{L}} \sum_{t=1}^{N}\left(x(t) - \sum_{i=1}^{L}\alpha_i v_{p_i}(\tau_i + M - t)\right)^2, \quad (40)$$

where all the sources are assumed to be active exactly L times and $v_p$ is an estimate of the time-reversed filter $a_p$, where $v_p(t)=\hat{a}_p(M+1-t)$. Because the source estimates (the atomic decomposition) are intrinsically linked to the filters, an alternating optimization is performed. An extension of K-SVD to the time-series case can use alternating optimization between matching pursuit and K-SVD. For conciseness, this combined algorithm can be called MP-SVD.

Let $T_\tau$ denote the linear operator such that $T_\tau v$ aligns the M-length filter v within an N-length signal. $T_\tau$ is an M by N matrix with a single 1 in each column. The transpose of this operator is denoted $T^*_\tau$ and is defined such that $T^*_\tau x$ extracts the M-length window from x starting at time $\tau$. Using the alignment operator the objective function can be written in terms of vectors as:

$$\min_{\{v_p\}_{p=1}^{P},\{(p_i,\alpha_i,\tau_i)\}_{i=1}^{L}} \left\| x - \sum_{i=1}^{L}\alpha_i T_{\tau_i} v_{p_i} \right\|_2^2. \quad (41)$$

To update the filters, we first assume we have an estimate of the components using the current filters. Let $x^{(p)}$ denote the signal comprising only the pth component and any error:

$$x^{(p)} = e + y_p = x - \sum_{q \in \{1,\ldots,P\}\backslash p} y_q, \quad (42)$$

where $y_p = \sum_{j \in \mathcal{I}_p} \alpha_j T_{\tau_j} v_p$ and $\mathcal{I}_p = \{i:p_i=p\}$. This single-filter signal can be used to update each filter, but because of the sparsity in time, only patches of the signal corresponding to source timings are used. These patches can be collected into a matrix and the updated filter can be selected as the singular vector of this matrix corresponding to the largest singular value. Assuming these were the correct timings, and none of the other filters changed, this update can minimize the reconstruction cost for these patches. The steps are detailed in the example algorithm in FIG. 10F. The non-overlapping approximation of matching pursuit can be substituted. In addition, two alternative approximations can be used to ameliorate the computational complexity.

Block-Based Approximation. A block-based approximation can be used to simplify the computational cost of running MP on the full signal after every update of the filters. MoTIF is an approximation method formed by partitioning the input signal into non-overlapping blocks and searching each block for the best alignment with the filter. As only a single alignment is identified in each patch, the method works well for sparse sources that are only active at most once per patch. For a filter of length M, the length of a patch is L≥2M−1 samples. This method works better for sparse sources or for sources with short filters.

The unconstrained optimization problem for the single-unit MoTIF can be written as:

$$\max_{\|v\|_2=1} \sum_{n=1}^{N} \max_{\tau \in P_n}(v^T x_\tau)^2, \quad (43)$$

where $P_n=\{1+L(n-1),\ldots,Ln\}$, $n=1,\ldots,N$ and $N=\lfloor T=L \rfloor$. Given the best alignment of the filter within each patch, the reconstruction cost can be minimized. The block-based approximation for MP-SVD can be solved by alternating between finding the alignments of the windows within the blocks based on the current filter, and updating the filter using SVD.

Block-based approximation minimizes the reconstruction cost of only one window in each patch. Computationally, this is a fast proxy for shift-invariant learning based on matching pursuit since it finds N occurrences in parallel. In the single filter case, it performs very well. In the multiple filter case, a generalized eigenvalue problem correlation in the filters can be minimized. In alternate implementations, the block-based approximation can also be used with MP-SVD. In either case, the method assumes each filter is active exactly once in each block. Except in the case of extreme sparsity, this assumption can yield poor results for multiple filter estimation.

Greedy Approach. A greedy approach can be used to learn a single filter using MP-SVD and then remove a set number of excitations of this filter from the training signal, before estimating the next filter. Using this iterative approach for approximation avoids the matching pursuit's joint search over both the best filter and best lag. The ability of this approach to find the true source filters may be limited as it is more likely to learn a filter that best approximates the average filter during the first iteration.

Synthetic Experiments. Experiments were conducted to compare the performance of algorithms for both single-source filter estimation, corresponding to a SISO system, and multiple source filter estimation, corresponding to a MISO system. In both cases, the true underlying filters are chosen as a set of Daubechies 4 (db4) wavelet packets. This ensured that the synthetic filters covered a range of frequency space with varying temporal characteristics. Two basic methodologies were compared for filter estimation: shift-invariant decomposition with mean-square error cost, and single-channel independent component analysis.

The source signals were independent, marked point processes with a homogeneous Poisson point process for the timing and a bimodal excitation amplitude distribution. The excitation amplitude distribution was a mixture of a Gaussian distributions with mean and variance of $$\left(1, \frac{1}{9}\right) \text{ and } \left(-1, \frac{1}{9}\right)$$

and equiprobable Bernoulli mixing. The shape of the resulting source-excitation amplitude distribution (the amplitude distribution when a source is active) is shown in FIG. 11. In the experiments, the rate of the Poisson process controls the sparsity of the sources, while the source excitation amplitude distribution was fixed.

For each run, a signal with 10,000 time points was created by convolving the source realizations with the selected filters and combining the results. The wavelet packets were chosen at a scale such that they were 226 elements long, and each filter was windowed to be 180 time points long, the filters were then normalized to have a norm of 180/2. Zero-mean, unit-variance white noise was added to the mixtures.

The shift-invariant decomposition was learned using matching pursuit (MP) for source estimation, and K-SVD on the aligned windows for filter estimation using the algorithm in FIG. 10F. The learning was performed using alternating optimization between approximate MP for source estimation and K-SVD for filter estimation. Two different computationally tractable approximations are used to speed up the matching pursuit: the first was the matching pursuit with no overlap with the algorithm in FIG. 10D, the second included block-based approximation of matching pursuit, e.g. MoTif. For conciseness, these are referred to as MP(no overlap)-SVD and MP(block)-SVD. As a baseline comparison, the greedy one-source-at-a-time approach was also applied using the algorithm in FIG. 10G. The greedy method used the no-overlap method for a single run of MP for each iteration update of the particular filter.

For ICA, both FastICA with 40-unit symmetric estimation and single-unit FastICA were used. The tan h non-linearity is used for both instances of FastICA. In practice, most of the filters in the 40-unit estimation are meaningless so the OMP-based filter selection with the algorithm in FIG. 10E was used to select a predefined number of filters.

Figure 12:
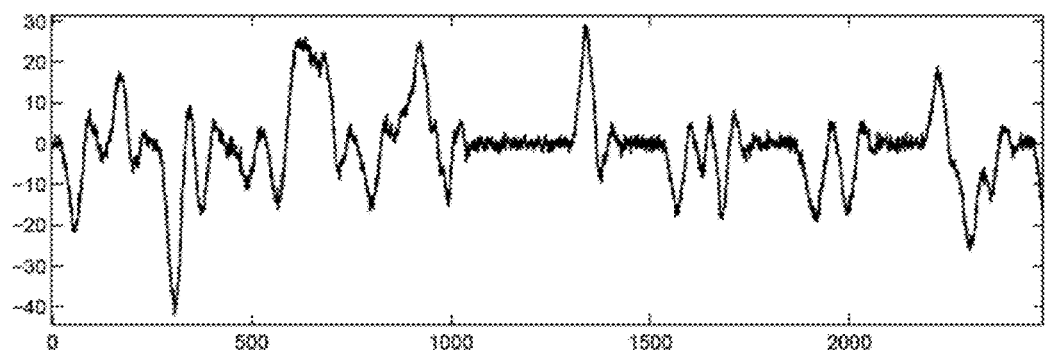
FIG. 12 is an example of a single source signal corresponding to a scaling function of Daubechies wavelet packets in accordance with various embodiments of the present disclosure.

Single-Source, Blind Filter Estimation. For a single source, the following source excitation rates were tested: 50%, 30%, 25%, 20%, 15%, 7%, 5%, 3%, 2%, 1%, 0.5%, and 0.1%. At a rate of 0.55% each filter was, on average, excited every 180 samples, the same as its length. This rate turned out to be close to the change point in the estimation performance. At the given signal and noise characteristics, the signal-to-noise ratio (SNR) was 36.5 dB for 50% excitation and 9.4 dB for 0.1% excitation. Thus, the signal-to-noise ratio was not a useful indicator because a signal with more overlap may prove more difficult to estimate. Referring to FIG. 12, shown is an example of a single-source signal corresponding to W1, the scaling function, of Daubechies 4 wavelet packets. The signal of FIG. 12 is at a source rate of 1% and SNR of 19.4 dB.

Figure 13A:
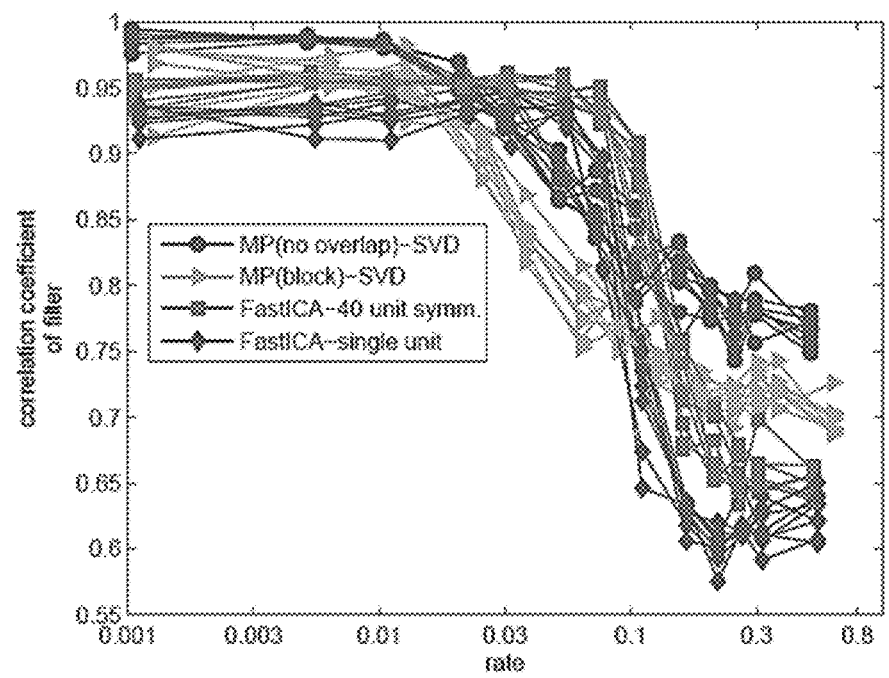
FIGS. 13A-13C and 14A-14D are examples of blind waveform estimation performance in accordance with various embodiments of the present disclosure.
Figure 13B:
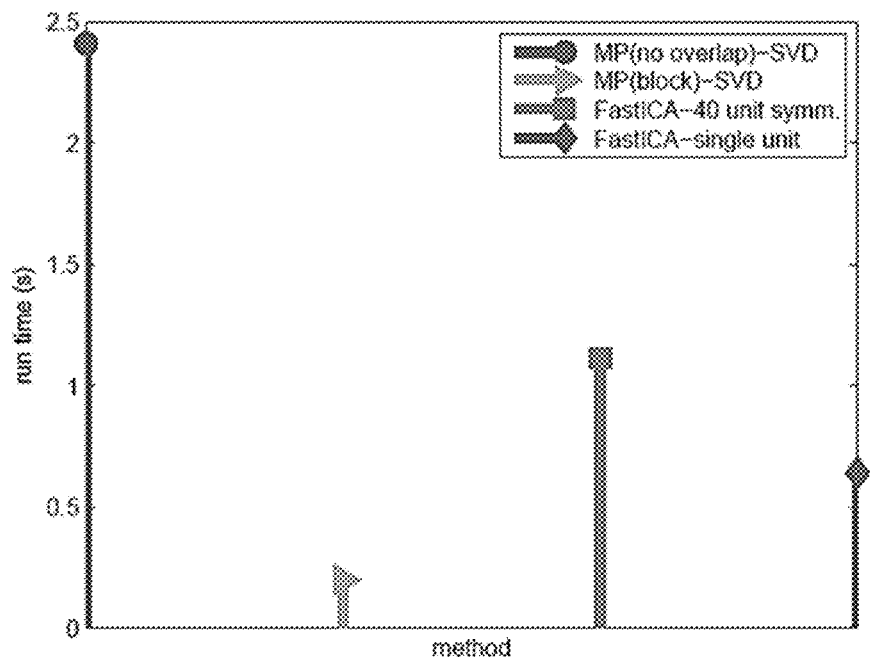
Figure 13C:
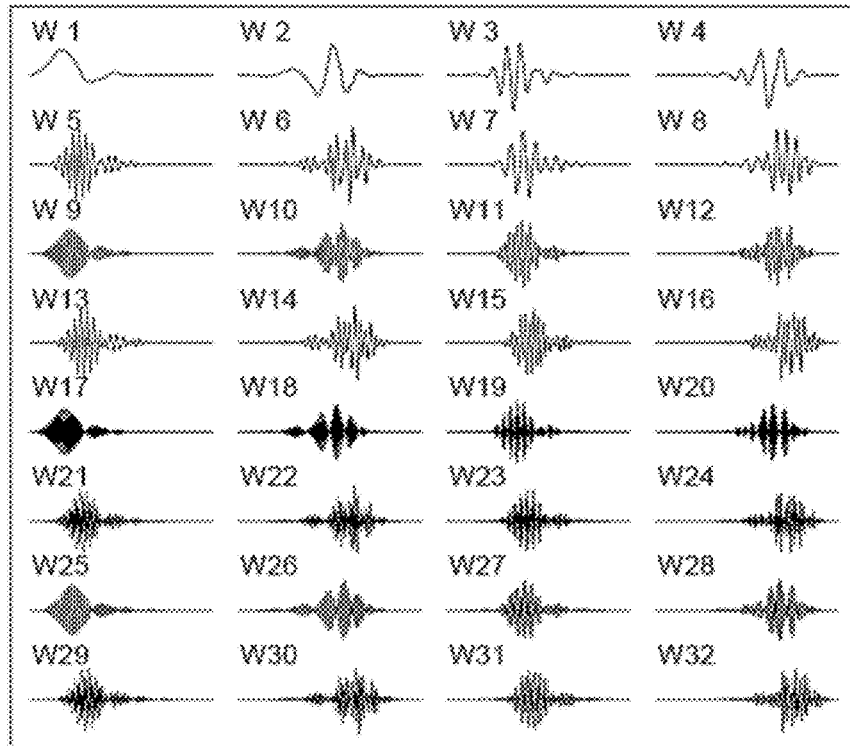

For each run, the filter estimation performance was quantified as the maximum correlation coefficient, across alignments, between the estimated filter and the true filter. This quantity was averaged across all 32 filters and the results are collected across 8 Monte Carlo generations of source and noise activity. The average computation time for the estimation is also recorded. The single-source blind waveform estimation performance is illustrated in FIGS. 13A and 13B. FIG. 13A shows the average correlation coefficient across the 32 waveforms for each method is recorded across 8 Monte Carlo runs. FIG. 13B shows the average run time to estimate one waveform for each method. The 32 true filters, Daubechies 4 (db4) wavelet packets are shown in FIG. 13C.

At high and low excitation rates, MP-SVD achieved the best performance. At extremely low rates of <1%, it achieved filter estimation with a correlation coefficient of nearly 1. Across sparsities, the 40-unit symmetric ICA estimation followed by the filter selection outperformed the single-unit ICA estimation. The ICA approaches exhibited a sharp increase in performance at 10%. In the range of rates between 3% and 10% multi-unit ICA outperformed the MP-SVD approach. At rates of 1% and below, the block-based MP-SVD approach performed at nearly the same level of performance with a much shorter computation time.

Multiple Source, Blind Filter Estimation. A subset of 11 filters was chosen for the multiple source case. The individual source excitation rate was sequentially varied as 10%, 7%, 5%, 3%, 2%, 1%, 0.5%, 0.1%, 0.05%, and 0.025%. This corresponds to an overall rate of excitation of 110%, 77%, 55%, 33%, 22%, 11%, 5.5%, 1.1%, 0.55%, and 0.275%. For the highest rate, on average the system was continually excited. The average SNR of a single component in this mixture was −10 dB. As the source excitation rates were equal, this remained a constant across all rates. For each run, the filter estimation performance was quantified using two indices: the first was the average of the correlation coefficient of each estimated filter to its best-matched true filter, and the second was the percentage of the true filters estimated with a correlation coefficient greater than 0.9. The first measure penalizes spurious filters that are not matched to any source. The second measure does not penalize spurious filters and allows an overcomplete filter estimation because the maximum is taken across all estimated filters. In addition, the computation time was recorded for each method.

Figure 14A:
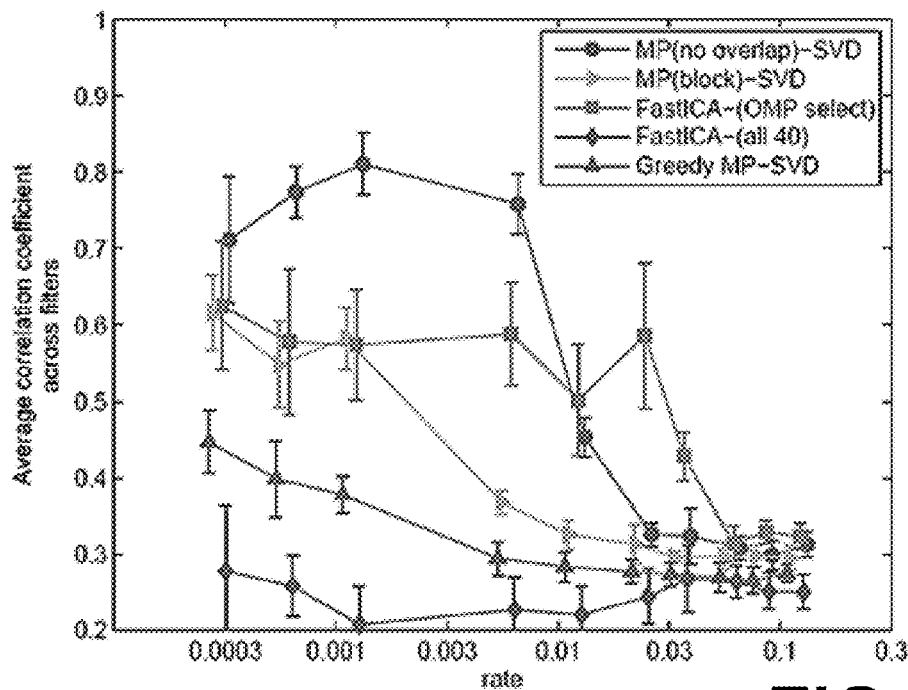
Figure 14B:
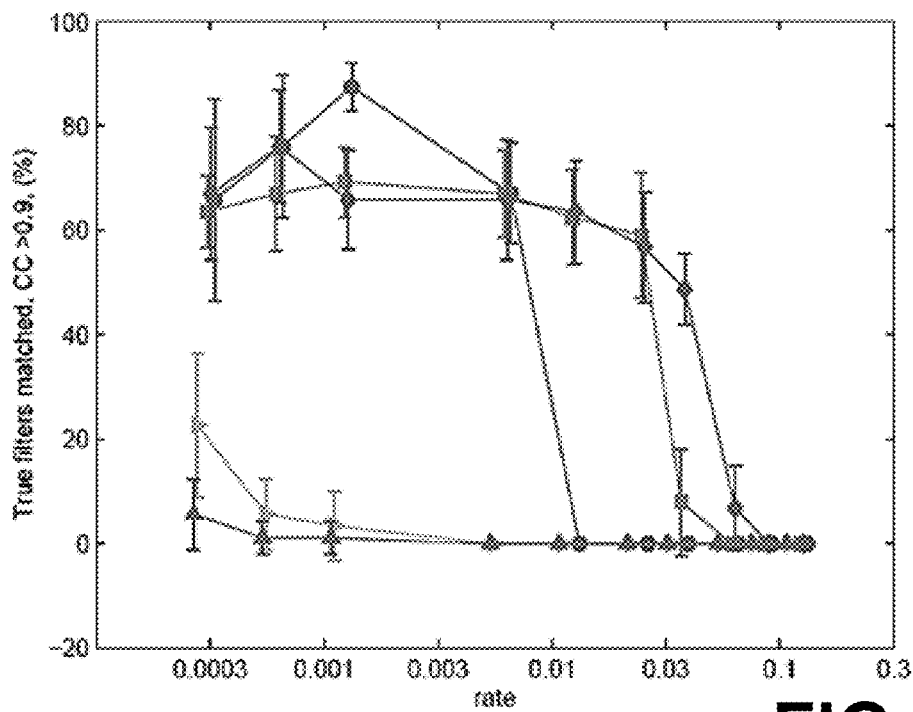
Figure 14C:
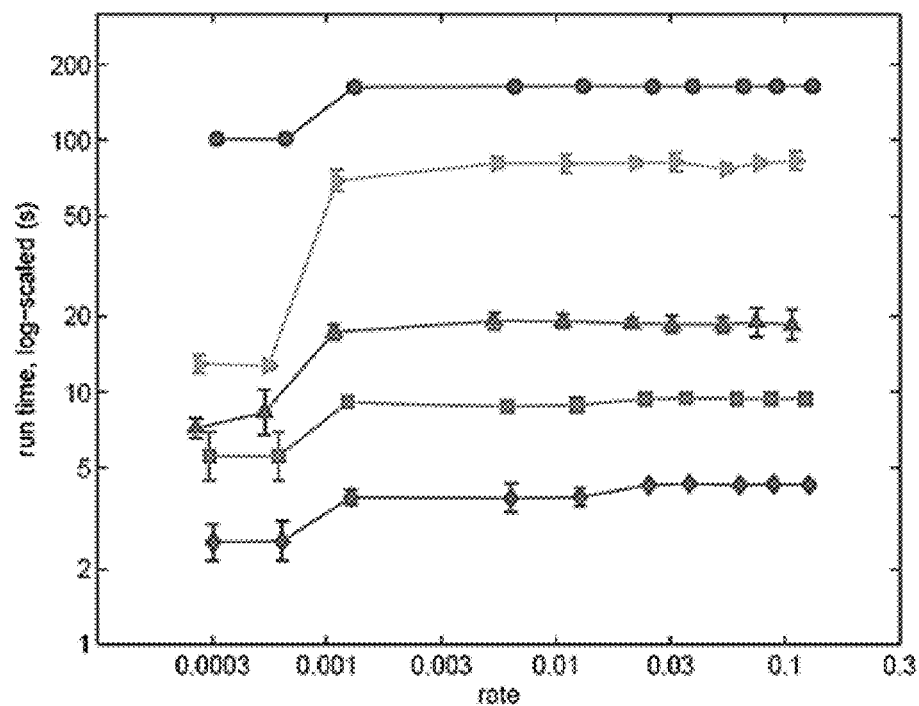
Figure 14D:
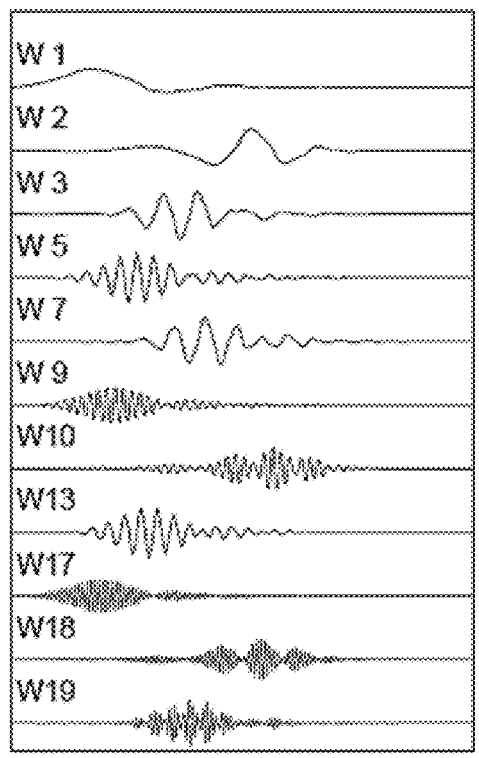

The multiple waveform, single-channel blind estimation performance is illustrated in FIGS. 14A through 14C. For each performance criterion, the average and standard-deviation across 8 Monte Carlo runs is shown as error-bars. FIG. 14A shows the average correlation coefficient of estimated filters to their best-matched true filter. FIG. 14B shows the percentage of the true filters matched, with correlation coefficient greater than 0.9. FIG. 14C shows the run time to estimate, and if necessary, select the group of filters. The 11 true filters, a subset of the Daubechies 4 (db4) wavelet packets, is shown in FIG. 14D.

The MP-SVD approaches achieved the highest performance at select rates, with an average correlation above 0.7 for rates below 1%. The matching performance was more sensitive to the rate, with a peak above 80%, but dropping to zero above 1%. ICA consistently matched 60% of the filters at rates below 3%. The average best-matched correlation coefficient was lower than MP-SVD at low rates, but was consistent across a range of sparsity levels. At extreme sparsity the block-based approximation for MP-SVD was able to perform as well as ICA in terms of average correlation coefficient, but is still more computationally expensive than ICA. The greedy approximation was the fastest MP-SVD-based approach but its performance is extremely poor. The ICA-based approach appeared to have the best tradeoff in terms of speed and consistent accuracy, with a run time of nearly 100 times less than MP-SVD. The better ICA approach performance at higher rates may be attributed to its avoidance of explicit modeling. The MP-SVD algorithm updates the filters based on the assumption that the other filters are perfectly represented. However, early on in the high rate case this is very unlikely, and the filter estimates can become entrapped at local minima of the overall objective function.

Here, matching pursuit that avoids overlap of the same filter has been used. This approximation may be another reason that MP-SVD was not able to perform as well as ICA for higher rate sources. However, running the full matching pursuit algorithm utilized much longer computation time and increased the convergence time. Often, the filters did not converge at high rates, which may be attributed to the same issue discussed in the previous paragraph, compounded by the self overlap. Indeed, in the case of overlap the update was not optimal.

These results confirm that both single-channel ICA and shift-invariant sparse coding are able to blindly estimate the underlying filters in a multiple-input single output system. Both approaches were limited to reasonable rates for the source excitations. This was reasonable since at high excitation rates, the sparse model is not meaningful as it would require as many parameters as samples in the original signal. For higher rates, continual excitation of the sources can be used to estimate auto-regressive and moving average models. These models would be able to describe the signals in terms of their time-varying spectral quantities. Thus, the correct model can be chosen based on a hypothesis of the underlying source excitations.

Decomposing Local Field Potentials. Multichannel local field potentials were recorded from the motor cortex of a bonnet macaque through a chronically implanted cortical micro-electrode array were analyzed. These signals were recorded as the subject passively observed a monitor that displayed cursor movements and colors that indicated upcoming reward delivery. Here, decompositions of a single channel and of multiple channels were performed on 15 minutes of the signal, divided into 60 second segments. The relationship with task timings and behavior was not analyzed. LFPs were collected on 32 electrodes implanted in M1. On this dataset, 8 of the LFP electrodes were excluded because of artifacts, which were associated with high impedance. These were electrodes 3, 9, 11, 13, 14, 19, 21, and 29. The remaining 24 channel signal was high-pass filtered with a cutoff of 4 Hz and notch filtered at 60, 120, 180, 240, and 300 Hz with a quality factor of 69. The data was downsampled by a factor of 3, such that the effective sampling rate is 666.67 Hz. At this rate, each 60 second window of data corresponded to 40,001 time points.

Single-channel Decomposition. For preliminary investigations, the single-channel blind filter estimation algorithms were applied to a select signal. After learning the filters on a single 60 second segment, multiple iterations of the approximation algorithms were applied to that segment and the other 14 segments. MP-SVD and FastICA used the non-overlapping convolution-based orthogonal matching pursuit to obtain the atomic decomposition. The greedy single-filter approximation was performed successively with each filter in the same order that they were estimated.

Figure 15A:
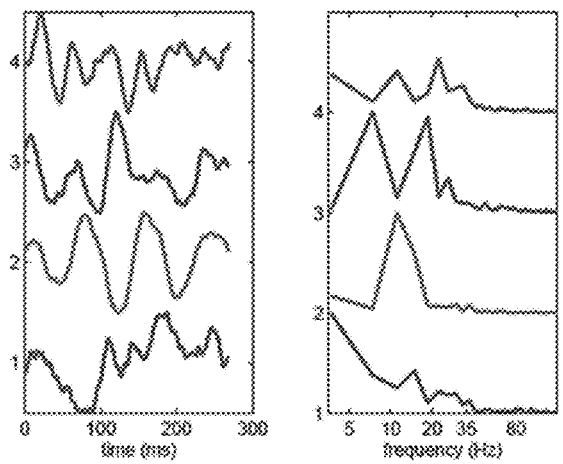
FIGS. 15A-15C, 19A-19C, and 25A-25C are examples of filters in accordance with various embodiments of the present disclosure.
Figure 15B:
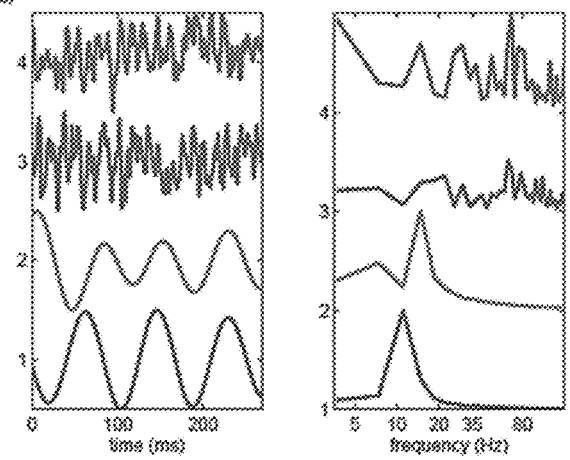
Figure 15C:
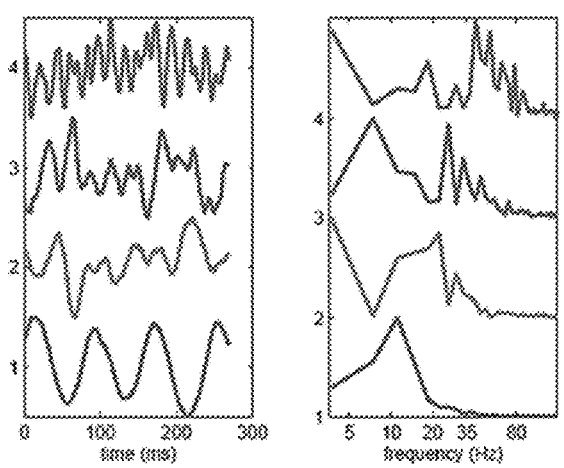

The number of filters to estimate was set to 4. The learned filters, and the magnitude of their frequency response, for the MP-SVD, FastICA-based, and greedy MP-SVD algorithms are shown in FIGS. 15A through 15C, respectively. The MP-SVD of FIG. 15A yielded 4 filters with wavelet-like or evoked-potential-shaped impulse responses. The frequency content of the filters was mainly below 35 Hz peaking, with one filter peaking around 10 Hz. For FastICA of FIG. 15B, the first two components resemble narrow-band waveforms with frequency content between 10 and 20 Hz. The other two components appear as high-frequency ripples. The greedy MP-SVD approximation of FIG. 15C yielded another sinusoidal-like component along with increasingly high-frequency waveforms. This progression makes sense as the greedy decomposition tries to explain as much as possible with each waveform by naturally following the skewed, 1/f power-spectral density for neural potentials.

The signal approximation error when the filters were used because the shift-invariant basis was calculated as proportion of variance explained (PVE). PVE is equal to one minus the normalized mean squared error. The PVE for the complete approximation and for each component individually are recorded in the Table in FIG. 16A. The table illustrates single-channel approximation performance as a proportion of variance explained. The greedy MP-SVD approach yielded the best approximation, followed by MP-SVD, and finally ICA. For MP-SVD and ICA, the distribution of variance explained across components was nearly uniform; whereas, greedy MP-SVD had a highly skewed energy distribution with the first component explaining the majority of the variance. The computation times for both learning the filters and performing the approximation are recorded in Table in FIG. 16B. The table time shows computation time for single-channel filter estimation and approximation on 60 seconds of data sampled at 666.67 Hz. The learning time is averaged across 2 runs. For the approximation time, the average and standard deviation were taken across 15 segments.

Figure 17A:
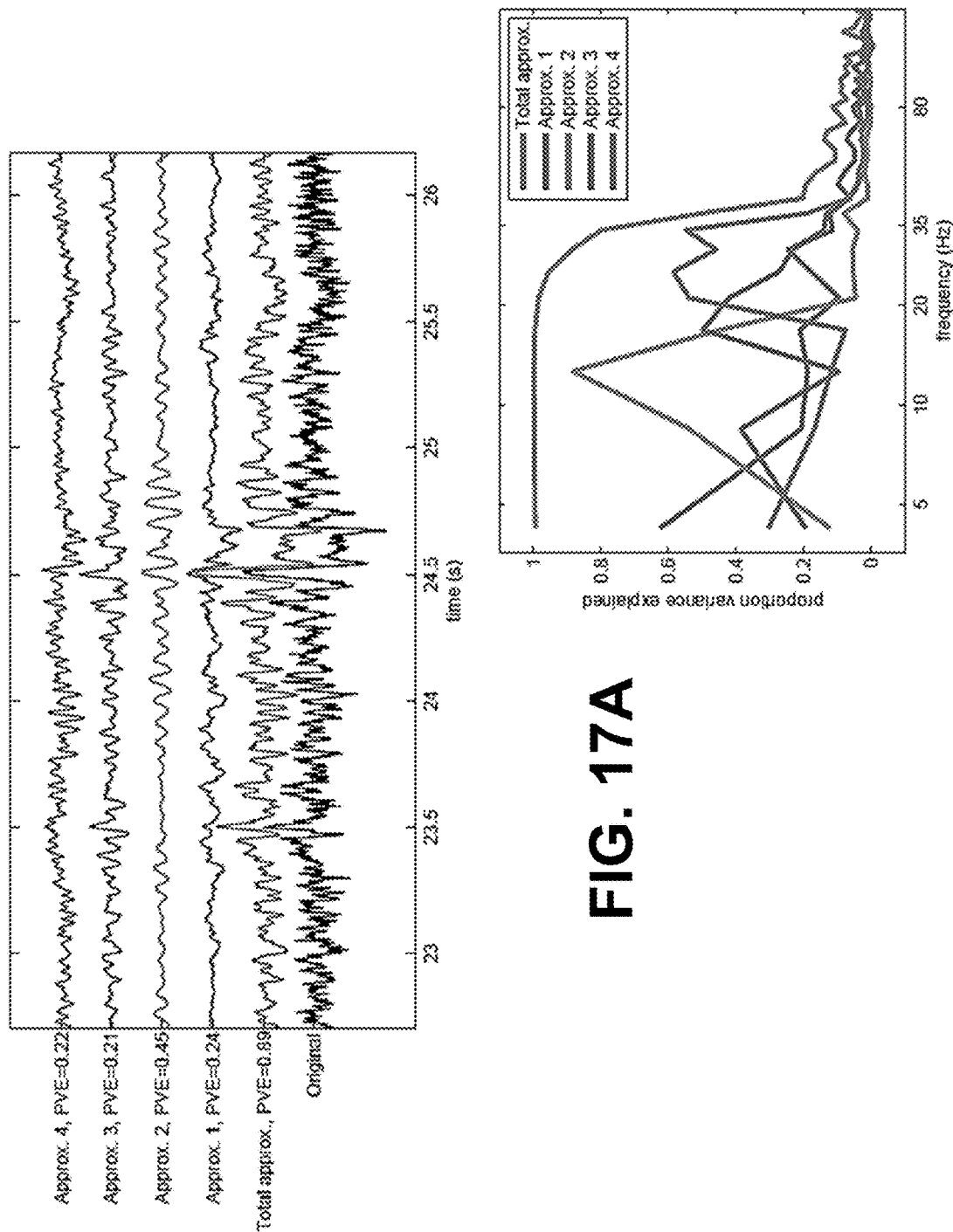
Figure 17B:
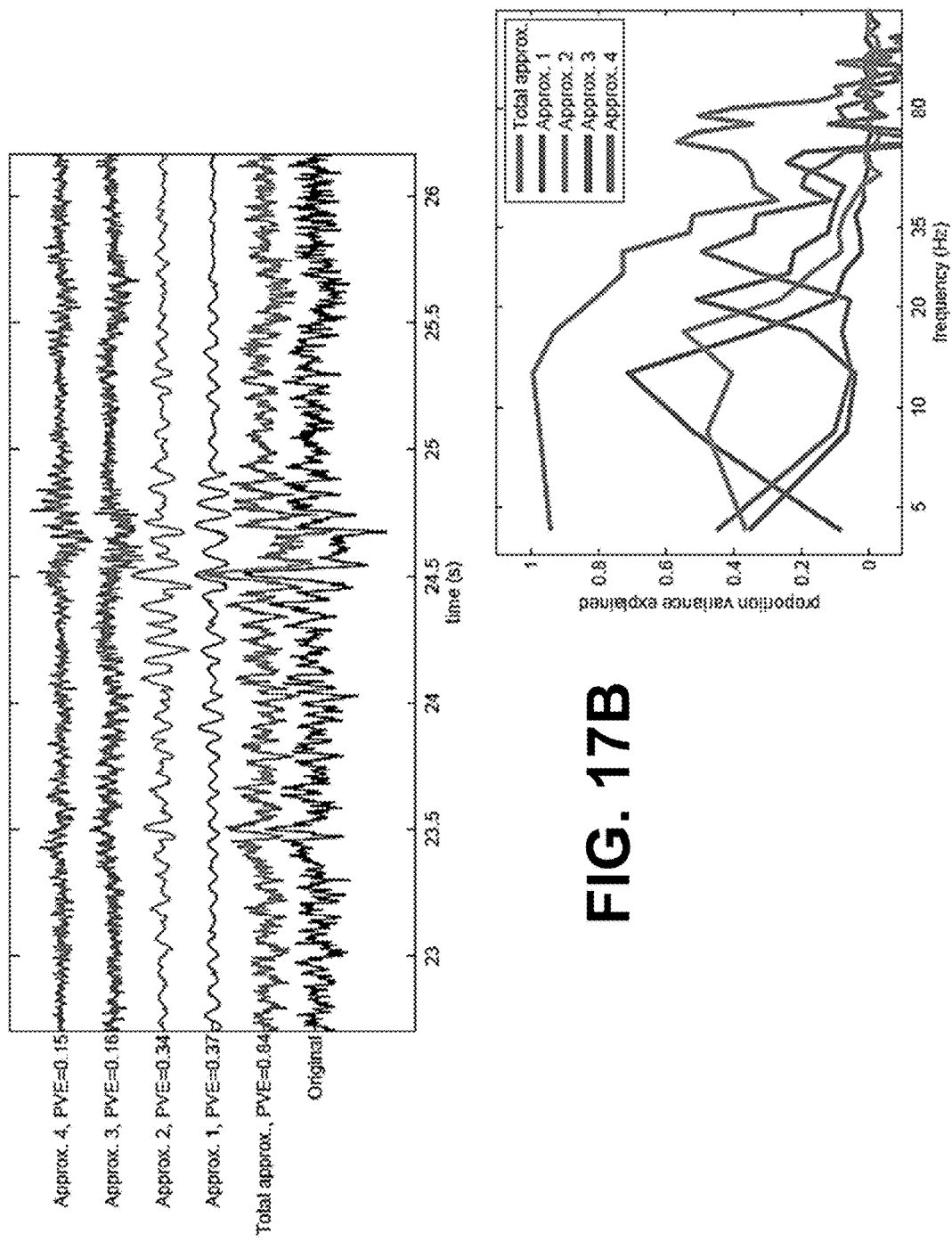
Figure 17C:
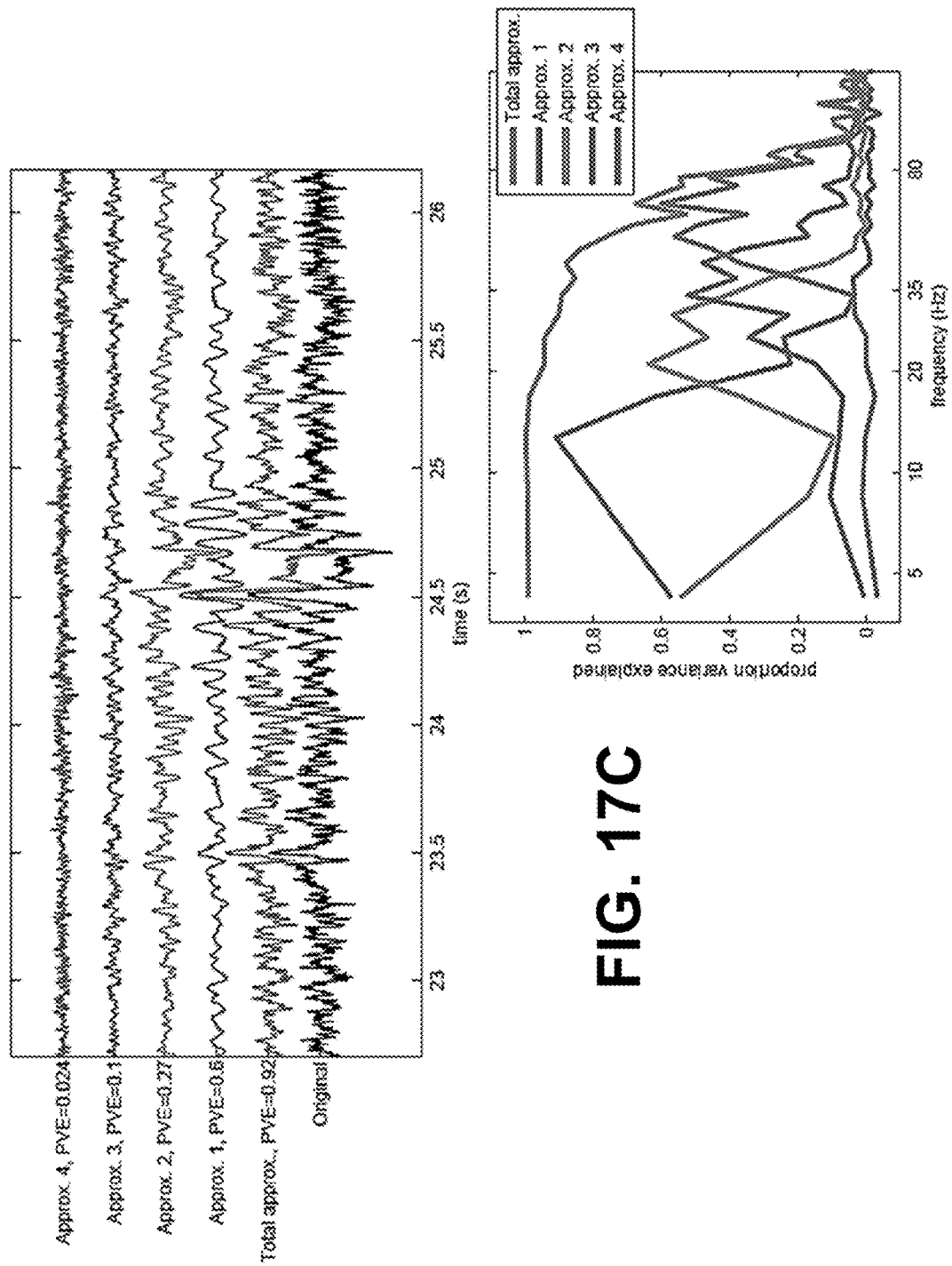

FIGS. 17A through 17C illustrates the analysis of single-channel decomposition of motor cortex LFP. The temporal and spectral aspects of the approximations are shown. On the left of each figure is the total approximation for each method and the individual components signals in a 3.5 second window of the data. On the right is the approximation performance across frequency as a proportion of variance explained. The total approximation using all filters and components for MP-SVD is displayed in FIG. 17A, for FastICA is displayed in FIG. 17B, and for greedy MP-SVD is displayed in FIG. 17C. The PVE was calculated across frequency using the Welch spectrogram with 270 ms Hamming windows with 150 ms overlap, for the complete approximation and each component. For the MP-SVD algorithm, the total approximation achieved nearly perfect reconstruction up to 25 Hz, and above 35 Hz the PVE rapidly diminishes. The first component, which has an evoked potential shape, explains most of the low-frequency response; the second component accounts for most of the variance around 15 Hz; and the fourth component is limited to 20 to 35 Hz. For FastICA, the total PVE was not as uniform, but the method was able to account for over 40% of the variance between 35 and 80 Hz, corresponding to the third and fourth components. The greedy approximation had the best coverage of the spectrum, tapering off above 80 Hz. In addition, the individual components neatly tiled the frequency space, with the low-frequency components being estimated first.

Model Complexity. In the previous analysis, the model complexity, in terms of the number of filters and number of atoms in the decomposition, was fixed a priori. The approximation performance varies across both of these parameters. The number of atoms in the decomposition is determined by the number of iterations of the orthogonal matching pursuit approximation. A small experiment was conducted on the initial 60 s segment of the single-channel LPF.

Figure 18A:
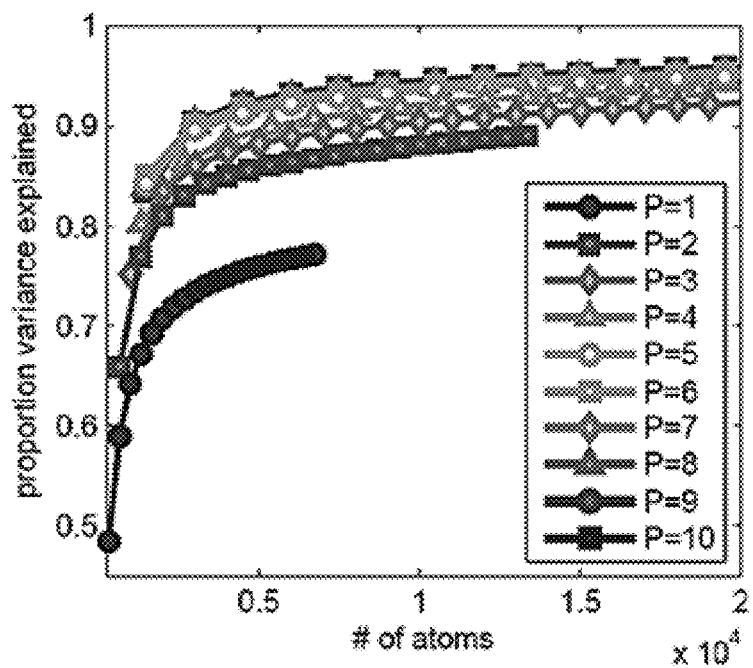
FIGS. 18A through 18C are examples of proportion of variance explained for various numbers of filters in accordance with various embodiments of the present disclosure.
Figure 18B:
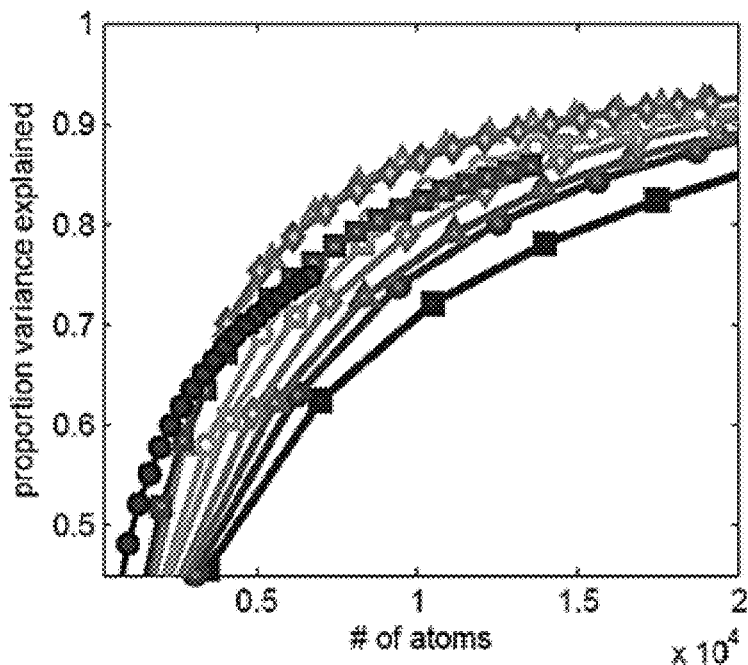
Figure 18C:
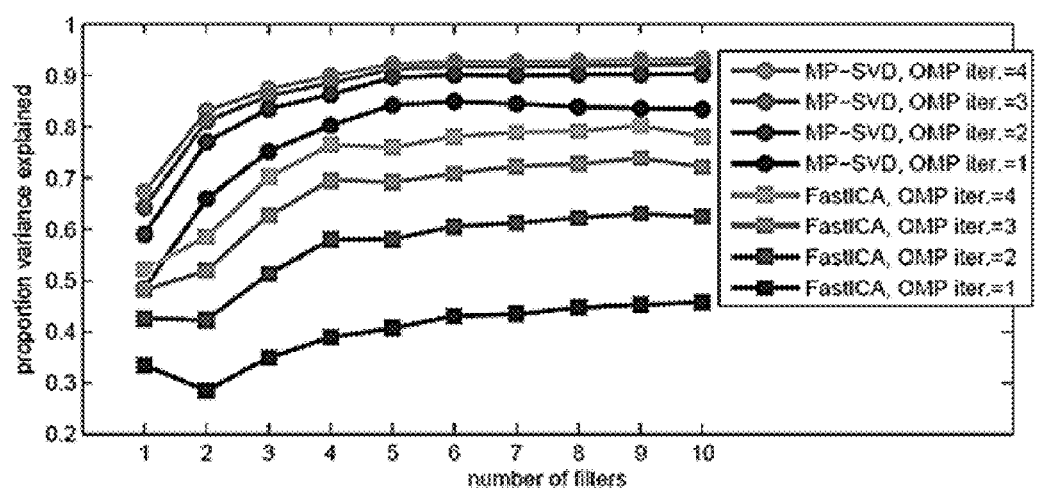

The proportion of variance explained were calculated for up to 10 components for both MP-SVD and ICA. FIGS. 18A and 18B illustrate the proportion of variance explained versus the number of atoms for various numbers of filters, denoted by K in the legend. FIG. 18A shows filters learned using the MP-SVD algorithm and FIG. 18B shows filters learned using single-channel FastICA. For the MP-SVD, learning 5 components appears to yield nearly the best performance, above 5 components there is marginal improvement. For ICA, the performance is not necessarily monotonic function of the number of components, 4 components appearing to perform the best across a range of atoms. In the non-overlapping approximation for matching pursuit, the number of atoms is a function of both the number of iterations and the number of bases. The performance across the number of iterations of the approximation (proportion of variance explained across approximation iterations versus the number of filters) is shown in FIG. 18C. The MP-SVD algorithm clearly outperforms ICA in terms of the variance-based measure. For the MP-SVD algorithm, above 5 components and 2 iterations there is diminishing marginal increase in performance.

Multichannel Decomposition. Using principal component analysis, all of the methods were extended to the multichannel case. For MP-SVD, the first principal component can be estimated at each step of the learning process at the same time that SVD is performed to update the filters. For the greedy approach the same can be done, but as only a single filter is updated for each greedy decomposition the spatial factor is allowed to vary between components. Finally, for ICA it is difficult to combine the multiway aspect directly, so the first principal component of the raw signal can be provided to single-channel ICA. This is most likely a suboptimal solution as for the other approaches the spatial component is tuned to the temporal filters estimated.

Figure 19A:
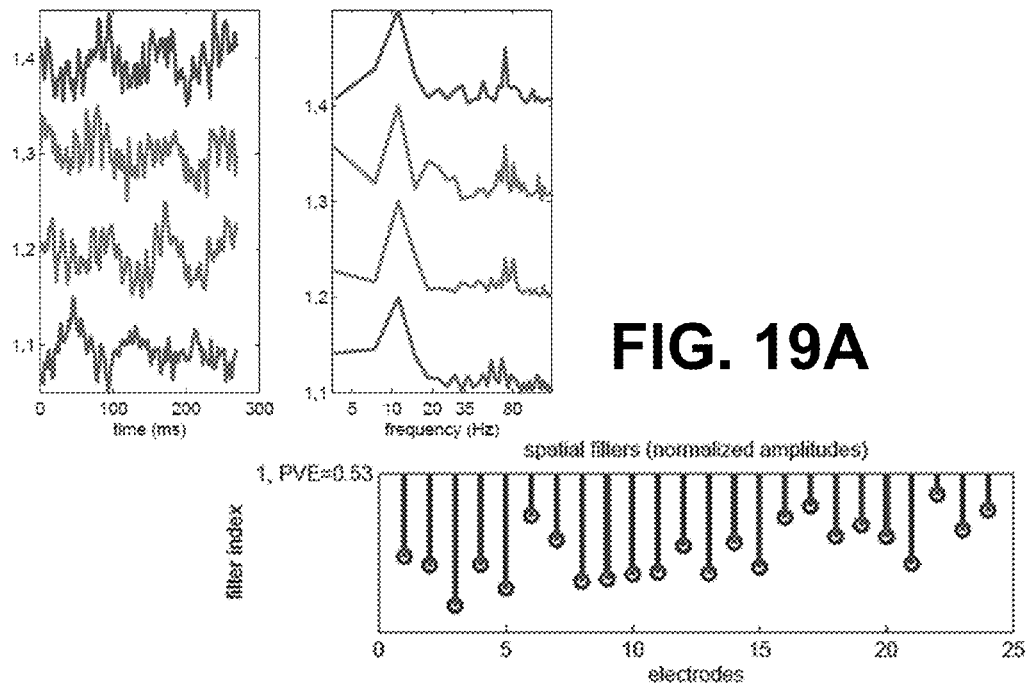
Figure 19B:
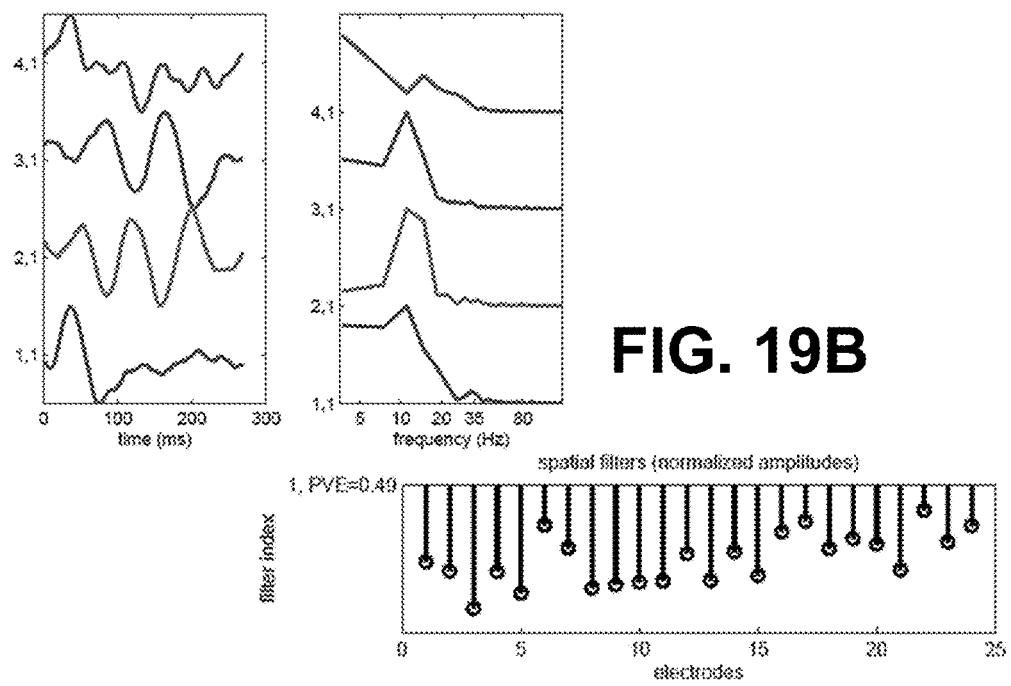
Figure 19C:
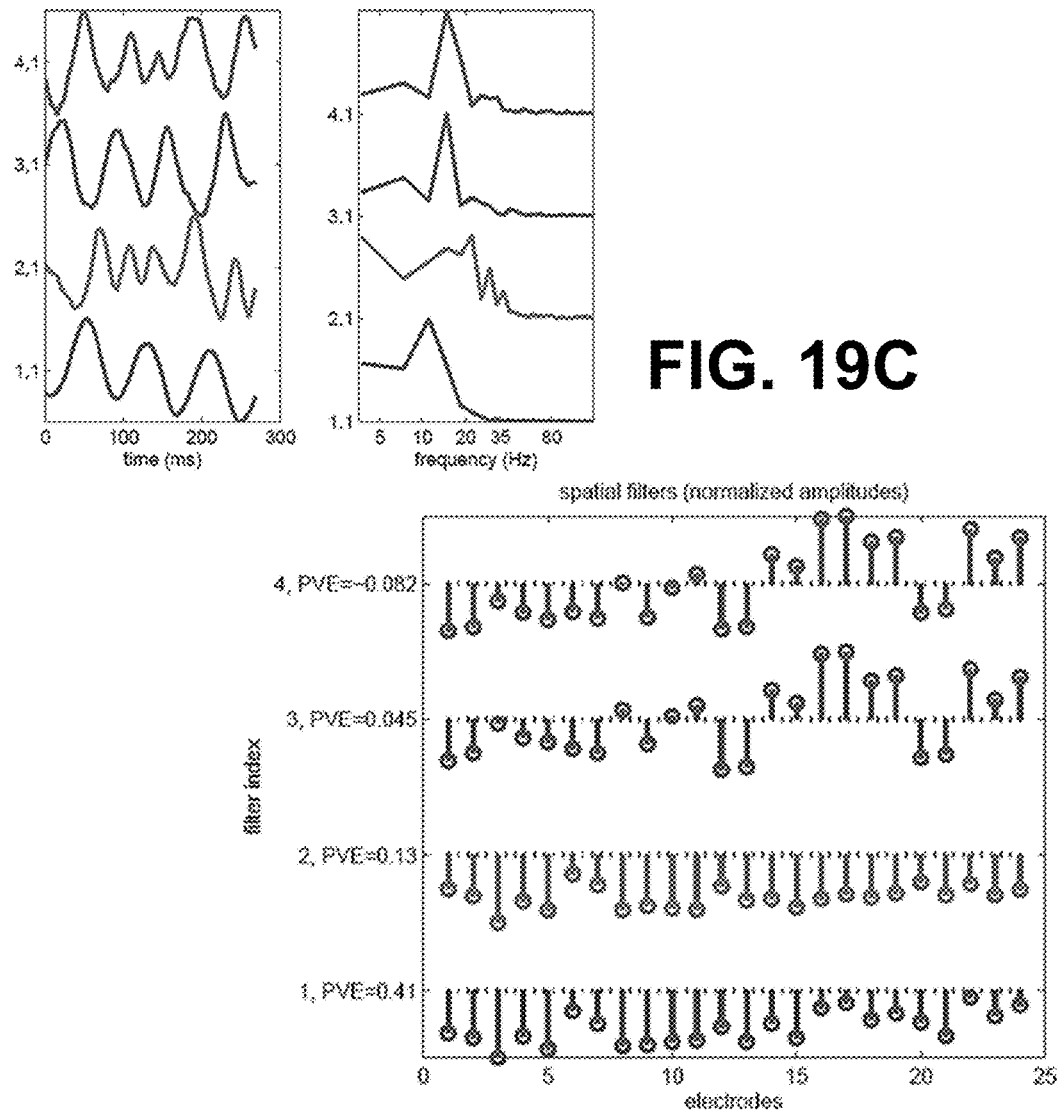

The temporal and spatial filters estimated from multichannel LFP recording of the motor cortex with the three approaches are shown in FIGS. 19A through 19C. The filters for PCA-MP-SVD are shown in FIG. 19A, filters for PCA-FastICA are shown in FIG. 19B, and filters for greedy PCA-MP-SVD are shown in FIG. 19C. In the multichannel case, all the filters had their peak frequency content at lower frequencies. The ICA filters appear as a mixture of the high-frequency and low-frequency oscillations, which were distinct components when applied to a raw single channel. The fact that the components and approximations corresponded to lower frequencies for the multichannel case is also apparent in the PVE across the spectrum.

Figure 20A:
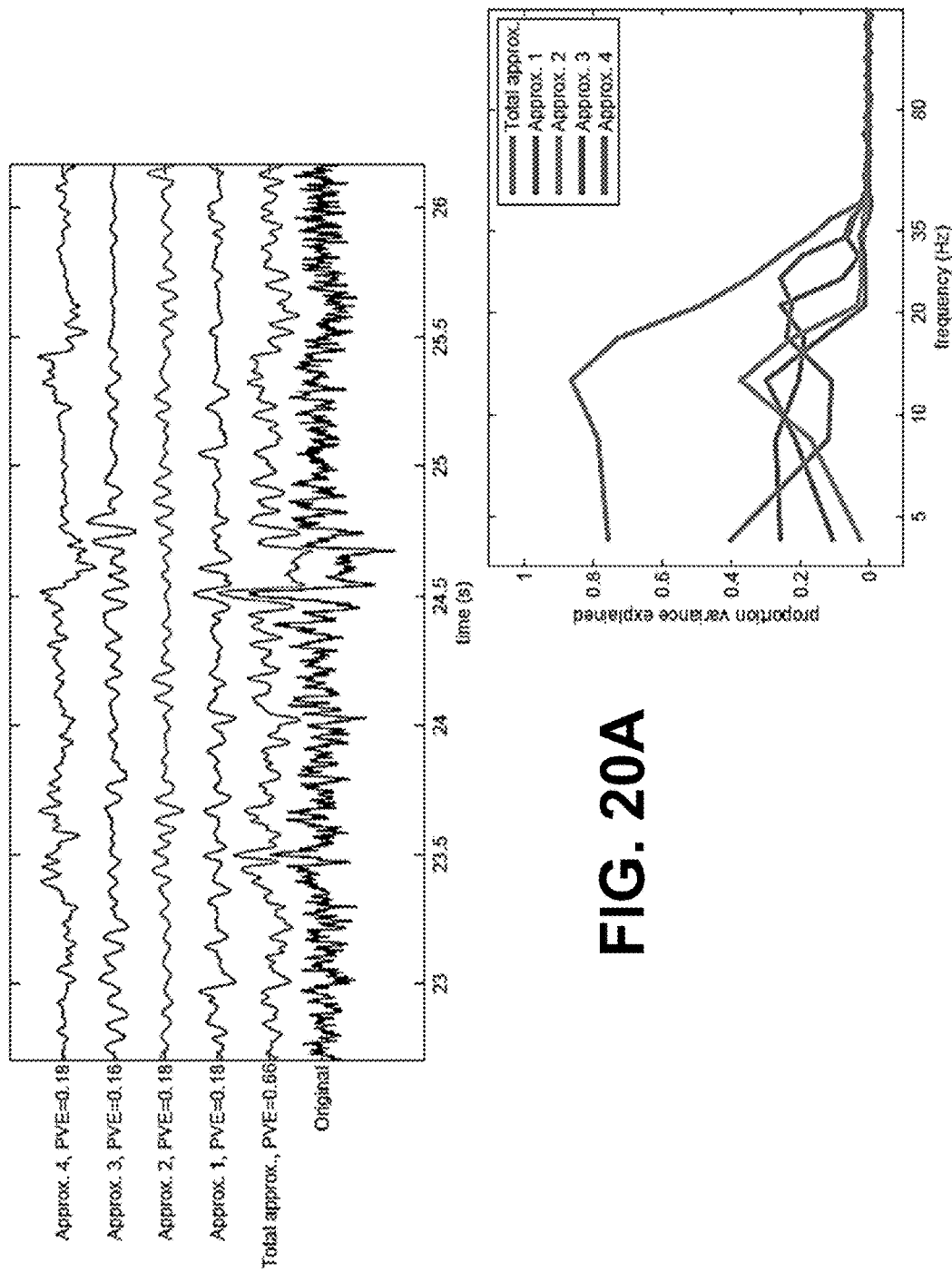
Figure 20B:
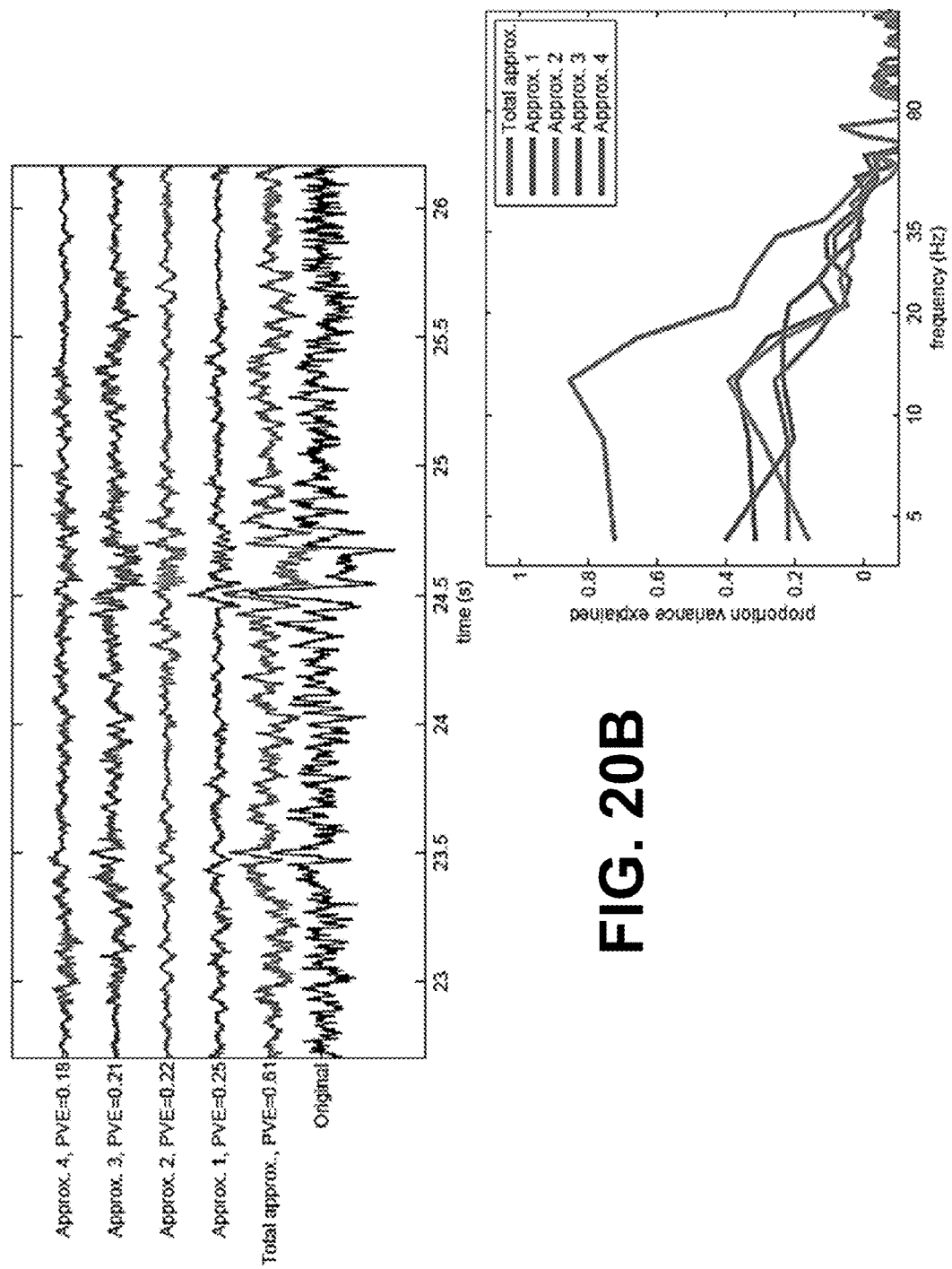
Figure 20C:
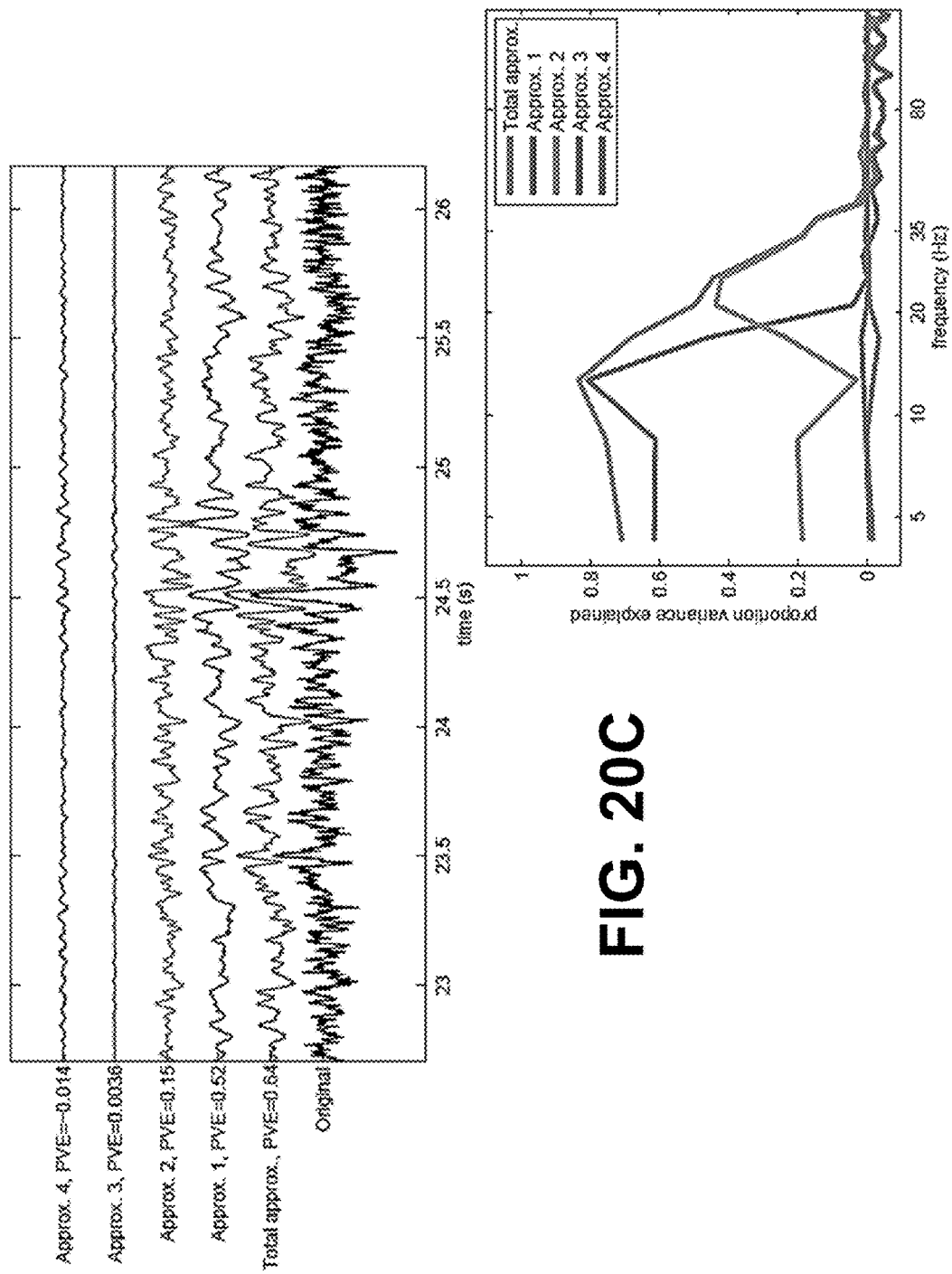

FIGS. 20A through 20C illustrate the analysis of select channel for the multichannel decomposition of motor cortex LFPs. On the left of each figure is the total approximation for each method and the individual components signals in a 3.5 second window of the data. On the right is the approximation performance across frequency as proportion of variance explained. The results using all filters and the components for each filter are each displayed for MP-SVD in FIG. 20A, for FastICA in FIG. 20B, and for greedy MP-SVD in FIG. 20C. All of the variance explained is in the frequency range below 40 Hz; whereas, in the single-channel case, ICA and the greedy MP-SVD were able to explain variance up to 80 Hz. This implies that the linear model across space is not a good model at frequencies above 40 Hz. Signals at these frequencies are unlikely to be phase-locked across the array.

The percentage variance explained across each component and across all channels is recorded in the Table in FIG. 20D. The Table shows the multichannel approximation performance as proportion of variance explained on a select channel and across all channels. Interestingly, the MP-SVD performed best for the select single-channel, but greedy MP-SVD, which has a separate spatial factor for each component, was able to account for an additional 4% of the variance. Again, MP-SVD and ICA yielded nearly equivariant components; whereas, greedy MP-SVD has a highly skewed energy distribution with the first component explaining the majority of the variance.

Approaches for blindly estimating MISO systems with sparse inputs were examined. The aspects of the problem compared existing algorithms on a synthetic test with varying sparsity, and explored applications in the decomposition of neural potentials. A variety of time-series analysis and machine learning tools were used: deconvolution, sparse coding, iterative approximation algorithms and atomic decomposition, alternating optimization, and FastICA. The blind filter estimation is essentially a modeling problem. In this framework, additional priors or constraints can be added on either the sources or the filters. The most common adjustment is forcing the sources to be strictly positive, or constraining both the sources and filters to be positive. These approaches can be important since in some applications the unconstrained models lead to uninterpretable components.

An approximation of matching pursuit was used to obtain the source estimates, and the number of atoms extracted corresponds to the sparsity of the sources. From the results on real data, this lead to components which uniformly contributed. Alternatives for matching pursuit can provide better sparse coding accuracy, but come at higher computational cost. The computational cost of matching pursuit is already a main source of the complexity. Alternative source estimation techniques allow alternative priors on the source distributions, which may lead to the extraction of different components. For instance, the greedy method proposed finds components with decreasing energy, but localized at increasingly higher frequencies. The benefit of the greedy method is that it learns an underlying set of filters that can be used on novel segments of the signal.

In terms of the neural potentials, the applied approaches can match the underlying generating process: recurrently activated waveforms that appear transiently in time. With classic time-frequency analysis, it is difficult to separate the contribution of unique sources in the local field potential. Using the blind system identification, both lower frequency components and high-frequency waveforms, even action potential waveforms, could be learned and matching pursuit can be applied to separate their contributions. On the segments of LFP analyzed, MP-SVD and the greedy approach for MP-SVD performed better than ICA. Even with increasing number of approximation iterations ICA was not able to match the approximation performance of MP-SVD. This is reasonable because MP-SVD is tuned to explain the signal in terms of mean squared error; whereas, ICA is only searching for 'independent' sources. Indeed, ICA choose filters at higher frequencies that may indeed be independent of the lower frequency sources MP-SVD estimated. Natural extensions of the single-channel case to the multichannel case were introduced. The resulting filters for the multiple channel case were lower frequency waveforms. This relates to the spatial localization of high-frequency components in the LFP. These interesting results indicate the capability of shift-invariant decompositions to provide new insight during exploratory analysis of neural potentials.

Trial-Wise Decompositions for Neural Potentials

The electrical potential of the brain is a combination of spatiotemporal oscillations in neural electric potentials, indicative of the communication between neural assemblies, intermixed with a broadband component of unsynchronized activity. Brain waves are often associated with rhythmic activity but can take the form of transient responses following a specific cognitive or sensory event, such as brief flash of light. Transient responses are localized in time and space. This localization is due to the brief involvement of the same neural circuits. The spatiotemporal patterns following presentation of a specific stimulus or condition are referred to as evoked potentials, and they can be indications of neural processing.

The recurrent characteristics of the evoked potentials to different stimuli or conditions can be represented by a spatiotemporal model. Then the stimuli or conditions can be compared using these models. This approach is particularly useful for investigating sensory and cognitive processing on a single-trial basis. Mathematically, this corresponds to evaluating the likelihood of single-trials on the various models. A particular application of these methods is brain computer interfaces wherein the intention of the user is determined based on their selective attention to various stimuli. This selective attention can be detected from the characteristics of the evoked potentials recorded on the scalp. Methods that reliably estimate a spatiotemporal model of the evoked potentials for each condition, or, alternatively, directly differentiate between neural response's to different conditions can be used to achieve this.

The simplest model for the evoked potential under specific conditions is that the neural response is a combination of the same spatiotemporal waveform and independent background activity and noise: signal plus independent noise. Under this assumption, the model can be estimated by averaging across multiple trials; however, much of the trial-to-trial variability cannot be explained by a simple average. For instance, the time between stimulus presentation and neural response may vary or the amplitude may vary across trials. Sometimes this effect results from physiological effects such as habituation. Additional free parameters can be added to the model to account for these trial-wise variations. A model can use a temporal waveforms whose exact temporal location may shift and whose amplitude may vary among the trials. Combining both of these, the estimation of the amplitude is then shift invariant. In reality, the shift is not simply a nuisance parameter, and both extracted parameters, the shift and the amplitude are useful for further analysis. Thus the model should be considered shift tolerant.

Models for evoked potentials are examined and extended. The multichannel case is explicitly addressed, and clear connections are made with tensor decompositions. An analysis of the model performance using model selection criteria is proposed as a consistent methodology to compare models based on different assumptions and with various degrees of freedom varies. Alternatively, the trial-varying parameters in the models are considered as features for single-trial classification between conditions. In this way, the model fitting performance can be used to guide the model, prior to any classification. The use of the condition or stimulus class information during model estimation is also considered. Model estimation is typically performed in an unsupervised manner across all trials, or in partially supervised case where only examples relating to a single class are used. In addition, the different forms of supervision may be used while fitting different modes of the model, e.g., the spatial factors or the temporal factors.

The methodology can be applied to datasets comprising local field potentials, such as those recorded from non-human primates during variable-reward experiments, where trials have the possibility of being rewarding or non-rewarding. The models can be used to analyze differences in the evoked potentials between the reward and non-rewarding trials, and gauge the models' performance by their single-trial classification between the two conditions. In addition, on one dataset the relationship between the timing of evoked potentials and the neural firing rates are assessed. Overall, shift-varying models can be used for the decomposition and classification of evoked potentials on a single-trial basis.

Mathematical Modeling Framework. A spatiotemporal model seeks to explain a window of multivariate time series of multichannel neural potential recordings. These neural recordings could be obtained from electroencephalogram, electrocorticogram, or the local field potential recorded by electrodes within brain tissue. The design of the model dictates the linear and non-linear processing of these signals.

Two levels of model parameter fitting are considered: at the bottom level, the parameters are fit for each trial, and at the top level, the parameters are fit across the trials. Borrowing nomenclature from signal processing, the term analysis is used to mean inferring any trial-varying coefficients for a given input. Analysis can be done on each trial independently; whereas, estimation refers to adjusting the model coefficients that are fixed across trials. In both cases, the coefficients are adjusted to minimize the cost function, for which the mean squared error can be used. The coefficients that are fixed across trials are referred to as factors. For clarity, coefficients that vary per trial will be indicated by a star superscript ($a^*$), or, when necessary to distinguish specific trials, with a trial indexing variable subscripted ($a_t$).

Tensor Representation. Assume a discrete sampling in time and space, and organize the evoked potential for a single trial into a matrix. Let $X=[x_1 x_2 \ldots x_M] \in \mathbb{R}^{L \times M}$ denote be a L length window of M channels of the spatiotemporal waveform for a particular trial. Let a set of n trials be denoted $\mathcal{X} = \{X_i\}_{i=1}^n$. Assuming all of the trials have the same dimensions, it is natural to treat this set of spatiotemporal evoked potentials as a three-way matrix, or tensor. Let $\mathcal{X}$ correspond to the tensor representation of the set of trials in $\mathcal{X}$; organized into trials by time by space with dimensions n×L×M.

Then $\mathcal{X}$ is a third-order (or order-3) tensor with 3 dimensions (or modes); a second-order tensor is a matrix; and a first-order tensor is a vector; and a scalar can be considered a zeroth-order tensor. Any tensor can be converted to a column vector by simply concatenating all of the entries $x=\text{vec}(\mathcal{X})$. In addition, the unfolding operation returns order-3 or higher tensor into a matrix. This allows the matrix operations to be applied to the tensor. For the third-order tensor $\mathcal{X}$ there are three possible unfoldings:
1. The 1-mode unfolding is a n×(M·L) matrix $X^{(1)}=[\text{vec}(X_1), \text{vec}(X_2), \ldots, \text{vec}(X_n)]^T$.
2. The 2-mode unfolding of $\mathcal{X}$ returns a $L \times (n \cdot M)$ matrix $X^{(2)}=[X_1, X_2, X_3, \ldots, X_n]$.
3. The 3-mode unfolding is a M×(n·L) matrix $X^{(3)}=[X_1^T, X_2^T, \ldots, X_n^T]$.

Tensors can be built out of lower-order vectors, matrices, or tensors using an outer product. Given an order-N $\mathcal{A}$ and an order-P tensor $\mathcal{B}$ the outer product of $\mathcal{A}$ and $\mathcal{B}$ is the order-(N+P) tensor $\mathcal{C} = \mathcal{A} \otimes \mathcal{B}$, with entries such that $\mathcal{C}_{i_1,i_2,\ldots,i_N,j_1,\ldots,j_P} = \mathcal{A}_{i_1,i_2,\ldots,i_N} \mathcal{B}_{j_1,j_2,\ldots,j_P}$. The tensors in the outer products are called factors, and tensors in linear combinations of tensors are referred to as components. Consider a series of outer products when each factor is a vector. An order-N tensor $\mathcal{X}$ is considered to be rank-1 if it is formed from the outer product of N vectors, i.e., it can written as $\mathcal{X} = a^1 \otimes a^2 \otimes \ldots \otimes a^N$. Otherwise, the rank is R and is equal to the minimal number of rank-1 tensors needed such that $\mathcal{X} = \Sigma_{r=1}^R a_r^1 \otimes \ldots \otimes a_r^N$. The set of factors $\{a_r^i\}_{i,r}$ form the canonical polyadic decomposition (CPD), which is also called CANDECOMP or PARAFAC.

Increasing the rank of the CPD introduces a new factor along each mode. Sometimes it may be desired to increase the number of factors only along certain modes. The Tucker model allows a different rank along each mode. Unlike the CPD, where a factor from each mode is associated with a single component, the Tucker decompositions relate the interaction between modes using a core tensor. The core tensor has the same number of modes and has dimensions equal to the ranks. The third-order Tucker model with core $\mathcal{G}$ and factors A, B, and C is written $\mathcal{X} = \mathcal{G} \times_1 A \times_2 \times_3 C$, where $\times_k$ denotes tensor multiplication along the kth mode. The CPD is the case of a Tucker model with equal ranks and a super-diagonal core. A tensor is super-diagonal if all entries that do not have the same index on each mode are non-zero, i.e., $\mathcal{A}_{i,j,k}=0$ if $i \neq j \neq k$.

Block term decompositions that share the benefits of the CPD with the added flexibility of the Tucker models can be used. The decompositions consider more general ranks, an order-3 tensor is rank-(L, L, 1) if it can be written as an outer product between a rank-L matrix A and a vector a, e.g., $\mathcal{X} = A \otimes a$. (The rank-1 term could be assigned to any mode by reordering the modes.) An order-3 tensor can be decomposed into a set of rank-($L_r$, $L_r$, 1) tensors as $\mathcal{X} = \sum_{r=1}^{R} A_r \otimes a_r$. Under certain conditions this is unique decomposition.

For real-valued third-order tensor, it is simple to consider the inner-product, norm, and Euclidean distance. The inner product of two tensors of the same size is:

$$\langle \mathcal{A}, \mathcal{B} \rangle_F = vec(\mathcal{A})^T vec(\mathcal{B}) = \sum_{i,j,k} \mathcal{A}_{i,j,k} \mathcal{B}_{i,j,k}. \quad (44)$$

The inner-product induces the Frobenius norm, which can be computed as:

$$\|\mathcal{A}\|_F = \sqrt{\langle \mathcal{A}, \mathcal{A} \rangle_F} = \sqrt{\sum_{i,j,k} \mathcal{A}_{i,j,k}^2}. \quad (45)$$

The squared Euclidean distance between two tensors is then $$\|\mathcal{A} - \mathcal{B}\|_F^2 = \sum_{i,j,k} (\mathcal{A}_{i,j,k} - \mathcal{B}_{i,j,k})^2. \quad (46)$$

Assuming $\mathcal{B}$ is an approximation of $\mathcal{A}$ and normalizing the squared Euclidean distance by the total number of entries N, yields the mean squared error of the approximation:

$$\frac{1}{N}\|\mathcal{A} - \mathcal{B}\|_F^2 = \sum_{i,j,k} \frac{1}{N} (\mathcal{A}_{i,j,k} - \mathcal{B}_{i,j,k})^2. \quad (47)$$

Returning to the evoked potentials case, consider bilinear models of a spatiotemporal waveform. A rank-1 model is the outer product between a single pair of vectors, with $A = u \otimes w = uw^T$, where $\otimes$ denotes the outer product. The factor u is the temporal component and w is the spatial component. To allow the amplitude to vary across trials, an additional scaling term may be added. The trial-varying amplitude is denoted $\alpha^*$ so that the approximation for a given trial is $\alpha^* A = \alpha^* u \otimes w$. Considering the full set of trials, the model is a rank-1 CPD, $\mathcal{X} = \overline{\alpha} \otimes u \otimes w$. FIGS. 21A and 21B show diagrams of third-order tensor models for sets of evoked potentials. In FIG. 21A, a rank-1 canonical polyadic decomposition (CPD) is shown that corresponds to the outer product between a spatial factor, temporal factor, and trial-varying amplitudes.

Instead of having a single temporal waveform to represent all the trials, a more general model assumes the temporal waveform on a given trial exists in some subspace. Consider the subspace spanned by the columns of B, a individual trial may have temporal aspect $u^* = Ba^*$, where the subspace coefficients are stored in $a^*$. The resulting model is $u^* \otimes w = Ba^* \otimes w$, which is still rank-1 across time and space, but has more degrees of freedom to describe the temporal aspects. In terms of a tensor model, the model is formed by first concatenating the subspace coefficients across all of the trial $A = [a_1, a_2, \ldots, a_N]^T$ into a matrix. Then if B is rank-D the model is a block term decomposition with rank-(D,D, 1), $\mathcal{X} = AB \otimes u$. FIG. 21B shows a rank-(3,3,1) block term decomposition that allows each trial to be the linear combination of three waveforms, but a single spatial factor.

For model estimation, a unique parameterization is important. Models involving both multiple factors are not uniquely defined if the norms of the factors involved are allowed to vary independently. Therefore, any models that use both scalar amplitudes and vectors or matrices fixed across trials are constrained to have unit norm $\|u\|_2 = \|w\|_2 = \|A\|_2 = 1$. This constraint also simplifies the mathematical analysis.

Figure 22:
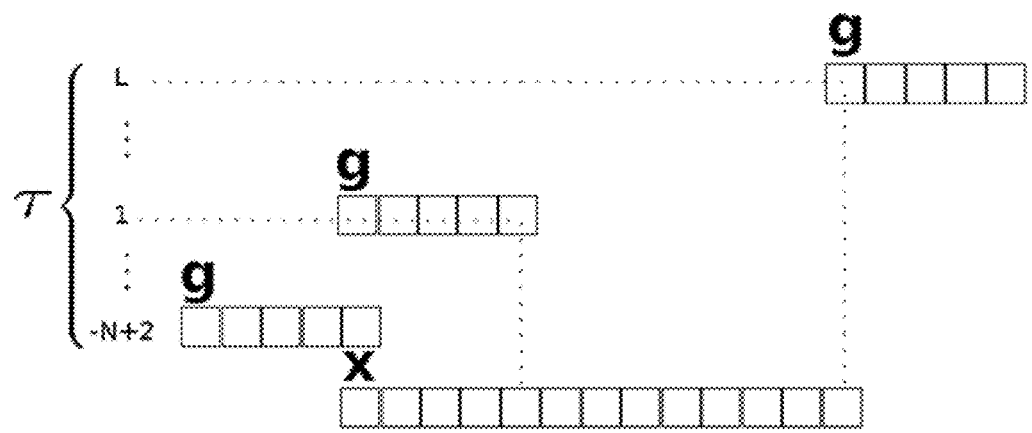
FIG. 22 illustrated an example of a range of alignments between temporal waveforms in accordance with various embodiments of the present disclosure.

Models with Variable Temporal Alignment. The time-series waveform can be modeled as a single waveform or a linear combination of multiple waveforms whose temporal alignment and scaling may vary per trial. More specifically, models where all of the waveforms have the same temporal alignment per trial are considered. These models include all time-series that can be formed by shifting the temporal waveform. Let $x \in \mathbb{R}^{L \times 1}$ and $g \in \mathbb{R}^{N \times 1}$, $N \leq L$ be discretely-sampled time series and waveform, respectively. Define $T_\tau$ to be the linear operator such that $T_\tau g$ temporally aligns a waveform g such that it starts at time $\tau$. Then $\tau - 1$ is the number of zeros that need to be pre-padded to g; if $\tau < 1$ the initial $1-\tau$ elements of g are truncated, and if $\tau > L - M + 1$ the final $\tau - (L - M + 1)$ elements are truncated. FIG. 22 illustrates the range of alignments between the temporal waveform and the signal. The possible alignment ranges for $\tau \in \{-N+2, \ldots, 1, \ldots, L\}$ of a waveform g of length N to the L-length signal x. $T_\tau$ is a L by N matrix with a single 1 in each column. Let $T_\tau^*$ denote the adjoint of this operator such that $\langle x, T_\tau g \rangle = \langle T_\tau^* x, g \rangle$. The adjoint selects an N-length window of time-series starting at time $\tau$, and $T_\tau^* = T_\tau^T$.

The best lag in terms of least squares can be found as:

$$\arg\min_\tau \|x - T_\tau g\|_2. \quad (48)$$

Squaring and expanding the norm yields:

$$\|x - T_\tau g\|_2^2 = \langle x - T_\tau g, x - T_\tau g \rangle \quad (49)$$
$$= \langle x, x \rangle + \langle T_\tau g, T_\tau g \rangle - 2 \langle x, T_\tau g \rangle. \quad (50)$$

Since the first term is constant and the third term has higher weighting than the second term, the solution to Equation (48) is equivalent to the solution to $\arg\max_\tau \langle x, T_\tau g \rangle$. This is useful since $\langle x, T_\tau g \rangle = (x*g)(1-\tau) = \sum_n x_n g_{n-\tau+1}$ where $*$ denotes the cross-correlation (e.g., convolution with the time-reversed filter) which can be computed across all lags using the fast Fourier transform.

Windowed Tensor Representation. Given a set of timings for all the trials $\{\tau_i\}_{i=1}^n$, let $\tilde{\mathcal{X}} = \{\tilde{\mathcal{X}}_i\}_{i=1}^n$ denote the set of matrices corresponding to the realigned potentials, $\tilde{\mathcal{X}}_i = T_{\tau_i}^* X_i$, $i=1, \ldots, n$. This set of windows can also be considered a tensor $\tilde{\mathcal{X}}$. The approximation of this tensor is denoted $\hat{\tilde{\mathcal{X}}}$.

First Model. Consider a model characterized by a fixed spatial vector $w \in \mathbb{R}^{M \times 1}$, a fixed temporal waveform $g \in \mathbb{R}^{N \times 1}$, $N \leq L$, a variable temporal alignment $\tau^* \in \mathbb{Z}$, and a variable scalar amplitude $\alpha^*$. For a set of n trials this model has $2n+N-1+M$ free parameters. The single-trial approximation is given by $\hat{X} = \alpha^* T_{\tau^*} g \otimes w$. The approximation of the windowed tensor is a rank-1 CPD: $\tilde{X} = \overline{\alpha} \otimes g \otimes w$, where $\overline{\alpha}$ is the vector of amplitudes across the trials. The analysis for this model comprises a static spatial projection of the spatiotemporal window $u = \sum_{m=1}^{M} w_m x_m = w^T X$, followed by finding the alignment that maximizes the norm of the coefficient. The temporal alignment $\tau^*$ is found via:

$$\tau^* = \text{argmax}_\tau |\langle u, T_\tau g \rangle|, \quad (51)$$

and the amplitude $\alpha^*$ is found via:

$$\alpha^* = |\langle u, T_{\tau^*} g \rangle|. \quad (52)$$

Second Model. Consider a model similar to the first model but characterized by a fixed set of D linearly independent temporal waveforms $G = [g_1, g_2, \ldots, g_D] \in \mathbb{R}^{N \times D}$, $N \leq L$, which forms a subspace for the temporal waveform. The model is still characterized by a variable temporal alignment $\tau^* \in \mathbb{Z}$, but now a variable vector of subspace coefficients $a^* = [\alpha^*_1, \ldots, \alpha^*_D]^T \in \mathbb{R}^{D \times 1}$ is used. For a set of n trials, this model has $n + n \cdot D + N \cdot D - D^2 + M$ free parameters. The single-trial approximation is given by $\hat{X} = T_{\tau^*} G a^* \otimes w$. The approximation of the windowed tensor is rank-(D,D,1) block term decomposition: $\tilde{X} = AG \otimes w$, where $A = [a_1, a_2, \ldots, a_n]$. The analysis of this model uses the pseudo-inverse of $T_\tau G$. Let B be a matrix with linearly independent columns then $B^\dagger = (B^T B)^{-1} B^T \in \mathbb{R}^{D \times N}$ is its pseudo-inverse. Again, the alignment that maximizes the norm of the subspace coefficient vector, and minimizes the reconstruction cost, is found via:

$$\tau^* = \text{argmax}_\tau \|(T_\tau G)^\dagger u\|_2, \text{ and} \quad (53)$$

$$a^* = (T_{\tau^*} G)^\dagger u. \quad (54)$$

Spatial Covariance-based Models. Models with fixed spatial covariance can be utilized, with the temporal waveform allowed to vary per trial. In terms of neurophysiology, a model with a single fixed spatial factor corresponds to a point source. It assumes the relevant portion of the neural response is a single point source corresponding to a specific neural population. The product with the spatial vector acts as a simple weighted average, reducing the signal to a univariate time series. In general, the spatial factors project the signal to a low dimensional subspace. In terms of synthesis the spatial factors form the subspace of approximations of the spatiotemporal waveform.

Single Source. Consider a model characterized only by the fixed spatial waveform $w \in \mathbb{R}^{M \times 1}$ and variable temporal waveform $u^* = [u^*_1, \ldots, u^*_L]^T \in \mathbb{R}^{L \times 1}$. For a set of n trials, this model has $n \cdot L + M - 1$ free parameters. The single-trial approximation is given by $\hat{X} = u^* \otimes w$. The approximation of the full tensor is a rank-1 Tucker-1 decomposition: $\hat{\mathcal{X}} = U \otimes w$, where $U = [u_1, u_2, \ldots, u_n]$. The analysis for this model comprises a static spatial projection of the spatiotemporal window $u^* = \sum_{m=1}^{M} w_m x_m = w^T X$.

Spatial Subspace. Consider a model similar to the previous model but characterized by a fixed set of E linearly independent spatial vectors $W = [w_1, w_2, \ldots, w_E] \in \mathbb{R}^{M \times E}$, which form a subspace for the spatial pattern. The model is characterized by a multivariate time-series $U^* = [u^*_1, \ldots, u^*_E]^T \mathbb{R}^{L \times E}$. For a set of n trials, this model has $n \cdot L \cdot E + M \cdot E - E^2$ free parameters. The single-trial approximation is given by $\hat{\mathcal{X}} = U^* W^T$. The previous model is a special case of this model when E=1. The approximation of the full tensor is a rank-E Tucker-1 decomposition: $\hat{\mathcal{X}} = \mathcal{U} \times_3 W$, where $\mathcal{U}$ is the tensor representation of the set of multivariate time-series across all trials $\{U_1\}_{i=1}^n$. The analysis of this model is given by $U^* = W^\dagger X$.

Fitting the Spatiotemporal Models. Model fitting can be performed in an alternating process where the analysis equations for each model provide an estimate of the coefficients on a given trial, and the model can be updated to best explain, in terms of minimizing the mean-squared error, the data given these coefficients. For the temporal factors, only non-discriminative model fitting is used, but the model can be fit using only trials of one condition. This partial supervisory information does not consider trials of other conditions. For the spatial factors, discriminative models based on the spatial covariance can be considered. Overall, the spatial and temporal factors are alternatively updated. For the models allowing temporal shift, only the windowed portion of the signal, corresponding to the alignment of the waveform on a particular trial, is used to update the model. For the first two models discussed, this window can be found after the signal has been projected to a single channel via the spatial factor. The window alignment can be selected for each given the current model. Recall that $\breve{\mathcal{X}} = \{\breve{\mathcal{X}}_i\}_{i=1}^n$ denotes the set of matrices corresponding to the realigned potentials, $\breve{\mathcal{X}}_i = T_{\tau_i}$, $i = 1, \ldots, n$ and as a tensor is denoted $\breve{\mathcal{X}}$.

Updating the Temporal Factors. After alignment each spatiotemporal matrix is multiplied by the spatial factors W and the resulting products are concatenated across trials into another matrix $U = [\breve{\mathcal{X}}_1 W, \breve{\mathcal{X}}_2 W, \ldots, \breve{\mathcal{X}}_n W] = \breve{\mathcal{X}}^{(2)} W$, where $\breve{\mathcal{X}}^{(1)}$ is the mode-2 unfolding of $\breve{\mathcal{X}}$. The waveforms are updated to be the D singular vectors corresponding to the D largest singular values of this matrix, which is the solution to the following optimization comprising the ratio of the determinants:

$$G = \text{argmax}_V \frac{|V^T U U^T V|}{|V^T V|}. \quad (55)$$

Choosing the updated filters in this way minimizes the mean-squared error of the model, as the singular value decomposition is the best approximation of matrix.

Updating the Spatial Factors. The spatial projection is also updated from the covariance of the set of aligned windows $\breve{\mathcal{X}}$. The spatial covariance, without removing the mean, is computed as $R_0 = \sum_i^n 1/n \breve{\mathcal{X}}_i^T \breve{\mathcal{X}}_i = 1/n \breve{\mathcal{X}}^{(3)} \breve{\mathcal{X}}^{(3)T}$, where $\breve{\mathcal{X}}^{(3)}$ is the mode-3 unfolding of $\breve{\mathcal{X}}$. For discrimination, we consider having an auxiliary matrix $R_1$, which is the spatial covariance during background or different conditions. This can be used to find projections which maximize a ratio of the variance between the conditions; replacing this auxiliary matrix with an identity matrix will simply minimize the error. The spatial projection is then found as a solution that maximizes the following ratio of matrix determinants:

$$W = \text{argmax}_V \frac{|V^T R_0^T V|}{|V^T R_1 V|}. \quad (56)$$

The solution to this optimization is chosen from the solutions $\{(\lambda_j, v_j)\}$ for the generalized eigenvalue problem $R_0 v_j = \lambda_j R_1 v_j$. The columns of W should be chosen as the E eigenvectors $v_j$ corresponding to the E largest generalized eigenvalues $\lambda_j$. In pattern recognition, this is known as the Fukunaga-Koontz transform, and in the EEG analysis it can be used for extracting features for motor imagery classification and is referred to as common spatial patterns (CSP).

Figure 23:
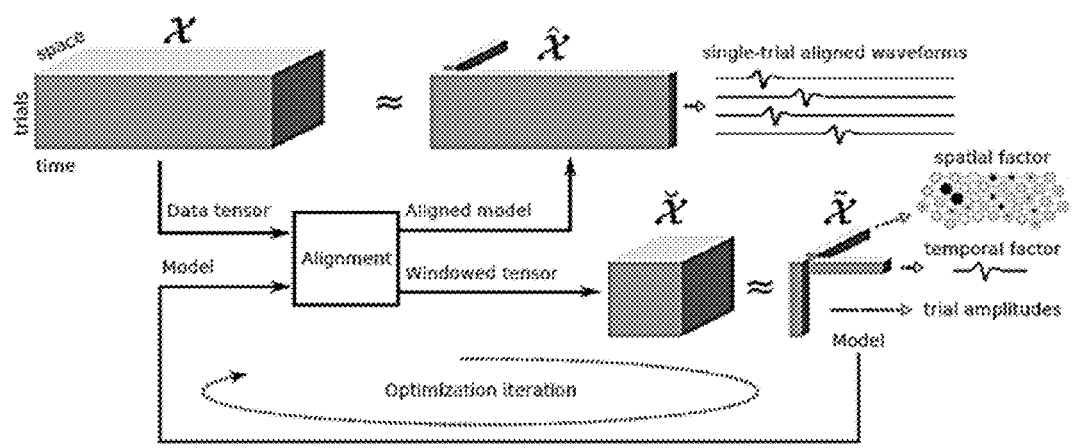
FIG. 23 is an example of an optimization process in accordance with various embodiments of the present disclosure.

An Alternating Optimization Algorithm. Given the updated model, the spatial factors and any trial-varying coefficients, alignment and amplitude coefficients, are re-estimated. One iteration cycle of the full optimization computes the following steps:

1. Alignment update via Equations (51) and (53)—Input: $\mathcal{X}$, W, G, and Output: $\tilde{\mathcal{X}}$ 2. Temporal factor update via Equations (55)—Input: $\tilde{\mathcal{X}}$, W, D, and Output: G 3. Spatial factor update via Equation (56)—Input: $\tilde{\mathcal{X}}$, $R_1$, E, and Output: W Ideally, after multiple iterations the factors and coefficients will lead to convergence. In practice, this may not always be the case, and the process can be stopped after a fixed number of iterations. Referring to FIG. 23, shown is a diagram of an example of the optimization process comprising temporal alignment and tensor decomposition. Here the model of the aligned tensor is a canonical polyadic decomposition (CPD). Although, the windows are approximated using the CPD, the aligned model cannot be considered a CPD, instead it is a "Tucker-1" model with specific structure.

Model Selection. The performance trade-off between different model structures or model orders can be quantitatively assessed using a model selection criterion. Depending on the sizes of the waveform and the fit of each model, a model that allows shifts may be more or less efficient than a fixed alignment model. The most straightforward approach to select a model is to test its ability to predict novel data. This cross-validation approach simply uses multiple divisions of the dataset into training and validation sets. A simple model may perform poorly; whereas, an overly complex model that over-fits (e.g., a model that is tuned to the particulars of the noise in the training samples not the general structure) may also perform poorly on novel data. However, with complex models that already involve alternative optimizations this approach utilizes excessive computation. In other implementations, model selection criteria balance the model fit and complexity: as fitting error decreases with model complexity, a penalty for the degrees of freedom in the model. The Bayesian Information Criterion (BIC) is a consistent way to compare tensor models of different structures. Whereas Akaike Information Criterion can be used, it is only applicable to nested models (e.g., models built by adding parameters to parent models), and should not be used to select among non-nested models. BIC is formulated in terms of the log-likelihood, but for a signal plus noise model where the noise is assumed to be i.i.d. zero-mean and Gaussian distributed only the mean-squared error (MSE) of Equation 47 is needed. In this case, the following optimization problem selects the optimal model from a set of models $\mathcal{M}$:

$$\underset{\hat{\mathcal{X}} \in \mathcal{M}}{\arg\min} BIC(\hat{\mathcal{X}}) = M \ln\left(\frac{1}{M}\|\mathcal{X} - \hat{\mathcal{X}}\|_F^2\right) + k(\hat{\mathcal{X}})\ln(M) + C, \quad (57)$$

where $\mathcal{X}$ denotes a tensor with M elements, $\hat{\mathcal{X}}$ is the tensor model with $k(\hat{\mathcal{X}})$ degrees of freedom, and C is a constant that is a function of the noise variance and is independent of $\hat{\mathcal{X}}$.

Single-Trial Classification. To quantify the information captured by the model we investigate single-trial classification. We specifically consider the binary case for two classes of conditions. In the classification setting, the dataset is divided into the training and testing set and only the training set is used to fit the factors of the spatiotemporal model. We used two model fitting paradigms:

1. Partially supervised modeling: model is trained using only one condition

2. Supervised modeling: spatial factors are trained to be discriminative between conditions, but temporal factors are trained using only one condition The learned spatial and temporal factors constrain the waveform of the evoked potential. The amplitude, power, and/or alignment of this waveform is extracted on all trials, both training and testing, and used as features for classification. Standard classifiers, such as nearest-neighbor, linear discriminant analysis, or support vector machines can then employ the training set examples of these trial-varying parameters to form classification decision boundaries.

Reward Representation in Striatal LFPs During a Reach Task. Using data from a reward expectation experiments, we test the method's ability to model the neural response during two different stimulus conditions (e.g., presentation of rewarding and non-rewarding objects) and discriminate between them.

Data Collection and Experimental Setup. A marmoset monkey, *Callithrix jacchus*, was trained to sit and reach for food items. After training, the subject underwent a craniotomy surgery while under isoflurane anesthesia. All surgical and animal care procedures were consistent with the National Research Council Guide for the Care and Use of Laboratory Animals. A 16-channel tungsten microelectrode array (Tucker-Davis Technologies, Alachua, Fla.) was implanted in both the motor cortex (M1) and the striatum, targeting the nucleus accumbens of the ventral striatum. Local field potentials were processed by a RZ2 processor (Tucker-Davis Technologies, Alachua, Fla.) and filtered through a cascaded 1 Hz high-pass and 500 Hz low-pass first order biquad filters with 12 dB/octave roll-off and stored with 1017.3 Hz sampling rate. The common average reference was used to improve the signal to noise ratio. Only the signals from the array in the stratium were used in the analysis. The local field potentials (LFPs) were digitally filtered with a 3rd-order Butterworth high-pass filter (cutoff of 0.1 Hz) to remove low-frequency content. To maintain zero-phase, filtering was done both forward and backward resulting in a 6th-order high-pass filter. The data was further filtered with a Gaussian window with length of 40 samples and standard deviation of 8 samples. This corresponds to a low-pass filter with a cutoff of 33.8 Hz.

The experiment comprised revealing objects held behind doors within reach and directly in front of the restrained subject. As the objects were either a mushroom piece, a rewarding object for which the subject would reach and eat, or a wooden bead, a non-rewarding target for which the subject would not reach, the set-up comprised both a go-no/go task coupled with a rewarding/non-rewarding task. Each trial began with the subject resting its hand on a touch pad for a random hold period. At the end of the hold period, the door would open revealing either a mushroom piece or a plastic bead in one of four boxed locations: top, bottom, left, and right. Once the door opens the subject sees the object and makes a decision to reach or not. Here, a dataset for a single session was analyzed. There were 83 trials in total; 40 trials with mushrooms and 43 trials with beads. The number of trials that an object was behind a certain door was pseudo-random with 20, 21, 23, and 19 trials for each door respectively. Only the data in the 1 second window when the door opens was used.

Model Design. For this experiment, strong modulation for the non-rewarding tasks was anticipated. Because of this, the model of the temporal waveforms was trained using only the non-rewarding trial. Based on this partial supervision, the model should be well-suited to explain the non-rewarding trials. In other implementations, discriminative spatial projections trained using both conditions, rewarding and non-rewarding, were compared. Three different spatiotemporal models were estimated using the training set. The first model used a single temporal waveform and spatial factor, a rank-1 model, and it was trained using partial supervision. The second model was also rank-1 but the spatial factor is discriminatively trained. The third model used a subspace of 4 temporal waveforms to approximate each response, and the model was trained using only the non-rewarding condition trials.

Figure 24A:
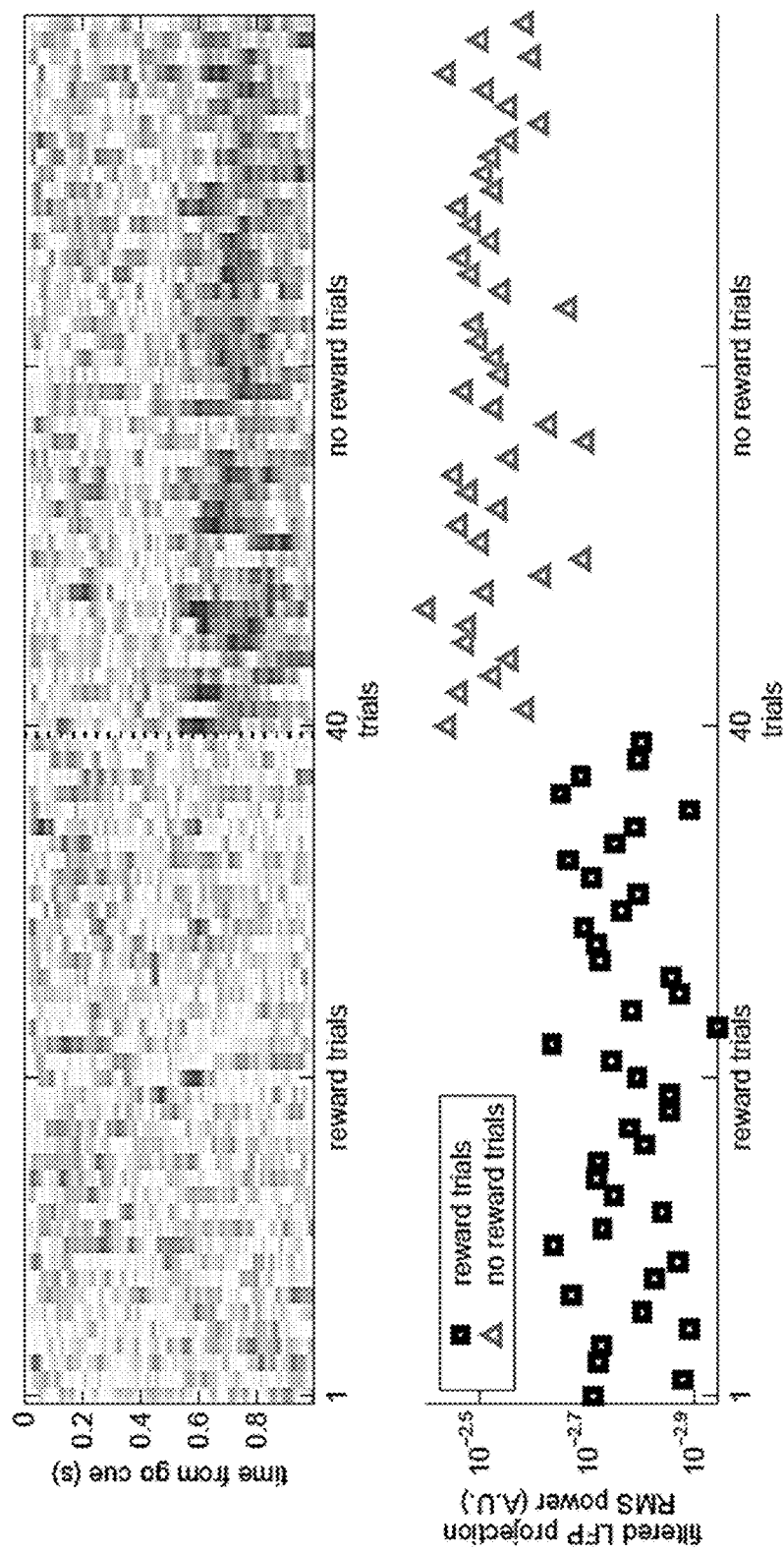
FIGS. 24A-24B, 26A-26C, 33 are examples of LFPs in accordance with various embodiments of the present disclosure.
Figure 24B:
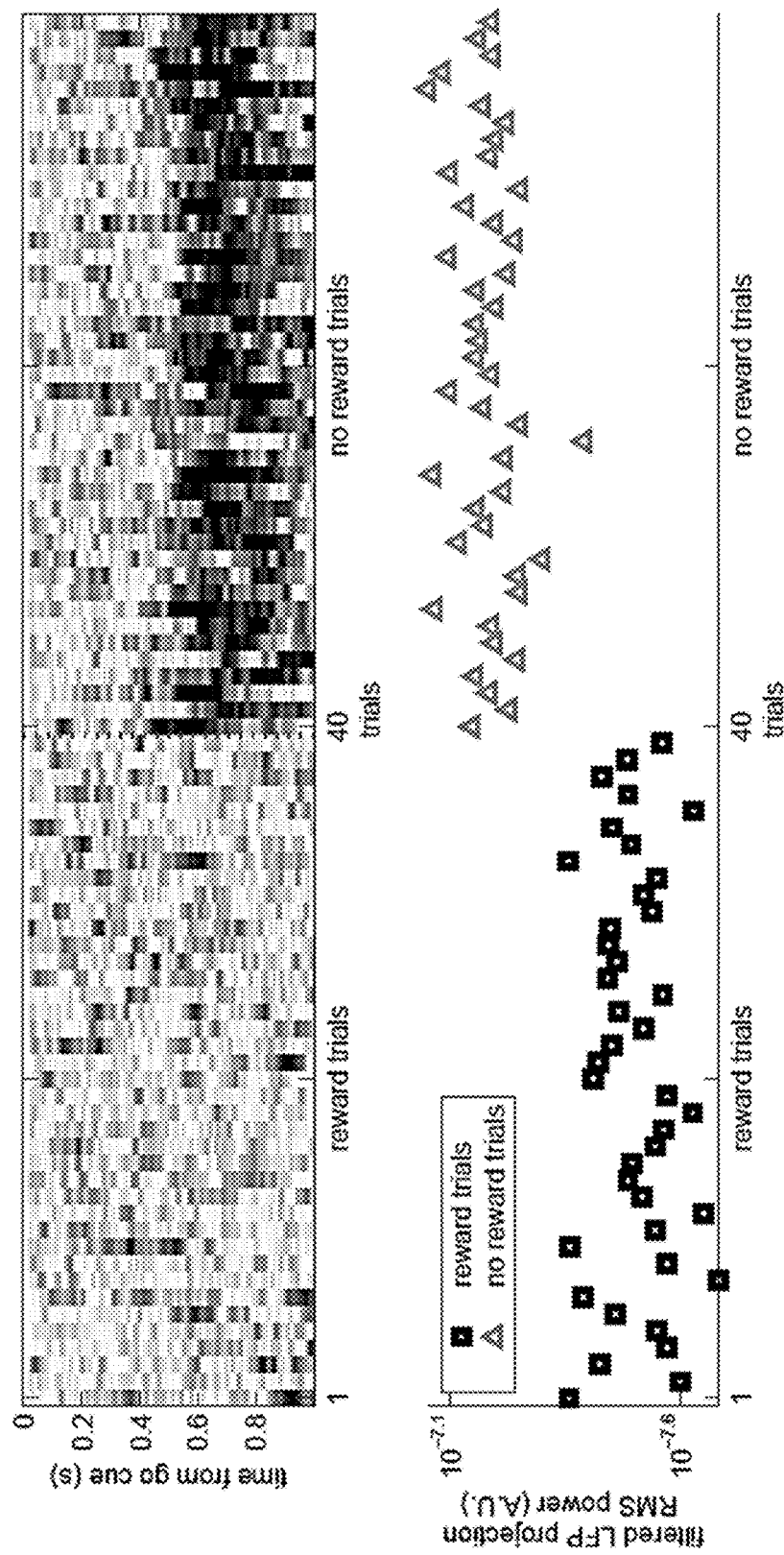

Results. The processing of LFPs using the spatial and temporal factors in spatiotemporal models is illustrated. First is a comparison of the temporal aspects of the LFP components after spatial projections, one trained in the semi-supervised manner and one trained discriminately. To quantify the differential variation between the two conditions, the root-mean-squared (RMS) power of the resulting temporal across all trials was computed. The results are shown in FIGS. 24A and 24B. LFPs are projected to a one-dimensional time series and the root-mean-squared, RMS, power is computed for each trial. FIG. 24A shows spatial filter that explain the maximum energy during the non-rewarding trials, e.g., first eigenvector of covariance matrix. FIG. 24B shows spatial filter that discriminates the two reward conditions, e.g., first generalized eigenvector.

Figure 25A:
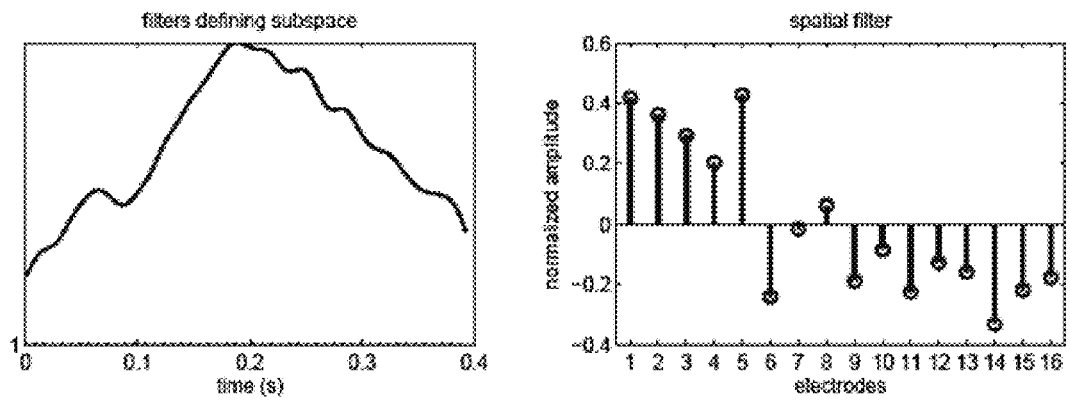
Figure 25B:
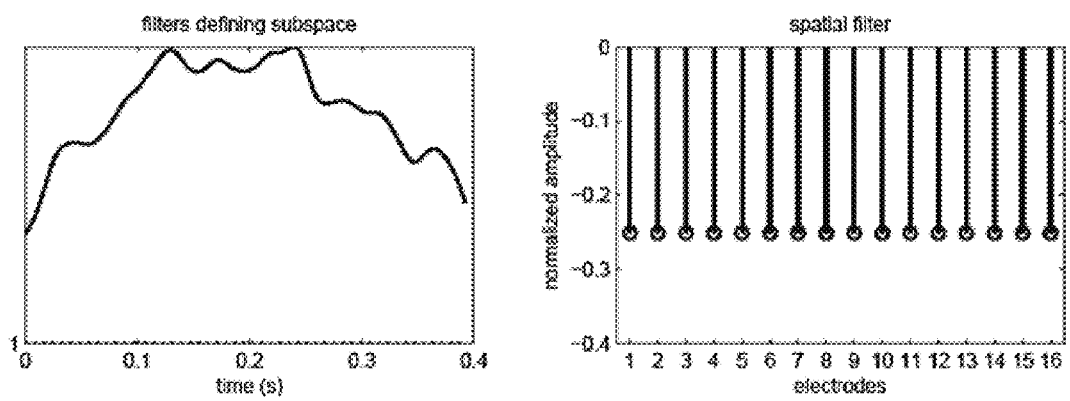
Figure 25C:
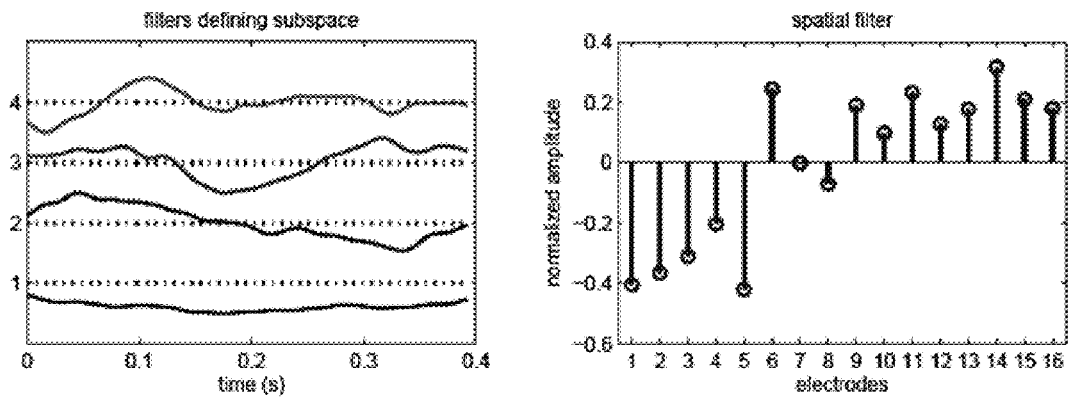

The temporal and spatial factors for the 3 spatiotemporal models were estimated using only the training set. The resulting factors are shown in FIGS. 25A through 25C, illustrating the spatial and temporal filters of the spatiotemporal decompositions with different ranks objectives. FIG. 25A shows a model trained to explain the maximum energy during the non-rewarding trials. FIG. 25B shows a model trained to be spatially discriminative; whereas the spatial filter is the projection that discriminates the conditions in terms of variance. In FIG. 25C, a model uses a temporal subspace to explain the maximum energy during the non-rewarding trials. A set of temporal filters were trained to span the subspace with the maximum energy during the non-rewarding trials.

Figure 26A:
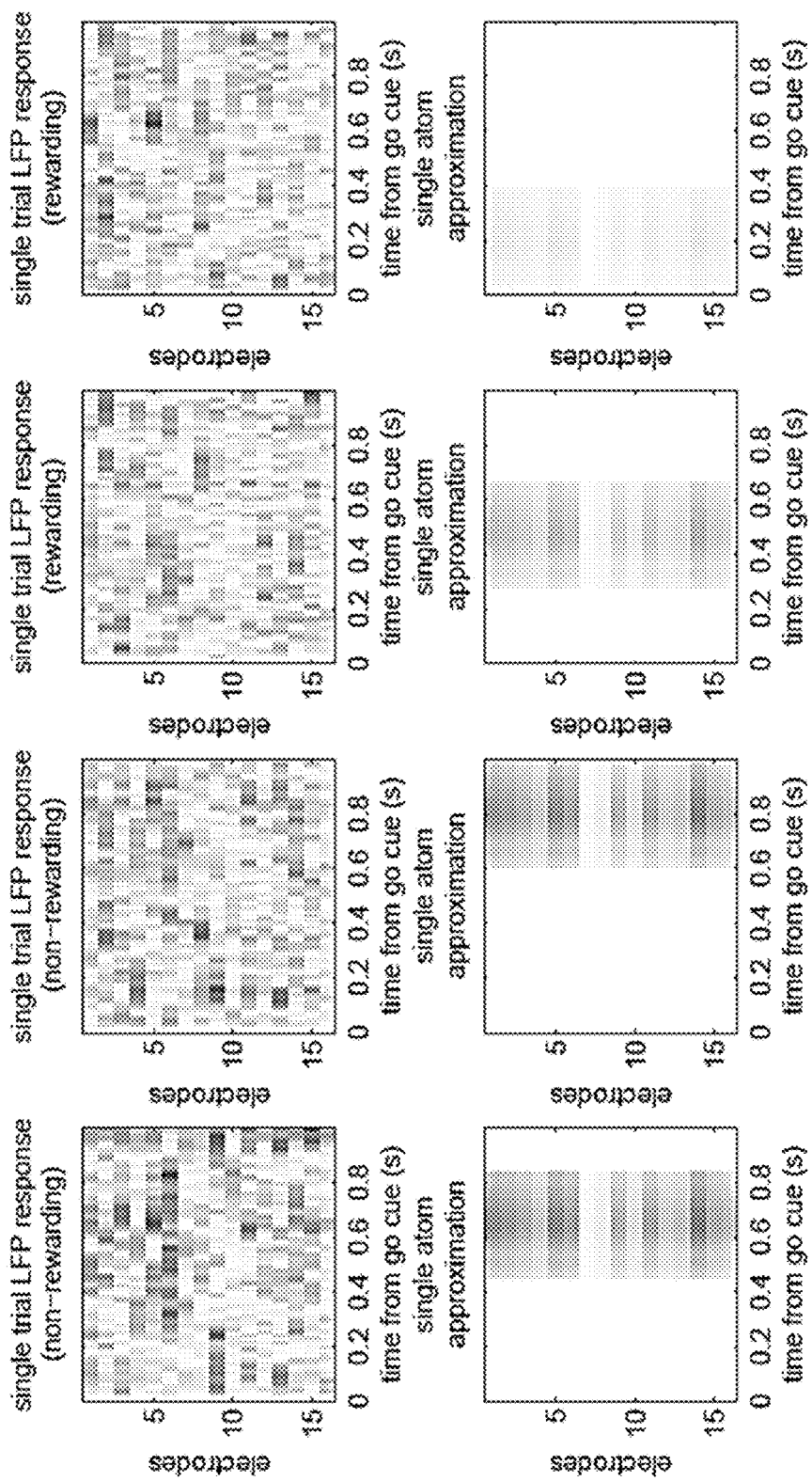
Figure 26B:
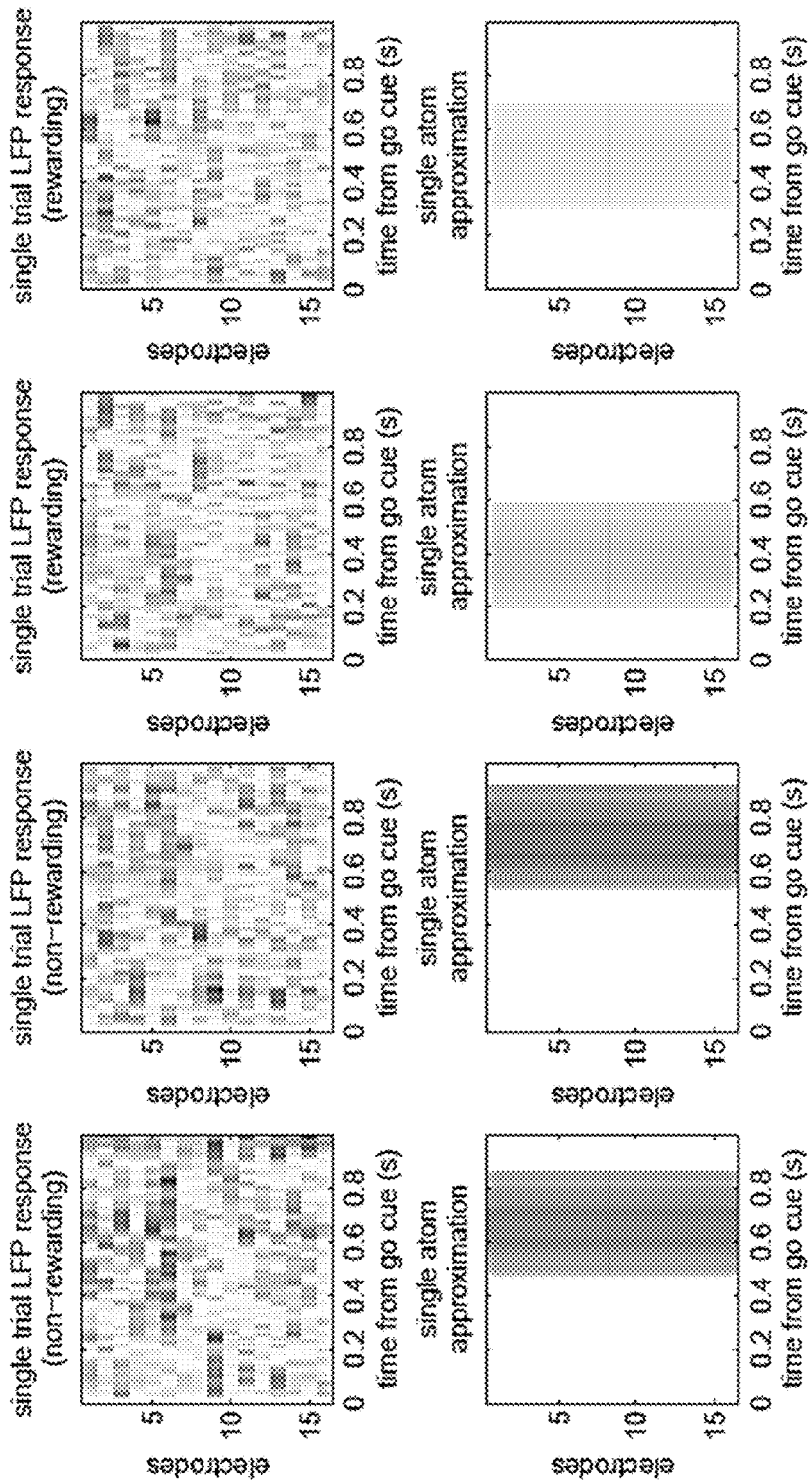
Figure 26C:
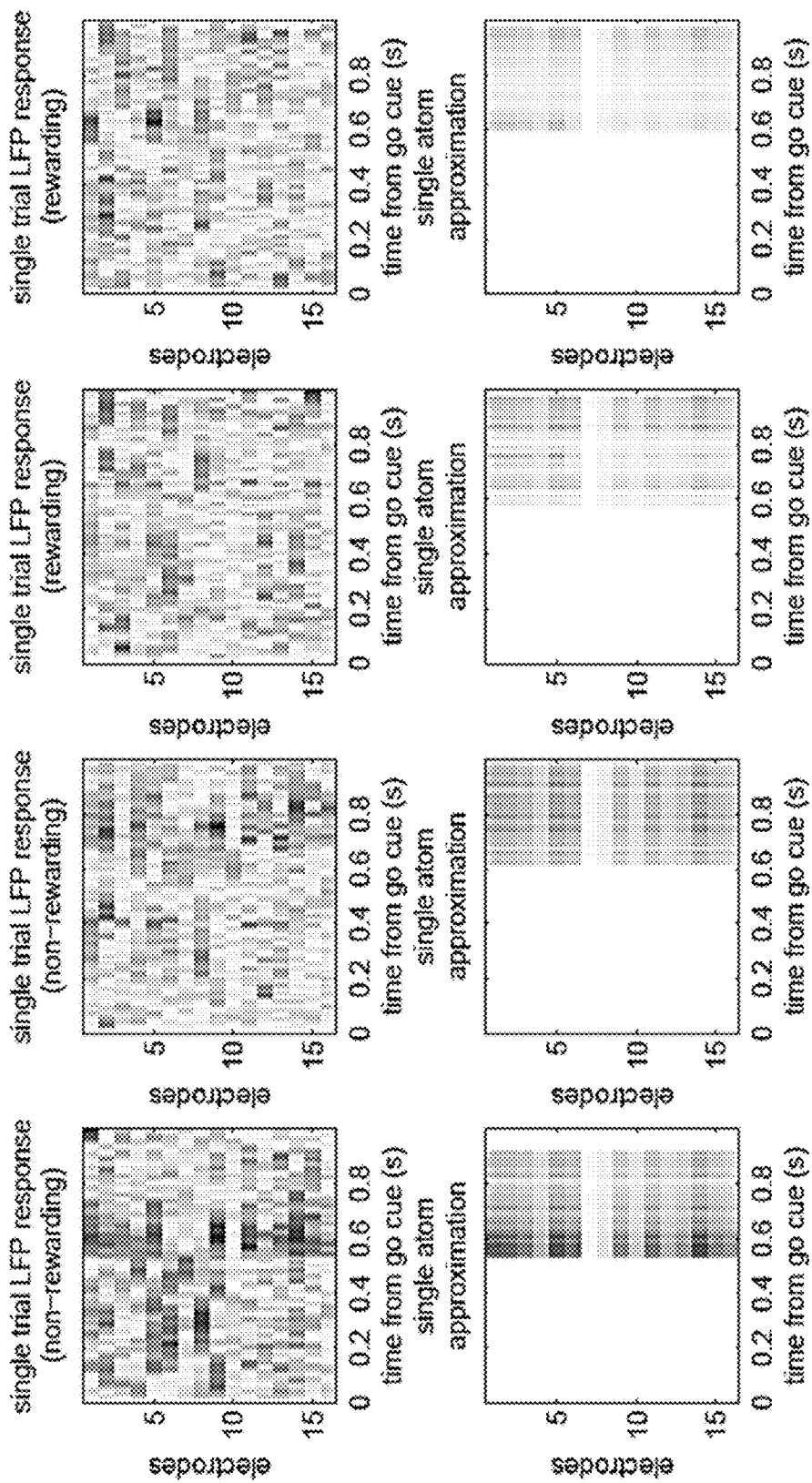
Figure 27A:
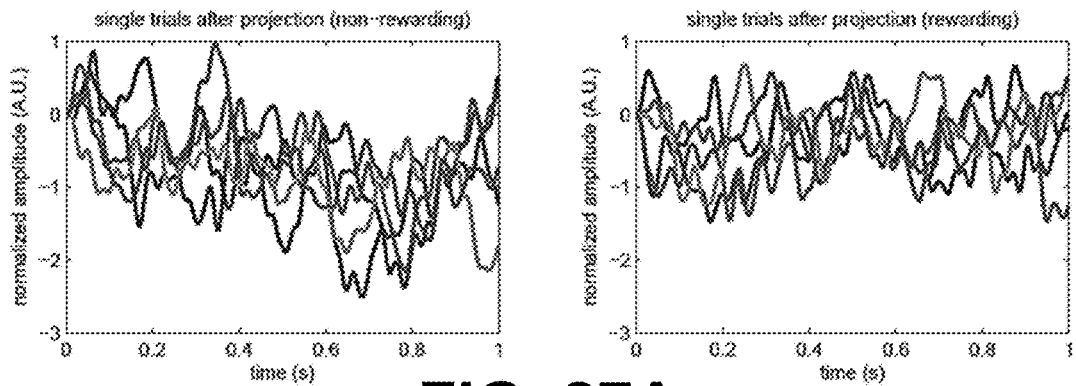
FIGS. 27A through 27D are examples of processing stages in accordance with various embodiments of the present disclosure.
Figure 27B:
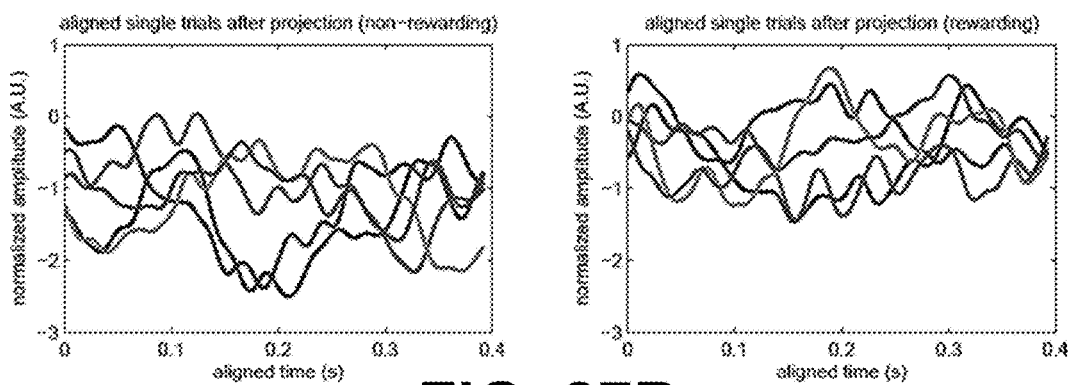
Figure 27C:
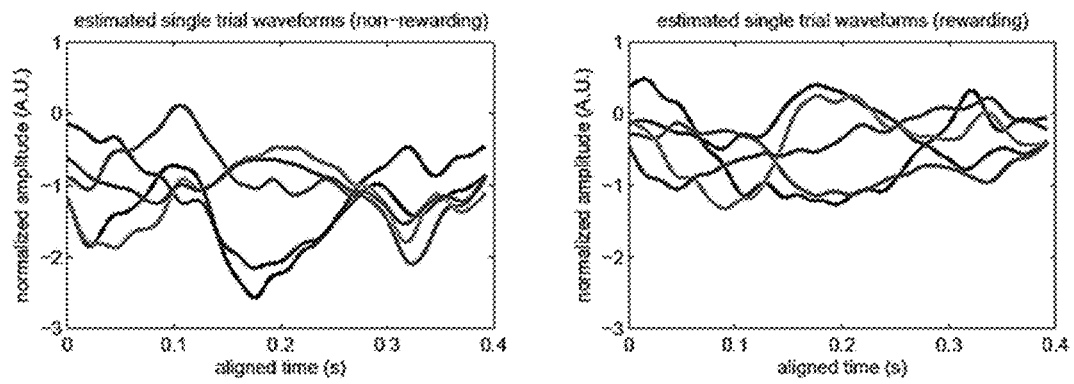
Figure 27D:
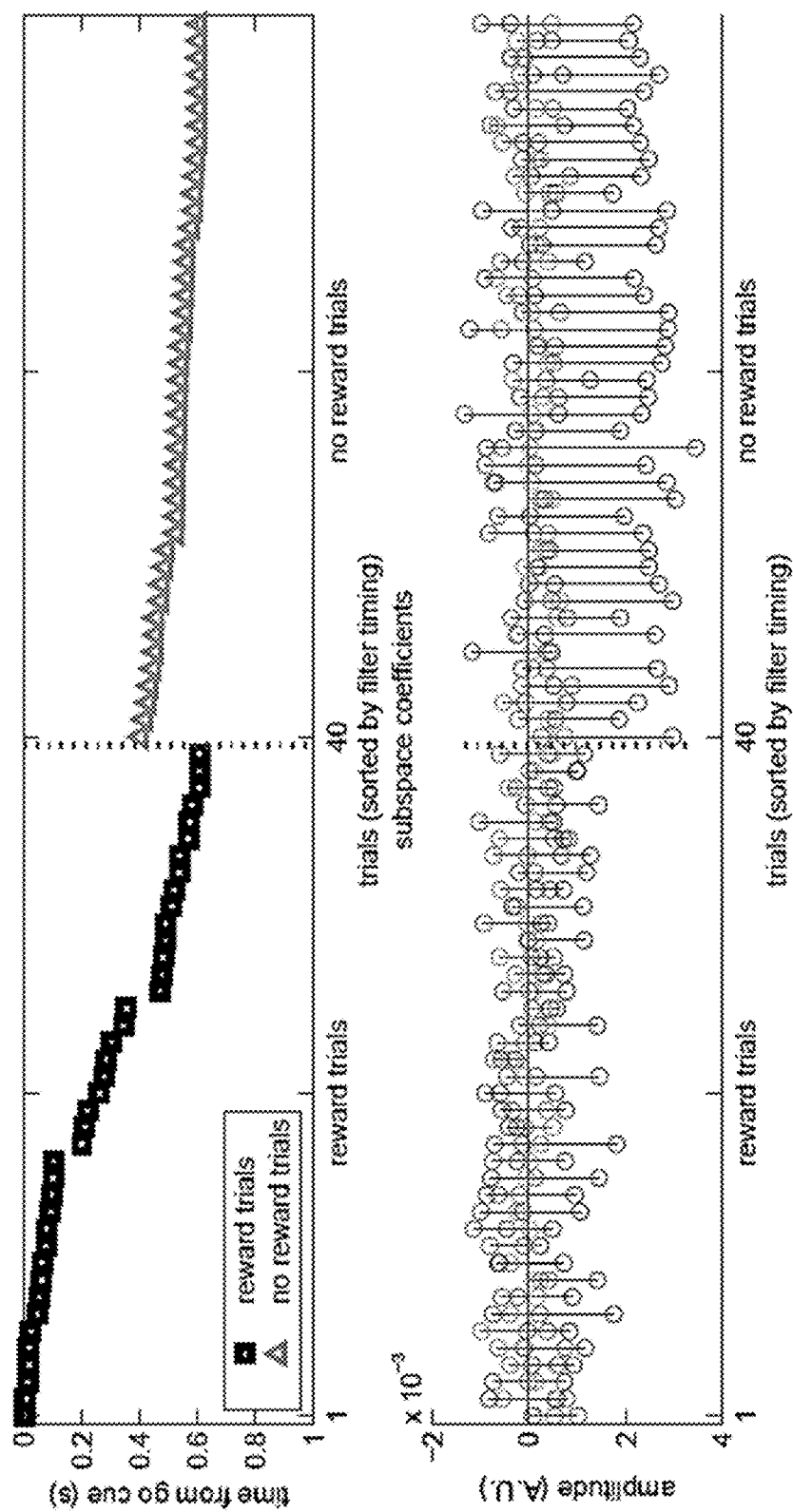

Single-atom approximations across select trials for each model are shown in FIGS. 26A through 26C. Single trials multichannel LFPs and rank-1, single-atom model approximations of four example trials, two from each reward condition are illustrated. FIG. 26A shows a model trained to explain the maximum energy during the non-rewarding trials. FIG. 26B shows a model trained to be spatially discriminative. In FIG. 26C, a model uses a temporal subspace to explain the maximum energy during the non-rewarding trials. The non-rewarding trials have larger amplitude oscillations, and more consistent timing. This fact can also be seen by examining the processing stages during the temporal subspace decomposition. FIGS. 27A through 27D illustrate the processing stages for the model using a temporal subspace. For each condition, 5 example trials are shown. FIG. 27A shows the one-dimensional signals after applying the spatial projection. FIG. 27B shows the windowed signal, where the timing is found by maximum energy in the subspace. FIG. 27C shows an approximation of the windowed signal using the four filters in the subspace. FIG. 27D shows an atomic representation, timing and amplitude coefficients, across all trials, separated by reward condition. The aligned windows have a more consistent waveform shape than the entire trials.

The consistency in waveform magnitude and alignment under the non-rewarding conditions can be seen by looking at the distribution of these features on individual trials. FIGS. 28A through 28C show timing and magnitude scatter plots for atomic decompositions of test set examples and normal distributions fitted to the training set. FIG. 28A illustrates a model trained to explain the maximum energy during the non-rewarding trials. FIG. 28B illustrates a model trained to be spatially discriminative. In FIG. 28C, a model uses a temporal subspace to explain the maximum energy during the non-rewarding trials. The concentrated points in the scatter plot indicate a clear mode in the temporal alignment of the waveform under the non-rewarding condition. Whereas in the rewarding condition the temporal alignment of the waveform is inconsistent, with almost uniform distribution of frame alignment. The same pattern of differential amplitude of the two conditions is also evident; this was seen using only a spatial projection in FIGS. 24A and 24B.

The classification performance was tested when using the models' trial-varying parameters as features. Specifically, 4 sets of 3 features were compared:
1. Time alignment of the temporal waveform
2. Scalar magnitude of temporal waveform (log-transformed)
3. Time-series RMS power after spatial projection (log-transformed)
4. A combination of (1) and (2)

Figure 29A:
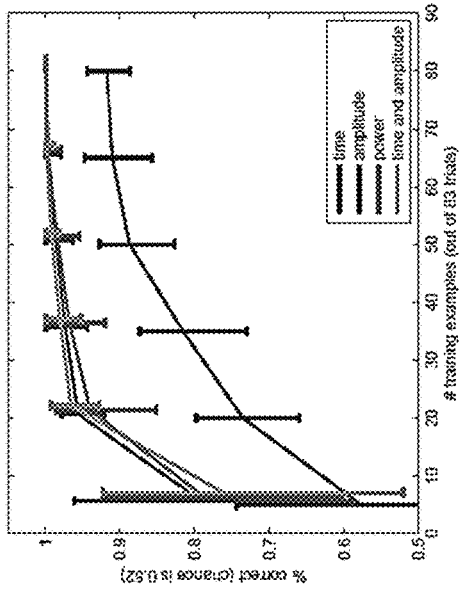
Figure 29B:
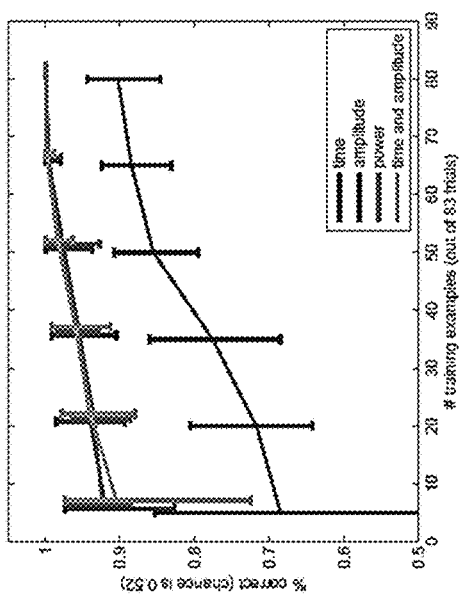
Figure 29C:
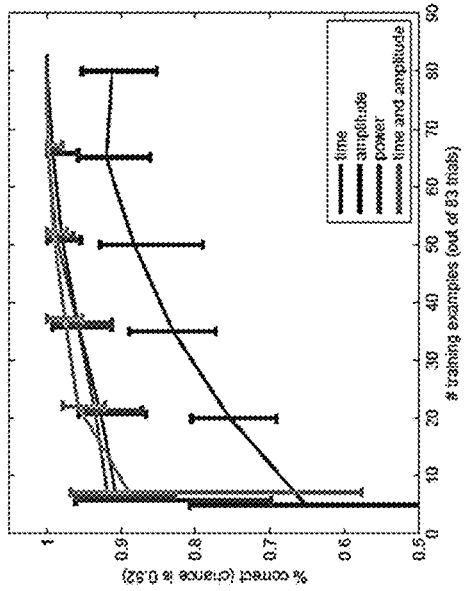
Figure 30A:
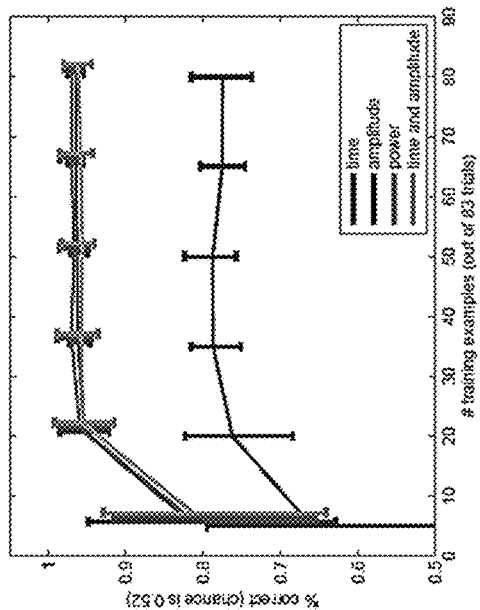
Figure 30B:
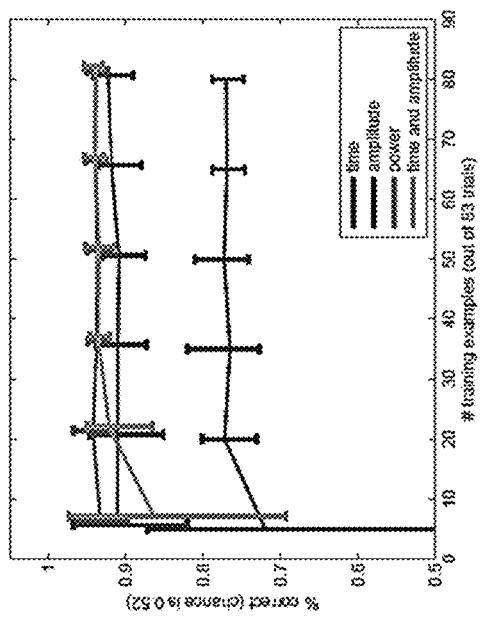
Figure 30C:
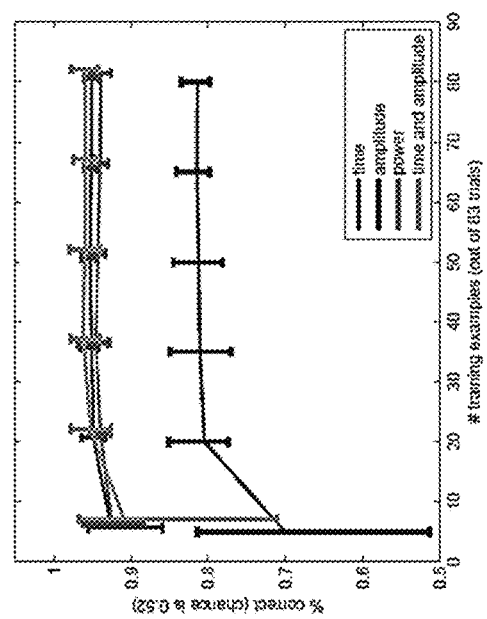

For classifiers, both non-parametric and parametric classifiers were used: first nearest neighbor (1NN) and linear discriminant analysis (LDA), respectively. For each, the number of training examples used for fitting the model and training the classifier were adjusted, and performed 20 Monte Carlo divisions the samples into training and testing sets. FIGS. 29A through 29C show nearest-neighbor classifier performance using different features while varying training set size and FIGS. 30A through 30C show linear discriminant analysis classification performance using different features while varying training set size. The average, 5th percentile, and 95th percentile across these 20 Monte Carlo divisions were indicated by the error bars in FIGS. 29A-29C and 30A-30C for the 1NN and LDA classifier, respectively. FIG. 29A shows a model trained to explain the maximum energy during the non-rewarding trials. FIG. 29B shows a model trained to be spatially discriminative. In FIG. 29C, a model uses a temporal subspace to explain the maximum energy during the non-rewarding trials. FIG. 30A shows a model trained to explain the maximum energy during the non-rewarding trials. FIG. 30B shows a model trained to be spatially discriminative. In FIG. 30C, a model uses a temporal subspace to explain the maximum energy during the non-rewarding trials. The 1NN classifier shows much higher performance, which increases with the number of training examples. A minimum of 20 training examples is needed for consistent performance.

Given the classifier type and training set size, we compare the performance using the different features and models. The Table of FIG. 31 shows classification performance for decoding object type across features and models, with the average and standard deviation in the classification accuracy (% correct) using the 1NN classifier and a training size of 20 is reported. Entries indicate the mean and standard deviation of percent correct computed across 20 Monte Carlo divisions of the trials into 20 for testing and 63 for testing. Chance rate was 52%. Results used a nearest-neighbor classifier. Model A was trained to explain the maximum energy during the non-rewarding trials. Model B was trained to be spatially discriminative. Model C used a temporal subspace to explain the maximum energy during the non-rewarding trials. Across the models, using both time and amplitude as features performs the best. Across all features except the time information, the model with a discriminative spatial performs the best. Using only the timing information, the model with a temporal subspace achieves higher performance. Throughout the models, using only the timing did not perform as well, but still was significantly above chance. For higher training set samples, as shown in FIGS. 29A through 29C, using the timing extracted from the subspace model as the sole feature achieves a classification rate of above 90%. This may mean that the timing (delay) of the evoked potential may be better estimated using the subspace model versus a single waveform.

A method for applying spatiotemporal models of evoked potentials in LFPs to extract features useful for discriminating between two different conditions was applied. These methods are more computationally expensive than using the power of the signal, but beyond the classification rate improvement they are able to provide clearer insight into the single-trial evoked potentials, in terms of both the variability of the timing and of waveform shape. In particular, the timing information was found to be most informative when using the subspace model.

Reward Expectation in the Motor Cortex During an Observation Task. An experiment involving a variable reward task is analyzed. The motivation of using the shift-varying decompositions on this task is to identify any pattern in the timing of the evoked potential between rewarding and non-rewarding trials. In addition, for dataset both LFPs and action potential timings were collected, and any correspondence between the timing extracted from the LFP and the action potentials was investigated.

Data Collection. 96 channels of neural data were collected from a macaque monkey during a single day's recording. The spiking units were identified on the 96 channels. LFPs were collected on 32 electrodes implanted in M1. On this dataset, 8 of the LFP electrodes were excluded because of artifacts, which were associated with high impedance. The remaining 24 channel signal was high-pass filtered with cutoff of 4 Hz and notch filtered at 60, 120, 180, 240, and 300 Hz with a quality factor of 69. The data was further filtered with a Gaussian window with length of 40 samples and standard deviation of 8 samples. This corresponds to a low-pass filter with a cutoff of 66.4 Hz.

During the experiment, the subject manually performed right-handed center-out reaching tasks using a Kinarm exoskeleton (BKIN Technologies) in a two-dimensional plane, while the left arm was restrained with a cuff. Visual feedback was provided by cursors representing the position of the tip of the subject's middle finger and targets were displayed to the subject. Targets were 4-5 cm from the center target and the targets were 1 cm in diameter. The experiment consisted of watching the center target for 300 ms until the peripheral target appeared and center target disappeared. During certain sessions, the subject's reaches were only for a single target to the right of the center. In addition, reward variability was introduced: only a subset of successful trials would end in a liquid reward—the unsuccessful reach trials never resulted in reward. Both center and reach targets changed color during the hold period to indicate whether the trial outcome would be rewarding or non-rewarding. The subject could learn to associate this color cue with the expected reward outcome. Unsuccessful trials were repeated, so the subject was motivated to complete all trials. The presentation of the reward outcomes was randomized.

This task was further abstracted by automating the cursor movement to the right target at a speed of 1 cm/s, such that subject had to only observe the movement. Eye tracking was performed using an IR sensitive camera and trials were aborted if gaze was not maintained. During this modified task, the subjects right arm (the reaching arm) was locked in place by securing the Kinarm exoskeleton and the left arm was still secured in a cuff. Here, a dataset for a single session was analyzed. There were 289 trials in total; 145 rewarding trials and 144 non-rewarding trials. The LFPs in the 2 second window following reach target appearance, and spike data 2.5 seconds before and 3 seconds after this cue, were used.

Spatiotemporal Model. A single spatiotemporal model was estimated using two-thirds of the trials. FIG. 32 shows the spatiotemporal models trained during reward expectation. The model used a subspace of 4 temporal waveforms to approximate each non-rewarding trial and the spatial factor is discriminatively trained with the spatial covariance estimated during rewarding trials. The resulting filters corresponding to the temporal and spatial factors are shown in FIG. 32. A set of four temporal filters were trained to span the subspace with the maximum energy during the non-rewarding trials. A single spatial filter was trained to be discriminative using the spatial covariance under both conditions.

Figure 33:
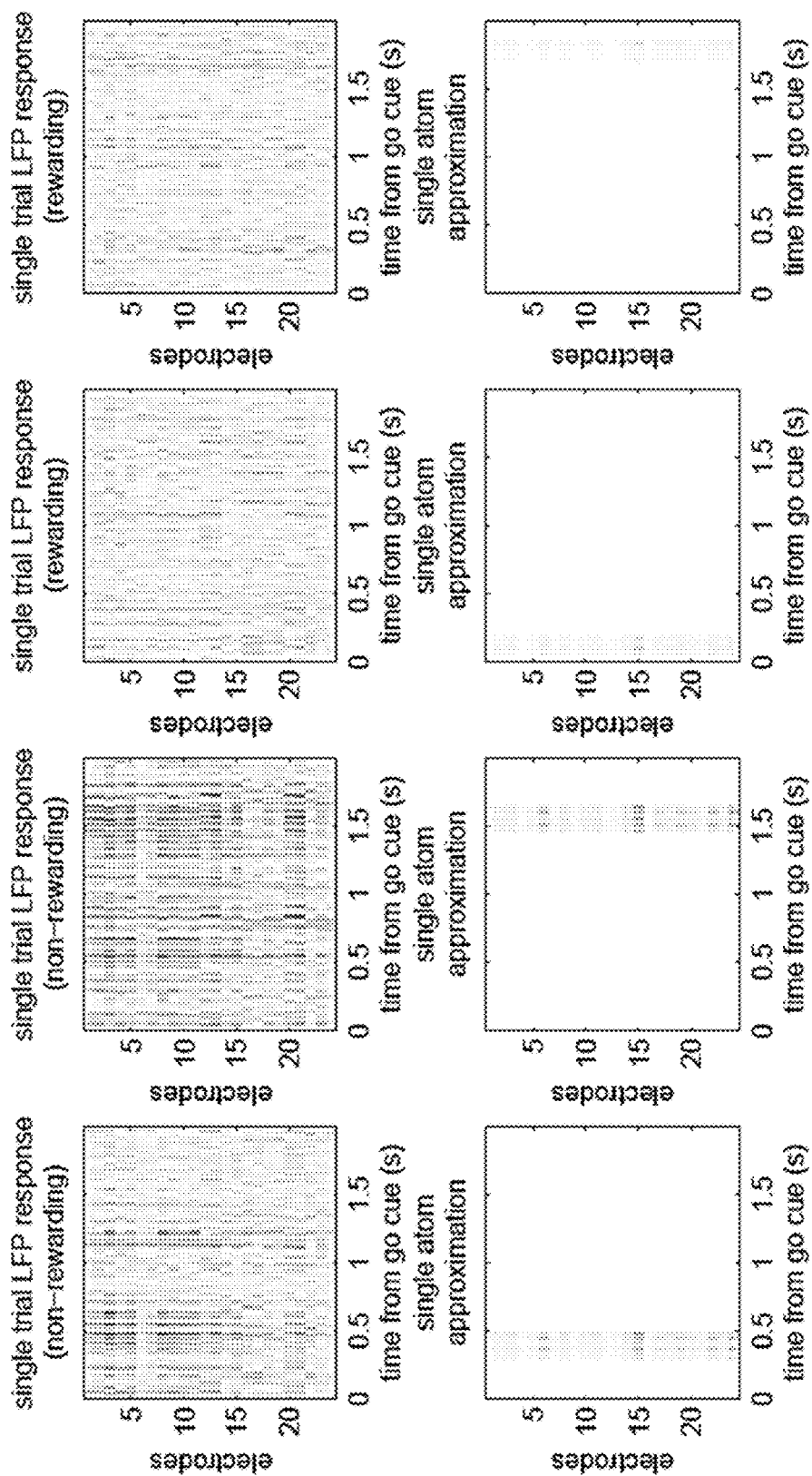
Figure 34:
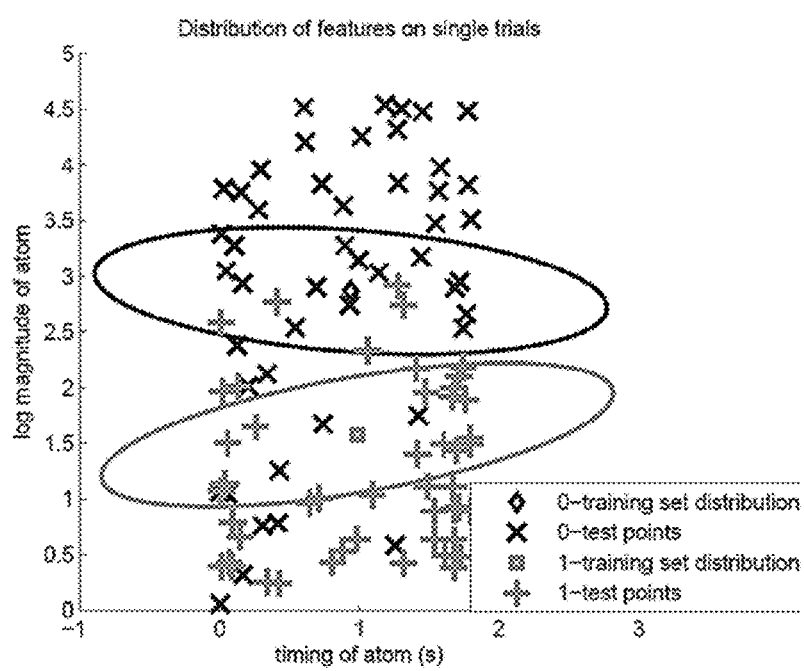

Example trials and the models approximations are shown in FIG. 33. Multichannel LFP and rank-1, single-atom approximations of four example trials are depicted, two from each reward condition. The distribution of the features, subspace magnitude and temporal alignment, for the training and testing sets (parameter distribution during reward expectation) are shown in FIG. 34. Timing and magnitude scatter plot for atomic decompositions of test set examples and normal distributions fitted to the training set. The two conditions are separable by their magnitude, with larger amplitude during the non-rewarding trials (as is intended by the modeling). The timing does not show a clear pattern; however, the timing extracted from the LFP event was used as a timing event for aligning histograms of the neural spike trains.

Aligning Peristimulus Time Histograms to the LFP Model's Temporal Alignment.

The peristimulus time histogram was used as an estimator for the time-varying firing rate during trials. The use of histogram assumes a time-locked, inhomogeneous Poisson point process where spike timings in a given trial are independent. The timings aligned to the LFP-event can be a better model for individual neural firing rate than the original cue timing. Two models were formed, one that realigns the spike-times to the LFP-event and the other that uses the original timings relative to the cue. In other implementations, a nested model can be formed using both timings, but here the disparate models with separate dependent variables has a clearer understanding.

The spike data was extracted 2.5 seconds before and 3 seconds after the reach target cue. Under the first model, a fixed width histogram was formed for the spikes in the 2 second window following the cue, and under the second model a fixed width histogram was formed for the spikes 1 second before and 1 second after the LFP event. For either model, any spikes that fall before these 2 second windows were pooled into a single bin, as are any spikes that follow after the window. The number of bins in the 2 second window was selected for each neuron and condition based on minimizing an cost function based on the mean and variance of the histogram. Specifically, for each spiking unit and condition the bin size is selected as the minimum of the optimal bin size across both models. The actual search was performed on the number of bins, ranging from 1 to 200, and the bin width was chosen to equally divide the 2 second window. If the optimal bin size was less than 250 ms, that condition/unit was excluded from further analysis. This yielded n=50 units under non-rewarding and n=57 units under rewarding.

Given the binning time structure, the spike train recorded on a given trial were converted into a vector of non-negative integers. The elements of this vector were assumed to be independent but Poisson distributed with a varying mean. To compare the two time alignments, leave-one-out cross validation of goodness-of-fit was performed using log-likelihood and check for a significantly better fit under one of the two time-structure models using Vuong's test, which simply performs a t-test on the paired log-likelihood values across all trials for the two models. For each condition, Bonferroni's correction was applied to the p-values to account for the multiple tests across neurons. A significance level was chosen at 1%.

Figure 35A:
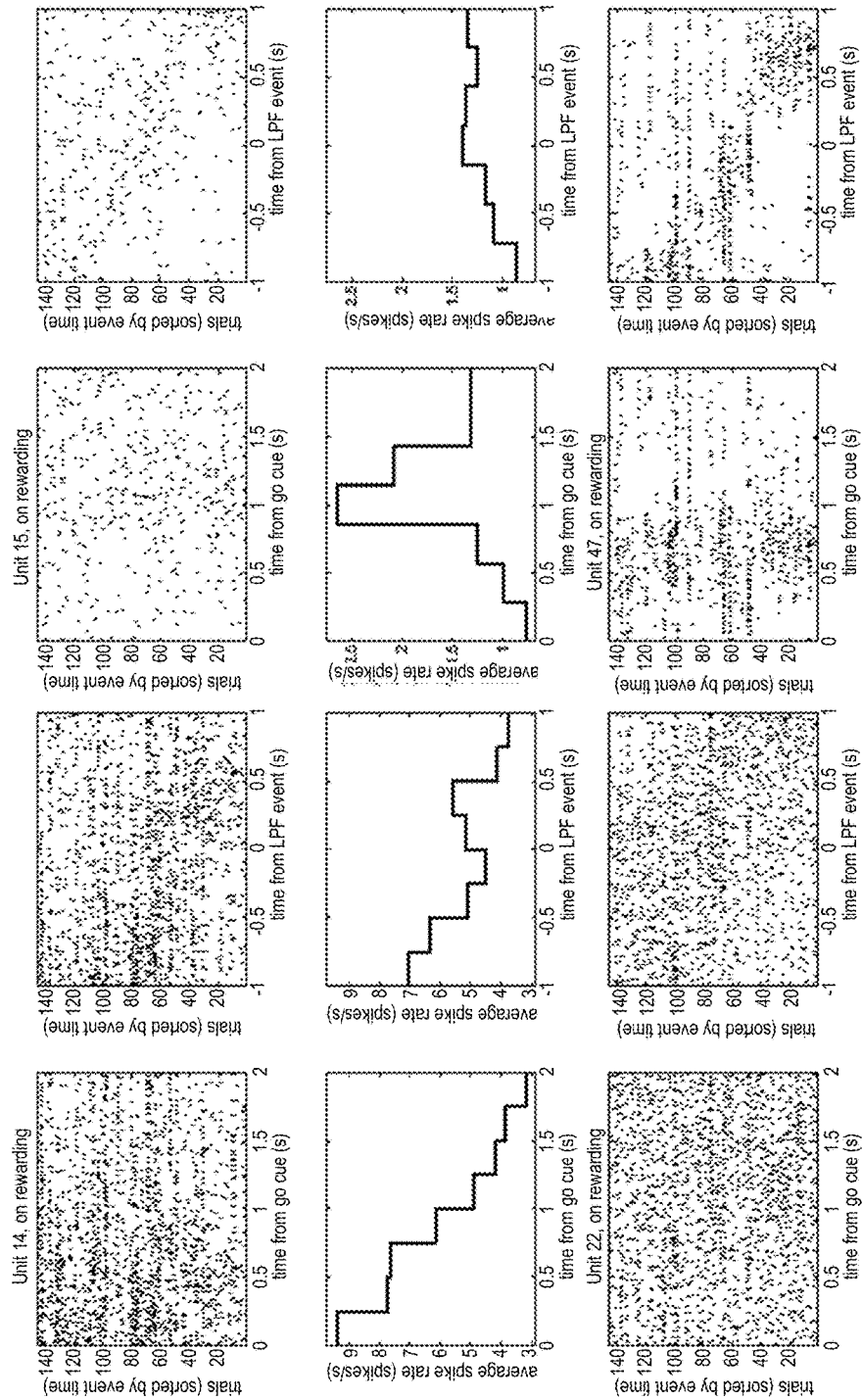
FIGS. 35A through 35C are spike trains and histograms for spiking units in accordance with various embodiments of the present disclosure.
Figure 35A:
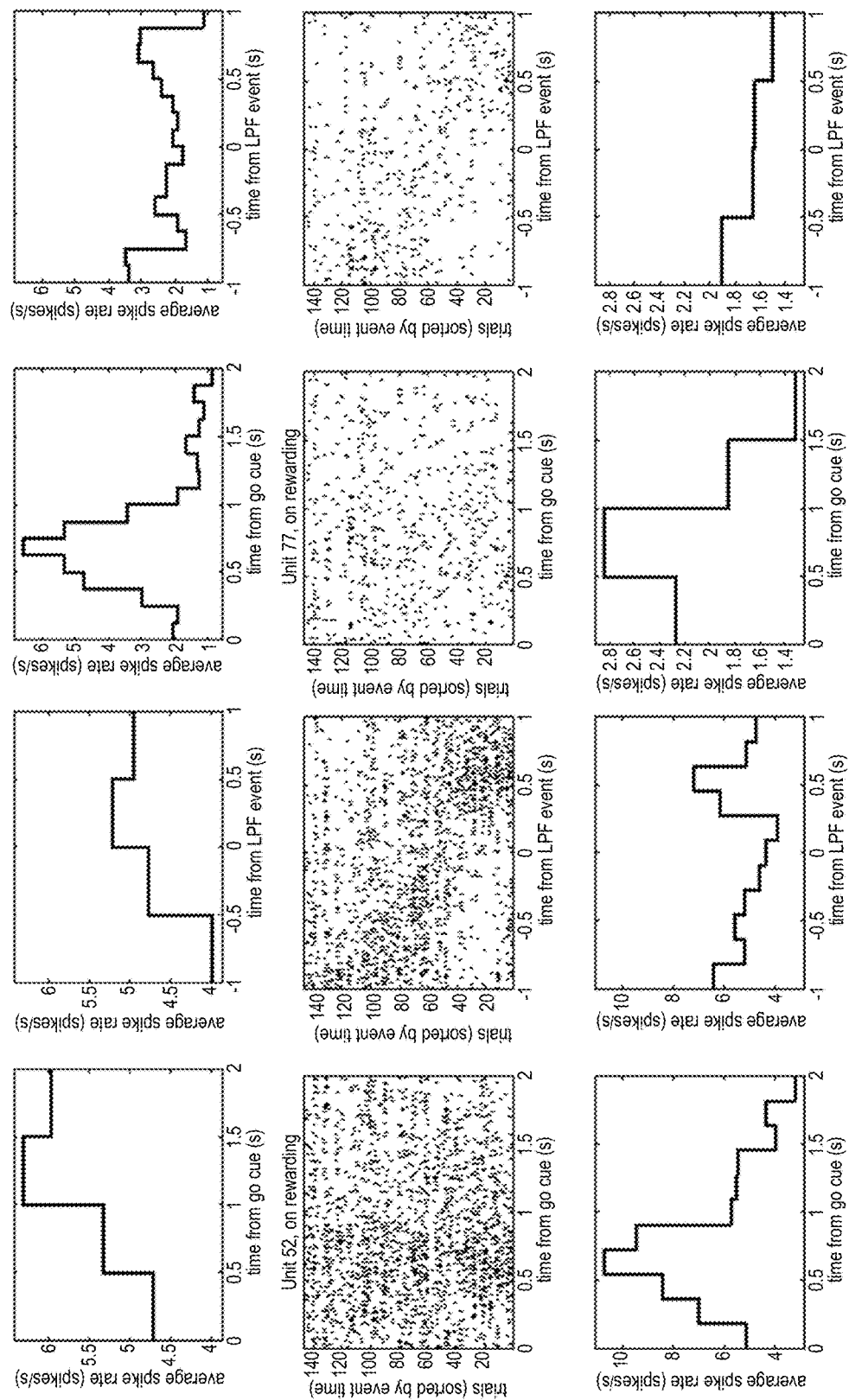
Figure 35B:
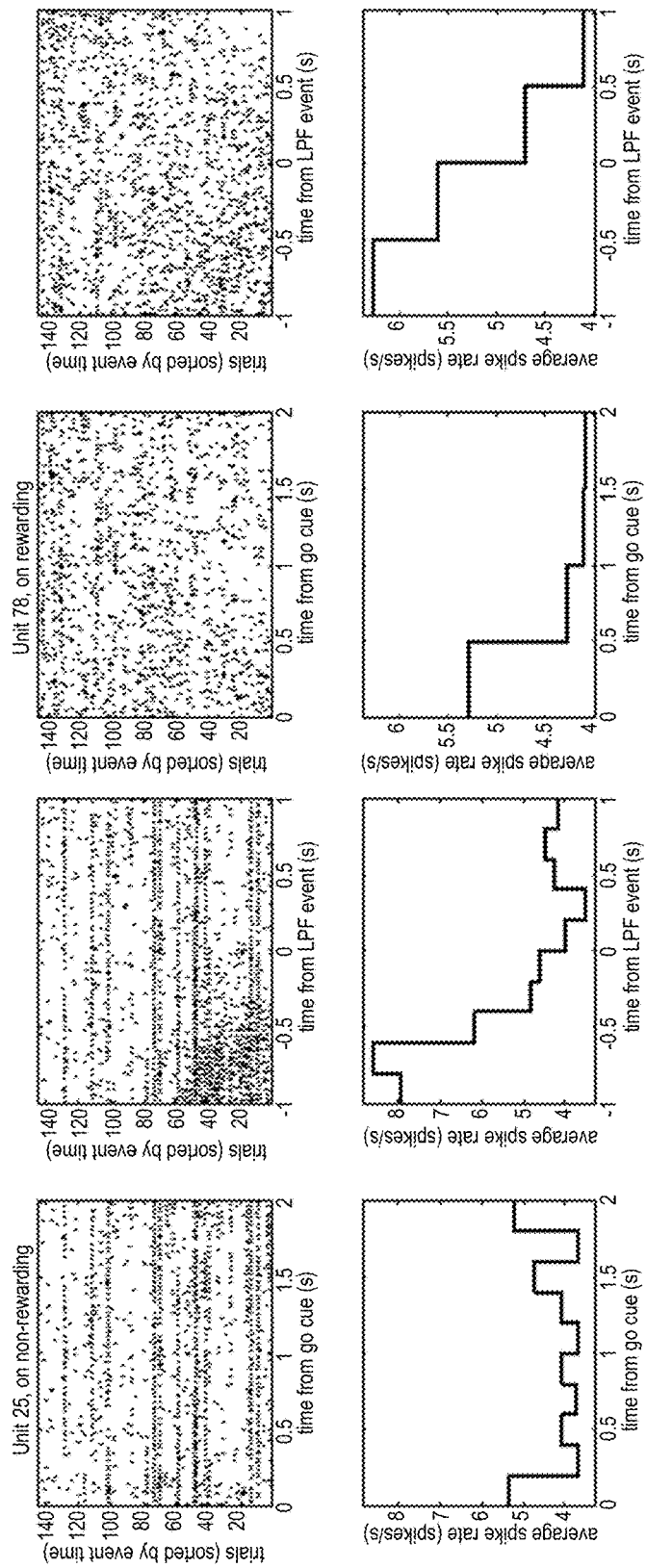
Figures 35C, 36:
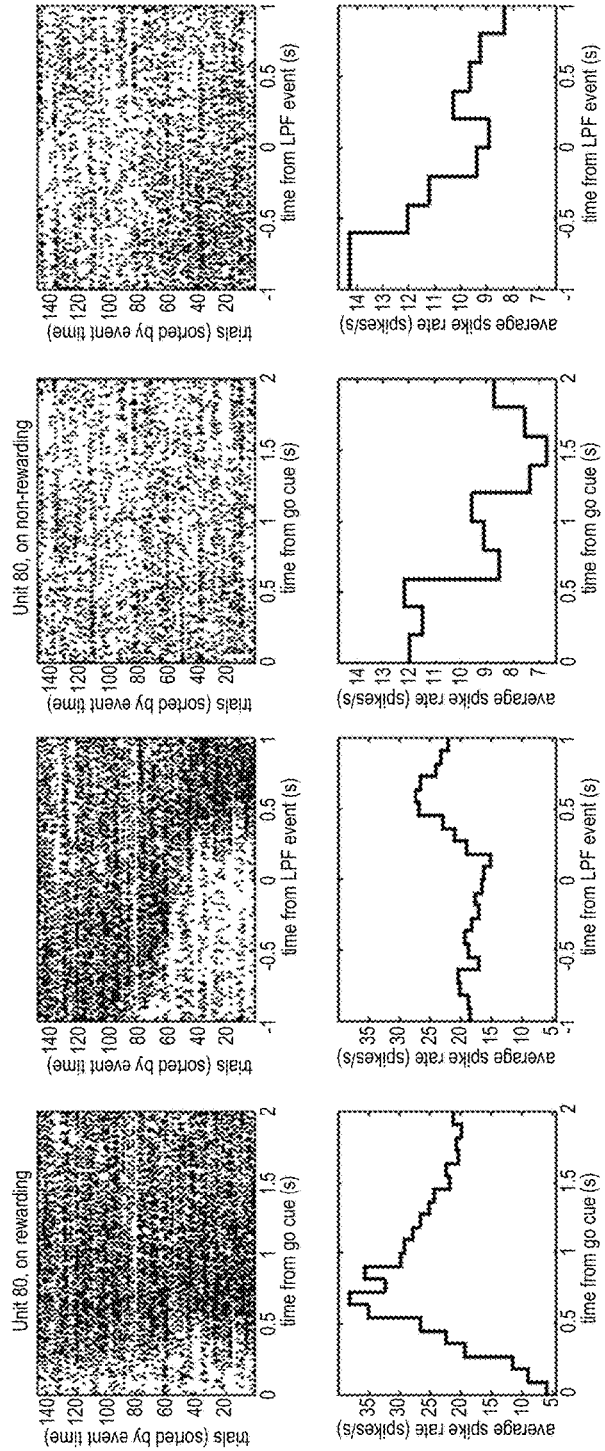
FIG. 36 is a table illustrating model fit in accordance with various embodiments of the present disclosure.

The spike trains and histograms for units which had significantly better fit under the original cue-aligned PSTH, under the LFP-event aligned PSTH, and a unit whose best model depended on the condition are shown in FIGS. 35A through 35C, respectively. FIG. 35A shows spike trains and histograms for spiking units for which the LFP-event provides a significantly better fit (Vuong's test, $p<10^{-5}$). A total of 3 units were identified (two under the non-rewarding condition and one under the rewarding condition). Two units are shown here and the remaining unit is shown in shown in FIG. 35C, which fit significantly better to the cue-time aligned model for rewarding conditions and the LFP-event aligned model for non-rewarding trials (Vuong's test, $p<10^{-5}$). FIG. 35B shows spike trains and histograms for spiking units for which the original cue-time aligned model provides a significantly better fit (Vuong's test, $p<10^{-5}$). A total of 7 units were identified (all under the rewarding condition). Six units are shown in FIG. 35B and the remaining unit is shown in FIG. 35C.

The Table of FIG. 36 summarizes the number of units assigned to each model per condition, with statistically better fits for each model. The results of the statistical test appear consistent with the modeling structure, as the LFP-event is based on a model of the non-rewarding conditions. It is interesting that the two units assigned to the LFP-event model under the non-rewarding condition have spike rates that increase preceding the LFP-event. This points to the fact that the spiking may be an indication of the upcoming LFP-event.

Model Selection. In the previous result sections, the model architecture for the evoked potentials were chosen a priori; the optimality of the model and model order were not considered. In this section, model selection was considered for the previously analyzed datasets along with the data from two subjects in the publicly available BCI Competition III dataset II provided by the Wadsworth Center, NYS Department of Health. Specifically, the two human subjects were using a P300 speller interface within the BCI2000 software. The aim of this analysis is to compare models with different underlying assumptions regarding the complexity of the structure in the neural response set. The following models were compared using different sizes of shiftable temporal waveforms and different ranks or number of components:

A bilinear approximation of the spatiotemporal average, i.e., the average across trials is approximated using the singular value decomposition with different ranks.

Woody's method for estimating an average temporal waveform that is allowed to shift between trials.

A shift-varying subspace approach proposed here: this is an extension of an amplitude and shift-varying waveform.

The differentially variable component analysis (dVCA) with a single spatial factor and run for a fixed number of iterations (11 full cycles).

An implemented greedy version of dVCA (gVCA) was also used. The original version of dVCA used an alternating optimization across components which does not always converge. This was replaced with a stage-wise greedy approximation wherein a component is completely learned before moving on to the next component. In the proposed greedy version, explicit spatial factors for each component can be naturally added; whereas, only a single spatial factor is used in the alternating version.

The canonical polyadic decomposition (CPD) with varying ranks that models the trial-varying spatiotemporal waveforms, but does not account for any shifts. The CPD is learned using a fast damped Gauss-Newton (Levenberg-Marquad) algorithm using a publically available implementation, which utilizes the MATLAB Tensor Toolbox.

The raw spatiotemporal average, or trial-wise principal component analysis, where the spatiotemporal waveform is vectorized, have orders of magnitude more parameters which are not considered because of their inefficiency.

Figure 37A:
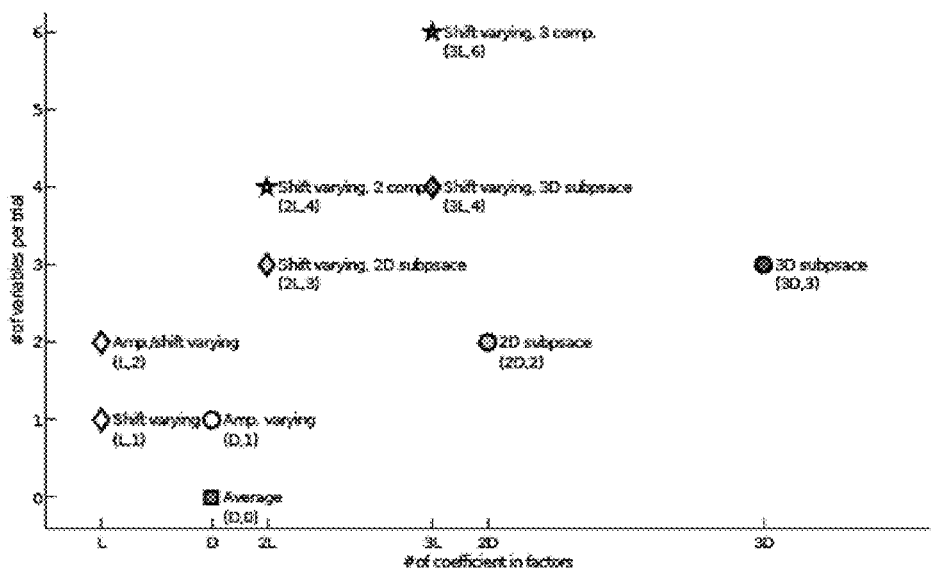
FIGS. 37A and 37B illustrate examples of number of parameters for various model types in accordance with various embodiments of the present disclosure.
Figure 37B:
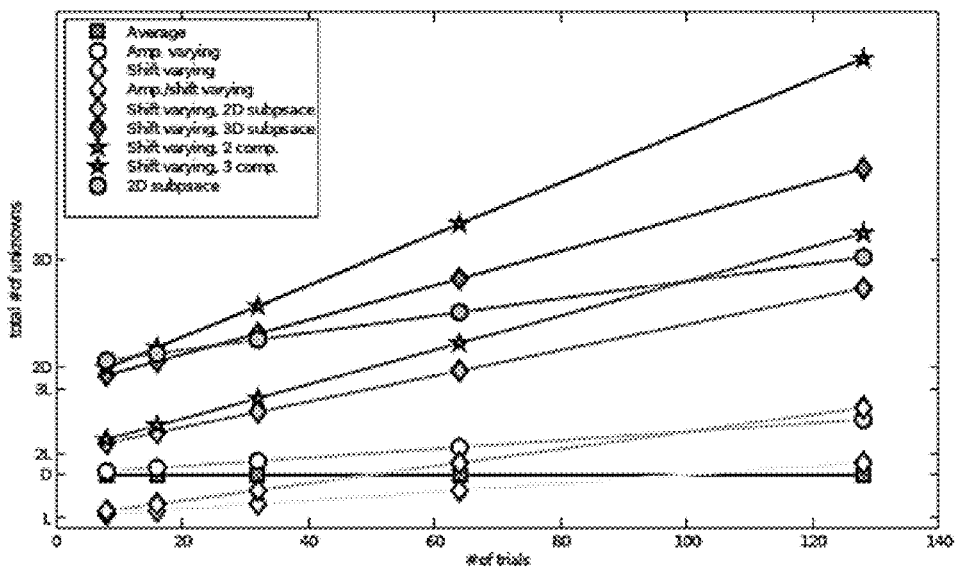

The Bayesian information criterion (BIC) of Equation (57) can be used to compare the different models and model orders in terms of mean squared error and degrees of freedom. For each model, different lengths were used for the temporal waveform and different number of components or ranks were used for the spatial and trial-varying components. The number of degrees of freedom used in calculating BIC takes into account both the number of trial-varying parameters (e.g., the trial amplitude, temporal alignment) along with the number of trial-invariant parameters (e.g., the number of spatial factors and the length of the temporal waveform). A diagram showing the correspondence between the model types and how the number trial-varying and trial-invariant parameters is shown in FIG. 37A. FIG. 37B also shows how the total number of parameters for a single-channel case increases with number of trials. FIG. 37A shows the number of trial-invariant coefficients in the factors and the number of variables allowed to change per trial. FIG. 37B is a graph of total number of parameters as function of the number of trials.

Figure 38A:
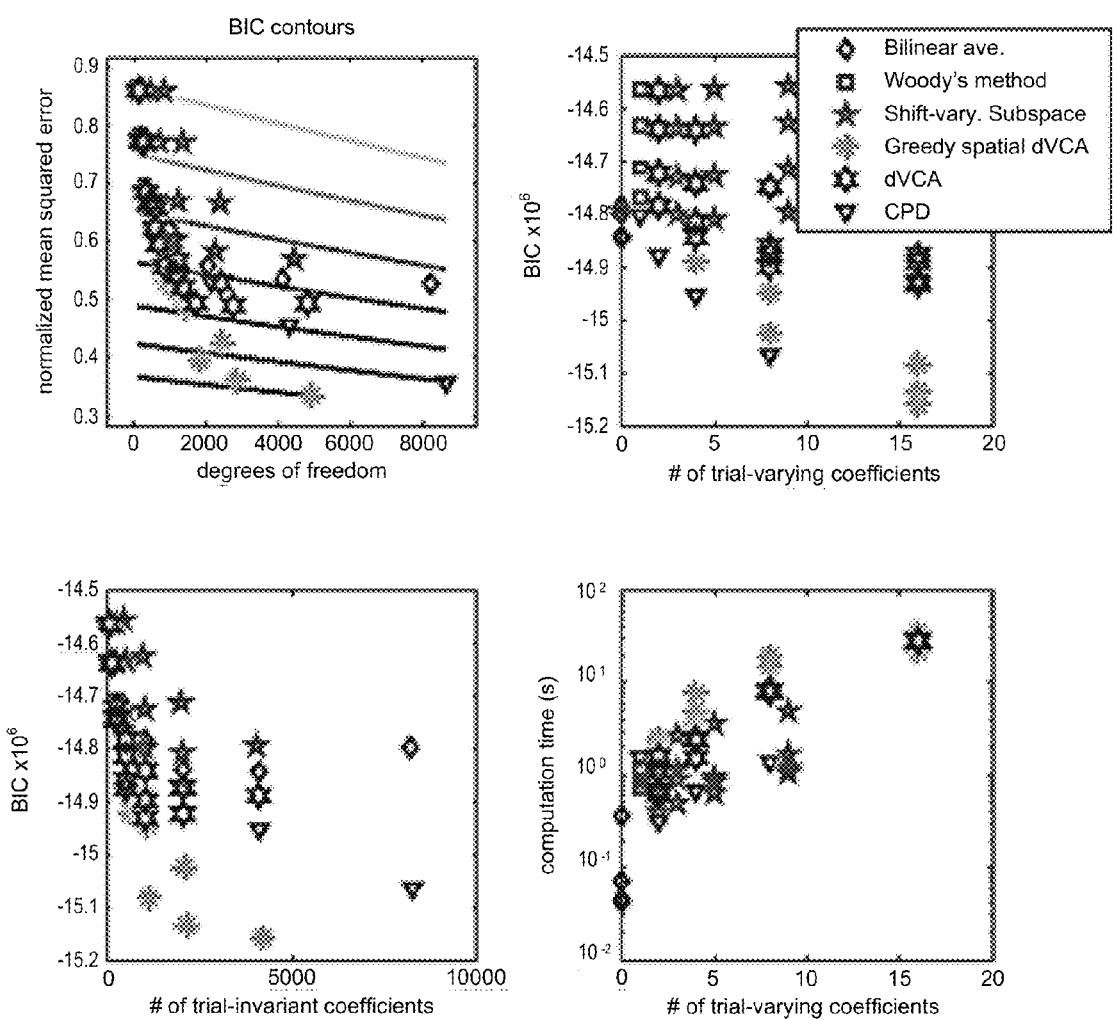
Figure 38B:
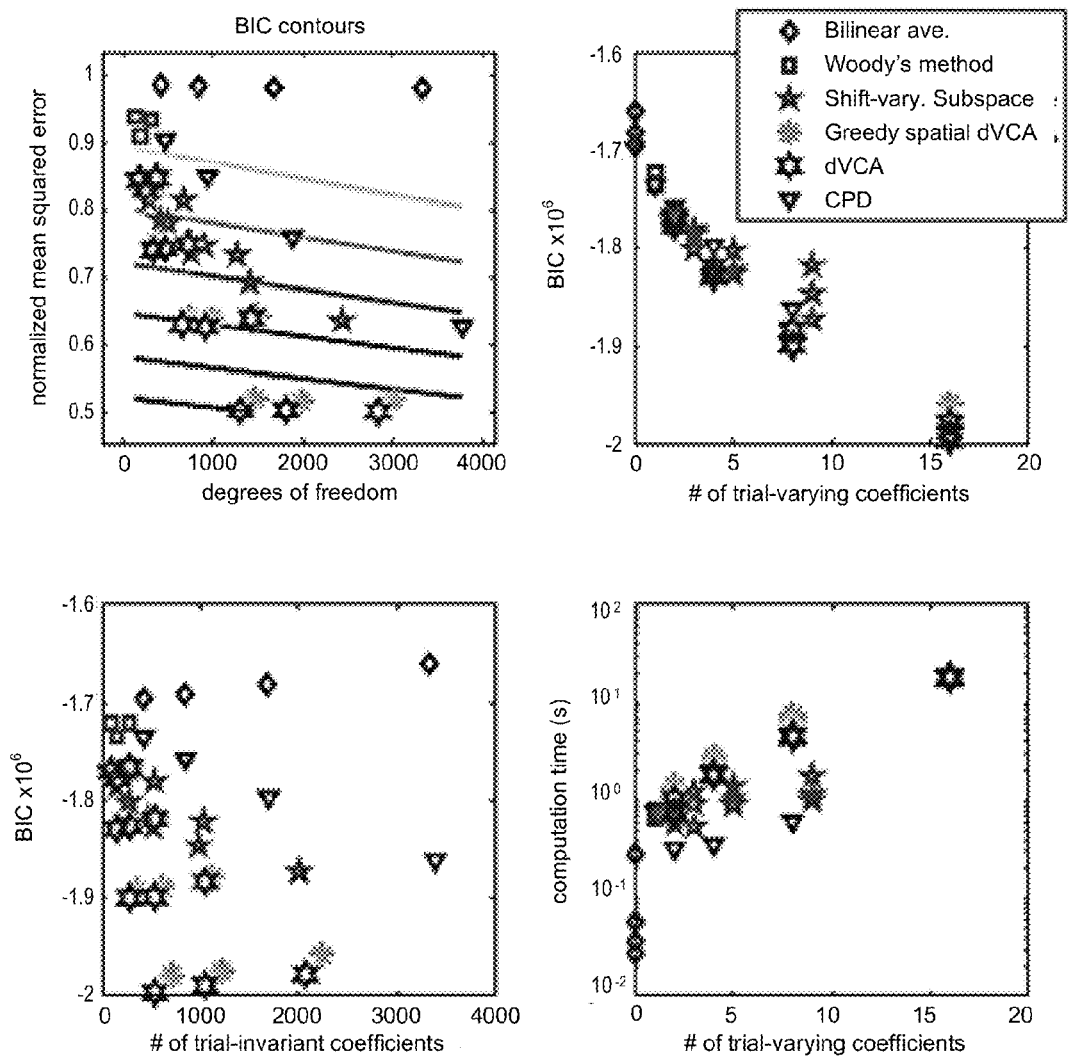
Figure 38C:
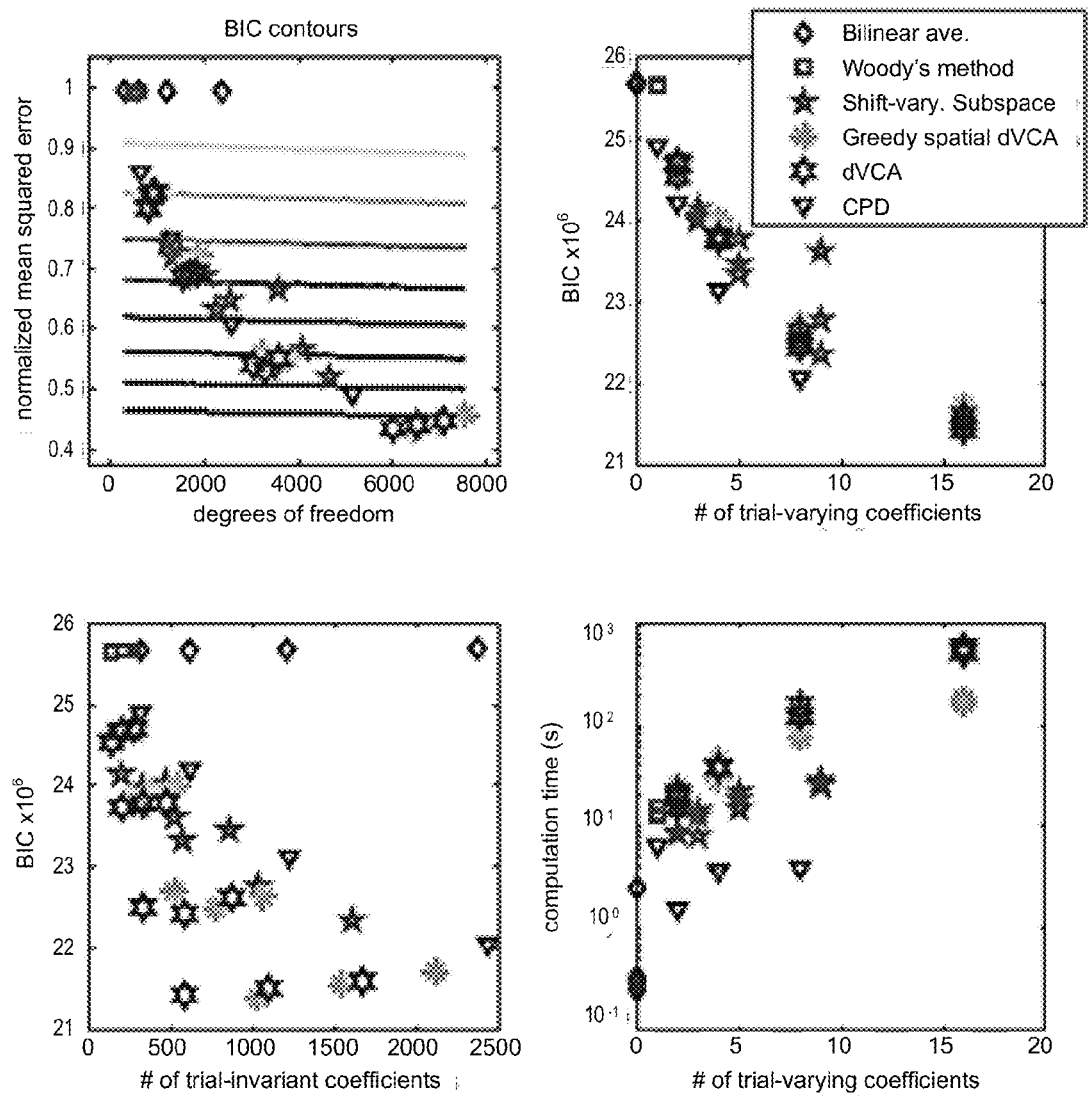
Figure 38D:
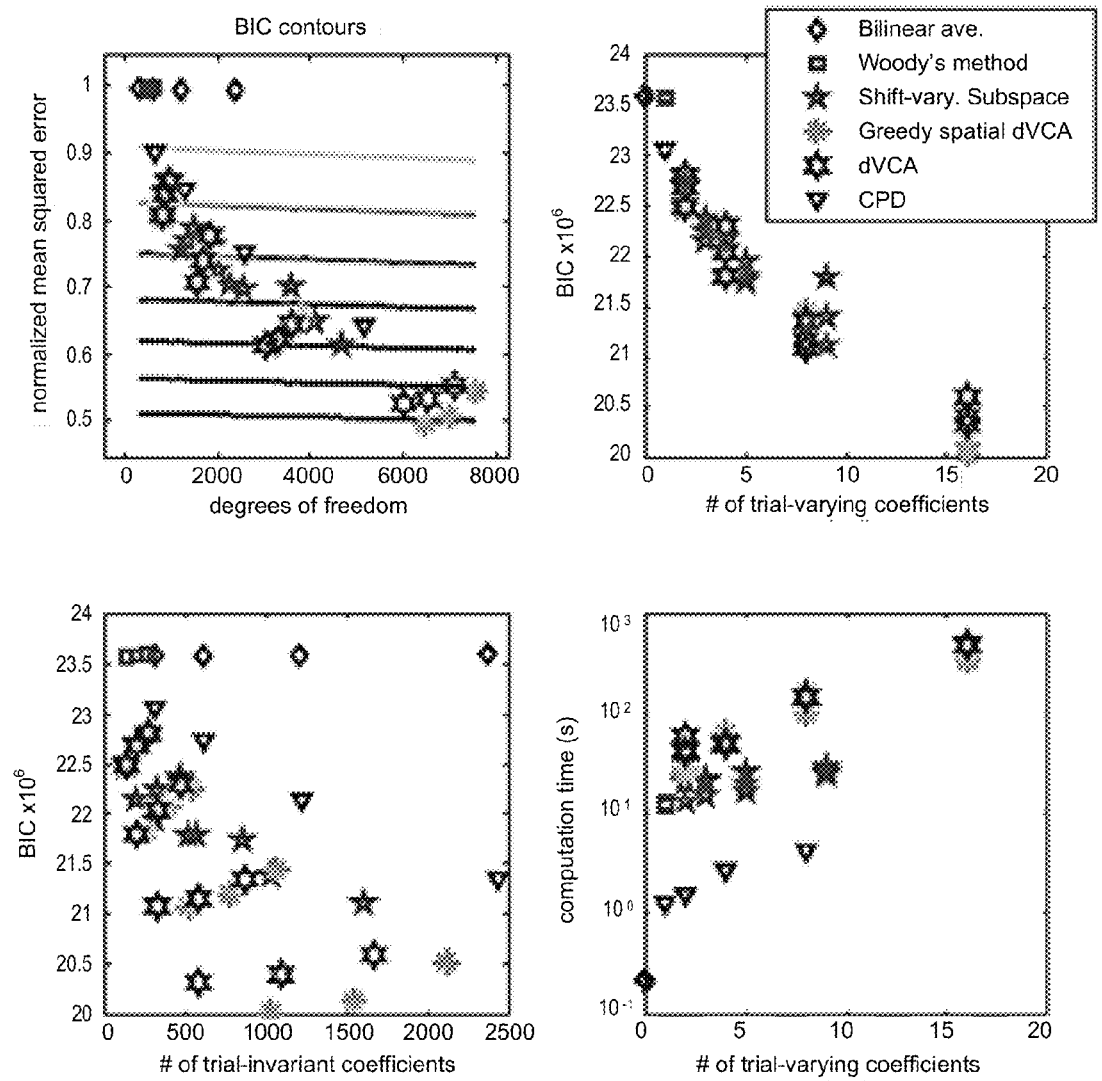

A comparison of the models was performed on three datasets:

LFPs recorded from the ventral striatum in a marmoset for the non-rewarding object trials LFPs recorded from the motor cortex in a macaque for a subset (the first 48 trials) of the non-rewarding passive observation trials EEGs recorded across the scalp for two human subjects (subject A and B) during a P300 evoked potentials experiment, the first 4 highlighted responses to the desired character across all 85 character presentations in the BCI Competition III Wadsworth BCI dataset For each model and dataset, the following values were calculated: the normalized mean squared error, the degrees of freedom, the BIC value, and the computation time. The results across all models and datasets are shown in FIGS. 38A through 38D. FIG. 38A shows the LFPs in ventral striatum for non-rewarding object trials, FIG. 38B shows the LFPs in motor cortex for non-rewarding passive observation trials, FIG. 38C shows the scalp EEG for subject A in the BCI dataset, and FIG. 38D shows the scalp EEG for subject B in the BCI dataset. For the models compared, the overall trend is that increasing parameters yields better performance. The fact that BIC has not reached a minimum for any model type indicates that the data supports complex structure that the simple models are not able to capture. To better understand the model performance with an interpretable number of components, a subset of the models with a fixed number of components are compared. For the shift-varying model the length of the temporal waveform that yields the lowest BIC (closer to optimal) is chosen.

The results for 2 and 8 components are presented in the Tables in FIGS. 39A and 39B, respectively. The dVCA model, under both optimization methods, offers the optimal model, in terms of BIC, for a fixed number of components: outperforming the tensor model and the single component with a temporal subspace. For 2 components, the original alternating optimization performed best on 3 out of the 4 subjects and the greedy optimization was the best for other dataset. For 8 components, the greedy optimization performed best on 3 out of the 4 subjects and the original alternating optimization was the best for other dataset. This switch may have been due to the fact that the alternating optimization was ran for a fixed number of iterations, and with a larger number of components the number of iterations needs to increase. However, it should be noted that even with a fixed number of iterations the run time for the dVCA models was substantially greater than the shift-varying subspace or tensor decompositions. The results indicate there is a clear trade-off between performance and computation time. In addition, the dVCA model is more difficult to interpret since multiple temporal shifts are estimated for each trial. Whether or not the increased explanatory power of dVCA would translate into discrimination as was seen in the shift-varying subspace is yet to be determined. Imposing additional constraints for discrimination is not straightforward on either the alternating or greedy optimization.

The models for evoked potentials have been guided by the neural responses, and have been constrained to trial-varying parameters that are easy to understand such as amplitude and time delays. This single-trial extraction of these parameters allows testing for trends across trials. Here we have used existing models and proposed new models for which the trial-varying parameters are treated as features for single-trial classification. This follows along the lines of previous research, but the spatial factor in the model was used as a spatial filter. In addition, in one instance the spatial filter was trained to explicitly discriminate between conditions. As opposed to the majority of the existing literature, the spatiotemporal neural signals have been considered across the trials as a tensor. Tensor decompositions are a natural model for evoked potentials. Here the use of shift-varying models has been combined with the tensor models using explicit estimation of shifts. This does not need approximations restricted to low-frequency signals. The same approximation has been used by shift-varying models for evoked potential models. A shift-varying model that does not need this approximation was introduced, and uses a temporal subspace to explain each single-trial waveform. After alignment of each trail, the model is a block term decomposition.

The tensor treatment also allows standard tensor decompositions to be compared to the shift-varying methods using standard model selection criterion. Through this analysis, it was confirmed that the additional computational cost of shift-varying decompositions is offset by increased model flexibility. From the results, it is clear that the shift-varying models are able to more parsimoniously explain the data: they have fewer coefficients, better fit, and are still more interpretable than standard tensor decompositions. Strictly in terms of model fit and model order selection, a range of tensor decompositions and evoked-potential models was considered including the differentially variable component analysis (dVCA) with multiple components. We also introduced a greedy version of this approach. In certain cases, the greedy approach was faster and had better performance: in terms of the model selection criterion. The main benefit is that it always converges and can naturally allow a different spatial factor for each component; future work should analyze whether these spatial factors indicate unique sources. The greedy approach comes with the caveat that it may increase the rank of the underlying model, such as for the CPD, resulting in a higher model being estimated than necessary. The single-trial modeling and classification was applied to two reward expectation datasets. For the dataset with both neural action potentials and LFPs, the coupling between these scales was evaluated. Specifically, models of the neural firing rate aligned to the experimental timing are compared to models aligned to the evoked potential alignment. Cross-validation is used to select which time events better explain the neural activity in terms of a simple peristimulus time histograms (PSTH) model for the firing rate.

Neural Decoding with Kernel-Based Metric Learning

When studying the nervous system, the choice of metric for the neural responses is a pivotal assumption. For instance, a well-suited distance metric enables one to gauge the similarity of neural responses to various stimuli and assess the variability of responses to a repeated stimulus (e.g., exploratory steps in understanding how the stimuli are encoded neutrally). Here, an approach is discussed where the metric is tuned for a particular neural decoding task. In particular, neural spike train metrics have been used to quantify the information content carried by the timing of action potentials. While a number of metrics for individual neurons exist, a method to optimally combine single-neuron metrics into multi-neuron, or population-based, metrics is lacking.

Metric-learning algorithms change the metric in the original space to achieve some specific objective, usually exploiting supervisory information. When the original space is composed of multiple independent dimensions possible ways to change the metric are the by removing dimensions, scaling dimensions, or rotating the axes of the space by using linear combinations of dimensions. A linear combination of dimensions corresponds to a linear projection which can be found by a number of supervised learning methods. Removing or weighting features corresponds to feature selection.

Metric learning is used as an intelligent preprocessing for classification methods that depend on a measure of similarity or dissimilarity to determine if two samples are of the same class. For instance, kernel machines or nearest-neighbor-based approaches compare novel samples relative to already observed samples but rely on a predefined similarity measure. These classifiers are highly dependent on the preprocessing and offer little insight into the importance of individual feature dimensions. Metric learning can improve the classification performance by adjusting the importance of individual features for the task, and these weights can be used to highlight the features or dimensions relevant for the objective. Furthermore, metric learning approaches can also improve kernel regression.

Classes of metrics that can be parameterized along spatiotemporal dimensions of neural responses are examined. For instance, consider which channels or time points in the neural response are most useful for distinguishing among conditions. Unlike previous metric-learning approaches that have concentrated on learning projections and weightings for scalar-valued variables, here metric learning is used where the weights correspond to different neurons in multiunit spike train metrics or vectors of spatial amplitudes from multichannel LFPs. With vector-valued data each individual metric is defined over a vector space. Using a weighted combination of these metrics we can form strictly spatial or temporal weightings for multivariate time series. In addition, we propose to optimize multi-neuron spike train metrics formed as combinations of spike train metrics defined for individual neurons. The parameters of multi-neuron spike train metrics may be optimized, instead of using pre-defined weightings.

Given the form of the projections or weightings, one must consider their optimization. A number of metric-learning cost functions have been posed in the literature, but a kernel-based measure of dependence known as centered alignment can be used. Centered alignment can be a useful measure for kernel-learning, and a similar but unnormalized kernel dependence measure, Hilbert Schmidt information criterion (HSIC), can be used for feature selection. Another kernel-based dependence measure formulated based on conditional entropy has also been shown to be useful for learning a Mahalanobis distance and a weighted product kernel. By replacing the kernel-based canonical correlation measure with centered kernel alignment, both matrix inversion and regularization can be avoided.

Using a kernel-based objective, the connection between optimizing weighted tensor product kernels and metric learning can be highlighted. Optimizing a metric in a kernel-based framework has the added benefit that it naturally optimizes the kernel itself for use in support vector machines. This can eliminate the need for the user to choose a kernel size through cross-validation or trial-and-error. Kernels also provide a straightforward way to form metrics corresponding to nonlinear projections. This is done by retrieving a metric from a unweighted sum of optimized kernels, which is an approach distinct from optimizing a convex sum of kernels. Ultimately, this leads to optimized multi-neuron spike train kernels formed as the product and the sum of product of single-unit spike train kernels.

Using the kernel-based dependence measure, multi-neuron metrics and metrics on local field potentials (LFPs) can be optimized. The approach is demonstrated on invasively recorded neural data comprising both spike trains and LFPs. The experimental paradigm comprises decoding the location of tactile stimulation on the forepaws of anesthetized rats. It is shown that the optimized metrics highlight the distinguishing dimensions of the neural response, significantly increase the decoding accuracy, and improve non-linear dimensionality reduction methods for exploratory neural analysis. The following disclosure will introduce the mathematical representation of the neural response and different metrics that use linear projections or weightings; kernel-based similarity measures can be formed from the metrics;
and a dependence measure introduced from the kernels. From these, metric-learning optimization can be formed. The classification performance of the proposed approach is verified on benchmark datasets, and show results on the experimental datasets.

Metrics and Similarity Functions. Neural Data Representation and Metrics. For the trial-wise classification of different conditions, a sample from each trial is the concatenation of the neural response across all selected time samples, electrode channels, or neural spiking units. Let $x=[x_{(1)} \ldots x_{(P)}]$ denote the P-dimensional neural response to a given trial, where parenthetical subscripts denote the response dimension: $x_{(i)}$ may be a scalar, vector, or set (in the case of spike trains). Let $x_j$ denote the neural response for the jth trial, $j \in \{1, \ldots, n\}$, and let $l_j \in \{1, \ldots, m\}$ denote the discrete class label corresponding to a certain class condition for the jth trial. The set $\{z_j=(x_j,l_j)\}_{j=1}^n$ represents a joint sample of the neural responses and labels. Briefly, a bivariate function $d(\cdot,\cdot)$ is a distance metric with domain $\mathcal{X} \times \mathcal{X}$ if it satisfies the following requirements:

1. $d(x, x') \geq 0 \ \forall x, x' \in \mathcal{X}$.
2. $d(x, x')=d(x', x) \ \forall x, x' \in \mathcal{X}$.
3. $d(x, x')=0$ if and only if $x=x'$.
4. $d(x, x^+) \leq d(x, x')+d(x', x^+) \ \forall x, x', x^+ \in \mathcal{X}$.

Functions that satisfy all but the third requirement can be considered pseudo-metrics. In metric learning, achieving a pseudo-metric may be useful since it allows points to be considered equivalent even if they differ on certain, hopefully irrelevant, aspects.

Consider the distances between pairs of neural responses along each dimension: the distance between samples x, x" on the ith dimension is denoted $d_i(x_{(i)}, x'_{(i)})$. For instance, this may be the Euclidean metric for scalars or vectors or a metric on spike trains.

A metric for the joint neural response is formed by combining these individual distances using a feature weighting, where the weights control the importance of the distance along each dimension. Let w denote a nonnegative P-dimensional weighting vector, such that $\forall i, w_i \geq 0$. The metric using this weighting can be formed as:

$$d_w^\gamma(x, x') = \sum_{i=1}^P w_i d_i^\gamma(x_{(i)}, x'_{(i)}), \qquad (58)$$

where the exponent $\gamma \geq 1$ controls how relatively large distances on individual dimensions contribute to the total distance. This is a weighted Euclidean metric if $\gamma=2$ and the metric for each dimension is the Euclidean or $\mathcal{L}_2$ metric.

If $w_i=0$, then the metric is a pseudo-metric since it does not satisfy the property that $d(x,x')=0$ if and only if $x=x'$. However, this invariance to certain dimensions is a goal of metric learning. For vector-valued data, the weighting is a special case of a linear transformation that is equivalent to globally scaling the input dimensions:

$$w_i d_i^\gamma(x_{(i)}, x'_{(i)}) = d_i^\gamma(w_i^{1/\gamma} x_{(i)}, w_i^{1/\gamma} x'_{(i)}).$$

If each neural response is a vector of scalars, define a more general Euclidean metric parameterized by a matrix $A \in \mathbb{R}^{P \times Q}$ using a linear projection of the samples $y=A^T x$, $y_{(j)}=\Sigma_j A_{i,j} x_{(i)}$, $j=1, \ldots, Q$. The Euclidean distance in the Q-dimensional feature space $d^2(y, y')=\Sigma_{j=1}^Q \|y_{(j)}-y'_{(j)}\|_2^2$ is equivalent to a Mahalanobis distance in the original space, with the inverse covariance matrix replaced by the symmetric positive definite matrix $AA^T$:

$$d_A^2(x,x')=d^2(A^Tx,A^Tx')=\|A^Tx-A^Tx'\|_2^2=(x-x')^TAA^T(x-x'). \quad (59)$$

As A has P·Q coefficients there are more degrees of freedom to distort the space according to this metric. This matrix is strictly positive definite if P=Q and $AA^T$ is full rank; otherwise, the metric is actually a pseudo-metric.

The special case of a weighted metric of Equation (58) appears if A is diagonal and square, with P diagonal entries $A_{i,j}=\sqrt{w_i}$. More generally, a Mahalanobis distance can be seen as a weighting over a squared distance matrix between all dimensions. Using properties of the trace, $$d_A^2(x,x') = tr[AA^T(x-x')(x-x')^T] = tr[AA^TD] = \sum_{i,j}[AA^T]_{i,j}D_{i,j}, \quad (60)$$

where $D_{i,j}=\|x_{(i)}-x_{(j)}\|_2^2 = \langle x_{(i)}, x_{(j)}\rangle - \langle x_{(i)}, x'_{(j)}\rangle - \langle x'_{(i)}, x_{(j)}\rangle + \langle x'_{(i)}, x'_{(j)}\rangle$. Unless A is diagonal this metric exploits the inner-product between different dimensions. Written in this form, it is clear how a Mahalanobis-type metric can be formed whenever all the dimensions of the neural response correspond, or can be mapped, to the same Hilbert space. Specifically, let $\phi: \mathcal{X} \to \mathcal{H}$ define a mapping from any element $x_{(i)}\in\mathcal{X}$ to an element in the Hilbert space $\phi(x_{(i)})\in\mathcal{H}$. The Mahalanobis-type metric in this space is defined by Equation (60) where $D_{i,j}=\langle \phi(x_{(i)}),\phi(x_{(j)})\rangle - \langle \phi(x_{(i)}),\phi(x'_{(j)})\rangle - \langle \phi(x'_{(i)}),\phi(x_{(j)})\rangle + \langle \phi(x'_{(i)}),\phi(x'_{(j)})\rangle$. As long as the inner-product can be defined between the dimensions, for instance by using the spike-train kernels discussed below, one can form metrics that use the distance between different spiking units. This would replicate the interaction between spikes on different units intrinsic to some multi-unit metrics. However, evaluating the inner-product between each pair of dimensions for every pair of samples can be computationally demanding.

Kernels. Kernel functions are bivariate measures of similarity based on the inner-product between samples embedded in a Hilbert space. Let the domain of the neural response be denoted $\mathcal{X}$ and consider a kernel $\kappa:\mathcal{X}\times\mathcal{X}\to\mathbb{R}$. If $\kappa$ is positive definite then there is an implicit mapping $\phi:\mathcal{X}\to\mathcal{H}$ that maps any element $x\in\mathcal{X}$ to an element in the Hilbert space $\phi(x)\in\mathcal{H}$ such that $\kappa(x,x')=\langle\phi(x),\phi(x')\rangle$.

To explore the similarity across the individual dimensions of the data, a joint similarity measure can be composed from the marginal similarity on each dimension. Let $X_i$ denote the neural response domain of the ith dimension and consider a positive-definite kernel $\kappa_i:\mathcal{X}_i\times\mathcal{X}_i\to\mathbb{R}$ and corresponding mapping $\phi_i:\mathcal{X}_i\to\mathcal{H}_i$ for this dimension. The similarity between a pair of samples x and x' on the ith dimension is $$\kappa_i(x_{(i)},x'_{(i)})=\langle\phi_i(x_{(i)}),\phi_i(x'_{(i)})\rangle.$$

Tensor-product kernel. The joint similarity over both dimensions i and j is computed by taking the product between the kernel evaluations $\kappa_{[ij]}(x_{(i,j)}, x'_{(i,j)})=\kappa_i(x_{(i)}, x'_{(i)})\cdot\kappa_j(x_{(j)}, x'_{(j)})$. The new kernel $\kappa_{[ij]}$ is called a tensor-product kernel since it corresponds to using a mapping function that is the tensor-product between the individual mapping functions $\phi_{[ij]}=\phi_i\otimes\phi_j$ where $\phi_{[ij]}(x_{(i,j)})\in\mathcal{H}_{[ij]}$. The product of positive-definite kernels is positive definite, and taking the product over all dimensions returns a positive-definite kernel over the joint space: $\kappa(x, x')=\prod_i \kappa_i(x_{(i)}, x'_{(i)})$.

Due to the product, if for one dimension $\kappa_i(x_{(i)}, x'_{(i)})\approx 0$ then $\kappa(x, x')\approx 0$. If some of the dimensions are noisy with respect to the task, then they will have a deleterious effect on the joint similarity measure. In order to separately weight the contribution of each dimension in the product, consider taking the kernel for the ith dimension to the $\theta_i\geq 0$ power $[\kappa_i(x_{(i)}, x'_{(i)})]^{\theta_i}$. As $\theta_i\to 0$, the influence of the ith dimension decreases, and $\theta_i=0 \Longrightarrow (\kappa_i(x_{(i)}, x'_{(i)}))^{\theta_i}=1$, thereby removing its effect altogether. Taking the product over all dimensions results in a weighted product kernel over the joint space:

$$\kappa_\theta = (x, x') = \prod_i [\kappa_i(x_{(i)}, x'_{(i)})]^{\theta_i}, \quad (61)$$

where $\theta=[\theta_1 \ldots \theta_P]$ denotes the nonnegative parameter vector. However, not all positive-definite kernels can be taken to an arbitrary power and still be positive definite. Only the class of positive-definite kernels that are infinitely divisible can be taken to arbitrary powers such that the resulting kernel $\kappa_\theta$ is positive definite.

Infinitely divisible kernels. There are many infinitely divisible kernels, but our interest in metric learning leads us to the special case of kernels that are functions of distances $\kappa_i(x, x')=f(d(x, x'))=f(u)$. Relying on the work of Schoenberg, I. J. (1938), "Metric spaces and positive definite functions," *Transactions of the American Mathematical Society*, 44(3), 522-536, who explored the connection between distance metrics and positive-definite kernel functions: a kernel that is a function of distance metric is only positive definite if the metric space can be isometrically embedded in Hilbert space. From Theorem 4 of Schoenberg, the most general function f(u) which is bound away from zero and whose positive powers $[f(u)]^\lambda$, $\lambda>0$ are positive definite is of the form $f(u)=\exp(c+\psi(u))$ where $\psi(u)$ is positive definite and c is a constant. For kernels of this form, positive powers simply scale the constant and function $$[f(u)]^\lambda=[\exp\{c+\psi(u)\}]^\lambda=\exp\{c'+\lambda\psi(u)\}, \lambda>0.$$

Thus, a class of kernels whose positive powers are all positive definite are of the form $\kappa(x, x')=f(d(x, x'))=\exp(c+h(x, x'))$ where $h(x, x')$ is positive definite. Given a metric $d(x, x')$, $\kappa(x, x')=\exp(0+h(x, x'))=\exp\{-g(d(x, x'))\}$ is positive definite for only certain choices of $g(\cdot)$. In particular, if $d_p(x, x')$ corresponds to a p-norm or an $\mathcal{L}_p$ metric, then $\kappa(x, x')=\exp(-d_p^p(x, x'))$ is positive definite for $0<p\leq 2$. Furthermore, the kernel $\kappa(x, x')=\exp(-d_p^\gamma(x, x'))$ is positive definite for $0<p\leq 2$ and $0<\gamma\leq p$. For $p<1$, $d_p$ is not actually a metric since it violates the triangle inequality; nonetheless, $d_p^\gamma$ is embeddable in a vector space for $0<\gamma\leq p$.

Clearly, the Gaussian kernel $\kappa$(x, x')=exp($-\theta d^2$(x, x')) is positive definite if and only if d(x, x') is a Euclidean or L2 metric; whereas, the Laplacian kernel $\kappa$(x, x')=exp($-\theta d$(x, x')) positive definite for an $\mathcal{L}_p$ metric with $1 \le p \le 2$.

Weighted product kernels. For kernels of this form, $\kappa_i^{\theta_i}$($x_{(i)}$, $x'_{(i)}$)=exp($-\theta_i d^\gamma$($x_{(i)}$, $x'_{(i)}$))), and substituting this equation into the weighted product kernel of Equation (61) yields:

$$\kappa_\theta(x, x') = \prod_{i=1}^P \exp(-\theta_j d^\gamma(x_{(i)}, x'_{(i)})) = \exp\left(-\sum_{i=1}^P \theta_i d^\gamma(x_{(i)}, x'_{(i)})\right), \quad (62)$$

where $\theta_i$ can now be regarded as a parameter of kernel $\kappa_i$. Letting $\theta$=w, $\kappa_\theta$(x, x')=exp($-d_w^\gamma$(x, x')); this shows the equivalence between the weighted metric of Equation (58) and parameterized product kernel of Equation (61).

Multivariate Gaussian kernel. Similarly, using the Mahalanobis metric of Equation (59) on scalar-valued data, a multivariate Gaussian kernel can be defined as the product of Q Gaussian kernels:

$$\kappa_A(x, x') = \exp(-d_A^2(x, x')) = \prod_{j=1}^Q \exp(-d^2(y_{(j)}, y'_{(j)})), \quad (63)$$

where $y_{(j)} = \Sigma_i A_{i,j} x_{(i)}$.

Sum of product kernels. For scalar-valued data the weighted and Mahalanobis metrics correspond to linear projections. A nonlinear metric can be formed from the direct sum of kernels, as the sum of positive-definite functions is itself a positive-definite function. Let $\Theta=[\theta^1, \theta^2, \ldots, \theta^Q]$ denote a matrix of different weighting vectors corresponding to a set of product kernels $\{\kappa_{\theta i}\}_{j=1}^Q$. Define $\kappa_\Theta$ as an unweighted sum of Q product kernels:

$$\kappa_\Theta(x, x') = \sum_{j=1}^Q \kappa_{\theta i}(x, x') = \sum_{j=1}^Q \prod_{i=1}^P \exp(-\theta_i^j d^\gamma(x_{(i)}, x'_{(i)})), \quad (64)$$

Let $\phi_\Theta$ denote the implicit mapping defined by the sum kernel. This mapping defines a metric between x and x' that corresponds to the $\mathcal{L}_2$ distance in the Hilbert space.

$$d_\Theta(x,x')=\|\phi_\Theta(x)-\phi_\Theta(x')\|_2 = \sqrt{\kappa_\Theta(x,x) - 2\kappa_\Theta(x,x') + \kappa_\Theta(x',x')}. \quad (65)$$

Kernel matrices. In terms of a group of samples, the $\gamma$ power of the distance matrix for the ith dimension is denoted $D_i^{\circ\gamma}$ where $[D_i^{\circ\gamma}]_{j,k} = d^\gamma(x_j(i), x_k(i))$ j, k∈{1, . . . , n}. The notation $D^{\circ 2}$ denotes that each element is squared $D^{\circ 2} = D \circ D$ where $\circ$ denotes the entry-wise (Hadamard) product, as opposed to the matrix product $D^2 = DD$. The kernel matrix for the ith dimension is $K_i = \exp(-\theta_i D_i^{\circ\gamma})$. The kernel matrix for the product and sum kernels are computed as $K_\theta = K_1 \circ K_2 \circ \ldots \circ K_P = e^{-\Sigma_i D_i^{\circ\gamma}}$ and $K_\Theta = K_{\theta^1} + K_{\theta^2} + \ldots K_{\theta^Q}$. The labels of the trials can also be represented by a kernel matrix L, where each entry $L_{j,k} = \delta(l_j, l_k)$ use the 0-1 kernel, $\delta(l, l')=1$ if l=l' and $\delta(l, l')=0$ if l≠l'.

Neural Metrics. Out of the many possible neural response metrics, consider the following metrics:

Temporal metrics for multivariate time-series: Each individual distance is the Euclidean distance between the vectors of instantaneous amplitudes across the channels. Each weight corresponds to a particular time lag. The weight adjusts the importance of the distance between the spatial patterns of the two samples at that particular time.

Spatiotemporal projections: A linear projection matrix is used to form a Mahalanobis distance.

Spike train metrics: Each individual distance is between spike trains on the same unit at different temporal precisions. The weight adjusts the importance of each unit at a particular temporal precision value. There are a number of spike train metrics, but we consider two different metrics:

Spike train alignment metric. The metric is the $\mathcal{L}_1$ or $\mathcal{L}_2$ version of the Victor-Purpura (VP) spike train distance.

Kernel-based spike metric. The metric is defined by the mapping $\phi$ induced by a spike train kernel. The memoryless cross-intensity (mCI) spike train kernel can be used. Let $x = \mathcal{T}$ and $x = \mathcal{T}'$ $$\kappa(x, x') = \langle \phi(x), \phi(x') \rangle = \sum_{t \in \mathcal{T}} \sum_{t' \in \mathcal{T}'} \exp(-q|t - t'|).$$

Then $\|\phi(x)-\phi(x')\|_2 = \sqrt{\kappa(x,x) - 2\kappa(x,x') + \kappa(x',x')}$ is an $\mathcal{L}_2$ metric. In alternate implementations, multichannel spike trains can be transformed to vectors in Euclidean space. First the spike timings for each unit, can be quantized into fixed-width, contiguous, and non-overlapping bins. Then the binned spike count vectors for each neuron can be concatenated and a spatiotemporal projection can be applied.

Based on these metrics, kernel functions can be used as measures of similarity. On each individual dimension, either the Gaussian kernel for the Euclidean and $\mathcal{L}_2$ distances or the Laplacian for $\mathcal{L}_1$ metrics such as the original Victor-Purpura metric can be used. The kernels for individual dimensions can be combined using the tensor product kernel in Equation (62). The sum of product kernels of Equation (64) comprises an unweighted sum of the weighted product kernels with different weightings. For the Mahalanobis metric of Equation (59), a multivariate Gaussian kernel of Equation (63) can be used.

Kernel-based Metric Learning. A kernel-based measure is introduced to quantify the joint information between neural responses and labels corresponding to stimuli or condition. The measures can be used as an objective function to optimize the metric used to evaluate the similarity among neural responses.

Kernel-based Measures of Dependence. Kernel target alignment measures the similarity between two kernel functions using their normalized inner-product. For jointly sampled data, the inner-product of kernel functions can define a measure of dependence between random variables. Unlike Pearson's correlation-coefficient which uses the values of the random variables, kernel-based dependence assesses the degree to which the similarity of example pairs, as defined by each kernel function, matches or aligns.

Consider the statistical alignment of two kernel functions. Let z∈$\mathcal{Z}$ denote a random variable and z' be an independent and identically distributed random variable. Let $\mathcal{K}_1$ and $\mathcal{K}_2$ be two kernel functions with implicit mappings $\phi_i: \mathcal{Z} \to \mathcal{H}_i$. A natural measure of similarity between these kernel functions is the expected value of their normalized inner product across pairs of realizations:

$$A(\kappa_1, \kappa_2) = \frac{E_{z,z'}[\kappa_1(z, z')\kappa_2(z, z')]}{\sqrt{E_{z,z'}[\kappa_1^2(z, z')]E_{z,z'}[\kappa_2^2(z, z')]}}. \quad (66)$$

Now, consider when $z=(x, y)$ represents a joint sample of $x \in \mathcal{X}$ and $y \in \mathcal{Y}$ and $\mathcal{K}_1$, $\mathcal{K}_2$ only depend on x and y, respectively: $\mathcal{K}_1(z, z') = \mathcal{K}_x(x, x')$ and $\mathcal{K}_2(z, z') = \mathcal{K}_y(y, y')$. The marginal behavior of the kernels can be expressed in terms of their mapping functions:

$$\phi_1(z) = (\phi_x \otimes 1_y)(x,y), \text{ where } \phi_x: \mathcal{X} \to \mathcal{H}_x, \text{ and } \forall y 1_y(y)=1 \quad (67)$$

$$\phi_2(z) = (1_x \otimes \phi_y)(x,y), \text{ where } \phi_y: \mathcal{Y} \to \mathcal{H}_y, \text{ and } \forall x 1_x(x)=1. \quad (68)$$

Then (69)

$$A(\kappa_1, \kappa_2) = \frac{E_{x,y}E_{x',y'}[\kappa_x(x, x')\kappa_y(y, y')]}{\sqrt{E_xE_{x'}[\kappa_x^2(x, x')]E_yE_{y'}[\kappa_y^2(y, y')]}}.$$

is a measure of statistical dependence between x and y, since it is higher when similar pairs of one variable correspond to similar pairs in the other variable. However, the measure performs poorly in practice without centering the kernels first.

Centering plays the same role as removing the mean when computing the correlation coefficient between scalar-valued random variables. The centered kernel alignment can be given by:

$$\rho(\kappa_1, \kappa_2) = A(\tilde{\kappa}_1, \tilde{\kappa}_2) \quad (70)$$

$$\tilde{\kappa}_j(z, z') = \langle \tilde{\phi}_i(z), \tilde{\phi}_i(z') \rangle \quad (71)$$
$$= \langle \phi_i(z) - E_z[\phi_i(z)], \phi_i(z') - E_z[\phi_i(z')] \rangle$$
$$= \kappa_i(z, z') - E_{z'}[\kappa_i(z, z')] - E_z[\kappa_i(z, z')] + E_{z,z'}[\kappa_i(z, z')].$$

Centering the mapping functions is key to a useful measure of dependence. The role of centering can be seen by expanding the numerator of the kernel target alignment in tensor product form:

$$E_{z,z'}[\kappa_1(z, z')\kappa_2(z, z')] = E_{z,z'}\langle (\phi_1 \otimes \phi_2)(z, z), (\phi_1 \otimes \phi_2)(z', z') \rangle \quad (72)$$
$$= \langle E_z[(\phi_1 \circ \phi_2)(z)], E_{z'}[(\phi_1 \circ \phi_2)(z')] \rangle$$
$$= \|E_z[(\phi_1 \circ \phi_2)(z)]\|_2^2$$

Writing the original kernel in terms of the centered kernel of Equation (71) yields:

$$E_z(\phi_1 \circ \phi_2)(z) = E_z(\tilde{\phi}_1 + E_{z'}[\phi_1(z')]) \circ (\tilde{\phi}_2 + E_{z'}[\phi_2(z')])(z)$$
$$= E_z(\tilde{\phi}_1 \circ \tilde{\phi}_2)(z) + \mu_1 \circ \mu_2 + \mu_2 \circ \tilde{\phi}_1(z) + \mu_1 \circ \tilde{\phi}_2(z)$$
$$= E_z(\tilde{\phi}_1 \circ \tilde{\phi}_2)(z) + \mu_1 \circ \mu_2$$

where $\mu_i = E_z(\phi_i(z))$ and $E_z(\tilde{\phi}_i(z)) = 0$. In terms of the marginal kernels:

Writing the original kernel in terms of the centered kernel of Equation 71 yields:

$$\mu_1 \circ \mu_2 = E_{x,y}[(\phi_x \otimes 1_y)(x,y)] \circ E_{x,y}[(1_x \otimes \phi_y)(x,y)] = (E_x \phi_x(x)) \otimes (E_y \phi_y(y)) = \mu_x \otimes \mu_y$$

which is only a measure of the marginal, not of their joint distribution, and thus its biases the norm in Equation (72) regardless of the dependence between x and y.

Again if $z = (x, y)$ and $\mathcal{K}_1(z, z') = \mathcal{K}_x(x, x')$ and $\mathcal{K}_2(z, z') = \mathcal{K}_y(y, y')$, then $\rho(\mathcal{K}_1, \mathcal{K}_2) = \rho_{\mathcal{K}_x, \mathcal{K}_y}(x, y)$ is a measure of statistical dependence between x and y:

$$\rho_{\kappa_x, \kappa_y}(x, y) = \frac{E_{x,y}E_{x',y'}[\tilde{\kappa}_x(x, x')\tilde{\kappa}_y(y, y')]}{\sqrt{E_xE_{x'}[\tilde{\kappa}_x^2(x, x')]E_yE_{y'}[\tilde{\kappa}_y^2(y, y')]}}, \quad (73)$$

for positive-definite-symmetric kernels, $\rho_{\mathcal{K}_x, \mathcal{K}_y} \in [0, 1]$. Centered alignment is essentially a normalized version of the Hilbert-Schmidt Information Criterion.

Correntropy coefficient. Additionally, centered alignment can be related to the localized similarity measure known as correntropy. Specifically, if x and y are in the same domain then a single shift-invariant kernel $\mathcal{K}$ can be used to define the correntropy coefficient $\eta_\mathcal{K}(x, y)$:

$$\eta_k(x, y) = \frac{E_{x,y}[\tilde{\kappa}(x - y)]}{\sqrt{E_{x,x'}[\tilde{\kappa}(x - x')]E_{y,y'}[\tilde{\kappa}(y - y)]}}$$

When $\mathcal{K}(x-y) = E_{x',y'}[\mathcal{K}_x(x, x')\mathcal{K}_y(y, y')]$, then $\rho_{\mathcal{K}_x, \mathcal{K}_y}(x, y) = \eta_\mathcal{K}(x, y)$. For instance, this is the case if $\mathcal{K}_x$ and $\mathcal{K}_y$ are Gaussian kernels and (x, y) is normally distributed. However, this approach is not applicable for metric learning where x and y correspond to two different domains, i.e., labels and neural responses.

Empirical estimation. An empirical estimate of the centered alignment can be computed directly from the kernel matrices K and L where $[K]_{i,j} = \mathcal{K}_x(x_i, x_j)$ and $[L]_{i,j} = \mathcal{K}_y(y_i, y_j)$:

$$\hat{\rho}(K, L) = \frac{\langle \tilde{K}, \tilde{L} \rangle}{\sqrt{\langle \tilde{K}, \tilde{K} \rangle \langle \tilde{L}, \tilde{L} \rangle}} = \frac{\langle \tilde{K}, \tilde{L} \rangle}{\|\tilde{K}\|_2 \|\tilde{L}\|_2}, \quad (74)$$

where $\tilde{K}$ and $\tilde{L}$ are the centered kernel matrices. The centered kernel is computed as:

$$[\tilde{K}]_{i,j} = [K]_{i,j} - \frac{1}{n}\sum_{i=1}^{n}[K]_{i,j} - \frac{1}{n}\sum_{j=1}^{n}[K]_{i,j} + \frac{1}{n^2}\sum_{i=1}^{n}\sum_{j=1}^{n}[K]_{i,j}. \quad (75)$$

Using matrix multiplication, $\tilde{K}=HKH$, where $$H = I - \frac{1}{n}\vec{1}\vec{1}^T$$

is the empirical centering matrix, 1 is the n×n identity matrix, and $\vec{1}$ is a vector of ones. The computational complexity of the centered alignment between two n×n kernel matrices is $\mathcal{O}(n^2)$.

Metric Learning Optimization Using Centered Alignment. For metric learning, the objective is to maximize the dependence between the neural data representation and the class label. Centered alignment can be used to evaluate the dependence in terms of the kernel representations. The 0-1 kernel on the labels can be fixed, and the parameters of a metric-based kernel can be optimized in order to maximize the centered alignment. For convenience, the logarithm of the centered alignment can be used as the objective. With or without the logarithm the kernel-based objective is a non-linear functions of the parameters, and we propose to use approximate inverse Hessian and stochastic gradient methods for optimization. The gradients are detailed below.

First, consider optimizing the sum and product kernels. As the product kernel of Equation (62) is the trivial case of the sum kernel of Equation (64), consider only the optimization of the sum kernel parameters $\Theta=[\theta_i^j]_{i=1,j=1}^{P,Q}$ in the following problem:

$$\underset{\Theta \geq 0}{\text{maximize}}\; \log(\rho_{K_\Theta,\delta}(x, l)). \tag{76}$$

When the empirical estimate of centered alignment is substituted the explicit objective function is:

$$f(\Theta)=\log(\hat{\rho}(K_\Theta,L))=\log(tr(K_\Theta HLH))-\log(\sqrt{tr(K_\Theta HK_\Theta H)})+k, \tag{77}$$

where $K_\Theta$ is the kernel matrix of the responses, L is the 0-1 kernel matrix of the labels, H is the centering matrix, and k is a constant that does not depend on $\Theta$. The gradient of the objective function with respect to the kernel matrix is:

$$G = \nabla_{K_\Theta} f(\Theta) = \frac{HLH}{tr(K_\Theta HLH)} - \frac{HK_\Theta H}{tr(K_\Theta HK_\Theta H)}. \tag{78}$$

The gradient kernel with respect to the kernel parameter $\theta_i^j$ is $$\frac{\partial K_\Theta}{\partial \theta_i^j} = -K_{\theta j} \circ D_i^{\circ \gamma}.$$

Then the gradient of the objective is:

$$\frac{\partial f(\Theta)}{\partial \theta_i^j} = tr((-K_{\theta j} \circ D_i^{\circ \gamma})G). \tag{79}$$

The non-negativity constraint on $\Theta$ can be removed by performing the optimization in terms of u where $\theta_i^j = 10^{u_i^j}$. The gradients can be made in terms of unconstrained optimization variables $u_i$ by $$\frac{\partial f(\Theta)}{\partial u_i^j} = \theta_i \log(10) \frac{\partial f(\Theta)}{\partial \theta_i^j}.$$

This yields an unconstrained optimization.

For the case of scalar-valued data we explore learning a Mahalanobis metric of Equation (63) using the logarithm of the empirical centered alignment as the objective:

$$\underset{A}{\text{maximize}}\; f(A) = \log(\hat{\rho}(K_A, L)). \tag{80}$$

The gradient of the objective function with respect to A is:

$$\nabla_A f(A) = -4X^T((G \circ K_A) - \text{diag}((G \circ K_A)\vec{1}))XA. \tag{81}$$

where X is an n×P matrix of the data, G is the gradient of the objective function with respect to the kernel matrix of Equation (78), and $\vec{1}$ is a vector of ones.

For the approximate inverse Hessian optimization, minFunc can be used with the default limited memory BFGS update. For the sum and product kernels, prior to optimization the individual matrices $D_i^{\circ \gamma}$ are all normalized such that the average across all elements is 1. For the product kernel all the weights are initialized to be $10^{-3}$ and for the sum of product kernels they are uniformly distributed in $10^{-3} \pm 10^4$. For the Mahalanobis distance, the optimization of A yields varying results depending on the initial value of A, but using the projection from Fisher discriminant analysis for initialization performs well in practice.

As an alternative optimization that can handle large sample sizes, a stochastic gradient can be used over small batches. A paradigm commonly used in feature selection can be utilized: at each iteration, one example is sampled and then a pre-specified number of examples of the same class and from differing classes are sampled to form the batch. For each batch, the weights are updated based on the gradient of the objective. Very small batches (even just four examples) are sufficient for learning the parameters of the product kernel, but to learn a Mahalanobis distance it was found that larges batches, in the hundreds, were used.

Benchmark Comparison. Using publicly available datasets, centered alignment metric learning to optimize a weighted metric was compared to a feature weighting method. The feature weighting is explicitly optimized to improve the k-nearest neighbor classification; this serves as a benchmark for centered alignment metric learning, which is not tuned to any particular classifier. The method was shown to consistently outperform other feature weighting methods. UCI machine learning datasets and classification scenario (one-third for training, one-third to choose k, number of nearest neighbors, through cross-validation, and one-third for testing) were used. However, the Monte Carlo divisions were increased to 200 for statistical comparison. As a sanity check, Euclidean distance after normalizing the variance of the features was also used. Both the L-BFGS optimization and the mini-batch were tested with 4 sample batches, 10,000 batches, and a step size of 0.01. The sequential quadratic program-based feature weighting was based on reported values for the mean error rate across 10 Monte Carlos divisions. The results of the benchmark comparison across the UCI datasets using different feature weightings are displayed in Table of FIG. 40. On these small scale problems, with maximum dimensions of 57, none of the compared methods consistently outperformed the best.

Considering the best of the two proposed optimization methods, centered alignment metric learning performs best on half of the datasets.

Decoding Forepaw Touch Location from Rat Somatosensory Cortex. Spike train metrics and temporally-weighted and spatiotemporal metrics on local field potentials were used to decode the location of touch on the forepaw of a rat. The spike trains and local field potentials from the forepaw region of the somatosensory cortex (S1) were used.

Data Collection. Cortical local field potentials and action potentials were recorded during natural tactile stimulation of forepaw digits and palm of 4 female Long-Evans rats under anesthesia. All animal procedures conformed to National Institutes of Health guidelines. After induction using isoflurane, urethane was used to maintain anesthetic depth. A 32-channel microelectrode array (Blackrock Microsystems) was inserted into the hand region of the primary somatosensory cortex (S1). The array was arranged in a 6×6 grid (excluding the four corners) with 400 μm spacing between neighboring electrodes. Another array was inserted into the VPL region of the thalamus, but the signals are not used here.

Using a motorized probe, the right forepaw was touched 225 times at up to 9 sites, e.g., 4 digits and 5 sites on the palm. For each touch site, the probe was positioned 4 mm above the surface of the skin and momentarily pressed down for 150 ms, as seen in the image of FIG. 41; this was repeated 25 times at random intervals. The 4 datasets had 3, 8, 9, and 9 touch sites resulting in 75, 200, 225, and 225 samples, respectively.

The LFPs were band-pass filtered with cutoffs (5 Hz, 300 Hz) and sampled at a rate of 1220.7 Hz. Then the LFPs were digitally filtered using a 3rd-order Butterworth high-pass filter with cutoff of 4 Hz and notch filters at 60 Hz and harmonics. For analysis, the neural response in a 270 ms window following each touch onset was used, which corresponds to 330 discrete time samples. For 32 channels, this results in 330.32=10,560 dimensions. Across the 4 datasets, automatic spike-sorting selected 95, 64, 64, and 38 multi-neuron units from the 32 channels. Of these, only 68, 62, 36, and 24 units were used, whose average firing rate was below 30 Hz in the 270 ms window following touch onset.

Results. Centered alignment metric learning (CAML) was examined for both spike trains and local field potentials (LFPs) using the cases discussed above. For LFPs and binned spike trains, multi-class Fisher discriminant analysis (FDA) and large-margin nearest neighbor (LMNN) was compared. For the linear projections, PCA was used to reduce the dimensionality to ½ of the number of samples in the dataset. The FDA solution is the set of eigenvectors corresponding to a generalized eigenvalue problem. The dimensions can be chosen as the maximum number of non-zero eigenvalues, which is one less than the number of classes. The FDA solution was used as the initial projection for LMNN and CAML Mahalanobis metric. An efficient MATLAB implementation of LMNN is publicly available, and besides the initialization (which greatly increased the performance) default parameters were used.

To compare classification performance, 20 Monte Carlo divisions of the datasets were made into training and testing sets. For training, two-thirds of the samples in each class were used, the remainder of the samples were used in testing. On each Monte Carlo run, the metrics were optimized on the training set. Testing set samples were labeled by either a one-nearest-neighbor (1-NN) or a support vector machine (SVM) classifier. SVM training and testing was performed using the libsvm (ver. 3.17) implementation with the user-provided kernel matrix. The regularization parameter was chosen through 5-fold cross-validation. For CAML the kernel is directly optimized as part of the metric learning, but for FDA, LMNN, and the unweighted metrics a Gaussian kernel was used with the kernel size chosen from a discrete set using 5-fold cross-validation. For CAML the kernel is directly optimized as part of the metric learning, but for FDA, LMNN, and the unweighted metrics a Gaussian kernel was used with the kernel size chosen from a discrete set using 5-fold cross-validation. The set of the highest performing methods for each dataset was found by selecting the best performing method and finding those that were not significantly different using a two-sample Welch test with significance of 0.05.

Learning multi-unit spike train metrics. Multiunit spike-train metrics using the single-unit Victor-Purpura (VP) and kernel-based (mCI) metrics were optimized for touch location classification. For each unit, the distance was computed with different values for the temporal precision value q (higher values of q require more precise alignment): for the Victor-Purpura distance the set $(0.01, 0.1, 1.0)$ s$^{-1}$ was used, and for the spike train kernel-based metrics (mCI) the set $(10^{-9}, 0.01, 0.1, 1, 10, 100)$ s$^{-1}$ was used. For the Victor-Purpura distance, the $\mathcal{L}_2$ version was used. Experiments with the original $\mathcal{L}_1$ version with a Laplacian kernel were also performed, but there was no significant difference. The classification rates for the weighted spike-train metrics (comparison of touch site classification accuracy using multi-unit spike train metrics) are provided in the Table of FIG. 42. With the CAML-optimized product kernel, the average classification rate increased by at least 8 percentage points for both metrics and both classifiers. For the sum kernel with 5 product kernels, the accuracy was further increased.

Figures 43A, 43B:
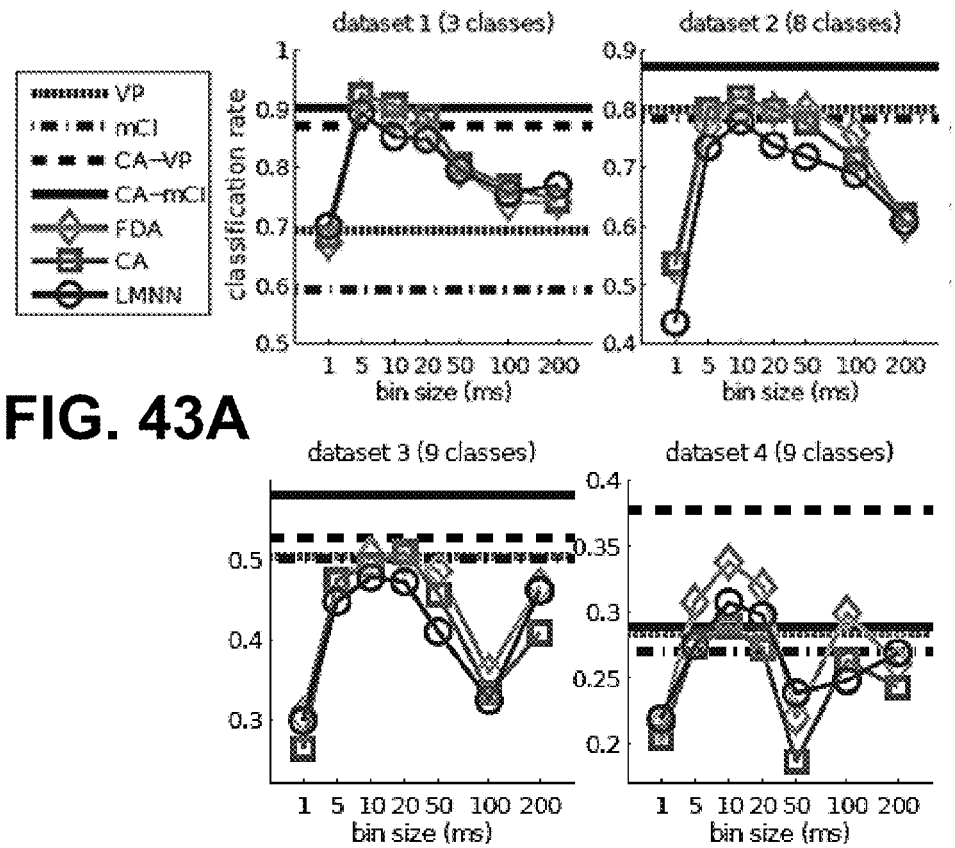

For binned spike trains, a Mahalanobis metric was optimized using FDA, CAML, and LMNN. The results across a range of different bin sizes are shown in FIG. 43A, which illustrates the comparison between multi-unit spike train metrics and binned spike count metrics with varying bin sizes. The SVM-based classification rate is shown for the unweighted Victor-Purpura (VP) and kernel-based (mCI) metrics, centered alignment metric learning optimized spike train metrics (CA-VP, CA-mCI), and Mahalanobis metrics on binned spike trains optimized with Fisher discriminant analysis (FDA), centered alignment (CA), and large margin nearest neighbor (LMNN). On three datasets the best binned metrics performed worse than the optimized spike-train metrics. For each dataset and method the performance using the bin size with the highest average accuracy is shown in the Table of FIG. 43B, which compares the touch site classification accuracy using binned spike trains and Euclidean or Mahalanobis-based metrics. On three of the datasets the Mahalanobis metric optimized with CAML tied or outperformed the FDA solution, and on all datasets using LMNN decreased performance.

Figure 44:
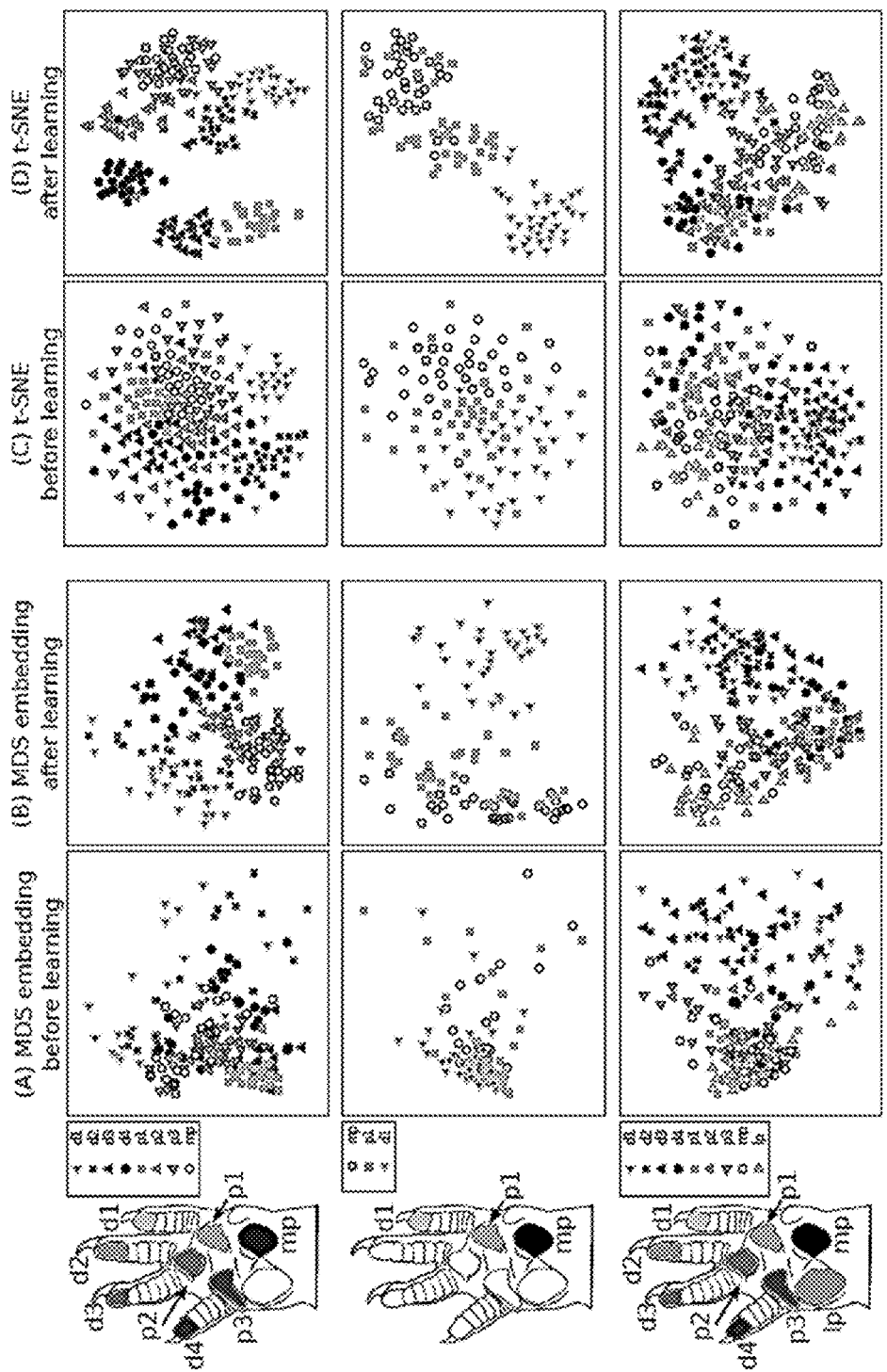

Classical multidimensional scaling (MDS) and t-distributed stochastic neighborhood embedding (t-SNE) was used to find a two-dimensional embedding of the distance matrices before and after training the metric. The embedding is formed without knowledge of the class labels. FIG. 44 illustrates a comparison of metric-based dimensionality reduction before and after using centered alignment metric learning (CAML) to optimize a weighted combination of Victor-Purpura spike train distances. For columns (A) and (B), a two-dimensional embedding was formed using multidimensional scaling (MDS) before and after learning. For columns (C) and (D), t-distributed stochastic neighborhood embedding (t-SNE) was used to form a nonlinear embedding where the algorithm's perplexity parameter was fixed at 10. From FIG. 44 it can be seen that metric learning with the product kernel increases distances among the different classes while decreasing the distances among samples within the same class.

Referring to FIG. 45, shown is an example of learned weights for spiking unit and temporal precision pairs for an optimized Victor-Purpura spike-train metric (CAML-VP), shown across the array as a Hinton diagram with the size of each square relative to the maximum weight of all units on the channel. Each subplot shows the weights for a different choice of the temporal precision value q. FIG. 45 illustrates how the optimized spike-train metric can be used to identify both the temporal precision and spiking units most useful for the decoding task. The weights for all temporal precision values were learned at the same time for dataset 2.

Learning LFP metrics. The classification rates for learning spatiotemporal metrics on LFP are tabulated in the Table of FIG. 46. Using CAML to optimize just a single temporal weighting improves the accuracy by 21 and 14.7 percentage points for 1-NN and SVM, respectively. Using a sum kernel composed of 5 product kernels further increased the performance by 2.2 and 4 percentage points. The optimized weights for a single product kernel are shown in FIG. 47. The learned temporal weighting of the optimized local field potential metric for decoding touch site across all datasets illustrated. Overall, using FDA to optimize, a linear projection was able to achieve the highest classification rates with average improvement over Euclidean distance by 33.5 and 23.4 percentage points for 1-NN and SVM.

A multiscale metric was learned as the weighted combination of the optimized spike distance and optimized LFP distance. On these datasets the combination of spiking and LFPs did not increase the classification rate versus using only LFPs, and the weight assigned to the spiking metric was insignificant compared to the weight assigned to the LFP metric. The average classification accuracy across the datasets was slightly lower than using just the LFP metric. From the results it can be seen that metric learning achieves three goals: increases the decoding accuracy, identifies important dimensions of the neural response, and improves the ability of manifold learning techniques to visualize the data in a low-dimensional space. For spike trains, the average performance of the optimized multi-unit spike train metrics exceeded those based on binning.

Here, a multi-neuron metric that is non-parametric has been optimized without the use of binning. In the framework of the kernel-based dependence measure, this optimization explicitly optimizes the contribution of each dimension using tensor product kernels for multi-neuron spike trains. On all the datasets the performance from using the unweighted multi-neuron spike train metrics was lower than using the optimized Mahalanobis metrics on the binned representation. In essence, a simple linear projection of binned spike trains performs better than binless metrics that are not optimized. The precision offered by binless methods is only realized after optimization. This highlights the advantage of metric learning versus naively combining the single-unit metrics.

FDA achieved the best performance for this touch decoding task using the time-locked evoked LFPs. FDA is well-suited for this setting since the class conditional LFP responses are approximately normally distributed—an underlying assumption for FDA. In addition, the FDA solution is also the fastest solution; consequently, FDA should always be the baseline for discrete decoding of sensory evoked LFPs. Alternatively, for binned spikes using CAML to further optimize the FDA projection marginally increased the classification performance. Overall, FDA and CAML outperformed LMNN in optimizing a Mahalanobis metric. One drawback of the Mahalanobis metric was the ability to analyze the projection matrices themselves. It is difficult to match and compare linear projections learned across multiple subjects or tasks, especially for high-rank projections. In this case using a weighted metric, which has lower accuracy but far fewer parameters, is more easily interpretable.

From FIG. 47, it is clear that the weighted metrics can be used to identify dimensions, in this case time lags, that are useful for discrimination. In addition, it appears that the optimization leads to a very sparse set of weights. In terms of neural decoding, the classification rate was compared, as a proxy for the information content, of the neural responses. Changing the underlying metric of the neural response space can improve the visualization results from unsupervised manifold learning algorithms. Indeed from FIG. 44, a user can immediately judge which classes are more similar or indistinguishable. The non-linear embeddings preserve some features of the stimulus space's topology, e.g., the separation between digit responses and palm responses in dataset 3 and the preservation of the relative arrangement of the three touch sites in dataset 2.

Decoding Reach Target from Monkey Premotor Cortex. Spike trains were recorded from the dorsal premotor cortex (PMd) cortex of a female bonnet macaque through chronically implanted cortical microelectrode arrays as the subject performed center-out reaching task. PMd is an area known to encode premeditation of movement. Only units whose average firing rates was greater than 2 Hz and less than 30 Hz during the reach trails are used for analysis; 38 units met this requirement. There were 150 trials among the 8 targets. The goal is to decode the intended reach target during a 300 ms hold period where the subject is shown the location of the goal target but before the reach has begun; this was insured because the hand must remain at the center target or the trial aborts and no reward is delivered. For comparison, the window of activity for the first 300 ms of the reach and a control window comprising the 300 ms hold period before the reach target are used. Decoding performance is gauged using metric and kernel-based classifiers. The mCI spike train kernel was used for the single-unit kernels and the corresponding metric; the temporal precision was set to 100 ms. Unweighted multi-unit metrics and kernels are compared to metrics optimized using CAML.

Classification across windows. The classification accuracy in the three windows (pre-cue (control), cued withhold, and movement) was calculated across 80 Monte Carlo divisions using two-thirds of the trials for testing and the remaining for testing. The statistics of the classification accuracy (in percent correct) are shown in the Table in FIG. 48. The optimized multi-unit metrics and kernels outperform the unweighted versions for the reach target decoding.

Visualization using metric-based embedding. Classical multidimensional scaling (MDS) was used to compare how well the unweighted and optimized metrics capture intrinsic relationship between the neural activity and the reach movements. FIGS. 49A through 49D visually illustrate metric-based dimensionality reduction on the premotor cortex data: before and after using centered alignment metric learning. Two-dimensional embedding was formed using multidimensional scaling (MDS) on different windows and different metrics. FIG. 49A shows the results using unweighted distance during the hold period, FIG. 49B shows the results using unweighted distance during the reach, FIG. 49C shows the results using the optimized distance during the hold period, and FIG. 49D shows the results using the optimized distance during the reach.

The visualization in FIGS. 49A-49D helps elucidate why the classification performance saturated around 55%: the neural responses are very similar for two distinct sets of reaches. The two groups are reaches between 9 o'clock and 2 o'clock and reaches between 3 o'clock to 8 o'clock, where the clock is in the horizontal plane with 12 o'clock as ventral movement along the subject's midline. The visualization provides a simple confirmation of the classification. This illustrates how dimensionality reduction can enable visualizations that are predictive of the classification performance. In some cases, a classifier may be able to perform better in a higher-dimensional space, yet the separation seen in the visualization suggests a lower bound on the classification accuracy.

Figure 50A:
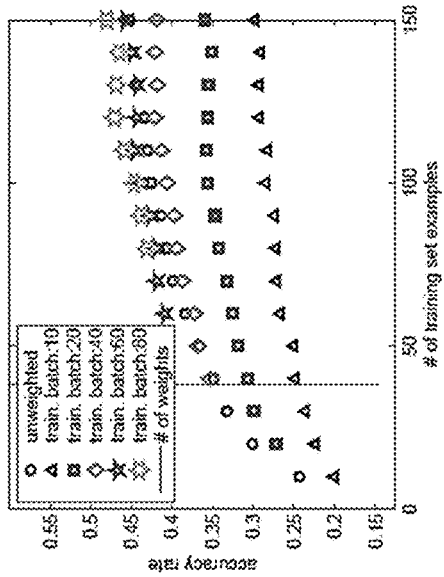
FIG. 50A through 50C are examples of reach target decoding performance in accordance with various embodiments of the present disclosure.
Figure 50B:
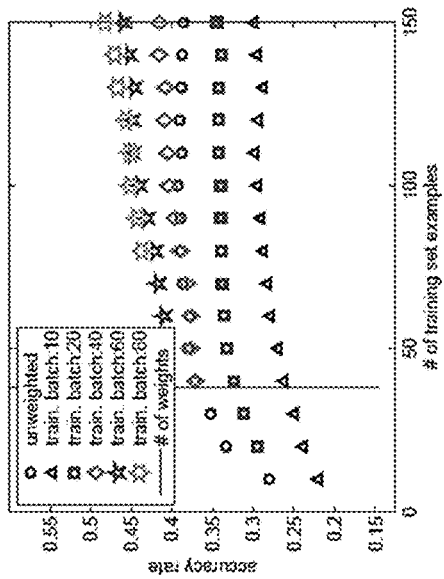
Figure 50C:
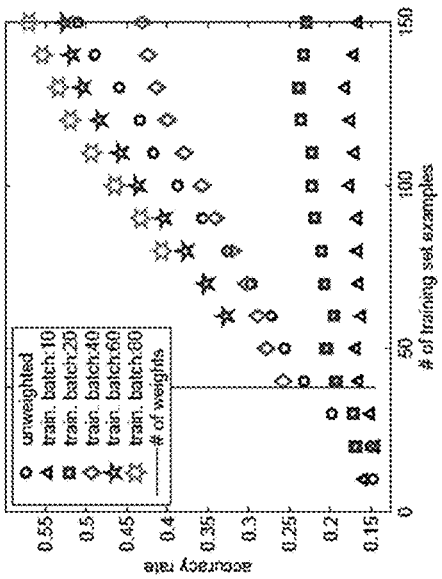
Figure 51A:
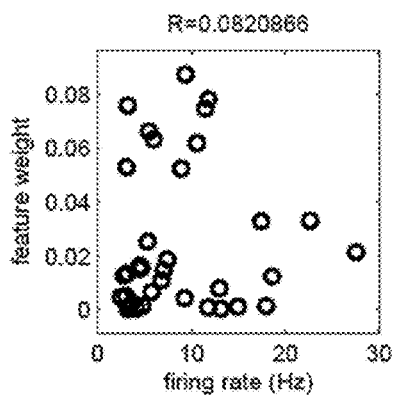
FIGS. 51A through 51D are examples of regression analysis in accordance with various embodiments of the present disclosure.
Figure 51B:
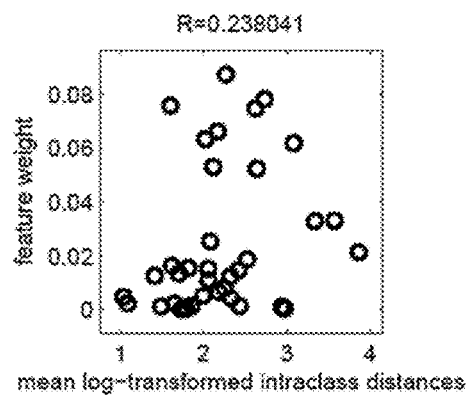
Figure 51C:
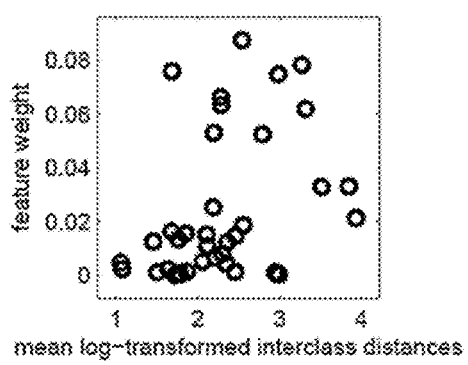
Figure 51D:
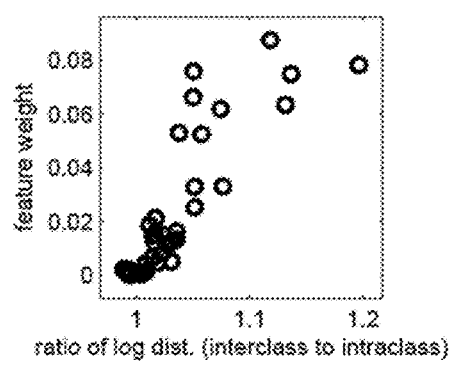

Effect of training set cardinality on performance of metric learning. The effect of training set size on both the metric-learning optimization and the classifiers was studied using more Monte Carlo experiments. The initial batch of samples given to CAML is varied along with the number of samples provided to the classifier. For each case, 80 Monte Carlo divisions are made and the averages are shown in FIGS. 50A through 50C. The reach target decoding performance across different sizes of training sets is shown. The unweighted multi-unit metric was compared to the weighted metric optimized by centered alignment metric learning: using different sizes of initial batches. FIG. 50A illustrates first nearest neighbor (1NN) classifier, FIG. 50B illustrates third nearest neighbor (3NN) classifier, and FIG. 50C illustrates Support vector machine (SVM) classifier. The results indicate that the metric learning optimization outperforms the unweighted distance only when there is least as many samples in its batch as there are optimized parameters. In this dataset there are 38 weights corresponding to the 38 units, so an initial batch of 40 samples was sufficient for 1 NN, but for SVM, 60 training samples (34% of the dataset) were needed.

Analysis of spike train unit weights. A regression analysis was performed between the optimized unit weights and measures of the single-unit firing rate and spike train distances. Besides the firing rates, the average of the log-normalized distances was computed for each unit between samples within the same class and samples of different classes. The log was used since single-trial distances are positive and right skewed. Since the weights should be indicative of the utility of a unit for discrimination, not the absolute value of the distances, the ratio of the interclass to intraclass log-normalized distances was also computed. Four different independent variables were tested: a unit's firing rate, unit's average log-transformed distances between samples in the same class, a unit's average log-transformed distances between samples in different classes, and the ratio of a unit's average log-transformed interclass distances to intraclass distance. There are n=38 feature weights corresponding to the single-units from PMd.

The scatter plots and correlation coefficients are reported in FIGS. 51A through 51D, which illustrate regression analysis between the optimized weights and different independent variables derived from the spike trains and metric. The correlation coefficient is denoted above each scatter plot. For FIG. 51A, the dependent variable is firing rate. For FIG. 51B, the dependent variable is the average of the log-transformed distances between samples in the same class, using the single-unit spike train distance. For FIG. 51C, the dependent variable is the average of the log-transformed distances between samples in different classes. For FIG. 51D, the dependent variable is the ratio between the average log-transformed distances for interclass versus intraclass. Only for the distance ratio was there a statistically significant correlation ($p<10^{-11}$) well below a significance level of 5/4=1.25% after Bonferroni's correction. This analysis shows, that in this dataset, the weights optimized with CAML indicate the single-units ability to discriminate between classes. This is a common aspect of all feature selection algorithms, beyond this relative ordering, CAML was able to find the absolute value to improve kernel classification without separately optimizing the kernel size.

Metric Learning for Neural Encoding. While neural decoding has been examined, the disclosed algorithms are also applicable to the neural encoding problem, wherein, the role of the stimulus and neural response are reversed. More specifically, for neural encoding, the metric on the neural response is fixed, the neural activity, e.g., the spiking of a single neuron, is treated as the target or label variable and a metric on the stimulus is adjusted. For instance, if the neuron is assumed to be a simple cell with a linear receptive field, then learning the receptive field is equivalent to learning a Mahalanobis distance on the stimulus space. The ideas that have been developed for metric-learning/supervised dimensionality reduction in the machine learning community are fundamentally similar to the algorithms for inferring the linear receptive fields of neurons in the computational neuroscience community, but the nomenclature and domain has differentiated them. Recently, researchers have begun to bridge this gap using kernel-based measures of dependence. To further highlight this connection, we replicated an experiment used to explain the maximally informative directions algorithm, using centered alignment metric learning to learn the neural encoding model.

Figure 52:
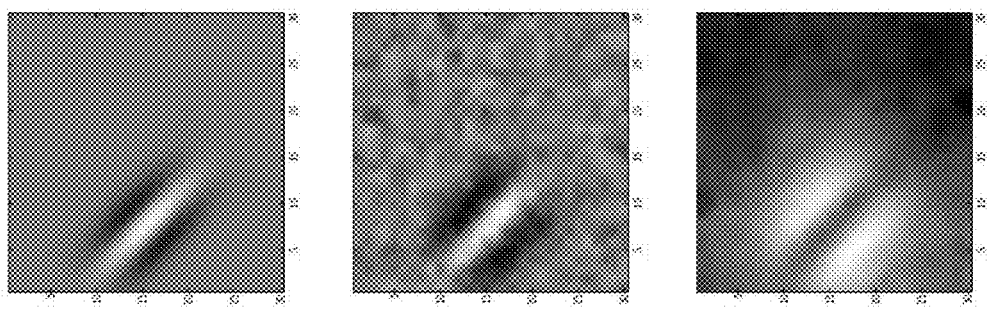
FIG. 52 is an example of filter estimation for a simple cell model in accordance with various embodiments of the present disclosure.

The underlying model corresponds to a predefined filter comprising 3 Gaussian bumps with equal covariance. FIG. 52 illustrates using metric learning to estimate the filter for a simple cell model. Here the Gaussian bumps are offset instead of being centered. This filter corresponds to the linear weights of a model simple cell, a stochastic neuron. The value of the inner product between an input image and the filter, denoted s, is proportional to the probability of the neuron spiking/firing or not. Specifically, a zero-mean Gaussian random variable e with variance a is added to the inner-product, if this sum is greater than the threshold b then a spike is generated. As input, patches are used from a database of natural images consisting of buildings, parks, trees, etc. Square patches of 30 by 30 pixels were randomly sampled from the images. The simulated cells parameters a and b are set relative to the standard deviation of s. Specifically, a=0.31σ(s) and b=1.8σ(s). The absence or presence of spike for a given patch is treated as a label. A set of 40,000 patches and the corresponding labels were given to the metric learning algorithm. Mini-batch optimization was run and the results are displayed in FIG. 52 for the Mahalanobis-based metric and a weighted metric. The images show (A) the true filter, (B) the learned projection using 100 sample batches and 2000 batches, and (C) the learned weighting using 100 sample batches and 2000 batches.

Kernels applicable to metric learning have been introduced, allowing the use of kernel-based dependence measure to optimize metrics. In the kernel-learning framework, changing the metric corresponds to changing the kernel. This leads to non-convex optimization, which can be solved using first-order methods. Adjusting the kernels is a distinct approach from the multiple kernel learning, where there is an explicit weight associated with each kernel in the sum and each summand kernel is chosen a priori (e.g., in the case of Gaussian kernel, the kernel size is not optimized and must be preselected). The main benefit of the multiple kernel learning is that a convex optimization problem can be posed to optimize the weights. Alternatively, the weighted product kernels and sum of weighted product kernels constitutes a much richer family of kernel functions than the weighted sum of kernels. Linear projections and weighted metrics are two special cases of metric learning that have received the most study. Indeed, the weighted combination of metrics was used in some of the earliest work on metric learning. We have gone beyond this by using a sum of weighted product kernels, which computes distances in the Hilbert space that correspond to nonlinear transformations of the data samples. The sum of weighed product kernels still has interpretable parameters, quite unlike kernelized projections, where the transformations are only defined in terms of the samples instead of the original dimensions. These metrics were optimized on a neural datasets consisting of both spike trains and local field potentials, for which metric learning improves both nearest neighbor and SVM classification accuracy over unweighted alternatives. Within the proposed framework, the optimized multi-unit spike train metrics, which avoid binning, outperform both unweighted multiunit metrics and metrics optimized for the binned spike trains. In addition, metric learning improves the quality of the visualizations (obtained via metric-based dimensionality reduction) for analyzing the relationship between high-dimensional neural data and target variables. The optimized weights themselves indicate the relative relevancy of different dimensions of the neural response. This can be used to explore how the weights of specific channels or neurons change for different tasks.

Figure 53:
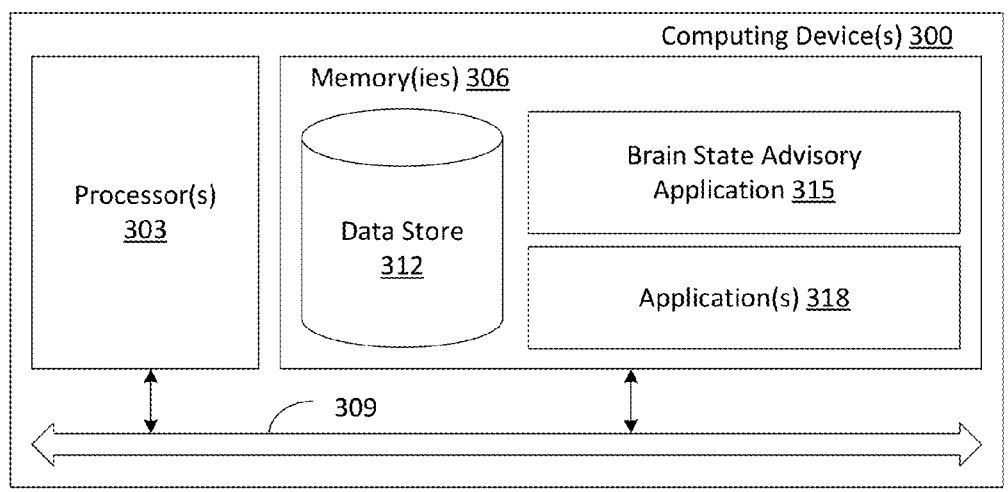
FIG. 53 is a schematic block diagram of a computing device in accordance with various embodiments of the present disclosure.

With reference to FIG. 53, shown is a schematic block diagram of a computing device 300 according to various embodiments of the present disclosure. The computing device 300 includes at least one processor circuit, for example, having a processor 303 and a memory 306, both of which are coupled to a local interface 309. To this end, the computing device 300 may comprise, for example, at least one server computer or like device. The local interface 309 may comprise, for example, a data bus with an accompanying address/control bus or other bus structure as can be appreciated.

Stored in the memory 306 are both data and several components that are executable by the processor 303. In particular, stored in the memory 306 and executable by the processor 303 may be a brain state advisory application 315 and/or other applications 318. Also stored in the memory 306 may be a data store 312 and other data. In addition, an operating system may be stored in the memory 306 and executable by the processor 303.

It is understood that there may be other applications that are stored in the memory 306 and are executable by the processor 303 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Delphi®, Flash®, or other programming languages.

A number of software components are stored in the memory 306 and are executable by the processor 303. In this respect, the term "executable" means a program file that is in a form that can ultimately be run by the processor 303. Examples of executable programs may be, for example, a compiled program that can be translated into machine code in a format that can be loaded into a random access portion of the memory 306 and run by the processor 303, source code that may be expressed in proper format such as object code that is capable of being loaded into a random access portion of the memory 306 and executed by the processor 303, or source code that may be interpreted by another executable program to generate instructions in a random access portion of the memory 306 to be executed by the processor 303, etc. An executable program may be stored in any portion or component of the memory 306 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 306 is defined herein as including both volatile and nonvolatile memory and data storage components. Volatile components are those that do not retain data values upon loss of power. Nonvolatile components are those that retain data upon a loss of power. Thus, the memory 306 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 303 may represent multiple processors 303 and the memory 306 may represent multiple memories 306 that operate in parallel processing circuits, respectively. In such a case, the local interface 309 may be an appropriate network that facilitates communication between any two of the multiple processors 303, between any processor 303 and any of the memories 306, or between any two of the memories 306, etc. The local interface 309 may comprise additional systems designed to coordinate this communication, including, for example, performing load balancing. The processor 303 may be of electrical or of some other available construction.

Although the brain state advisory application 315, application(s) 318, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Although FIG. 1 shows a specific order of execution, it is understood that the order of execution may differ from that which is depicted. For example, the order of execution of two or more blocks may be scrambled relative to the order shown. Also, two or more blocks shown in succession in FIG. 1 may be executed concurrently or with partial concurrence. Further, in some embodiments, one or more of the blocks shown in FIG. 1 may be skipped or omitted (in favor, e.g., measured travel times). In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the brain state advisory application 315 and/or application(s) 318, that comprises software or code can be embodied in any non-transitory computer-readable medium for use by or in connection with an instruction execution system such as, for example, a processor 303 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A method for determination of a clinical diagnostic condition of a subject's brain through a brain computer interface, comprising:
    monitoring brainwave activity of a subject at multiple spatial locations via neural electric recordings, the brainwave activity being monitored at multiple temporal scales, where the brainwave activity comprises spike trains and local field potentials obtained via multichannel neural monitoring of the subject;
    identifying, by at least one computing device, phasic events from neural waveforms of the brainwave activity, where the phasic events comprise temporally localized brain rhythms of the neural waveforms that are identified based upon a subject specific dictionary of filters associated with the subject;
    generating, by the at least one computing device, a multidimensional metric by:
        spatiotemporal integration of the phasic events, and
        projection of results of the spatiotemporal integration to a lower dimensional space using metric learning to generate the multidimensional metric;
    classifying, by the at least one computing device, a brain state of the subject based upon the multidimensional metric and a subject specific dynamical model of the brainwave activity of the subject, the brain state being a health state or a disease state of the subject; and
    generating, by the at least one computing device, an indication of the brain state of the subject, the indication identifying the health state or disease state of the subject.

2. The method of claim 1, wherein the brain state is classified based upon the subject specific dynamical model estimated through blind signal processing of the brainwave activity of that subject.

3. The method of claim 2, wherein the blind signal processing is based upon blind waveform estimation of a single channel of the brainwave activity of the subject.

4. The method of claim 2, wherein the blind signal processing is based upon separate blind waveform estimation of multiple individual channels of the brainwave activity of the subject.

5. The method of claim 1, wherein the subject specific dictionary of filters comprises a set of filters determined through unsupervised blind waveform estimation of the brainwave activity of the subject by the at least one computing device.

6. The method of claim 5, wherein the set of filters comprise temporal and spatial filters.

7. The method of claim 1, wherein the brain state is classified with a temporal precision given by a sampling rate used for monitoring the brainwave activity.

8. The method of claim 1, wherein the phasic events are identified based upon the subject specific dictionary of filters.

9. The method of claim 1, wherein the spatiotemporal integration comprises pooling of energy between adjacent channels with similar neural waveforms.

10. The method of claim 1, wherein the projection to the lower dimensional space is implemented using a supervised dimensionality reduction algorithm.

11. The method of claim 1, wherein the brain state of the subject is classified based at least in part upon a projection of the subject specific dynamical model.

12. The method of claim 1, wherein the brain state of the subject is classified based at least in part upon landmark points corresponding to classified brain states of the subject.

13. A method for determination of a clinical diagnostic condition of a subject's brain through a brain computer interface, comprising:

monitoring brainwave activity of a subject at multiple spatial locations, the brainwave activity being monitored by recording neural signals at multiple temporal scales, where the brainwave activity comprises spike trains and local field potentials obtained via multichannel neural monitoring of the subject;

decomposing, by at least one computing device, the neural signals of the brainwave activity to generate filtered components based upon a subject specific dictionary of filters associated with the subject, the subject specific dictionary of filters comprising filters determined through unsupervised blind waveform estimation of the brainwave activity of that subject by the at least one computing device;

modeling, by the at least one computing device, brain states of the subject based at least in part upon the filtered components from the brainwave activity and timing of the spike trains to provide a subject specific dynamical model of the brainwave activity of the subject;

classifying, by the at least one computing device, a brain state of the subject based upon a multidimensional metric determined from the brainwave activity and the subject specific dynamical model of the brainwave activity, the brain state being a health state or a disease state of the subject, where the multidimensional metric is determined from spatiotemporal integration of the filtered components and projection of results of the spatiotemporal integration to a lower dimensional space using metric learning; and generating, by the at least one computing device, an indication of the brain state of the subject, the indication identifying the health state or disease state of the subject.

14. The method of claim 13, wherein the filtered components comprise phasic events identified based upon the subject specific dictionary of filters.

15. The method of claim 13, wherein the filters of the subject specific dictionary of filters comprise waveforms tuned to neural signals of the brainwave activity of the subject.

16. The method of claim 15, wherein the neural signals comprise monitored EEG signals of the subject.

17. The method of claim 13, wherein the brain states of the subject are modeled using the multidimensional metric.

18. The method of claim 8, wherein the neural waveforms comprise EEG waveforms.

* * * * *